(12) United States Patent
Subramaniam et al.

(10) Patent No.: US 7,420,101 B2
(45) Date of Patent: Sep. 2, 2008

(54) NUCLEIC ACID SEQUENCES TO PROTEINS INVOLVED IN TOCOPHEROL SYNTHESIS

(75) Inventors: Sai S. Subramaniam, Framingham, MA (US); Steven C. Slater, Acton, MA (US); Katherine Karberg, Cambridge, MA (US); Ridong Chen, Maryland Heights, MO (US); Henry E. Valentin, Cambridge, MA (US); Yun-Hua Huang Wong, Chesterfield, MO (US)

(73) Assignee: Calgene LLC, St. Louis, MO (US)

( * ) Notice: Subject to any disclaimer, the term of this patent is extended or adjusted under 35 U.S.C. 154(b) by 246 days.

(21) Appl. No.: 11/092,140

(22) Filed: Mar. 29, 2005

(65) Prior Publication Data

US 2005/0262590 A1 Nov. 24, 2005

Related U.S. Application Data

(63) Continuation of application No. 09/688,069, filed on Oct. 14, 2000, now Pat. No. 6,872,815.

(51) Int. Cl.
*A01H 5/00* (2006.01)
*A01H 5/10* (2006.01)
*C12N 15/05* (2006.01)
*C12N 15/29* (2006.01)
*C12N 15/52* (2006.01)
*C12N 15/82* (2006.01)

(52) U.S. Cl. ............... 800/287; 536/23.1; 536/23.2; 536/23.6; 435/419; 435/468; 800/298; 800/306; 800/312; 800/314; 800/317.4; 800/320.1; 800/320.2; 800/320.3

(58) Field of Classification Search ............... None
See application file for complete search history.

(56) References Cited

U.S. PATENT DOCUMENTS

| | | | |
|---|---|---|---|
| 4,727,219 A | 2/1988 | Brat et al. | |
| 5,304,478 A | 4/1994 | Bird et al. | |
| 5,429,939 A | 7/1995 | Misawa et al. | |
| 5,432,069 A | 7/1995 | Gruninger et al. | |
| 5,545,816 A | 8/1996 | Ausich et al. | |
| 5,618,988 A | 4/1997 | Hauptmann et al. | |
| 5,684,238 A | 11/1997 | Ausich et al. | |
| 5,693,507 A | 12/1997 | Daniell et al. | |
| 5,750,865 A | 5/1998 | Bird et al. | |
| 5,792,903 A | 8/1998 | Hirschberg et al. | |
| 5,876,964 A | 3/1999 | Croteau et al. | |
| 5,908,940 A | 6/1999 | Lane et al. | |
| 6,281,017 B1 | 8/2001 | Croteau et al. | |
| 6,303,365 B1 | 10/2001 | Martin et al. | |
| 6,541,259 B1 * | 4/2003 | Lassner et al. | 435/468 |
| 2002/0069426 A1 | 6/2002 | Boronat et al. | |
| 2002/0108148 A1 | 8/2002 | Boronat et al. | |
| 2003/0148300 A1 | 8/2003 | Valentin et al. | |
| 2003/0150015 A1 | 8/2003 | Norris et al. | |
| 2003/0154513 A1 | 8/2003 | van Eenennaam et al. | |
| 2003/0166205 A1 | 9/2003 | van Eenennaam et al. | |
| 2003/0170833 A1 | 9/2003 | Lassner et al. | |
| 2003/0176675 A1 | 9/2003 | Valentin et al. | |
| 2003/0213017 A1 | 11/2003 | Valentin et al. | |
| 2004/0018602 A1 | 1/2004 | Lassner et al. | |
| 2004/0045051 A1 | 3/2004 | Norris et al. | |

FOREIGN PATENT DOCUMENTS

| | | |
|---|---|---|
| CA | 2339519 | 2/2000 |
| CA | 2343919 | 3/2000 |
| CA | 2372332 | 11/2000 |
| DE | 198 35 219 | 8/1998 |
| EP | 0 531 639 | 3/1993 |
| EP | 0 674 000 | 9/1995 |
| EP | 0 723 017 | 7/1996 |
| EP | 0 763 542 | 3/1997 |
| EP | 1 033 405 | 9/2000 |
| EP | 1 063 297 | 11/2000 |
| FR | 2 778 527 | 11/1999 |
| GB | 560 529 | 4/1944 |
| WO | WO 91/02059 | 2/1991 |
| WO | WO 91/09128 | 6/1991 |
| WO | WO 91/13078 | 9/1991 |
| WO | WO 9318158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |

(Continued)

OTHER PUBLICATIONS

Broun et al. Science vol. 282 Nov. 13, 1998; pp. 1315-1317.*

(Continued)

*Primary Examiner*—Russell Kallis
(74) *Attorney, Agent, or Firm*—Sonnenschein Nath & Rosenthal LLP

(57) ABSTRACT

Nucleic acid sequences and methods are provided for producing plants and seeds having altered tocopherol content and compositions. The methods find particular use in increasing the tocopherol levels in plants, and in providing desirable tocopherol compositions in a host plant cell.

52 Claims, 40 Drawing Sheets

FOREIGN PATENT DOCUMENTS

| | | |
|---|---|---|
| WO | WO 95/18220 | 7/1995 |
| WO | WO 95/23863 | 9/1995 |
| WO | WO 95/34668 | 12/1995 |
| WO | WO 96/02650 | 2/1996 |
| WO | WO 96/06172 | 2/1996 |
| WO | WO 96/13149 | 5/1996 |
| WO | WO 96/13159 | 5/1996 |
| WO | WO 96/36717 | 11/1996 |
| WO | WO 9638567 | 12/1996 |
| WO | WO 97/17447 | 5/1997 |
| WO | WO 97/27285 | 7/1997 |
| WO | WO 98/06862 | 2/1998 |
| WO | WO 99/04622 | 2/1999 |
| WO | WO 99/06580 | 2/1999 |
| WO | WO 99/07867 | 2/1999 |
| WO | WO 00/01650 | 1/2000 |
| WO | WO 00/08169 | 2/2000 |
| WO | WO 00/08187 | 2/2000 |
| WO | WO 00/10380 | 3/2000 |
| WO | WO 00/11165 | 3/2000 |
| WO | WO 00/14207 | 3/2000 |
| WO | WO 00/17233 | 3/2000 |
| WO | WO 00/22150 | 4/2000 |
| WO | WO 00/28005 | 5/2000 |
| WO | WO 00/32757 | 6/2000 |
| WO | WO 00/34448 | 6/2000 |
| WO | WO 00/42205 | 7/2000 |
| WO | WO 00/46346 | 8/2000 |
| WO | WO 00/61771 | 10/2000 |
| WO | WO 00/63389 | 10/2000 |
| WO | WO 00/63391 | 10/2000 |
| WO | WO 00/65036 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 8/2001 |
| WO | WO 01/62781 | 8/2001 |
| WO | WO 01/79472 | 10/2001 |
| WO | WO 01/88169 | 11/2001 |
| WO | WO 02/00901 A1 | 1/2002 |
| WO | WO 02/26933 | 4/2002 |
| WO | WO 02/29022 | 4/2002 |
| WO | WO 02/31173 | 4/2002 |
| WO | WO 02/33060 | 4/2002 |
| WO | WO 02/46441 | 6/2002 |
| WO | WO 02/072848 | 9/2002 |
| WO | WO 02/089561 | 11/2002 |
| WO | WO 03034812 | 5/2003 |
| WO | WO 03047547 | 6/2003 |

OTHER PUBLICATIONS

Porfirova et al. PNAS Sep. 17, 2002, vol. 99, No. 19, pp. 12495-12500.*
Sattler S, Plant Physiology; Aug. 2003; vol. 132, pp. 2184-2195.*
Addlesee et al., 'Cloning, sequencing and functional assignment of the chlorophyll biosyntheses gene,: chlP, of Synechocystis sp. PCC 6803', FEBS Letters 389 (1996) 126-130.
Arango et al., "Tocopherol synthesis from homogentisate in Capsicum anuum L. (yellow pepper) chromoplast membranes: evidence for tocopherol cyclase", Biochem J. 336:531-533 (1998).
Arigoni et a! , 'Terpenoid biosynthesis from 1 deoxy-D-xylulose in higher plants by intramolecular skeletal rearrangement', Proc. Natl. Acad. Sd. USA, 94:10600-10605 (1997).
Baker et al., Sequence and characterization of the gcpE gene of Escherichia colt, FEMS Microbiology Letters, 94:175180 (1992).
Bayley et aL, Engineering 2,4-D resistance into cotton, Theor Appl Genet, 83:645-649 (1992).

Bentley, R., 'The Shikimate Pathway—A Metabolic Tree with Many Branches,' Critical Reviews™ in Biochemistry and Molecular Biology; vol. 25, Issue 5, 307-384 (1990).
Bevan et al., TREMBL Database Accession No. 065524.
Bevan etal., Database EMBL, Accession No. AL035394 (Feb. 9, 1999) (XP 002153686).
Bevan, M., 'Binary Agrobacterium vectors for plant transformation', Nucleic Acids Research; 12:8711-872i (1984).
Beyer at at, Phytoene-forming activities in wild-type and transformed rice endosperm, IRRN 21:2-3, p. 44-45 (Aug.-Dec. 1996).
Bork at at, 'Go hunting in sequence databases but watch out for the traps', TIG 12,10:425 427 (Oct. 1996).
Bork et al., TIG, 10:425-427, 1996.
Bouvier at at, 'Dedicated Roles of Plastid Transketolases during the Early Onset of Isoprenoid Biogenesis in Pepper Fruits', Plant Physiol.,117:1423 1431 (1998).
Bramley et al, Biochemical characterization of transgenic tomato plants in which carotenoid synthesis has been inhibitied through the expression of antisense RNA to pTOM5, The Plant Journal, 2(3), 343-349 (1992).
Broun et al., Science, vol. 282, 1998.
Chen et al., EMBL Sequence Database Accession No. AI995392.
Desprez et al., Database EMBL, Accession No. Z34566 (Jun. 25, 1994) (XP 002169121).
Doerks et al., TIG, 14:248-250, 1998.
Fiedler et al., Planta, 155:511-515, 1982.
Gaubier et al., "A Chlorophyll Synthetase Gene from Arabidopsis thaliana," Mol. Gen. Genet., 249:58-64 (1995).
Gaubier et al., Database EMBL Accession No. Q33833 (Nov. 1, 1996) (XP 002169117).
Kaneko et al., Database TREMBL, Accession No. P73726 (Feb. 1, 1997) (XP 002169263).
Kaneko et al., Database TREMBL, Accession No. P73727 (Feb. 1, 1997) (XP 002169264).
Kaneko et al., EMBL Sequence Database Accession No. D90909.
Kaneko\t al., Database TREMBL, Accession No. P73962 (Jul. 15, 1998) (XP 002169129).
Kuntz et aL, "Identification of a eDNA for the Plastid-Located Geranylgeranyl Pyrophosphate Synthase from Capsicum annuum: Correlative Increase in Enzyme Activity and Transcript Level during Fruit Ripening," The Plant Journal, 2(1):25-34 (1992).
Li et al., "Identification of a Maize Endosperm-Specific cDNA Encoding Farnesyl Pyrophosphate Synthetase," Gene, 171:193-196 (1996).
Lin et al., Database EMBL, Accession No. A0003672 (Dec. 11, 1997) (XP 002153688).
Lin et al., Database EMBL, Accession No. AC003673 (Dec. 11, 1997) (XP 002153685).
Lin et al., Database EMBL, Accession No. AO004077 (Feb. 3, 1998) (XP 002169118).
Lopez et al., "Sequence of the bchG Gene from Chloroflexus aurantiacus: Relationship between Chlorophyll Synthase and Other Polyprenyltransferases," Journal of Bacteriology, 178(!1):3369-3373 (1996).
Malakhov et al., Database TREMBL, Accession No. Q55207 (Nov. 1, 1996) (XP 002169125).
Marshall et al., Phytochem, 24:1705-1711, 1985.
Murata et al., Database EMBL, Accession No. D13960 (Mar. 28, 1996) (XP 00 2169124).
Newman et al., Database EMBL, Accession No. R30625 (Aug. 11, 1995) (XP 002153690).
Newman et al., Database EMBL, Accession No. T44803 (Feb. 4, 1995) (XP 002169120).
Norris et al., "Genetic Dissection of Carotenoid Synthesis in Arabidopsis Defines Plastoquinone as an Essential Component of Phytoene Desaturation," The Plant Cell, 7:2139-2149 (1995).
Oster et al., "The G4 Gene of Arabindopsis thaliana Encodes a Chlorophyll Synthase of Etiolated Plants," Bot. Acta, 110:420-423(1947).
Oster et al., Database Biosis, Accession No. PREV199800047824 (Oct. 1997) (XP 002153691).

Porfirova et al., "Isolation of an *Arabidopsis* mutant lacking vitamin e and identification of a cyclase essential for all tocopherol biosynthesis," *PNAS*, 99:12495-12500, 2002.

Rounsley et al., Database EMBL, Accession No. B24116 (Oct. 13, 1997) (XP 002153687).

Rounsley et al., Database EMBL, Accession No. B29398 (Oct. 13, 1997) (XP 002153689).

Rounsley et al., Database TREMBL, Accession No. O64684 (Aug. 1, 1998) (XP 002169119).

Scolnik et al., Database EMBL, Accession No. L40577 (Apr. 15, 1995) (XP 002153692).

Shoemaker et al. Database EMBL, Accession No. AI988542 (Sep. 7, 1999) (XP 00 2169132).

Shoemaker et al., Database EMBL, Accession No. AI938569 (Aug. 3, 1999) (XP 002169133).

Shoemaker et al., Database EMBL, Accession No. AW306617 (Jan. 21, 2000) (XP 00 2169134).

Shoemaker, Database EMBL, Accession No. AI748688 (Jun. 29, 1999) (XP 002169135).

Smith et al., *Nature Biotechnology*, 15:1222-1223, 1997.

Soll et al., *Arch Biochem. Biophys*, 264:544-550, 1980.

Spurgeon et al., *Biosynthesis of Isoprenoid Compounds*, 1:1-46, 1981.

Stocker et al., "Identification of the Tocopherol-Cyclase in the Blue-Green Algae *Anabaena variabilis* Kutzing (*Cyanobacteria*)" 76:1729-1738 (1993).

Stocker et al., "The Substrate Specificity of Tocopherol Cyclase", *Bioorganic & Medicinal Chemistry* 4(7):1129-1134 (1996).

Svab et al., *PNAS USA*, 87:8526-8530, 1990.

Svab et al., *PNAS USA*, 90:913-917, 1993.

Tabata et al., Database EMBL, Accession No. D64001 (Sep. 30, 1995) (XP 002169126).

Tabata et al., Database EMBL, Accession No. D64006 (Sep. 30, 1995) (XP 002169122).

Tabata, Database EMBL, Accession No. D90909 (Oct. 31, 1996) (XP 002169130).

Tabata, Database EMBL, Accession No. D90911 (Oct. 31, 1996) (XP 002169128).

Tabata, Database TREMBL, Accession No. Q55145 (Nov. 1, 1996) (XP 002169127).

Tabata, Database TREMBL, Accession No. Q55500 (Nov. 1, 1996) (XP 002169123).

Walbot et al., Database EMBL, Accession No. AI795655 (Jul. 7, 1999) (XP 002169131).

Zhu et al., "Geranylgeranyl Pyrophosphate Synthase Encoded by the Newly Isolated Gene GGPS6 from *Arabidopsis thaliana* is Localized in Mitochondria," *Plant Molecular Biology*, 35:331-341 (1997).

Karunanandaa et al., "Metabolically enhanced oilseed crops with enhanced seed tocopherol". *Metabol. Eng.* 7:384-400, 2005.

Valentin et al., "The *Arabidopsis* vitamin E pathway gene5-1 Mutant Reveals a Critical Role for Phytol Kinase in Seed Tocopherol Biosynthesis", *Plant Cell* 18:212-224; 2006.

* cited by examiner

```
              *        20         *        40         *        60         *        80
ATPT2    : ------------MESLLSSSLVSAAGGFCWKKQNLKLHSLSEIRVLRCDSSKVVAKPKFRNNLVRPDGQGSSLLLYPKHKSRFRVNATAGQ :  80
SLR1736  : ---------------------------------------------------------------------------------------- :   -
ATPT3    : MAFFGLSRVSRLLKSSVSVTPSSSSALLQSQHKSLSNPVTTHYTNPFTKCYPSWNDNYQVWSKGRELHQEKFFGVGWNYRLICGMSSS :  89
SLR0926  : ---------------------------------------------------------------------------------------- :   -
ATPT4    : ---------------------MWRRSVVYRFSSRISVSSSLPNRLIPWSRELCAVNSFSQP----PVSTESTAKLGITGVRSDANRVFATA :  67
SLL1899  : ---------------------------------------------------------------------------MVTS :   4
ATPT12   : ------------MTSILNTVSTIHSSRVTSVDRVGVLSRNSDSVEFT-------------------RRRSGFSTLIYESPGRRFVVRAAETDT :  63
SLR0056  : ---------------------------------------------------------------------------MSDT :   4
ATPT8    : ---------------------------------------------------------------------------MVLA :   4
SLR1518  : ---------------------------------------------------------------------------MTES :   4

*       100         *       120         *       140         *       160          1
ATPT2    : PEAFDSNSKQK-------------------SFRDSLDAFYR---------FSRPHTVGTVLSLS----VSFLAVEKVS--DISPLFTGLE : 140
SLR1736  : ------------------------------------MATIQAFWR---------FSRPHTLGTTLSAVY----LLTILGDN-SVNSPASDLFG :  49
ATPT3    : SSVLEGKPKKDDKEKSDGVVVKKASWIDLYLPEEVRGYAKLARLDKPIGTWLAWPCS--------IALADPS--LPSFKYHALFGC : 170
SLR0926  : --------------------------------PLWLTIIYL---------LRWHKPAGRLLMIPAA---VCLAQ--G-LPPLPGTAL :  56
ATPT4    : TAAATATATTG-------------------EISSRVAALAGLGHHYAR---------CYWELSKAKLSMLVVATSG----TGYILGTNAAISFPGCYTCAG : 138
SLL1899  : TKIHRQHDSMG-------------------AVCKSYYQLTKP---------RIIPLLTTAAS-I-----ASER--VDLPKIITLG :  60
ATPT12   : DKVKSQTPDKAP----------AGGSSINQLLGIKGAS---------QETNKWKIRLQLTKPVTPPLVWGVVCGPAASNFHWTPEDAKSHLC : 139
SLR0056  : QNT-GQNQAKA-----------------RQLLGMKGAAP---------GESSIWKIRLQLMKPITIPLIWGVVCGASSGYIWSVEDFKATC :  73
ATPT8    : EVPKLASAAEY------------------FFKRGVQGKQF---------RSTILLEATALNRVP-------EALIGEST-DIVTSERVRQR :  63
SLR1518  : SPLAPSTAPAT------------------RKLWLAAIKP---------PMYTAVVPITVG-------SAVYGLTG--QWHGDFTIFLL :  59

*       180         *       200         *       220         *       240         *       260
ATPT2    : AVVAALMNIYIVGNQLSDVEIDKVNKPYLPLASGEYSNTGIAASFSIMSFWLGWIVGSWPLFWALFVSFLGTYS-INPLR : 228
SLR1736  : AWLACLLGNVYIVGLNQLMDVIDRINKPNLPLANGDFSAQGRWGLCGVASAIWGLG-LWLGLTVGLSLIGTIY---SPPVR : 134
ATPT3    : GALL--RGAGCTLNDLLDQHDTKVDTKLRIASGLT-PFQGGFLGLQLLGLG------ILLQLNNYSRNLGAS--SLLVF : 246
SLR0926  : GTLA--TSGLGCVNDLMDRLDPQVETKQRLAARAS-VQVGGVAVALLCAG----LFYLTPDSFWLCVI--APIV : 132
ATPT4    : TMVI--AASANSLNQLEISNDLSKMKTMLRLPSGRSVPHAQPRHAFALALGVSFL--LSKTNMLAAGLASN---LLYAF : 215
SLL1899  : GTLA--AASAQTLNCLDQIDYEMLTRARIPAGKVDAINEPYRPISGAISEPEVITQWVLLGGGIGILD-VWGHTTPIVFYIALG : 137
ATPT12   : MMMSGPCTGYTQTINDWDRIDAINEPYRPISGAISPQVVTQLILIVAGGVYGLD-VWQHDFPLMLLTLG--GSLSY : 223
SLR0056  : MLLSGPLTGYTQTLNDFDRIDDADTRGVGSLNVVMGNKMSVAGDFLSRACGAL--ALKNTEVVALATVEHLVTGETM : 157
ATPT8    : GIAE---TEMIHVASLHDDVIDDADTRGVGSLNVVMGNKMSVAGDFLSRACGAL--ALKNTEVVALATVEHLVTGETM : 144
SLR1518  : SADA---IAWINLSNVGDSTGIDVRAHSVVNLTGNRNLVFLSNFFLAGLGLMSMS--WRAQDWTVLEIGV---IFGY : 138
```

Alignment 1

```
Query-         12194 CACACGTTCTCGTCCTTTTCTTCTTCCTCTCTGCATTCTTCACAGAGTTTGTCACCACCA
genomic
ATCEA4C371+        1 ------------------------------------------------------------C est
                                                                                          :first
Met
Query-         12134 ▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓▓ATGGA
                     || |||||||-||||||||||||||||||||||||||||||||||||||||||||||||
ATCEA4C371+        2 ACCCCAAACATCACAATTTCACATTCTTTTGCATATTTCTTCTTCTTCTTCCATTATGGA Query-         12075 GATACGGAGCTTGATTGTTTCTATGAACCCTAATTTATCTTCCTTTGAGCTCTCTCGCCC
                     ||||||||||||||||||||||||||||||||||||||||||||||||||||||||||||
ATCEA4C371+       62 GATACGGAGCTTGATTGTTTCTATGAACCCTAATTTATCTTCCTTTGAGCTCTCTCGCCC Query-         12015 TGTATCTCCTCTCACTCGCTCACTAGTTCCGTTCCGATCGACTAAACTAGTTCCCCGCTC
                     ||||||||||||||||||||||||||||||||||||||||||||||||||||||||||||
ATCEA4C371+      122 TGTATCTCCTCTCACTCGCTCACTAGTTCCGTTCCGATCGACTAAACTAGTTCCCCGCTC Query-         11955 CATTTCTAGGGTTTCG▓▓▓▓▓ATCTCCACCCCGAATAGTGAAACTGACAAGATCTCCGT
                     ||||||||||||||||||||||||||||||||||||||||||||||||||||||||||||
ATCEA4C371+      182 CATTTCTAGGGTTTCGGCGTCGATCTCCACCCCGAATAGTGAAACTGACAAGATCTCCGT Query-         11895 TAAACCTGTTTACGTCCCGACGTCTCCCAATCGCGAACTCCGGACT▓▓▓▓▓▓▓▓▓▓GTA
                     ||||||||||||||||||||||||||||||||||||||||||||||||||||||||---
ATCEA4C371+      242 TAAACCTGTTTACGTCCCGACGTCTCCCAATCGCGAACTCCGGACT▓▓▓▓▓▓▓▓▓▓
                                                               Synecho seq aligns from
here Query-         11835 AATTGATCCATTCCATTCCATTTCTCTTCTCTTGTTTGTTTTATTAAGCTCCAATTTCAG
ATCEA4C371+      299 ------------------------------------------------------------

~~ 60 bp removed ~~~
Query-         11715 ***********************************************************TTTG
ATCEA4C371+      299 ---------
PIR:T04448         1                                                                ----

Query-         11655 GTGGCTCACCATTCGACGACTACTTTTGAATTTGAGTTTTTGAAAAATGCAATTTAACAT
ATCEA4C371+      299 ------------------------------------------------------------
PIR:T04448         1 ---------------------------------------------::::::::::::::
                                                                      M Q F N I
                                                               arab sequence which is incorrect Query-         11595 CAGAGAGTTTTTTTTTTTATGGTTGATAACTTATTGTTTAACTTTTGAAAAATGCAG▓▓▓
ATCEA4C371+      299 ------------------------------------------------------|||
                                                                             ▓▓▓
PIR:T04448         6 :::::::::::::::::::::::::::::::::::::::::::::::::::::::::::
                     R  E  F  F  F  L  W  L  I  T  Y  C  L  T  F  E  K  C  R  Y Query-         11535 CCATTTCGATGGAACACCTCGGAAGTTCTTCGAGGGATGGTATTTCAGGGTTTCCATCCC
                     ||||||||||||||||||||||||||||||||||||||||||||||||||||||||||||
ATCEA4C371+      302 CCATTTCGATGGAACACCTCGGAAGTTCTTCGAGGGATGGTATTT▓▓▓▓▓TCCATCCC
PIR:T04448        26 H  F  D  G  T  P  R  K  F  F  E  G  W  Y  F  ▓▓  S  I  P
```

Figure 31A

```
Query-       11475 AGAGAAGAGGGAGAGTTTTTGTTTTATGTATTCTGTGGAGAATCCTGCATTTCGGCAGAG
                  ||||||||||||||||||||||||||||||||||||||||||||||||||||||||||||
ATCEA4C371+    362 AGAGAAGAGGGAGAGTTTTTGTTTTATGTATTCTGTGGAGAATCCTGCATTTCGGCAGAG
                  ::::::::::::::::::::::::::::::::::::::::::::::::::::::::::::
PIR:T04448      46  E  K  R  E  S  F  C  F  M  Y  S  V  E  N  P  A  F  R  Q  S Query-       11415 TTTGTCACCATTGGAAGTGGCTCTATATGGACCTAGATTCACTGGTGTTGGAGCTCAGAT
                  ||||||||||||||||||||||||||||||||||||||||||||||||||||||||||||
ATCEA4C371+    422 TTTGTCACCATTGGAAGTGGCTCTATATGGACCTAGATTCACTGGTGTTGGAGCTCAGAT
                  ::::::::::::::::::::::::::::::::::::::::::::::::::::::::::::
PIR:T04448      66  L  S  P  L  E  V  A  L  Y  G  P  R  F  T  G  V  G  A  Q  I Query-       11355 TCTTGGCGCTAATGATAAATATTTATGCCAATACGAACAAGACTCTCACAATTTCTGGGG
                  |||||||||||||||||||||||||||||||||||||||||||||||||||||||
ATCEA4C371+    482 TCTTGGCGCTAATGATAAATATTTATGCCAATACGAACAAGACTCTCACAATTTC-----
                  :::::::::::::::::::::::::::::::::::::::::::::::::::::::
PIR:T04448      86  L  G  A  N  D  K  Y  L  C  Q  Y  E  Q  D  S  H  N  F  W  G
ATCEA4C371+        Exon       11538      11301   Confidence:  100 100

Query-       11295 AGGTAACTCCTTGACCCTTAAAATGCTGTGTCATGACAATAAGAAATCATATCTGAGTCT
ATCEA4C371+    537  ------------------------------------------------------------
PIR:T04448          :.------------------------------------------------------------
PIR:T04448     106  D
                   Exon       11609      11294   Confidence:  100 100

Query-       11235 TTTCTCTACTTCTAGTACTAATGTTCGTTATTGTTGTTAAAGATCTAAGTCTTATCTGAA
PIR:T04448     107 ------------------------------------------------------------

Query-       11175 TTTTGTTACATTTTGGTTCTGGTGCTTTCTCAACATGAATTTGTATATATGACTTTAAAG
PIR:T04448     107 ------------------------------------------------------------

Query-       11115 ATTGCTTACCTAAAGTTTTTACTCATGCATAGATCGACATGAGCTAGTTTTGGGGAATAC
PIR:T04448     107 -----------------------------------::::::::::::::::::::::::
                                                      R  H  E  L  V  L  G  N  T Query-       11055 TTTTAGTGCTGTGCCAGGCGCAAAGGCTCCAAACAAGGAGGTTCCACCAGAGGTTCTCAC
                  ::::::::::::::::::::::::::::::::::::::::::::::::::::--------
PIR:T04448     116  F  S  A  V  P  G  A  K  A  P  N  K  E  V  P  P  E
PIR:T04448         Exon       11083      11004   Confidence:  96 100

Query-       10995 TCCTCCCTTGTTGGTTACTTTGTTATCTGTTAAATAGTTTTCCAATTGTATCCGGATAGT
PIR:T04448     133 ------------------------------------------------------------

Query-       10935 GTTCTACTTCTCCTTGTAGAAAATCTCAAGTTTTTGTTACTCTTGCTATTCTCTTGGATG
PIR:T04448     133 ------------------------------------------------------------

Query-       10875 TTGATTTGTAAAGCATGTCGTTTTATTGTAGGAATTTAACAGAAGAGTGTCCGAAGGGTT
                  ---------------------------------:::::::::::::::::::::::::::
PIR:T04448     133                                  E  F  N  R  R  V  S  E  G  F Query-       10815 CCAAGCTACTCCATTTTGGCATCAAGGTCACATTTGCGATGATGGCCGGTAATTATATGA
                  ::::::::::::::::::::::::::::::::::::::::::::::::.-----------
PIR:T04448     143  Q  A  T  P  F  W  H  Q  G  H  I  C  D  D  G  R
PIR:T04448         Exon       10844      10768   Confidence:  100 100

Query-       10755 TTCTATGCACAACAAGAATTCACTATATTATAAATATTGGATATTGAGTATTTTTGTTGA
PIR:T04448     159 ------------------------------------------------------------
```

Figure 31B

```
Query-      10635 TGAAATCTGCTCGTTGGGAGTATAGTACTCGTCCCGTTTACGGTTGGGGTGATGTTGGGG
                  ::::::::::::::::::::::::::::::::::::::::::::::::::::::::::::
PIR:T04448    166   K  S  A  R  W  E  Y  S  T  R  P  V  Y  G  W  G  D  V  G  A Query-      10575 CCAAACAGAAGTCAACTGCAGGCTGGCCTGCAGCTTTTCCTGTATTTGAGCCTCATTGGC
                  ::::::::::::::::::::::::::::::::::::::::::::::::::::::::::::
PIR:T04448    186   K  Q  K  S  T  A  G  W  P  A  A  F  P  V  F  E  P  H  W  Q Query-      10515 AGATATGCATGGCAGGAGGCCTTTCCACAGGTGTGAGCTTTGCTTGATTGACTTAAAGTT
                  :::::::::::::::::::::::::::::.------------------------------
PIR:T04448    206   I  C  M  A  G  G  L  S  T  G
PIR:T04448        Exon      10655     10486   Confidence:  96 100

Query-      10455 AATAAATAGACGGTTAAGTTTACTTGCCTAGTACTAACAGAAAATTAAGAAAGAAACCAC
                  ------------------------------------------------------------
PIR:T04448    216

Query-      10395 CCTCTTTCTATCAGCAGAAACTGCTATTGTAGTTCTTATTTTTTCTCTTGTATTTGCAGG
                  -----------------------------------------------------------.
PIR:T04448    216

Query-      10335 GTGGATAGAATGGGGCGGTGAAAGGTTTGAGTTTCGGGATGCACCTTCTTATTCAGAGAA
                  .:::::::::::::::::::::::::::::::::::::::::::::::::::::::::::
PIR:T04448    216   W  I  E  W  G  G  E  R  F  E  F  R  D  A  P  S  Y  S  E  K Query-      10275 GAATTGGGGTGGAGGCTTCCCAAGAAAATGGTTTTGGGTAAAACATTTCATCCTTTTGCT
                  :::::::::::::::::::::::::::::::::::::-----------------------
PIR:T04448    236   N  W  G  G  G  F  P  R  K  W  F  W
PIR:T04448        Exon      10336     10239   Confidence:  96 100

Query-      10215 ACATTTCTTGTTGCAGACTTTAGTTAGCTAGTGGACCTGTGTATACACCCACATGTAGTA
                  ------------------------------------------------------------
PIR:T04448    248

Query-      10155 TACTTGTTTGATAGCTTTATTTGTCAATGTCTCTTTACAGGTCCAGTGTAATGTCTTTGA
                  ------------------------------------------:::::::::::::::::
PIR:T04448    248                                             V  Q  C  N  V  F  E Query-      10095 AGGGGCAACTGGAGAAGTTGCTTTAACCGCAGGTGGCGGGTTGAGGCAATTGCCTGGATT
                  ::::::::::::::::::::::::::::::::::::::::::::::::::::::::::::
PIR:T04448    255   G  A  T  G  E  V  A  L  T  A  G  G  G  L  R  Q  L  P  G  L Query-      10035 GACTGAGACCTATGAAAATGCTGCACTGGTATGCACTTATAAGATCTTCTTAAGCAATGA
                  :::::::::::::::::::::::::::::::-----------------------------
PIR:T04448    275   T  E  T  Y  E  N  A  A  L
PIR:T04448        Exon      10115     10008   Confidence: 100 100

Query-       9975 CAGTGAGTATTAGAAGGCAGATAGTTTACAAAAGCTCTGGGCCCTTGTAAATCTGCAGGT
                  -----------------------------------------------------------::
PIR:T04448    284                                                              V Query-       9915 TTGTGTACACTATGATGGAAAAATGTACGAGTTTGTTCCTTGGAATGGTGTTGTTAGATG
                  :::::::::::::::::::::::::::::::::::::::::::::::::::::::::::
PIR:T04448    285   C  V  H  Y  D  G  K  M  Y  E  F  V  P  W  N  G  V  V  R  W
GSDB:S:495-   532                                                            ------|||||
                                                                                   tagatg
```

Figure 31C

```
Query-       9855 GGAAATGTCTCCCTGGGG TTATTGGTATATAACTGCAGAGAACGAAAACCATGTGGTAA
                  ::::::::::::::::::  ::::::::::::::::::::::::::::::::::::::----
PIR:T04448    305 E  M  S  P  W  G    Y  W  Y  I  T  A  E  N  E  N  H  V
                  ||||||-||||||||||||-||||||||||||||||||||||| || ||||||||||||----
GSDB:S:495-   526 ggaaat tctccctgggggttattggtatataactgcagagaNcgNaaaccatgtg
PIR:T04448        Exon       9917       9801   Confidence: 100 100
GSDB:S:495-       Exon       9861       9801   Confidence:  93  93

Query-       9796 ATTTGTTTTACTAGTTTCATTCAGTTTTACTTTTGACATCATATCATTCCCTTATGGCTA
                  ----------------------------------------------------------
PIR:T04448    323 ----------------------------------------------------------
GSDB:S:495-   471 -

Query-       9736 GATTCCAACACCCGATGAATGTCTTGTGACAGGTGGAACTAGAGGCAAGAACAAATGAAG
                                                   :::::::::::::::::::::::::::
PIR:T04448    323                                  V  E  L  E  A  R  T  N  E  A
                  ---------------------------------|||||||||||||| |||||||||||||
GSDB:S:495-   471                                  gtggaactagaggcNagaacaaatgaag Query-       9676 CGGGTACACCTCTGCGTGCTCCTACCACAGAAGTTGGGCTAGCTACGGCTTGCAGAGATA
                  :::::::::::::::::::::::::::::::::::::::::::::::::::::::::::
PIR:T04448    333    G  T  P  L  R  A  P  T  T  E  V  G  L  A  T  A  C  R  D  S
                  ||||||||||||||||||||||||||||||||||||||||||||||||||||||||||||
GSDB:S:495-   443 cgggtacacctctgcgtgctcctaccacagaagttgggctagctacggcttgcagagata Query-       9616 GTTGTTACGGTGAATTGAAGTTGCAGATATGGGAACGGCTATATGATGGAAGTAAAGGCA
                  :::::::::::::::::::::::::::::::::::::::::::::::::::::::::::
PIR:T04448    353    C  Y  G  E  L  K  L  Q  I  W  E  R  L  Y  D  G  S  K  G  K
                  ||||||||||||||||||||||||||||||||||||||||||||||||||||||||||||
GSDB:S:495-   383 gttgttacggtgaattgaagttgcagatatgggaacggctatatgatggaagtaaaggca Query-       9556 AGGTATGTATGCTAATGTGATCCAATCCCTGTAGTTAAAAGTCTTAACAAATCCTAAGGC
                  ::---------------------------------:::::::::::::::::::::::::
PIR:T04448    373                                      L  K  V  L  T  N  P  K  A
                  ||----------------------------------------------------------
GSDB:S:495-   323 ag
PIR:T04448        Exon       9704       9555   Confidence: 100 100
GSDB:S:495-       Exon       9704       9555   Confidence:  98 100

Query-       9496 AGTGAAAGAAGATTATGAACGTTTGTTATGGTTAACAATGATGCAGGTGATATTAGAGAC
                  ::::::::::::::::::::::::::::::::::::::::::::::::::::::::::::
PIR:T04448    382 V  K  E  D  Y  E  R  L  L  W  L  T  M  M  Q  V  I  L  E  T
                  ----------------------------------------------|||||||||||||||
GSDB:S:495-   321                                               gtgatattagagac
```

Figure 31D

```
Query-       9436 AAAGAGCTCAATGGCAGCAGTGGAGATAGGAGGAGGACCGTGGTTTGGGACATGGAAAGG
                  ::::::::::::::::::::::::::::::::::::::::::::::::::::::::::
PIR:T04448    402  K  S  S  M  A  A  V  E  I  G  G  G  P  W  F  G  T  W  K  G
                  |||||||||||||||| |||||||||||||||||||||||||||||||||||||||||
GSDB:S:495-   307 aaagagctcaatggcaNcagtggagataggaggaggaccgtggtttgggacatggaaagg Query-       9376 AGATACGAGCAACACGCCCGAGCTACTAAAACAGGCTCTTCAGGTCCCATTGGATCTTGA
                  ::::::::::::::::::::::::::::::::::::::::::::::::::::::::::
PIR:T04448    422  D  T  S  N  T  P  E  L  L  K  Q  A  L  Q  V  P  L  D  L  E
                  ||||||||||||||||||||||||||||||||||||||||||||||||||||||||||
GSDB:S:495-   247 agatacgagcaacacgcccgagctactaaaacaggctcttcaggtcccattggatcttga Query-       9316 AAGCGCCTTAGGTTTGGTCCCTTTCTTCAAGCCACCGGGTCTGTAA
(stop)
                  :::::::::::::::::::::::::::::::::::::::::::---------------
PIR:T04448    442  S  A  L  G  L  V  P  F  F  K  P  P  G  L
                  ||||||||||||||||||||||||||||||||||||||||||||||||||||||||||
GSDB:S:495-   187 aagcgccttaggtttggtcccttcttcaagccaccgggtctgtaacattgatgagtgtt
PIR:T04448        Exon      9522      9274  Confidence: 100 100

Query-       9256
PIR:T04448    456
                  ||||||||||||||||||||||||||||||||||||||||||||||||||||||||||
GSDB:S:495-   127 ttgtttgttgatagagacccatgtgatgaatgaagccttagtcatgtcattgctagcttc Query-       9196 ACTATTATGTATGTATGATTTTAGTTCGTTCGGTCCTTGTGGTAAATGATACGGGCCAGT
                  ||||||||||||||||||||||||||||||||||||||||||||||||||||||||||
GSDB:S:495-    67 actattatgtatgtatgattttagttcgttcggtccttgtggtaaatgatacgggccagt Query-       9136 GTAAAGTCTAGTTCAATAAAAGCCTTGAGTCGCATAATTTCAATTTCAAATTGCATC
                  |||||||------------------------------------------------
GSDB:S:495-     7 gtaaagt
GSDB:S:495-       Exon      9450      9130  Confidence: 98 100
```

ATCEA4C37145_1  3063693/emb|CAA18584.1| 4.0e-43 (AL022537) putative protein
[Arabidopsis thaliana]

PIR:T04448 sPIR-T04448 shypothetical protein F4D11.30 - Arabidopsis thaliana;
g3063693|emb|CAA18584.1 (AL022537) putative protein [Arabidopsis thaliana]_F4D11.30

GSDB:S:4955486|AI995392|AI995392|701673779 A. thaliana, Columbia Col-0, inflorescence-
1 Arabidopsis thaliana cDNA clone 701673779, mRNA sequence.

Figure 31E

```
slr1737_SYNSP_S74814_    ----------------------------------------------M
slr1737_ARATH_T04448_    MEIRSLIVSMNPNLSSFELSRPVSPLTRSLVPFRSTKLVPRSISRVSASI
CFI_ARATH_P41088_        -------------------------------------------------- slr1737_SYNSP_S74814_    KFP----------------------PHSGYHWQGQS-PFFEGWYVRLL
slr1737_ARATH_T04448_    STPNSETDKISVKPVYVPTSPNRELRTPHSGYHFDGTPRKFFEGWYFRVS
CFI_ARATH_P41088_        ------------------------------------------------ slr1737_SYNSP_S74814_    LPQSGESFAFMYSIENPASDHHYGGGAVQILGPATK----KQENQEDQLV
slr1737_ARATH_T04448_    IPEKRESFCFMYSVENPAFRQSLSPLEVALYGPRFTGVGAQILGANDKYL
CFI_ARATH_P41088_                              MSSSNACASPSPFPA----VTKLHVDSVslr1737_SYNSP_S74814_    WRTFPSVKKFWASPRQFALG-HWGKCRDNRQ-AKPLLSEEFFATVKEGYQ
slr1737_ARATH_T04448_    CQYEQDSHNFWGDRHELVLGNTFSAVPGAKAPNKEVPPEEFNRRVSEGFQ
CFI_ARATH_P41088_        --TFVPSVKSPASSNPLFLG-GAGVRGLDIQ-GK------FVIFTVIGVY slr1737_SYNSP_S74814_    IHQNQHQGQIIHGDR--------HCRWQFTVEPEVTWGSPNRFPRATAGW
slr1737_ARATH_T04448_    ATPFWHQGHICDDGRTDYAETVKSARWEYSTRPVYGWGDVGAKQKSTAGW
CFI_ARATH_P41088_        LEGNAVPSLSV-------------KWKGKTTEELTESIPFFREIVTGAF slr1737_SYNSP_S74814_    LSFLPLFDPGWQILLAQGRAHGWLKWQREQYEFDHALVYAEKNWGHSFPS
slr1737_ARATH_T04448_    PAAFPVFEPHWQICMAGGLSTGWIEWGGERFEFRDAPSYSEKNWGGGFPR
CFI_ARATH_P41088_        EKFIKVT-------------M------------KLPLTGQQYSEKVTENC slr1737_SYNSP_S74814_    RWFWLQANYFPDHPG-LSVTAAGGERIVLGRPE---EVALIGLHHQGNFY
slr1737_ARATH_T04448_    KWFWVQCNVFEGATGEVALTAGGGLRQLPGLTETYENAALVCVHYDGKMY
CFI_ARATH_P41088_        VAIWKQLGLYTDCEA-KAV-----EKFLEIFKE---ET------------ slr1737_SYNSP_S74814_    EFGPGHGTVTWQVAPWGRHQLKASNDRYWVKLSGKTDKKGSLVHTP-TAQ
slr1737_ARATH_T04448_    EFVPWNGVVRWEMSPWGYWYITAENENHVVELEARTNEAGTPLRAPTTEV
CFI_ARATH_P41088_        -FPPG-SSILFALSPTGSLTVAFSKDDS-IPETGIAVIENKLLAEA-VLE slr1737_SYNSP_S74814_    GLQLNCRDTTRGYLYLQLGSVGHG-----LIVQGETDTAGLEVGG-----
slr1737_ARATH_T04448_    GLATACRDSCYGELKLQIWERLYDGSKGKVILETKSSMAAVEIGGGPWFG
CFI_ARATH_P41088_        --SIIGKNGVSPGTRLSVAERLSQ-----LMMKNKDEKEVSDHSL----- slr1737_SYNSP_S74814_    ----DWGLTEENLSKKT-----------VPF------
slr1737_ARATH_T04448_    TWKGDTSNTPELLKQALQVPLDLESALGLVPFFKPPGL
CFI_ARATH_P41088_        ----EEKLAKEN-------------------------
```

Figure 35

NUCLEIC ACID SEQUENCES TO PROTEINS INVOLVED IN TOCOPHEROL SYNTHESIS

The present application is a continuation application of U.S. patent application Ser. No. 09/688,069, filed Oct. 14, 2000, now U.S. Pat. No. 6,872,815, the entire contents of which are herein incorporated by reference.

TECHNICAL FIELD

The present invention is directed to nucleic acid and amino acid sequences and constructs, and methods related thereto.

BACKGROUND

Isoprenoids are ubiquitous compounds found in all living organisms. Plants synthesize a diverse array of greater than 22,000 isoprenoids (Connolly and Hill (1992) *Dictionary of Terpenoids*, Chapman and Hall, New York, N.Y.). In plants, isoprenoids play essential roles in particular cell functions such as production of sterols, contributing to eukaryotic membrane architecture, acyclic polyprenoids found in the side chain of ubiquinone and plastoquinone, growth regulators like abscisic acid, gibberellins, brassinosteroids or the photosynthetic pigments chlorophylls and carotenoids. Although the physiological role of other plant isoprenoids is less evident, like that of the vast array of secondary metabolites, some are known to play key roles mediating the adaptive responses to different environmental challenges. In spite of the remarkable diversity of structure and function, all isoprenoids originate from a single metabolic precursor, isopentenyl diphosphate (IPP) (Wright, (1961) *Annu. Rev. Biochem.* 20:525-548; and Spurgeon and Porter, (1981) in *Biosynthesis of Isoprenoid Compounds*, Porter and Spurgeon eds (John Wiley, New York) Vol. 1, pp 1-46).

A number of unique and interconnected biochemical pathways derived from the isoprenoid pathway leading to secondary metabolites, including tocopherols, exist in chloroplasts of higher plants. Tocopherols not only perform vital functions in plants, but are also important from mammalian nutritional perspectives. In plastids, tocopherols account for up to 40% of the total quinone pool.

Tocopherols and tocotrienols (unsaturated tocopherol derivatives) are well known antioxidants, and play an important role in protecting cells from free radical damage, and in the prevention of many diseases, including cardiac disease, cancer, cataracts, retinopathy, Alzheimer's disease, and neurodegeneration, and have been shown to have beneficial effects on symptoms of arthritis, and in anti-aging. Vitamin E is used in chicken feed for improving the shelf life, appearance, flavor, and oxidative stability of meat, and to transfer tocols from feed to eggs. Vitamin E has been shown to be essential for normal reproduction, improves overall performance, and enhances immunocompetence in livestock animals. Vitamin E supplement in animal feed also imparts oxidative stability to milk products.

The demand for natural tocopherols as supplements has been steadily growing at a rate of 10-20% for the past three years. At present, the demand exceeds the supply for natural tocopherols, which are known to be more biopotent than racemic mixtures of synthetically produced tocopherols. Naturally occurring tocopherols are all d-stereomers, whereas synthetic α-tocopherol is a mixture of eight d,l-α-tocopherol isomers, only one of which (12.5%) is identical to the natural d-α-tocopherol. Natural d-α-tocopherol has the highest vitamin E activity (1.49 IU/mg) when compared to other natural tocopherols or tocotrienols. The synthetic α-tocopherol has a vitamin E activity of 1.1 IU/mg. In 1995, the worldwide market for raw refined tocopherols was $1020 million; synthetic materials comprised 85-88% of the market, the remaining 12-15% being natural materials. The best sources of natural tocopherols and tocotrienols are vegetable oils and grain products. Currently, most of the natural Vitamin E is produced from γ-tocopherol derived from soy oil processing, which is subsequently converted to α-tocopherol by chemical modification (α-tocopherol exhibits the greatest biological activity).

Methods of enhancing the levels of tocopherols and tocotrienols in plants, especially levels of the more desirable compounds that can be used directly, without chemical modification, would be useful to the art as such molecules exhibit better functionality and bioavailability.

In addition, methods for the increased production of other isoprenoid derived compounds in a host plant cell is desirable. Furthermore, methods for the production of particular isoprenoid compounds in a host plant cell is also needed.

SUMMARY OF THE INVENTION

The present invention is directed to sequences to proteins involved in tocopherol synthesis. The polynucleotides and polypeptides of the present invention include those derived from prokaryotic and eukaryotic sources.

Thus, one aspect of the present invention relates to prenyltransferase, and in particular to isolated polynucleotide sequences encoding prenyltransferase proteins and polypeptides related thereto. In particular, isolated nucleic acid sequences encoding prenyltransferase proteins from bacterial and plant sources are provided.

In another aspect, the present invention provides isolated polynucleotide sequences encoding tocopherol cyclase, and polypeptides related thereto. In particular, isolated nucleic acid sequences encoding tocopherol cyclase proteins from bacterial and plant sources are provided.

Another aspect of the present invention relates to oligonucleotides which include partial or complete prenyltransferase or tocopherol cyclase encoding sequences.

It is also an aspect of the present invention to provide recombinant DNA constructs which can be used for transcription or transcription and translation (expression) of prenyltransferase or tocopherol cyclase. In particular, constructs are provided which are capable of transcription or transcription and translation in host cells.

In another aspect of the present invention, methods are provided for production of prenyltransferase or tocopherol cyclase in a host cell or progeny thereof. In particular, host cells are transformed or transfected with a DNA construct which can be used for transcription or transcription and translation of prenyltransferase or tocopherol cyclase. The recombinant cells which contain prenyltransferase or tocopherol cyclase are also part of the present invention.

In a further aspect, the present invention relates to methods of using polynucleotide and polypeptide sequences to modify the tocopherol content of host cells, particularly in host plant cells. Plant cells having such a modified tocopherol content are also contemplated herein. Methods and cells in which both prenyltransferase and tocopherol cyclase are expressed in a host cell are also part of the present invention.

The modified plants, seeds and oils obtained by the expression of the prenyltransferase or tocopherol cyclase are also considered part of the invention.

BRIEF DESCRIPTION OF THE DRAWINGS

FIG. 1 provides an amino acid sequence alignment between ATPT2, ATPT3, ATPT4, ATPT8, and ATPT12 are performed using ClustalW.

FIG. 21 provides an amino acid sequence alignment using ClustalW between the *Synechocystis* prenyltransferase sequences.

FIG. 22 provides an amino acid sequence of the ATPT2, ATPT3, ATPT4, ATPT8, and ATPT12 protein sequences from *Arabidopsis* and the slr1736, slr0926, sll1899, slr0056, and the slr1518 amino acid sequences from *Synechocystis*.

FIG. 31 is a sequence alignment of the *Arabidopsis* homologue with the sequence of the public database.

FIG. 35 is a sequence alignment of slr1737, slr1737 *Arabidopsis* homologue and the *Arabidopsis* chalcone isomerase.

DETAILED DESCRIPTION OF THE INVENTION

Figure 2:
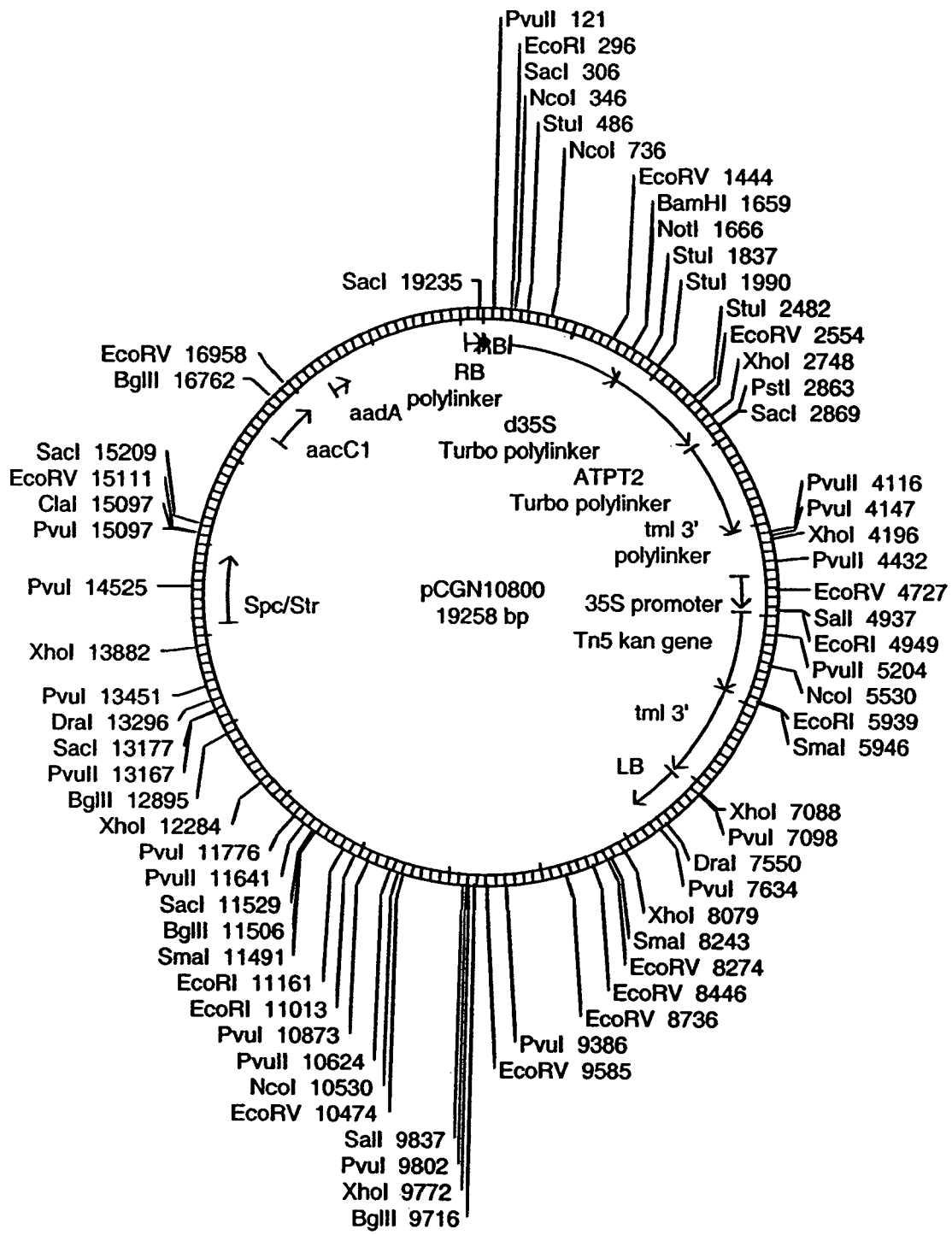
FIG. 2 provides a schematic picture of the expression construct pCGN10800.

The present invention provides, inter alia, compositions and methods for altering (for example, increasing and decreasing) the tocopherol levels and/or modulating their ratios in host cells. In particular, the present invention provides polynucleotides, polypeptides, and methods of use thereof for the modulation of tocopherol content in host plant cells.

The biosynthesis of α-tocopherol in higher plants involves condensation of homogentisic acid and phytylpyrophosphate to form 2-methyl-6 phytylbenzoquinol that can, by cyclization and subsequent methylations (Fiedler et al., 1982, *Planta*, 155: 511-515, Soll et al., 1980, *Arch. Biochem. Biophys*. 204: 544-550, Marshall et al., 1985 *Phytochem*., 24: 1705-1711, all of which are herein incorporated by reference in their entirety), form various tocopherols.

The *Arabidopsis* pds2 mutant identified and characterized by Norris et al. (1995), is deficient in tocopherol and plastiquinone-9 accumulation. Further genetic and biochemical analysis suggested that the protein encoded by PDS2 may be responsible for the prenylation of homogentisic acid. The PDS2 locus identified by Norris et al. (1995) has been hypothesized to possibly encode the tocopherol phytyl-prenyltransferase, as the pds2 mutant fails to accumulate tocopherols.

Norris et al. (1995) determined that in *Arabidopsis* pds2 lies at the top of chromosome 3, approximately 7 centimorgans above long hypocotyl2, based on the genetic map. ATPT2 is located on chromosome 2 between 36 and 41 centimorgans, lying on BAC F19F24, indicating that ATPT2 does not correspond to PDS2. Thus, it is an aspect of the present invention to provide novel polynucleotides and polypeptides involved in the prenylation of homogentisic acid.

This reaction may be a rate limiting step in tocopherol biosynthesis, and this gene has yet to be isolated.

U.S. Pat. No. 5,432,069 describes the partial purification and characterization of tocopherol cyclase from *Chlorella protothecoides, Dunaliella salina* and wheat. The cyclase described as being glycine rich, water soluble and with a predicted MW of 48-50 kDa. However, only limited peptide fragment sequences were available.

In one aspect, the present invention provides polynucleotide and polypeptide sequences involved in the prenylation of straight chain and aromatic compounds. Straight chain prenyltransferases as used herein comprises sequences which encode proteins involved in the prenylation of straight chain compounds, including, but not limited to, geranyl geranyl pyrophosphate and farnesyl pyrophosphate. Aromatic prenyltransferases, as used herein, comprises sequences which encode proteins involved in the prenylation of aromatic compounds, including, but not limited to, menaquinone, ubiquinone, chlorophyll, and homogentisic acid. The prenyltransferase of the present invention preferably prenylates homogentisic acid.

In another aspect, the invention provides polynucleotide and polypeptide sequences to tocopherol cyclization enzymes. The 2,3-dimethyl-5-phytylplastoquinol cyclase (tocopherol cyclase) is responsible for the cyclization of 2,3-dimethyl-5-phytylplastoquinol to tocopherol.

Isolated Polynucleotides, Proteins, and Polypeptides

A first aspect of the present invention relates to isolated prenyltransferase polynucleotides. Another aspect of the present invention relates to isolated tocopherol cyclase polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

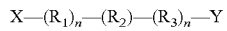

wherein, at the 5' end, X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably those of SEQ ID NOs: 1, 3, 5, 7, 8, 10, 11, 13-16, 18, 23, 29, 36, and 38. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond to the prenyltransferase or tocopherol cyclase EST sequences. The oligonucleotides are used as primers in polymerase chain reaction (PCR) techniques to obtain 5' and 3' terminal sequence of prenyltransferase or tocopherol cyclase genes. Alternatively, where oligonucleotides of low degeneracy can be prepared from particular prenyltransferase or tocopherol cyclase peptides, such probes may be used directly to screen gene libraries for prenyltransferase or tocopherol cyclase gene sequences. In particular, screening of cDNA libraries in phage vectors is useful in such methods due to lower levels of background hybridization.

Typically, a prenyltransferase or tocopherol cyclase sequence obtainable from the use of nucleic acid probes will show 60-70% sequence identity between the target prenyltransferase or tocopherol cyclase sequence and the encoding sequence used as a probe. However, lengthy sequences with as little as 50-60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20-50% deviation (i.e., 50-80% sequence homology) from the sequences used as probe. Oligonucleotide probes can be considerably shorter than the entire nucleic acid sequence encoding an prenyltransferase or tocopherol cyclase enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related prenyltransferase or tocopherol cyclase genes. Shorter probes are often particularly useful for polymerase chain reactions (PCR), especially when highly conserved sequences can be identified. (See, Gould, et al., *PNAS USA* (1989) 86:1934-1938.).

Another aspect of the present invention relates to prenyltransferase or tocopherol cyclase polypeptides. Such polypeptides include isolated polypeptides set forth in the Sequence Listing, as well as polypeptides and fragments thereof, particularly those polypeptides which exhibit prenyltransferase or tocopherol cyclase activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., *SIAM J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76-80 (1994); Birren, et al., *Genome Analysis*, 1: 543-559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.*, 215:403-410 (1990)). The well known Smith Waterman algorithm can also be used to determine identity.

Parameters for polypeptide sequence comparison typically include the following:

Algorithm: Needleman and Wunsch, *J. Mol. Biol.* 48:443-453 (1970)

Comparison matrix: BLOSSUM62 from Hentikoff and Hentikoff, *Proc. Natl. Acad. Sci USA* 89:10915-10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, J. Mol. Biol. 48:443-453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

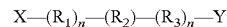

$$X-(R_1)_n-(R_2)-(R_3)_n-Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably those encoded by the sequences provided in SEQ ID NOs: 2, 4, 6, 9, 12, 17, 19-22, 24-28, 30, 32-35, 37, and 39. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in the Sequence Listing set forth herein.

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Ile; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called pro-proteins.

Plant Constructs and Methods of Use

Of particular interest is the use of the nucleotide sequences in recombinant DNA constructs to direct the transcription or transcription and translation (expression) of the prenyltransferase or tocopherol cyclase sequences of the present invention in a host plant cell. The expression constructs generally comprise a promoter functional in a host plant cell operably linked to a nucleic acid sequence encoding a prenyltransferase or tocopherol cyclase of the present invention and a transcriptional termination region functional in a host plant cell.

A first nucleic acid sequence is "operably linked" or "operably associated" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of plant functional promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810-812; Rogers, U.S. Pat. No. 5,378,619). In addition, it may also be preferred to bring about expression of the prenyltransferase or tocopherol cyclase gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res*. 1:209:219 (1991)), phaseolin, zein, soybean trypsin inhibitor, ACP, stearoyl-ACP desaturase, soybean α' subunit of β-conglycinin (soy 7s, (Chen et al, *Proc. Natl. Acad. Sci*., 83:8560-8564 (1986))) and oleosin.

It may be advantageous to direct the localization of proteins conferring prenyltransferase or tocopherol cyclase to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP.

Such transit peptides are known in the art. See, for example, Von Heijne et al. (1991) *Plant Mol. Biol. Rep*. 9:104-126; Clark et al. (1989) *J. Biol. Chem*. 264:17544-17550; della-Cioppa et al. (1987) *Plant Physiol* 84:965-968; Romer et al. (1993) *Biochem. Biophys. Res Commun*. 196: 1414-1421; and, Shah et al. (1986) *Science* 233:478-481.

Depending upon the intended use, the constructs may contain the nucleic acid sequence which encodes the entire prenyltransferase or tocopherol cyclase protein, or a portion thereof. For example, where antisense inhibition of a given prenyltransferase or tocopherol cyclase protein is desired, the entire prenyltransferase or tocopherol cyclase sequence is not required. Furthermore, where prenyltransferase or tocopherol cyclase sequences used in constructs are intended for use as probes, it may be advantageous to prepare constructs containing only a particular portion of a prenyltransferase or tocopherol cyclase encoding sequence, for example a sequence which is discovered to encode a highly conserved prenyltransferase or tocopherol cyclase region.

The skilled artisan will recognize that there are various methods for the inhibition of expression of endogenous sequences in a host cell. Such methods include, but are not limited to, antisense suppression (Smith, et al (1988) *Nature* 334:724-726), co-suppression (Napoli, et al (1989) *Plant Cell* 2:279-289), ribozymes (PCT Publication WO 97/10328), and combinations of sense and antisense Waterhouse, et al. (1998) *Proc. Natl. Acad. Sci. USA* 95:13959-13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the prenyltransferase or tocopherol cyclase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the prenyltransferase or tocopherol cyclase sequences directly from the host plant cell plastid. Such constructs and methods are known in the art and are generally described, for example, in Svab, et al. (1990) *Proc. Natl. Acad. Sci. USA* 87:8526-8530 and Svab and Maliga (1993) *Proc. Natl. Acad. Sci. USA* 90:913-917 and in U.S. Pat. No. 5,693,507.

The prenyltransferase or tocopherol cyclase constructs of the present invention can be used in transformation methods with additional constructs providing for the expression of other nucleic acid sequences encoding proteins involved in the production of tocopherols, or tocopherol precursors such as homogentisic acid and/or phytylpyrophosphate. Nucleic acid sequences encoding proteins involved in the production of homogentisic acid are known in the art, and include but not are limited to, 4-hydroxyphenylpyruvate dioxygenase (HPPD, EC 1.13.11.27) described for example, by Garcia, et al. ((1999) *Plant Physiol.* 119(4):1507-1516), mono or bifunctional tyrA (described for example by Xia, et al. (1992) *J. Gen Microbiol*. 138:1309-1316, and Hudson, et al. (1984) *J. Mol. Biol.* 180:1023-1051), Oxygenase, 4-hydroxyphenylpyruvate di-(9CI), 4-Hydroxyphenylpyruvate dioxygenase; p-Hydroxyphenylpyruvate dioxygenase; p-Hydroxyphenylpyruvate hydroxylase; p-Hydroxyphenylpyruvate oxidase; p-Hydroxyphenylpyruvic acid hydroxylase; p-Hydroxyphenylpyruvic hydroxylase; p-Hydroxyphenylpyruvic oxidase), 4-hydroxyphenylacetate, NAD(P)H:oxygen oxidoreductase (1-hydroxylating); 4-hydroxyphenylacetate 1-monooxygenase, and the like. In addition, constructs for the expression of nucleic acid sequences encoding proteins involved in the production of phytylpyrophosphate can also be employed with the prenyltransferase or tocopherol cyclase constructs of the present invention. Nucleic acid sequences encoding proteins involved in the production of phytylpyrophosphate are known in the art, and include, but are not limited to geranylgeranylpyrophosphate synthase (GGPPS), geranylgeranylpyrophosphate reductase (GGH), 1-deoxyxylulose-5-phosphate synthase, 1-deoxy-D-xylolose-5-phosphate reductoisomerase, 4-diphosphocytidyl-2-C-methylerythritol synthase, isopentyl pyrophosphate isomerase.

The prenyltransferase or tocopherol cyclase sequences of the present invention find use in the preparation of transformation constructs having a second expression cassette for the expression of additional sequences involved in tocopherol biosynthesis. Additional tocopherol biosynthesis sequences of interest in the present invention include, but are not limited to gamma-tocpherol methyltransferase (Shintani, et al. (1998) *Science* 282(5396):2098-2100), tocopherol cyclase, and tocopherol methyltransferase.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a prenyltransferase or tocopherol cyclase nucleic acid sequence.

Plant expression or transcription constructs having a prenyltransferase or tocopherol cyclase as the DNA sequence of interest for increased or decreased expression thereof may be employed with a wide variety of plant life, particularly, plant life involved in the production of vegetable oils for edible and industrial uses. Particularly preferred plants for use in the methods of the present invention include, but are not limited to: *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Most especially preferred are temperate oilseed crops. Temperate oilseed crops of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of prenyltransferase or tocopherol cyclase constructs in plants to produce plants or plant parts, including, but not limited to leaves, stems, roots, reproductive, and seed, with a modified content of tocopherols in plant parts having transformed plant cells.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

To confirm the activity and specificity of the proteins encoded by the identified nucleic acid sequences as prenyltransferase or tocopherol cyclase enzymes, in vitro assays are performed in insect cell cultures using baculovirus expression systems. Such baculovirus expression systems are known in the art and are described by Lee, et al. U.S. Pat. No. 5,348,886, the entirety of which is herein incorporated by reference.

In addition, other expression constructs may be prepared to assay for protein activity utilizing different expression systems. Such expression constructs are transformed into yeast or prokaryotic host and assayed for prenyltransferase or tocopherol cyclase activity. Such expression systems are known in the art and are readily available through commercial sources.

In addition to the sequences described in the present invention, DNA coding sequences useful in the present invention can be derived from algae, fungi, bacteria, mammalian sources, plants, etc. Homology searches in existing databases using signature sequences corresponding to conserved nucleotide and amino acid sequences of prenyltransferase or tocopherol cyclase can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as *Synechocystis, Shewanella*, yeast, *Pseudomonas, Rhodobacteria*, etc., that lack specific biochemical reactions, or that have been mutated. The sequences of the DNA coding regions can be optimized by gene resynthesis, based on codon usage, for maximum expression in particular hosts.

For the alteration of tocopherol production in a host cell, a second expression construct can be used in accordance with the present invention. For example, the prenyltransferase or tocopherol cyclase expression construct can be introduced into a host cell in conjunction with a second expression construct having a nucleotide sequence for a protein involved in tocopherol biosynthesis.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to *Agrobacterium* infection may be successfully transformed via tripartite or binary vector methods of *Agrobacterium* mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad. Sci., U.S.A.* (1980) 77:7347-7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride, et al. (*Plant Mol. Biol.* (1990) 14:269-276), wherein the pRiHRI (Jouanin, et al., *Mol. Gen. Genet.* (1985) 201:370-374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the expression construct of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the prenyltransferase or tocopherol cyclase expression construct, or alternatively, transformed plants, one expressing the prenyltransferase or tocopherol cyclase construct and one expressing the second construct, can be crossed to bring the constructs together in the same plant.

Transgenic plants of the present invention may be produced from tissue culture, and subsequent generations grown from seed. Alternatively, transgenic plants may be grown using apomixis. Apomixis is a genetically controlled method of reproduction in plants where the embryo is formed without union of an egg and a sperm. There are three basic types of apomictic reproduction: 1) apospory where the embryo develops from a chromosomally unreduced egg in an embryo sac derived from the nucleus, 2) diplospory where the embryo develops from an unreduced egg in an embryo sac derived from the megaspore mother cell, and 3) adventitious embryony where the embryo develops directly from a somatic cell. In most forms of apomixis, pseudogamy or fertilization of the polar nuclei to produce endosperm is necessary for seed viability. In apospory, a nurse cultivar can be used as a pollen source for endosperm formation in seeds. The nurse cultivar does not affect the genetics of the aposporous apomictic cultivar since the unreduced egg of the cultivar develops parthenogenetically, but makes possible endosperm production. Apomixis is economically important, especially in transgenic plants, because it causes any genotype, no matter how heterozygous, to breed true. Thus, with apomictic reproduction, heterozygous transgenic plants can maintain their genetic fidelity throughout repeated life cycles. Methods for the production of apomictic plants are known in the art. See, U.S. Pat. No. 5,811,636, which is herein incorporated by reference in its entirety.

The nucleic acid sequences of the present invention can be used in constructs to provide for the expression of the sequence in a variety of host cells, both prokaryotic eukaryotic. Host cells of the present invention preferably include monocotyledenous and dicotyledenous plant cells.

In general, the skilled artisan is familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Maliga et al., *Methods in Plant Molecular Biology*, Cold Spring Harbor Press (1995), the entirety of which is herein incorporated by reference; Birren et al., *Genome Analysis: Analyzing DNA*, 1, Cold Spring Harbor, N.Y., the entirety of which is herein incorporated by reference).

Methods for the expression of sequences in insect host cells are known in the art. Baculovirus expression vectors are recombinant insect viruses in which the coding sequence for a chosen foreign gene has been inserted behind a baculovirus promoter in place of the viral gene, e.g., polyhedrin (Smith and Summers, U.S. Pat. No. 4,745,051, the entirety of which is incorporated herein by reference). Baculovirus expression vectors are known in the art, and are described for example in Doerfler, *Curr. Top. Microbiol Immunol*. 131:51-68 (1968); Luckow and Summers, *Bio/Technology* 6:47-55 (1988a); Miller, *Annual Review of Microbiol*. 42:177-199 (1988); Summers, *Curr. Comm. Molecular Biology*, Cold Spring Harbor Press, Cold Spring Harbor, N.Y. (1988); Summers and Smith, *A Manual of Methods for Baculovirus Vectors and Insect Cell Culture Procedures*, Texas Ag. Exper. Station Bulletin No. 1555 (1988), the entireties of which is herein incorporated by reference)

Methods for the expression of a nucleic acid sequence of interest in a fungal host cell are known in the art. The fungal host cell may, for example, be a yeast cell or a filamentous fungal cell. Methods for the expression of DNA sequences of interest in yeast cells are generally described in "Guide to yeast genetics and molecular biology", Guthrie and Fink, eds. Methods in enzymology, Academic Press, Inc. Vol 194 (1991) and Gene expression technology", Goeddel ed, Methods in Enzymology, Academic Press, Inc., Vol 185 (1991).

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include, but are not limited to, viral promoters such as that from Simian Virus 40 (SV40) (Fiers et al., *Nature* 273:113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells are well known in the art, and may include viral replicons, or sequences which insure integration of the appropriate sequences encoding epitopes into the host genome. Plasmid vectors that greatly facilitate the construction of recombinant viruses have been described (see, for example, Mackett et al, *J. Virol*. 49:857 (1984); Chakrabarti et al., *Mol. Cell. Biol*. 5:3403 (1985); Moss, In: *Gene Transfer Vectors For Mammalian Cells* (Miller and Calos, eds., Cold Spring Harbor Laboratory, N.Y., p. 10, (1987); all of which are herein incorporated by reference in their entirety).

The invention also includes plants and plant parts, such as seed, oil and meal derived from seed, and feed and food products processed from plants, which are enriched in tocopherols. Of particular interest is seed oil obtained from transgenic plants where the tocopherol level has been increased as compared to seed oil of a non-transgenic plant.

The harvested plant material may be subjected to additional processing to further enrich the tocopherol content. The skilled artisan will recognize that there are many such processes or methods for refining, bleaching and degumming oil. U.S. Pat. No. 5,932,261, issued Aug. 3, 1999, discloses on such process, for the production of a natural carotene rich refined and deodorised oil by subjecting the oil to a pressure of less than 0.060 mbar and to a temperature of less than 200.degree. C. Oil distilled by this process has reduced free fatty acids, yielding a refined, deodorised oil where Vitamin E contained in the feed oil is substantially retained in the processed oil. The teachings of this patent are incorporated herein by reference.

The invention now being generally described, it will be more readily understood by reference to the following examples which are included for purposes of illustration only and are not intended to limit the present invention.

EXAMPLES

Example 1

Identification of Prenyltransferase or Tocopherol Cyclase Sequences

PSI-BLAST (Altschul, et al. (1997) *Nuc Acid Res* 25:3389-3402) profiles were generated for both the straight chain and aromatic classes of prenyltransferases. To generate the straight chain profile, a prenyl-transferase from *Porphyra purpurea* (Genbank accession 1709766) was used as a query against the NCBI non-redundant protein database. The *E. coli* enzyme involved in the formation of ubiquinone, ubiA (genbank accession 1790473) was used as a starting sequence to generate the aromatic prenyltransferase profile. These profiles were used to search public and proprietary DNA and protein data bases. In *Arabidopsis* six putative prenyltransferases of the straight-chain class were identified, ATPT1, (SEQ ID NO:9), ATPT7 (SEQ ID NO:10), ATPT8 (SEQ ID NO:11), ATPT9 (SEQ ID NO:13), ATPT10 (SEQ ID NO:14), and ATPT11 (SEQ ID NO:15), and six were identified of the aromatic class, ATPT2 (SEQ ID NO:1), ATPT3 (SEQ ID NO:3), ATPT4 (SEQ ID NO:5), ATPT5 (SEQ ID NO:7), ATPT6 (SEQ ID NO:8), and ATPT12 (SEQ ID NO:16). Additional prenyltransferase sequences from other plants related to the aromatic class of prenyltransferases, such as soy (SEQ ID NOs: 19-23, the deduced amino acid sequence of SEQ ID NO:23 is provided in SEQ ID NO:24) and maize (SEQ ID NOs:25-29, and 31) are also identified. The deduced amino acid sequence of ZMPT5 (SEQ ID NO:29) is provided in SEQ ID NO:30.

Searches are performed on a Silicon Graphics Unix computer using additional Bioaccellerator hardware and GenWeb software supplied by Compugen Ltd. This software and hardware enables the use of the Smith-Waterman algorithm in searching DNA and protein databases using profiles as queries. The program used to query protein databases is profilesearch. This is a search where the query is not a single sequence but a profile based on a multiple alignment of amino acid or nucleic acid sequences. The profile is used to query a sequence data set, i.e., a sequence database. The profile contains all the pertinent information for scoring each position in a sequence, in effect replacing the "scoring matrix" used for the standard query searches. The program used to query nucleotide databases with a protein profile is tprofilesearch. Tprofilesearch searches nucleic acid databases using an amino acid profile query. As the search is running, sequences in the database are translated to amino acid sequences in six reading frames. The output file for tprofilesearch is identical to the output file for profilesearch except for an additional column that indicates the frame in which the best alignment occurred.

The Smith-Waterman algorithm, (Smith and Waterman (1981) supra), is used to search for similarities between one sequence from the query and a group of sequences contained in the database. E score values as well as other sequence information, such as conserved peptide sequences are used to identify related sequences.

To obtain the entire coding region corresponding to the *Arabidopsis* prenyltransferase sequences, synthetic oligonucleotide primers are designed to amplify the 5' and 3' ends of partial cDNA clones containing prenyltransferase sequences. Primers are designed according to the respective *Arabidopsis* prenyltransferase sequences and used in Rapid Amplification of cDNA Ends (RACE) reactions (Frohman et al. (1988) *Proc. Natl. Acad. Sci. USA* 85:8998-9002) using the Marathon cDNA amplification kit (Clontech Laboratories Inc, Palo Alto, Calif.).

Figure 1:
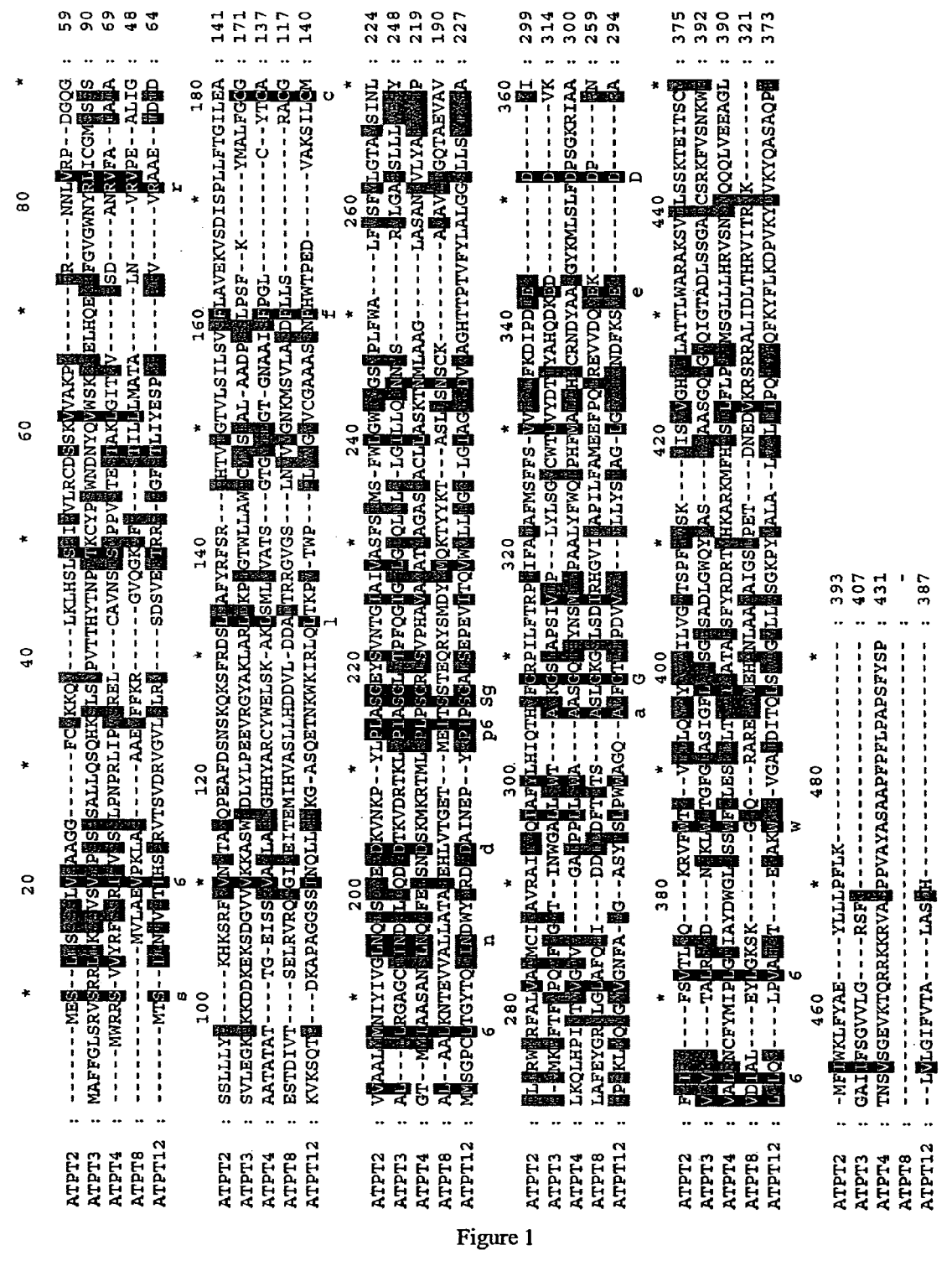

Amino acid sequence alignments between ATPT2 (SEQ ID NO:2), ATPT3 (SEQ ID NO:4), ATPT4 (SEQ ID NO:6), ATPT8 (SEQ ID NO:12), and ATPT12 (SEQ ID NO:17) are performed using ClustalW (FIG. 1), and the percent identity and similarities are provided in Table 1 below.

TABLE 1

|  |  | ATPT2 | ATPT3 | ATPT4 | ATPT8 | ATPT12 |
|---|---|---|---|---|---|---|
| ATPT2 | % Identity |  | 12 | 13 | 11 | 15 |
|  | % similar |  | 25 | 25 | 22 | 32 |
|  | % Gap |  | 17 | 20 | 20 | 9 |
| ATPT3 | % Identity |  |  | 12 | 6 | 22 |
|  | % similar |  |  | 29 | 16 | 38 |
|  | % Gap |  |  | 20 | 24 | 14 |
| ATPT4 | % Identity |  |  |  | 9 | 14 |
|  | % similar |  |  |  | 18 | 29 |
|  | % Gap |  |  |  | 26 | 19 |
| ATPT8 | % Identity |  |  |  |  | 7 |
|  | % similar |  |  |  |  | 19 |
|  | % Gap |  |  |  |  | 20 |
| ATPT12 | % Identity |  |  |  |  |  |
|  | % similar |  |  |  |  |  |
|  | % Gap |  |  |  |  |  |

Example 2

Preparation of Prenyl Transferase Expression Constructs

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence CGCGATTTAAATG-GCGCGCCCTGCAGGCGGCCGCCTG-CAGGGCGCGCCATTTAAAT (SEQ ID NO:40) was ligated into the cloning vector pBC SK+ (Stratagene) after digestion with the restriction endonuclease BssHII to construct vector pCGN7765. Plamids pCGN3223 and pCGN7765 were digested with NotI and ligated together. The resultant vector, pCGN7770, contains the pCGN7765 backbone with the napin seed specific expression cassette from pCGN3223.

The cloning cassette, pCGN7787, essentially the same regulatory elements as pCGN7770, with the exception of the napin regulatory regions of pCGN7770 have been replaced with the double CAMV 35S promoter and the tml polyadenylation and transcriptional termination region.

A binary vector for plant transformation, pCGN5139, was constructed from pCGN1558 (McBride and Summerfelt, (1990) Plant Molecular Biology, 14:269-276). The polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A series of turbo binary vectors are constructed to allow for the rapid cloning of DNA sequences into binary vectors containing transcriptional initiation regions (promoters) and transcriptional termination regions.

The plasmid pCGN8618 was constructed by ligating oligonucleotides 5'-TCGAGGATCCGCGGCCGCAAGCTTC-CTGCAGG-3' (SEQ ID NO:41) and 5'-TCGACCTGCAG-GAAGCTTGCGGCCGCGGATCC-3' (SEQ ID NO:42) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGGC-CGCGGATCC-3' (SEQ ID NO:43) and 5'-TCGAGGATC-CGCGGCCGCAAGCTTCCTGCAGG-3' (SEQ ID NO:44) into SalI/XhoI-digested pCGN7770. A fragment containing the napin promoter, polylinker and napin 3' region was removed from pCGN8619 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAGCTTC-CTGCAGGAGCT-3' (SEQ ID NO:45) and 5'-CCTGCAG-GAAGCTTGCGGCCGCGGATCC-3' (SEQ ID NO:46) into SalI/SacI-digested pCGN7787. A fragment containing the d35S promoter, polylinker and tml 3' region was removed from pCGN8620 by complete digestion with Asp718I and partial digestion with NotI.

The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTTGCGGC-CGCGGATCCAGCT-3' (SEQ ID NO:47) and 5'-GGATC-CGCGGCCGCAAGCTTCCTGCAGG-3' (SEQ ID NO:48) into SalI/SacI-digested pCGN7787. A fragment containing the d35S promoter, polylinker and tml 3' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tml 3' was closest to the blunted HindIII site was subjected to sequence analysis to confirm both the insert orientation and the integrity of cloning junctions. The resulting plasmid was designated pCGN8625.

The plasmid construct pCGN8640 is a modification of pCGN8624 described above. A 938 bp PstI fragment isolated from transposon Tn7 which encodes bacterial spectinomycin and streptomycin resistance (Fling et al. (1985), *Nucleic Acids Research* 13(19):7095-7106), a determinant for *E. coli* and *Agrobacterium* selection, was blunt ended with Pfu polymerase. The blunt ended fragment was ligated into pCGN8624 that had been digested with SpeI and blunt ended with Pfu polymerase. The region containing the PstI fragment was sequenced to confirm both the insert orientation and the integrity of cloning junctions.

The spectinomycin resistance marker was introduced into pCGN8622 and pCGN8623 as follows. A 7.7 Kbp AvrII-SnaBI fragment from pCGN8640 was ligated to a 10.9 Kbp AvrII-SnaBI fragment from pCGN8623 or pCGN8622, described above. The resulting plasmids were pCGN8641 and pCGN8643, respectively.

The plasmid pCGN8644 was constructed by ligating oligonucleotides 5'-GATCACCTGCAGGAAGCTTGCGGC-CGCGGATCCAATGCA-3' (SEQ ID NO:49) and 5'-TTG-GATCCGCGGCCGCAAGCTTCCTGCAGGT-3' (SEQ ID NO:50) into BamHI-PstI digested pCGN8640.

Synthetic oligonulceotides were designed for use in Polymerase Chain Reactions (PCR) to amplify the coding sequences of ATPT2, ATPT3, ATPT4, ATPT8, and ATPT12 for the preparation of expression constructs and are provided in Table 2 below.

TABLE 2

| Name | Restriction Site | Sequence | SEQ ID NO: |
|---|---|---|---|
| ATPT2 | 5' NotI | GGATCCGCGGCCGCACAATGGAGTC TCTGCTCTCTAGTTCT | 51 |
| ATPT2 | 3' SseI | GGATCCTGCAGGTCACTTCAAAAAA GGTAACAGCAAGT | 52 |
| ATPT3 | 5' NotI | GGATCCGCGGCCGCACAATGGCGTT TTTTGGGCTCTCCCGTGTTT | 53 |
| ATPT3 | 3' SseI | GGATCCTGCAGGTTATTGAAAACTT CTTCCAAGTACAACT | 54 |
| ATPT4 | 5' NotI | GGATCCGCGGCCGCACAATGTGGCG AAGATCTGTTGTT | 55 |
| ATPT4 | 3' SseI | GGATCCTGCAGGTCATGGAGAGTAG AAGGAAGGAGCT | 56 |
| ATPT8 | 5' NotI | GGATCCGCGGCCGCACAATGGTACT TGCCGAGGTTCCAAAGCTTGCCTCT | 57 |
| ATPT8 | 3' SseI | GGATCCTGCAGGTCACTTGTTTCTG GTGATGACTCTAT | 58 |
| ATPT12 | 5' NotI | GGATCCGCGGCCGCACAATGACTTC GATTCTCAACACT | 59 |
| ATPT12 | 3' SseI | GGATCCTGCAGGTCAGTGTTGCGAT GCTAATGCCGT | 60 |

The coding sequences of ATPT2, ATPT3, ATPT4, ATPT8, and ATPT12 were all amplified using the respective PCR primers shown in Table 2 above and cloned into the TopoTA vector (Invitrogen). Constructs containing the respective prenyltransferase sequences were digested with NotI and Sse8387I and cloned into the turbobinary vectors described above.

The sequence encoding ATPT2 prenyltransferase was cloned in the sense orientation into pCGN8640 to produce the plant transformation construct pCGN10800 (FIG. 2). The ATPT2 sequence is under control of the 35S promoter.

Figure 3:
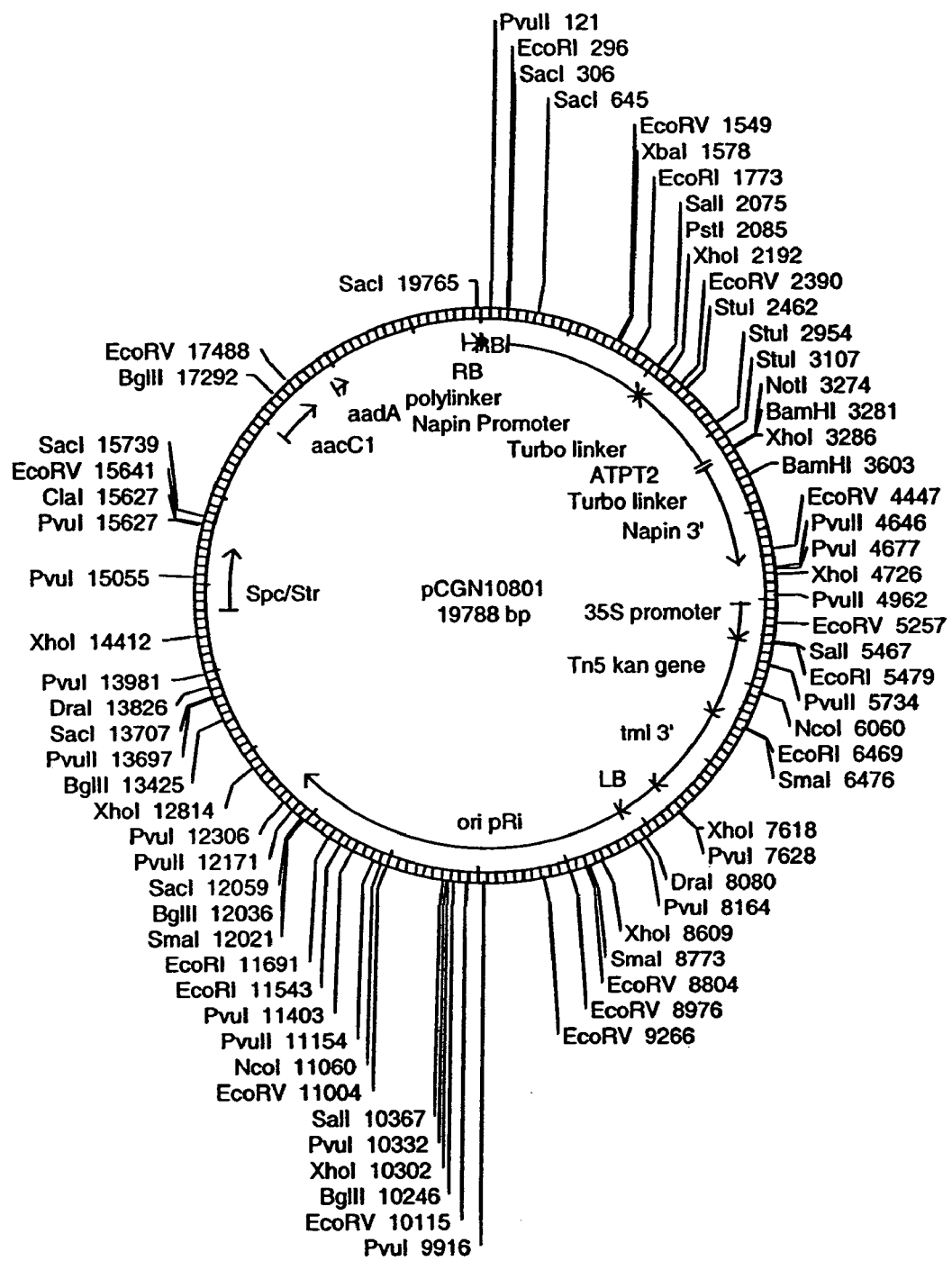
FIG. 3 provides a schematic picture of the expression construct pCGN10801.

The ATPT2 sequence was also cloned in the antisense orientation into the construct pCGN8641 to create pCGN10801 (FIG. 3). This construct provides for the antisense expression of the ATPT2 sequence from the napin promoter.

The ATPT2 coding sequence was also cloned in the sense orientation into the vector pCGN8643 to create the plant transformation construct pCGN10822

Figure 4:
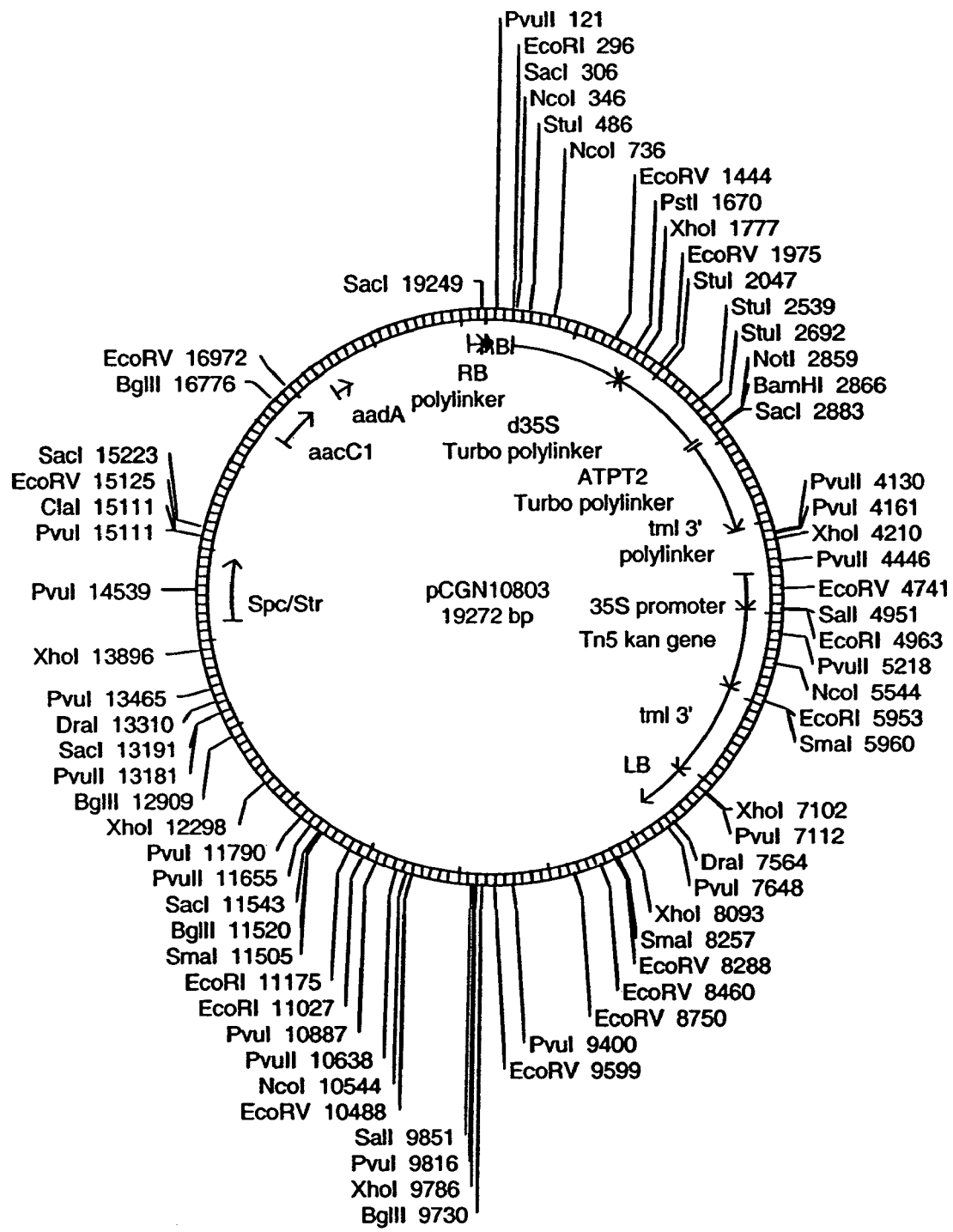
FIG. 4 provides a schematic picture of the expression construct pCGN10803.

The ATPT2 coding sequence was also cloned in the antisense orientation into the vector pCGN8644 to create the plant transformation construct pCGN10803 (FIG. 4).

Figure 5:
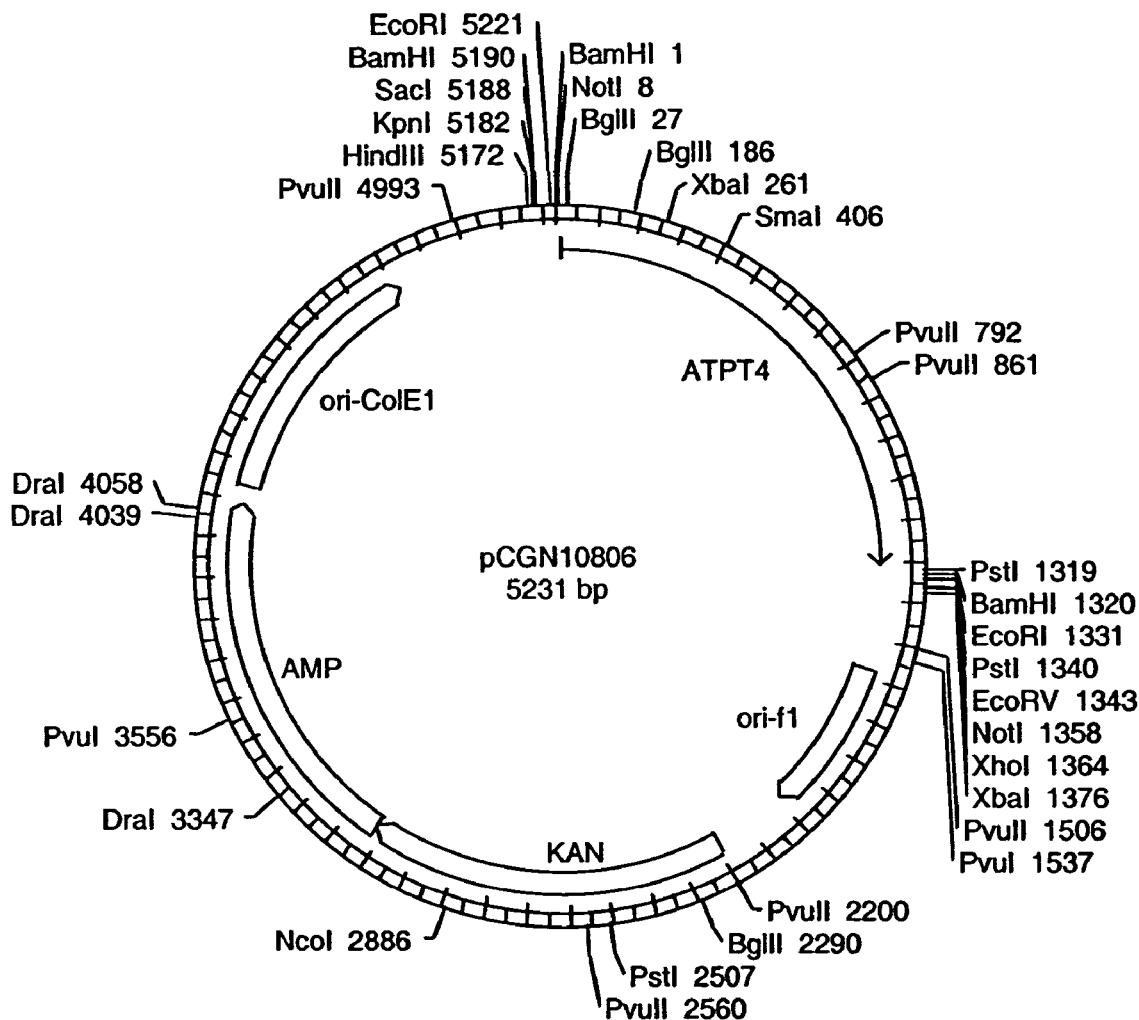
FIG. 5 provides a schematic picture of the construct pCGN10806.
Figure 6:
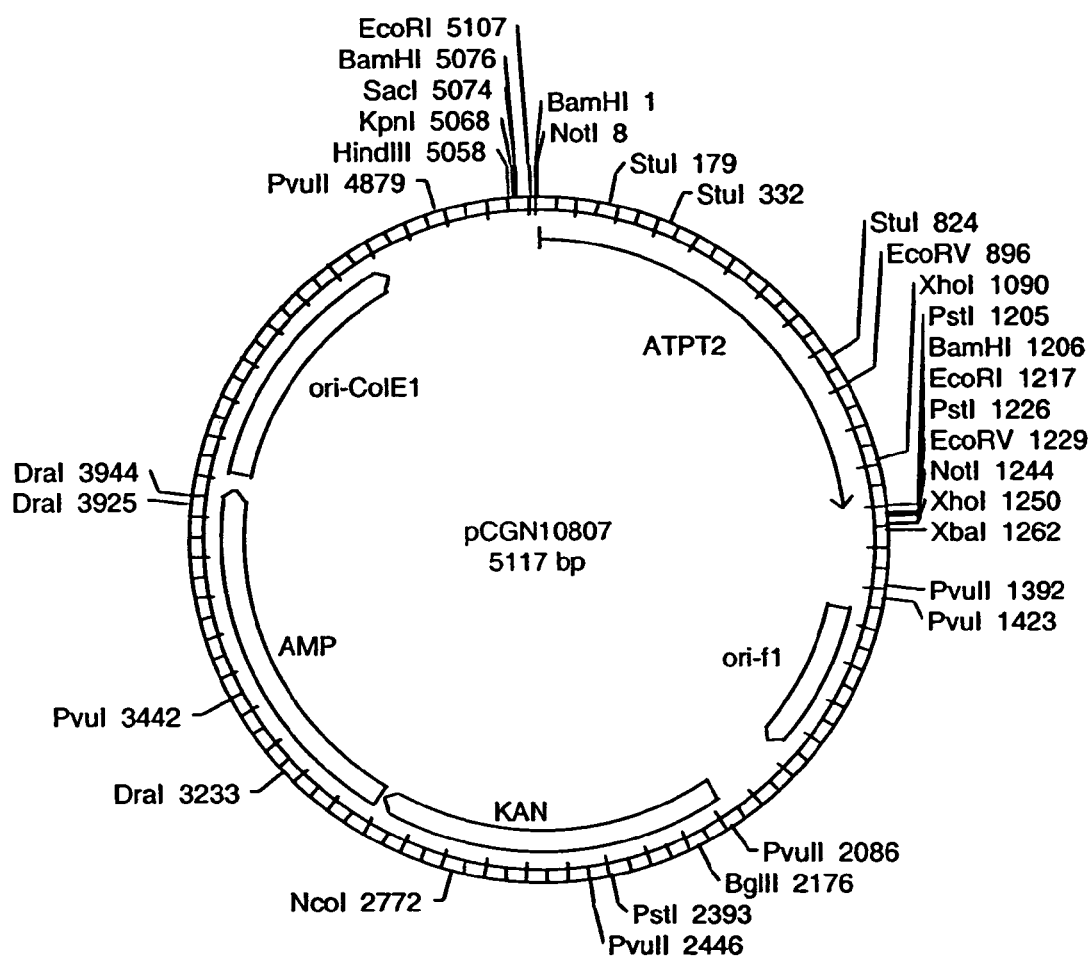
FIG. 6 provides a schematic picture of the construct pCGN10807.
Figure 7:
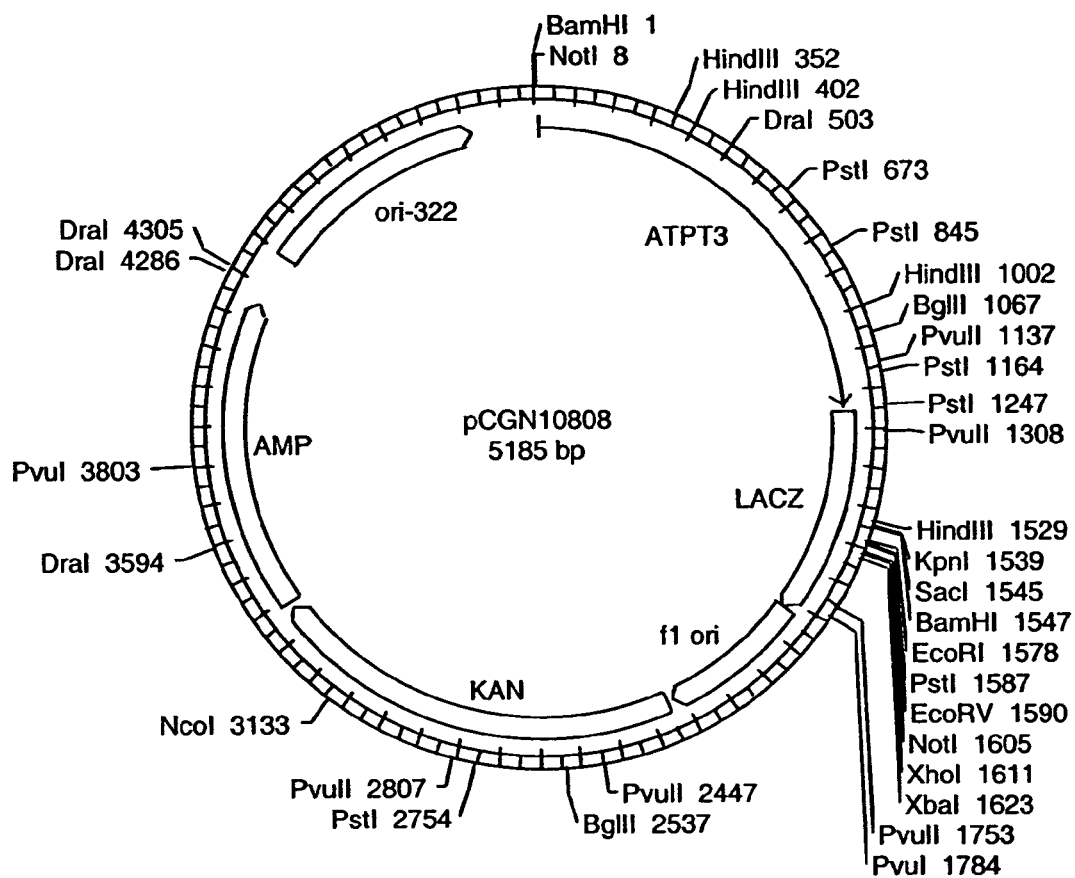
FIG. 7 provides a schematic picture of the construct pCGN10808.
Figure 8:
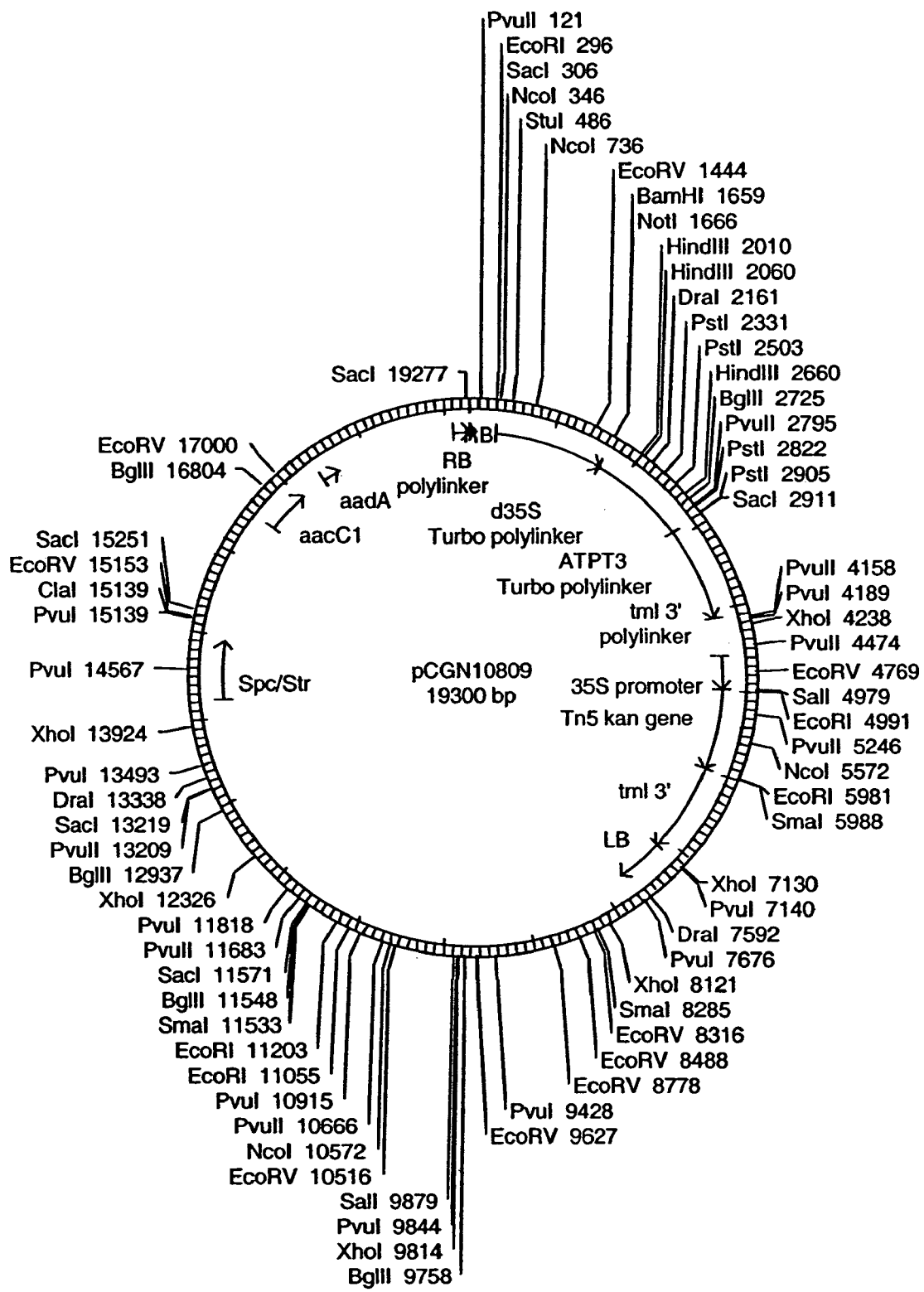
FIG. 8 provides a schematic picture of the expression construct pCGN10809.
Figure 9:
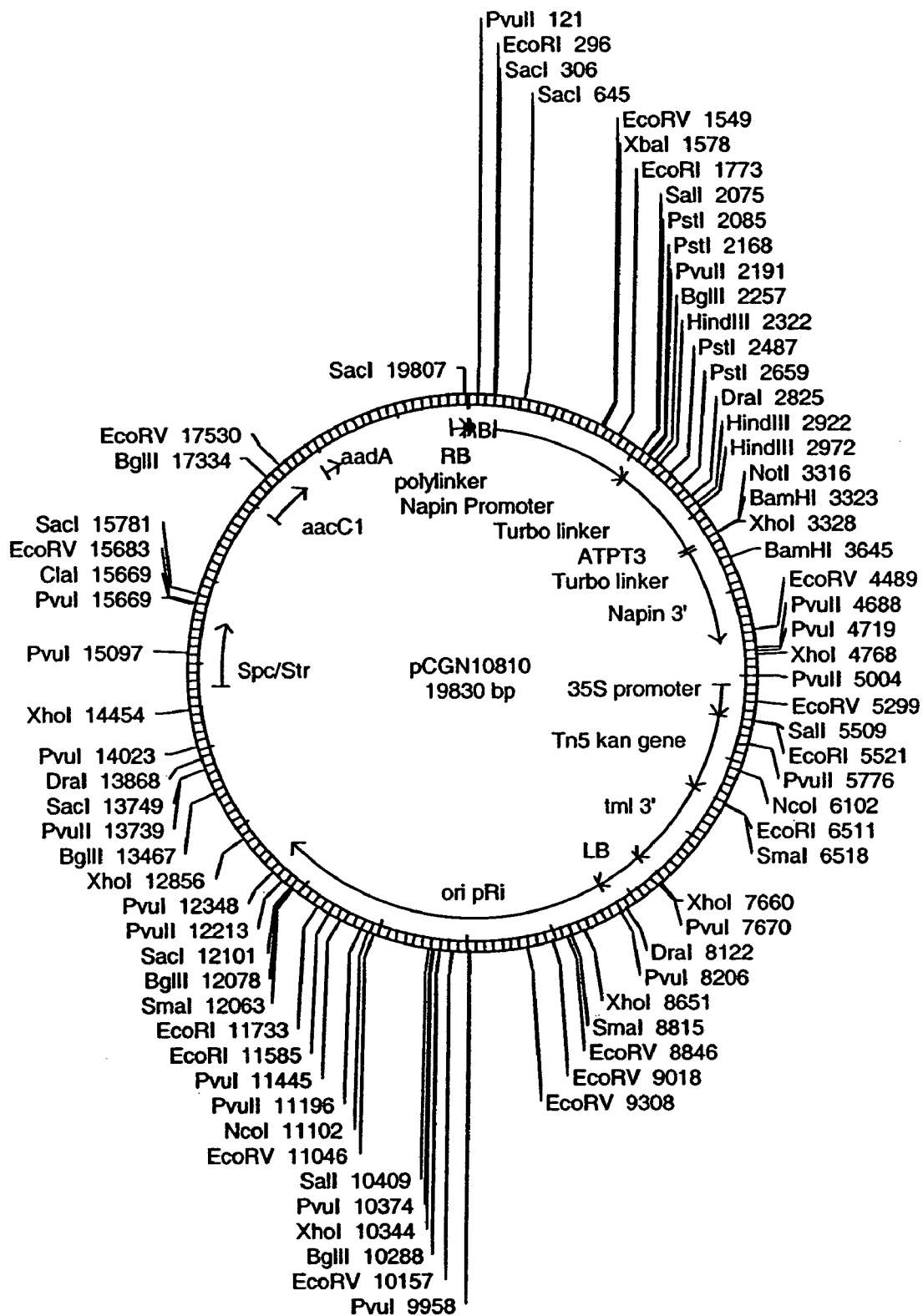
FIG. 9 provides a schematic picture of the expression construct pCGN10810.
Figure 10:
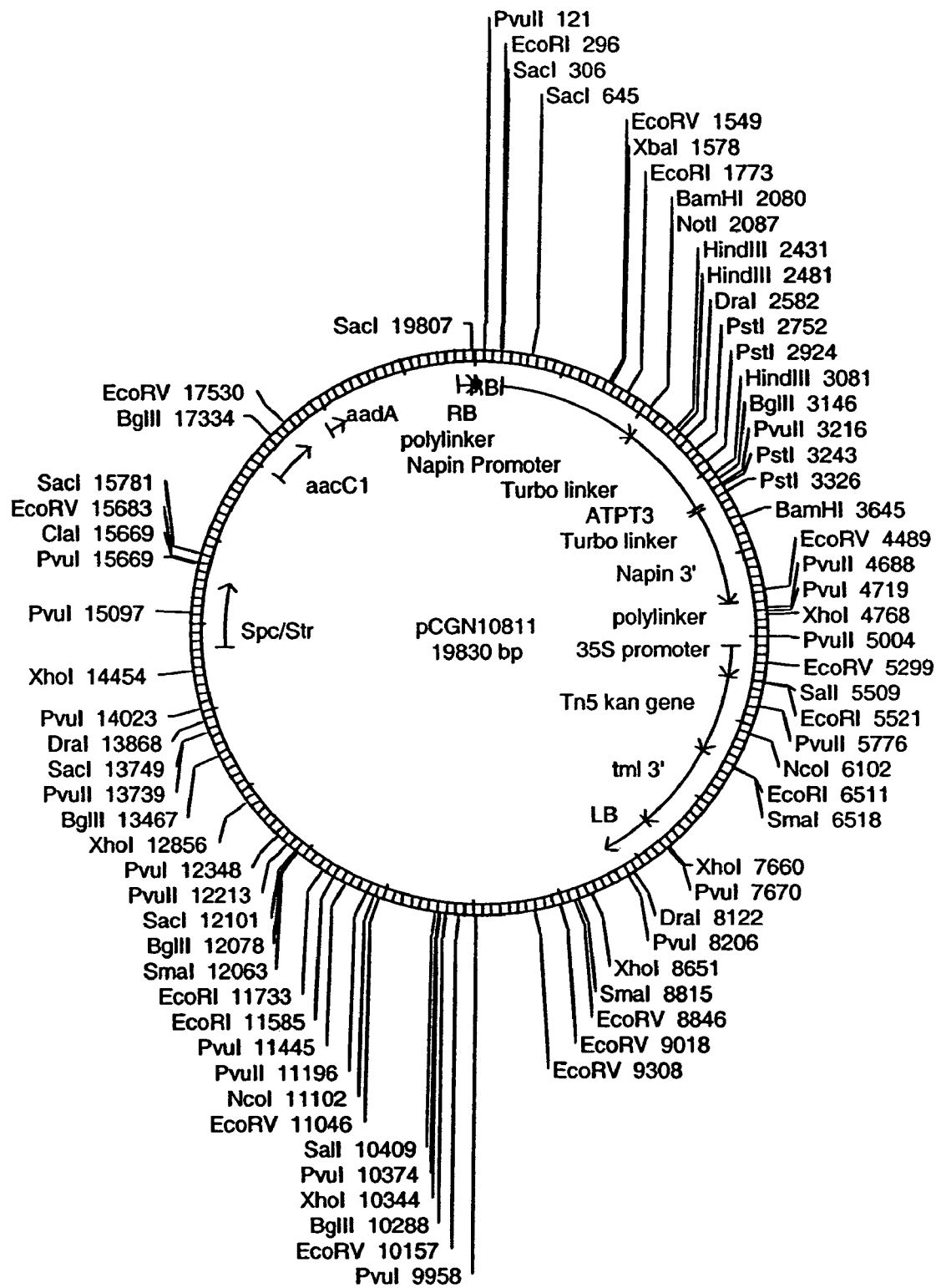
FIG. 10 provides a schematic picture of the expression construct pCGN10811.
Figure 11:
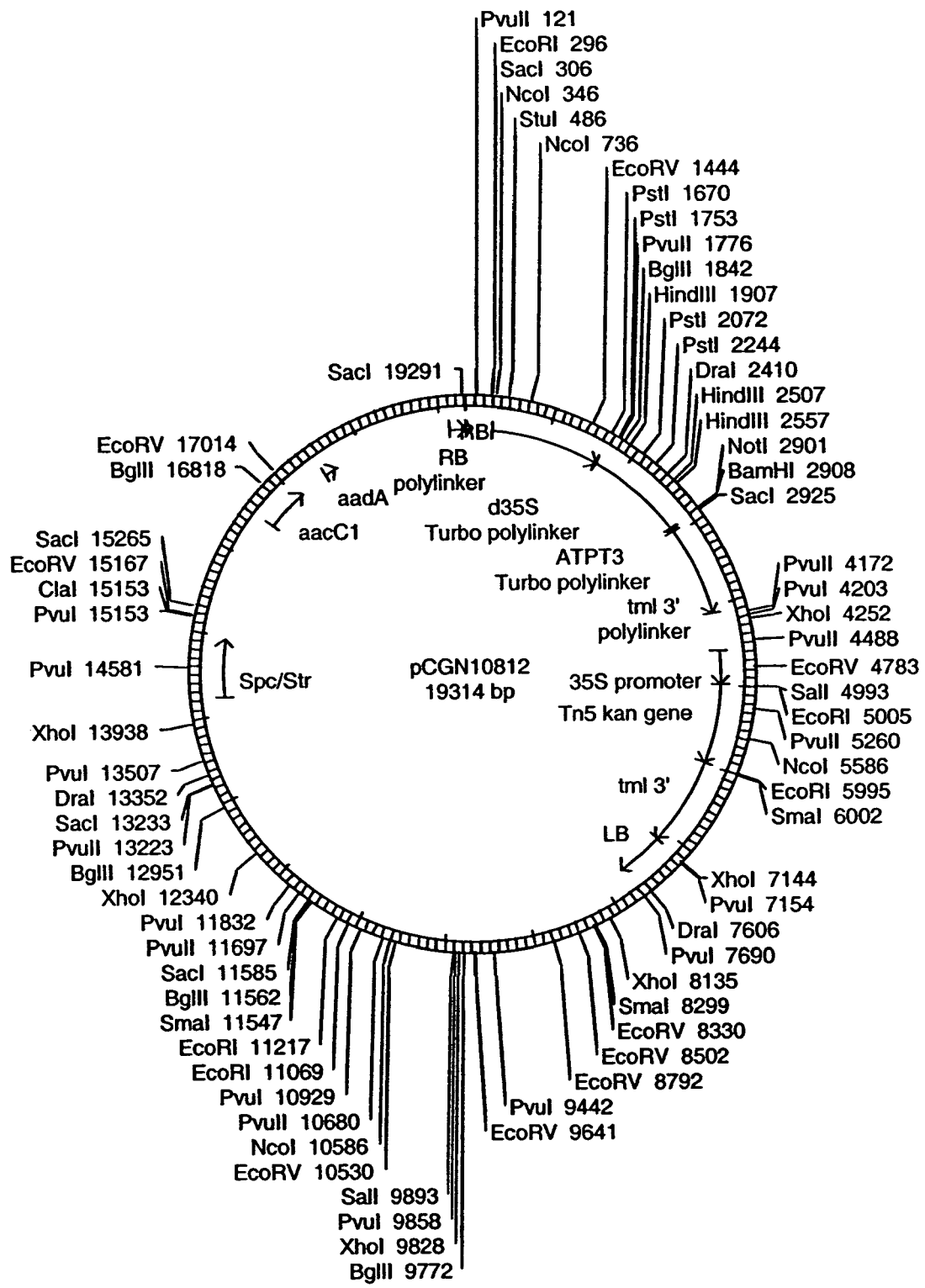
FIG. 11 provides a schematic picture of the expression construct pCGN10812.
Figure 12:
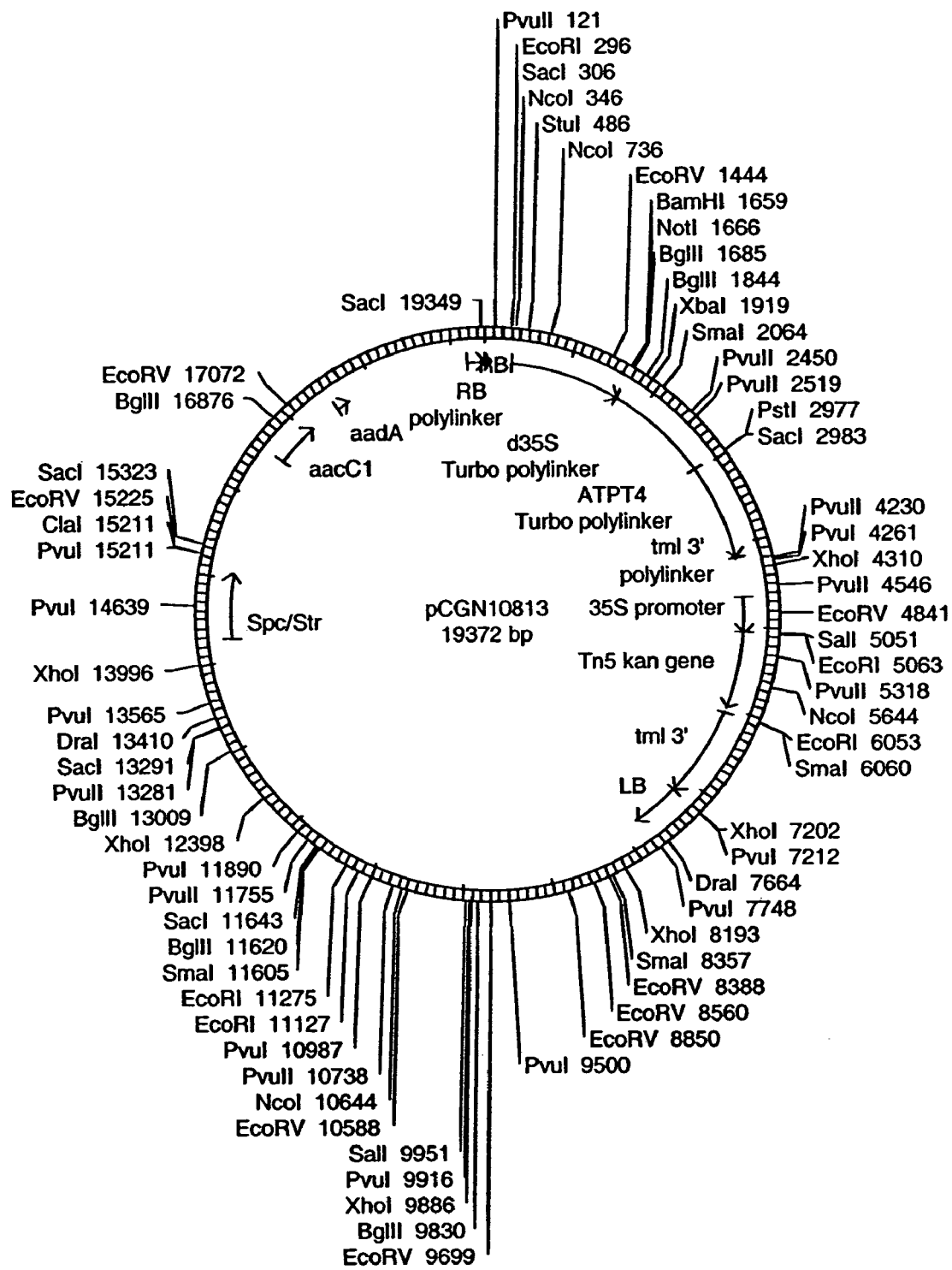
FIG. 12 provides a schematic picture of the expression construct pCGN10813.
Figure 13:
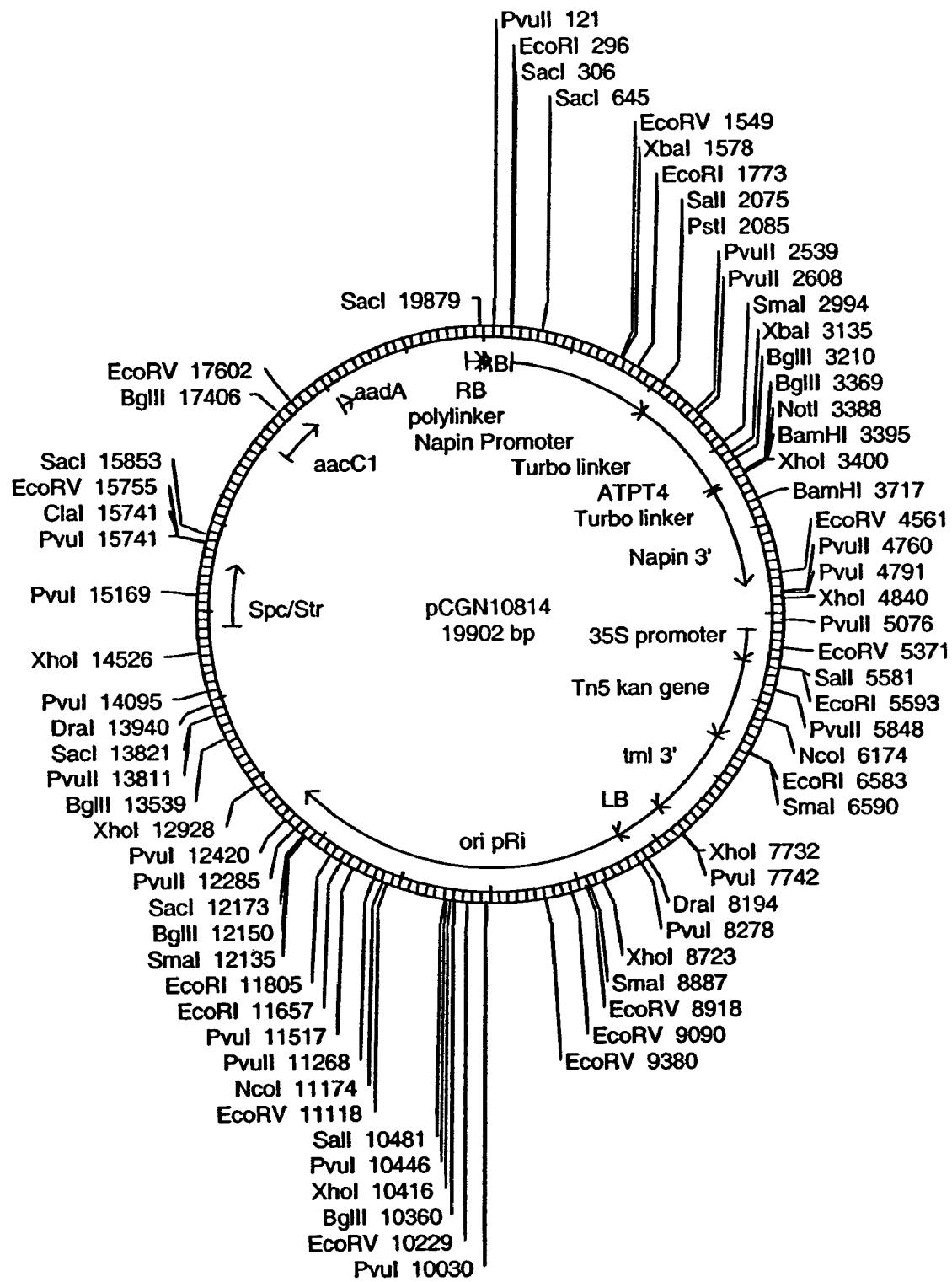
FIG. 13 provides a schematic picture of the expression construct pCGN10814.
Figure 14:
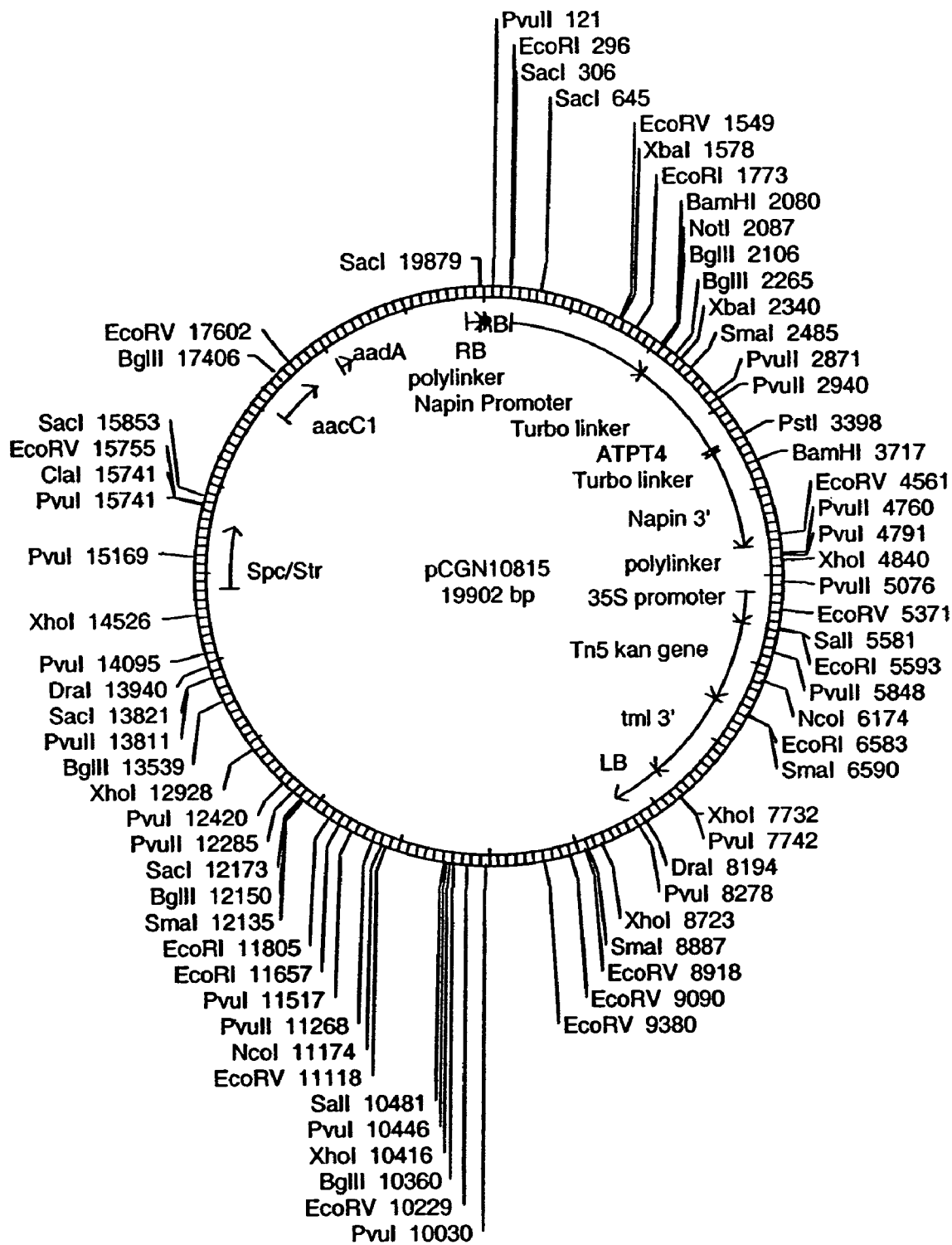
FIG. 14 provides a schematic picture of the expression construct pCGN10815.
Figure 15:
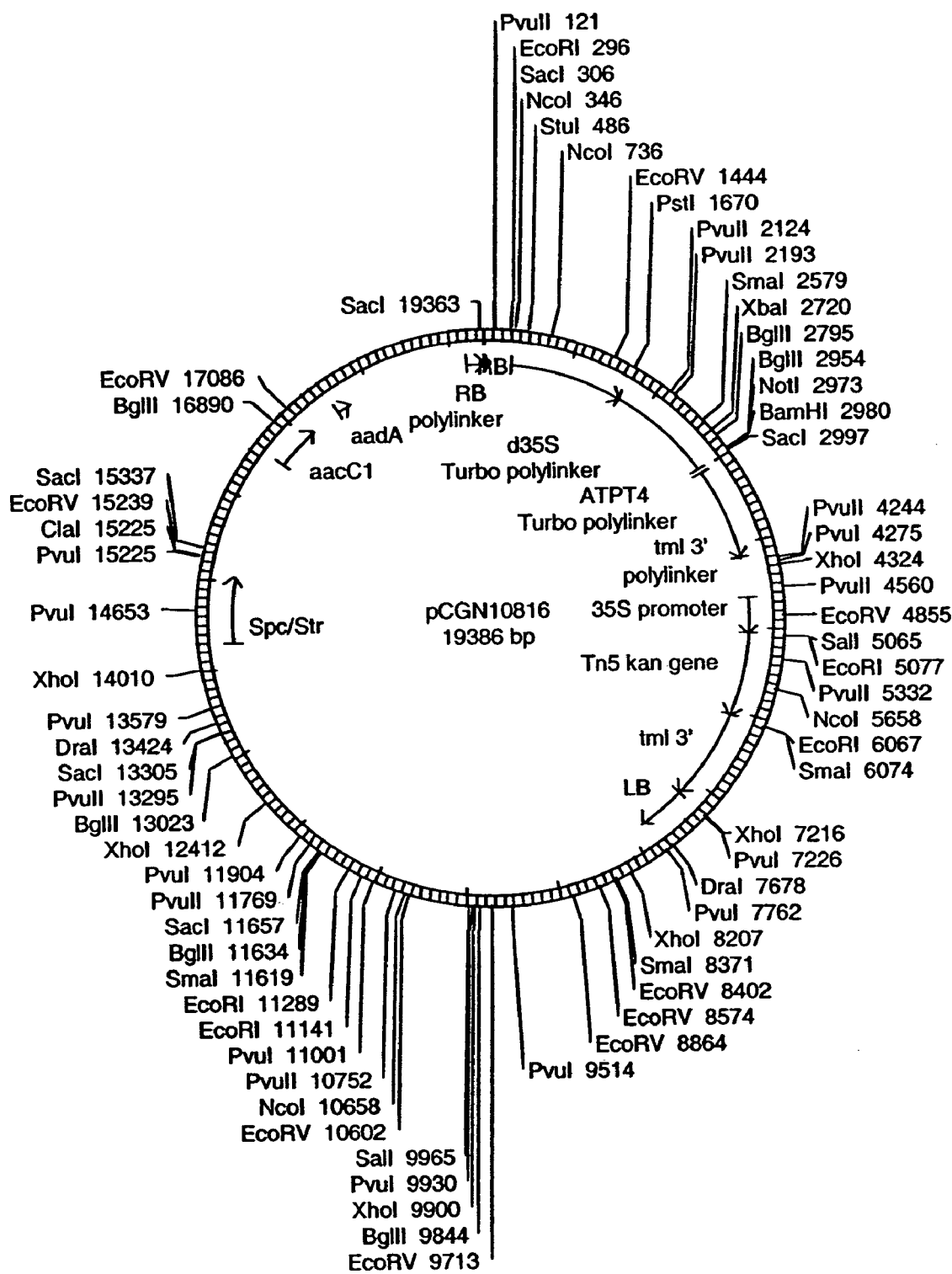
FIG. 15 provides a schematic picture of the expression construct pCGN10816.
Figure 16:
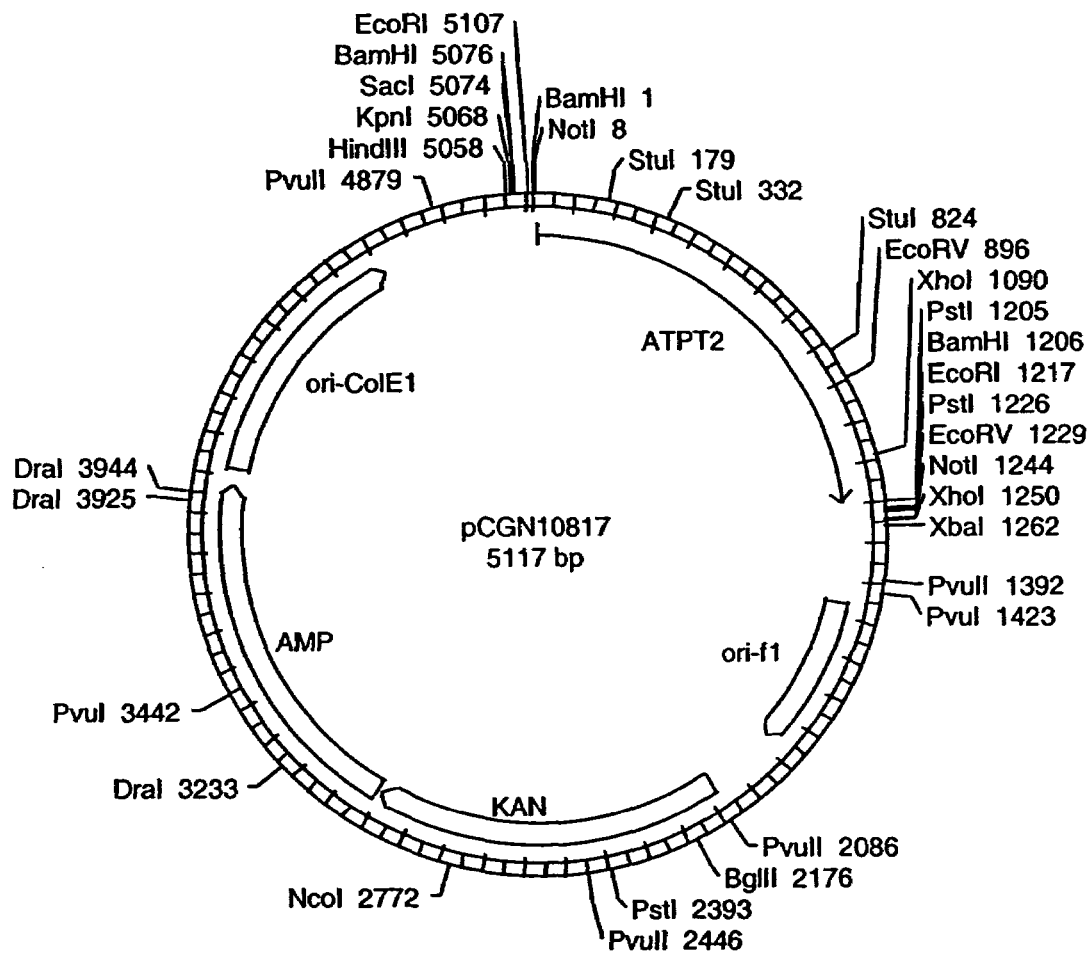
FIG. 16 provides a schematic picture of the expression construct pCGN10817.
Figure 17:
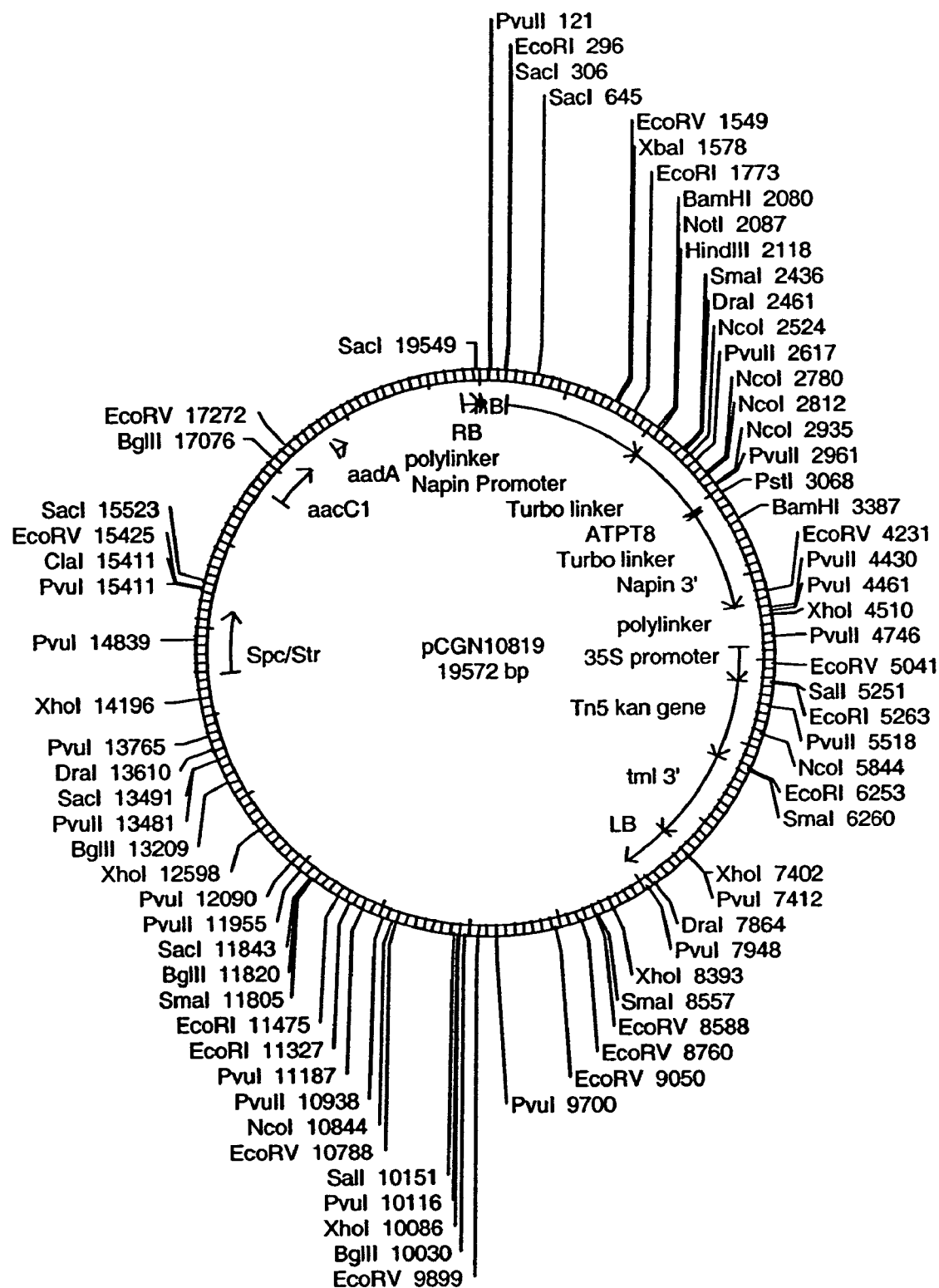
FIG. 17 provides a schematic picture of the expression construct pCGN10819.
Figure 18:
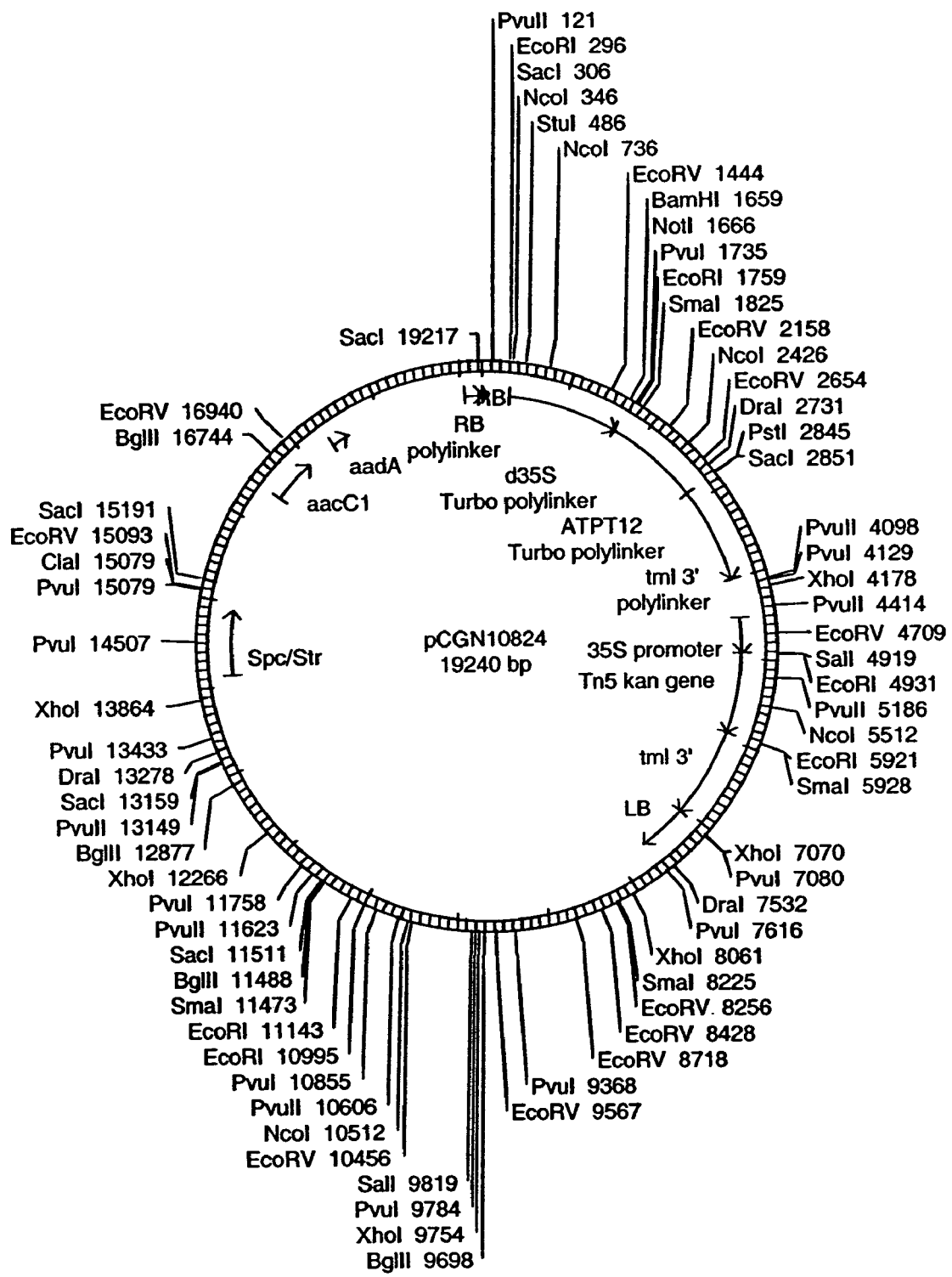
FIG. 18 provides a schematic picture of the expression construct pCGN10824.
Figure 19:
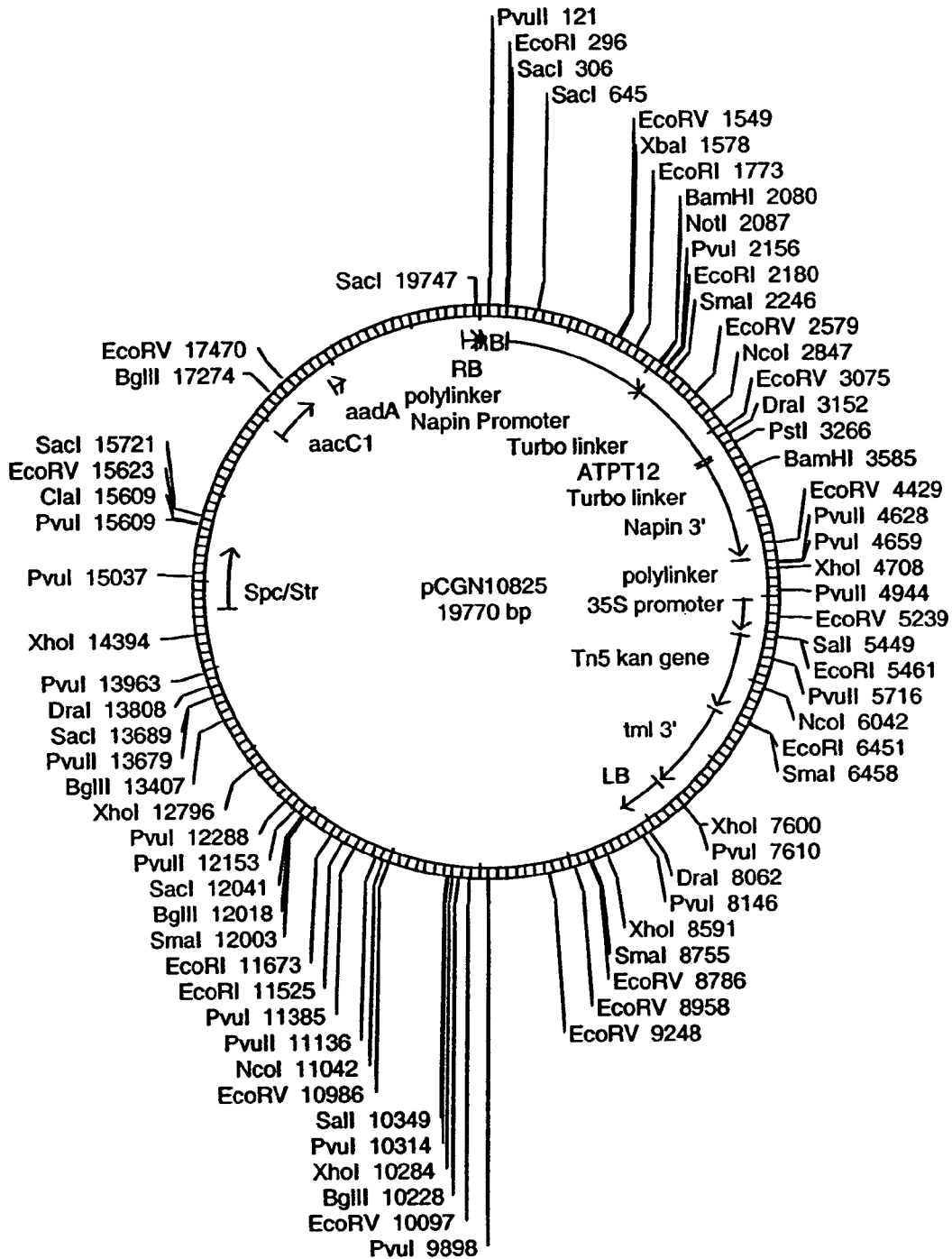
FIG. 19 provides a schematic picture of the expression construct pCGN10825.
Figure 20:
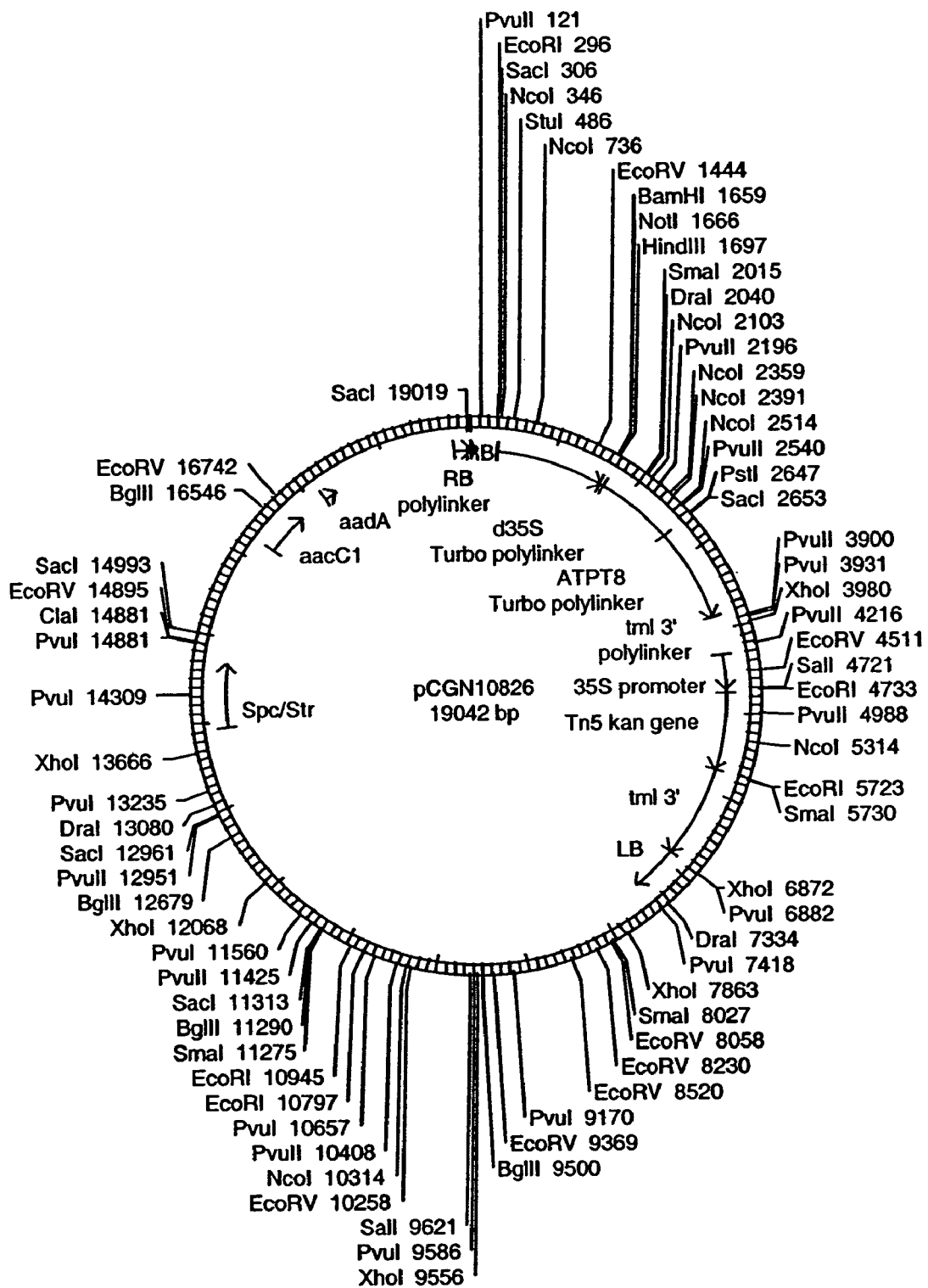
FIG. 20 provides a schematic picture of the expression construct pCGN10826.

The ATPT4 coding sequence was cloned into the vector pCGN864 to create the plant transformation construct pCGN10806 (FIG. 5). The ATPT2 coding sequence was cloned into the vector TopoTA™ vector from Invitrogen, to create the plant transformation construct pCGN10807 (FIG. 6). The ATPT3 coding sequence was cloned into the TopoTA vector to create the plant transformation construct pCGN10808 (FIG. 7). The ATPT3 coding sequence was cloned in the sense orientation into the vector pCGN8640 to create the plant transformation construct pCGN10809 (FIG. 8). The ATPT3 coding sequence was cloned in the antisense orientation into the vector pCGN8641 to create the plant transformation construct pCGN10810 (FIG. 9). The ATPT3 coding sequence was cloned into the vector pCGN8643 to create the plant transformation construct pCGN10811 (FIG. 10). The ATPT3 coding sequence was cloned into the vector pCGN8644 to create the plant transformation construct pCGN10812 (FIG. 11). The ATPT4 coding sequence was cloned into the vector pCGN8640 to create the plant transformation construct pCGN10813 (FIG. 12). The ATPT4 coding sequence was cloned into the vector pCGN8641 to create the plant transformation construct pCGN10814 (FIG. 13). The ATPT4 coding sequence was cloned into the vector pCGN8643 to create the plant transformation construct pCGN10815 (FIG. 14). The ATPT4 coding sequence was cloned in the antisense orientation into the vector pCGN8644 to create the plant transformation construct pCGN10816 (FIG. 15). The ATPT8 coding sequence was cloned in the sense orientation into the vector pCGN8643 to create the plant transformation construct pCGN10819 (FIG. 17). The ATPT12 coding sequence was cloned into the vector pCGN8640 to create the plant transformation construct pCGN10824 (FIG. 18). The ATPT12 coding sequence was cloned into the vector pCGN8643 to create the plant transformation construct pCGN10825 (FIG. 19). The ATPT8 coding sequence was cloned into the vector pCGN8640 to create the plant transformation construct pCGN10826 (FIG. 20).

Example 3

Plant Transformation with Prenyl Transferase Constructs

Transgenic *Brassica* plants are obtained by *Agrobacterium*-mediated transformation as described by Radke et al. (*Theor. Appl. Genet.* (1988) 75:685-694; *Plant Cell Reports* (1992) 11:499-505). Transgenic *Arabidopsis thaliana* plants may be obtained by *Agrobacterium*-mediated transformation as described by Valverkens et al., (*Proc. Nat. Acad. Sci.* (1988) 85:5536-5540), or as described by Bent et al. ((1994), *Science* 265:1856-1860), or Bechtold et al. ((1993), *C.R. Acad. Sci, Life Sciences* 316:1194-1199). Other plant species may be similarly transformed using related techniques.

Alternatively, microprojectile bombardment methods, such as described by Klein et al. (*Bio/Technology* 10:286-291) may also be used to obtain nuclear transformed plants.

Example 4

Identification of Additional Prenyltransferases

Additional BLAST searches were performed using the ATPT2 sequence, a sequence in the class of aromatic prenyltransferases. ESTs, and in some case, full-length coding regions, were identified in proprietary DNA libraries.

Soy full-length homologs to ATPT2 were identified by a combination of BLAST (using ATPT2 protein sequence) and 5' RACE. Two homologs resulted (SEQ ID NO:95 and SEQ ID NO:96). Translated amino acid sequences are provided by SEQ ID NO:97 and SEQ ID NO:98.

A rice est ATPT2 homolog is shown in SEQ ID NO:99 (obtained from BLAST using the wheat ATPT2 homolog).

Other homolog sequences were obtained using ATPT2 and PSI-BLAST, including est sequences from wheat (SEQ ID NO:100), leek (SEQ ID NOs:101 and 102), canola (SEQ ID NO:103), corn (SEQ ID NOs:104, 105 and 106), cotton (SEQ ID NO:107) and tomato (SEQ ID NO:108).

A PSI-Blast profile generated using the *E. coli* ubiA (genbank accession 1790473) sequence was used to analyze the *Synechocystis* genome. This analysis identified 5 open reading frames (ORFs) in the *Synechocystis* genome that were potentially prenyltransferases; slr0926 (annotated as ubiA (4-hydroxybenzoate-octaprenyltransferase, SEQ ID NO:32), sll1899 (annotated as ctaB (cytocrome c oxidase folding protein, SEQ ID NO:33), slr0056 (annotated as g4 (chlorophyll synthase 33 kd subunit, SEQ ID NO:34), slr1518 (annotated as menA (menaquinone biosynthesis protein, SEQ ID NO:35), and slr1736 (annotated as a hypothetical protein of unknown function (SEQ ID NO:36).

4A. *Synechocystis* Knock-Outs

To determine the functionality of these ORFs and their involvement, if any, in the biosynthesis of tocopherols, knockouts constructs were made to disrupt the ORF identified in *Synechocystis*.

Synthetic oligos were designed to amplify regions from the 5' (5'-TAATGTGTACATTGTCGGCCTC (17365') (SEQ ID NO:61) and 5'-GCAATGTAACATCAGAGATTTTGAGA-CACAACGTGGCTTTCCACAATTCCCCGCACC GTC (1736kanpr1)) (SEQ ID NO:62) and 3' (5'-AG-GCTAATAAGCACAAATGGGA (17363') (SEQ ID NO:63) and 5'-GGTATGAGTCAGCAACACCTTCTTCAC-GAGGCAGACCTCAGC GGAATTGGTTTAGGT-TATCCC (1736kanpr2)) (SEQ ID NO:64) ends of the slr1736 ORF. The 1736kanpr1 and 1736kanpr2 oligos contained 20 bp of homology to the slr1736 ORF with an additional 40 bp of sequence homology to the ends of the kanamycin resistance cassette. Separate PCR steps were completed with these oligos and the products were gel purified and combined with the kanamycin resistance gene from puc4K (Pharmacia) that had been digested with HincII and gel purified away from the vector backbone. The combined fragments were allowed to assemble without oligos under the following conditions: 94° C. for 1 min, 55° C. for 1 min, 72° C. for 1 min plus 5 seconds per cycle for 40 cycles using pfu polymerase in 100 ul reaction volume (Zhao, H and Arnold (1997) *Nucleic Acids Res.* 25(6):1307-1308). One microliter or five microliters of this assembly reaction was then amplified using 5' and 3' oligos nested within the ends of the ORF fragment, so that the resulting product contained 100-200 bp of the 5' end of the *Synechocystis* gene to be knocked out, the kanamycin resistance cassette, and 100-200 bp of the 3' end of the gene to be knocked out. This PCR product was then cloned into the vector pGemT easy (Promega) to create the construct pMON21681 and used for *Synechocystis* transformation.

Primers were also synthesized for the preparation of *Synechocystis* knockout constructs for the other sequences using the same method as described above, with the following primers. The ubiA 5' sequence was amplified using the primers 5'-GGATCCATGGTT GCCCAAACCCCATC (SEQ ID NO:65) and 5'-GCAATGTAACATCAGAGA TTTTGAGA-CACAACGTGGCTTTGGGTAAGCAACAATGACCGGC (SEQ ID NO:66). The 3' region was amplified using the synthetic oligonucleotide primers 5'-GAATTCTCAAAGC-CAGCCCAGTAAC (SEQ ID NO:67) and 5'-GGTAT-GAGTC AGCAACACCTTCTTCACGAGGCAGACCT-CAGCGGGTGCGAAAAGGGTTTTCCC (SEQ ID NO:68). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-CCAGTGGTTTAGGCTGTGTGGTC (SEQ ID NO:69) and 5'-CTGAGTTGGATGTATTGGATC (SEQ ID NO:70)), so that the resulting product contained 100-200 bp of the 5' end of the *Synechocystis* gene to be knocked out, the kanamycin resistance cassette, and 100-200 bp of the 3' end of the gene to be knocked out. This PCR product was then cloned into the vector pGemT easy (Promega) to create the construct pMON21682 and used for *Synechocystis* transformation.

Primers were also synthesized for the preparation of *Synechocystis* knockout constructs for the other sequences using the same method as described above, with the following primers. The sll1899 5' sequence was amplified using the primers 5'-GGATCCATGGTTACTT CGACAAAAATCC (SEQ ID NO:71) and 5'-GCAATGTAACATCAGAG ATTTTGAGACACAACGTGGCTTTGCTAG-GCAACCGCTTAGTAC (SEQ ID NO:72). The 3' region was amplified using the synthetic oligonucleotide primers 5'-GAATTCTTAACCCAACAGTAAAGTTCCC (SEQ ID NO:73) and 5'-GGTATGAGTCAGC AACACCTTCT-TCACGAGGCAGACCTCAGCGCCGGCAT-TGTCTTTTACATG (SEQ ID NO:74). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-GGAACCCTTG-CAGCCGCTTC (SEQ ID NO:75) and 5'-GTATGC-CCAACTGGTGCAGAGG (SEQ ID NO:76)), so that the resulting product contained 100-200 bp of the 5' end of the *Synechocystis* gene to be knocked out, the kanamycin resistance cassette, and 100-200 bp of the 3' end of the gene to be knocked out. This PCR product was then cloned into the vector pGemT easy (Promega) to create the construct pMON21679 and used for *Synechocystis* transformation.

Primers were also synthesized for the preparation of *Synechocystis* knockout constructs for the other sequences using the same method as described above, with the following primers. The slr0056 5' sequence was amplified using the primers 5'-GGATCCATGTCTGACACACAAAATACCG (SEQ ID NO:77) and 5'-GCAATGTAACATCA-GAGATTTTGAGACACAACGTG-GCTTTCGCCAATACCAGCCACC AACAG (SEQ ID NO:78). The 3' region was amplified using the synthetic oligonucleotide primers 5'-GAATTCTCAAATCCCCGCATG-GCCTAG (SEQ ID NO:79) and 5'-GGTATGAGTCAGCAA-CACCTTCTTCACGAGGCAGACCTCAGCGGCCTAC GGCTTGGA CGTGTGGG (SEQ ID NO:80). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-CACTTG-GATTCCCCTGATCTG (SEQ ID NO:81) and 5'-GCAATACCCGCTTGGAAAACG (SEQ ID NO:82)), so that the resulting product contained 100-200 bp of the 5' end of the *Synechocystis* gene to be knocked out, the kanamycin resistance cassette, and 100-200 bp of the 3' end of the gene to be knocked out. This PCR product was then cloned into the vector pGemT easy (Promega) to create the construct pMON21677 and used for *Synechocystis* transformation.

Primers were also synthesized for the preparation of *Synechocystis* knockout constructs for the other sequences using the same method as described above, with the following primers. The slr1518 5' sequence was amplified using the primers 5'-GGATCCATGACCGAAT CTTCGCCCCTAGC (SEQ ID NO:83) and 5'-GCAATGTAACATCA-GAGATTTTGA GACACAACGTGGCTTTCAATCCTAG-GTAGCCGAGGCG (SEQ ID NO:84). The 3' region was amplified using the synthetic oligonucleotide primers 5'-GAATTCTTAGCCCAGGCC AGCCCAGCC (SEQ ID NO:85) and 5'-GGTATGAGTCAGCAACACCTTCT-TCACGA GGCAGACCTCAGCGGGGAAT-TGATTTGTTTAATTACC (SEQ ID NO:86). The amplification products were combined with the kanamycin resistance gene from puc4K (Pharmacia) that had been digested with HincII and gel purified away from the vector backbone. The annealed fragment was amplified using 5' and 3' oligos nested within the ends of the ORF fragment (5'-GCGATCGCCAT-TATCGCTTGG (SEQ ID NO:87) and 5'-GCAGACTG-GCAATTATCAGTAACG (SEQ ID NO:88)), so that the resulting product contained 100-200 bp of the 5' end of the *Synechocystis* gene to be knocked out, the kanamycin resistance cassette, and 100-200 bp of the 3' end of the gene to be knocked out. This PCR product was then cloned into the vector pGemT easy (Promega) to create the construct pMON21680 and used for *Synechocystis* transformation.

4B. Transformation of *Synechocystis*

Cells of *Synechocystis* 6803 were grown to a density of approximately $2 \times 10^8$ cells per ml and harvested by centrifugation. The cell pellet was re-suspended in fresh BG-11 medium (ATCC Medium 616) at a density of $1 \times 10^9$ cells per ml and used immediately for transformation. One-hundred microliters of these cells were mixed with 5 ul of mini prep DNA and incubated with light at 30 C for 4 hours. This mixture was then plated onto nylon filters resting on BG-11 agar supplemented with TES pH8 and allowed to grow for 12-18 hours. The filters were then transferred to BG-11 agar+ TES+5 ug/ml kanamycin and allowed to grow until colonies appeared within 7-10 days (Packer and Glazer, 1988). Colonies were then picked into BG-11 liquid media containing 5 ug/ml kanamycin and allowed to grow for 5 days. These cells were then transferred to BG-11 media containing 10 ug/ml kanamycin and allowed to grow for 5 days and then transferred to Bg-11+kanamycin at 25 ug/ml and allowed to grow for 5 days. Cells were then harvested for PCR analysis to determine the presence of a disrupted ORF and also for HPLC analysis to determine if the disruption had any effect on tocopherol levels.

PCR analysis of the *Synechocystis* isolates for slr1736 and sll1899 showed complete segregation of the mutant genome, meaning no copies of the wild type genome could be detected in these strains. This suggests that function of the native gene is not essential for cell function. HPLC analysis of these same isolates showed that the sll1899 strain had no detectable reduction in tocopherol levels. However, the strain carrying the knockout for slr1736 produced no detectable levels of tocopherol.

Figure 21:
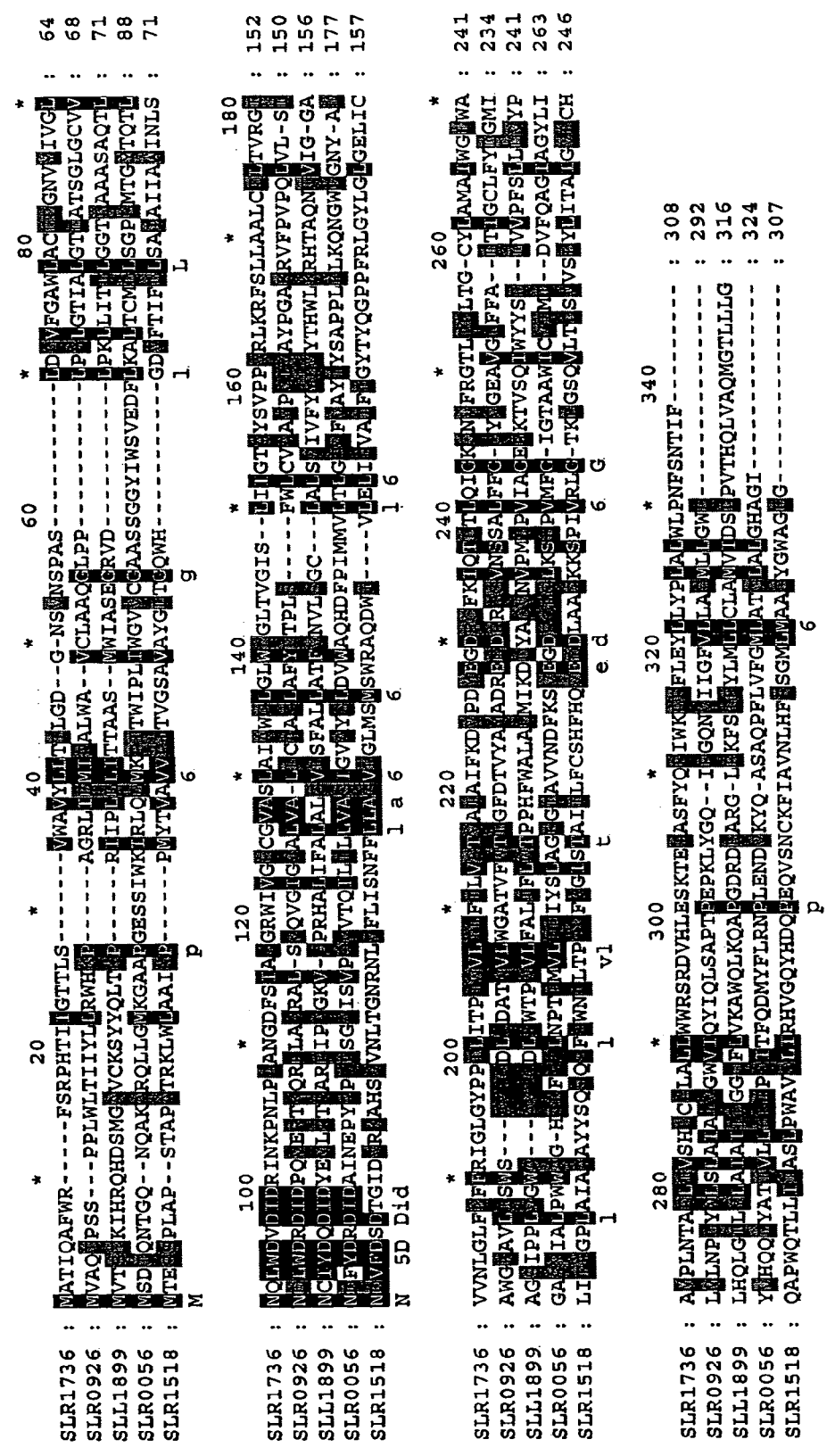

The amino acid sequences for the *Synechocystis* knockouts are compared using ClustalW, and are provided in Table 3 below. Provided are the percent identities, percent similarity, and the percent gap. The alignment of the sequences is provided in FIG. 21.

TABLE 3

|  |  | Slr1736 | slr0926 | sll1899 | slr0056 | slr1518 |
|---|---|---|---|---|---|---|
| slr1736 | % identity |  | 14 | 12 | 18 | 11 |
|  | % similar |  | 29 | 30 | 34 | 26 |
|  | % gap |  | 8 | 7 | 10 | 5 |
| slr0926 | % identity |  |  | 20 | 19 | 14 |
|  | % similar |  |  | 39 | 32 | 28 |
|  | % gap |  |  | 7 | 9 | 4 |
| sll1899 | % identity |  |  |  | 17 | 13 |
|  | % similar |  |  |  | 29 | 29 |
|  | % gap |  |  |  | 12 | 9 |
| slr0056 | % identity |  |  |  |  | 15 |
|  | % similar |  |  |  |  | 31 |
|  | % gap |  |  |  |  | 8 |
| slr1518 | % identity |  |  |  |  |  |
|  | % similar |  |  |  |  |  |
|  | % gap |  |  |  |  |  |

Figure 22B:
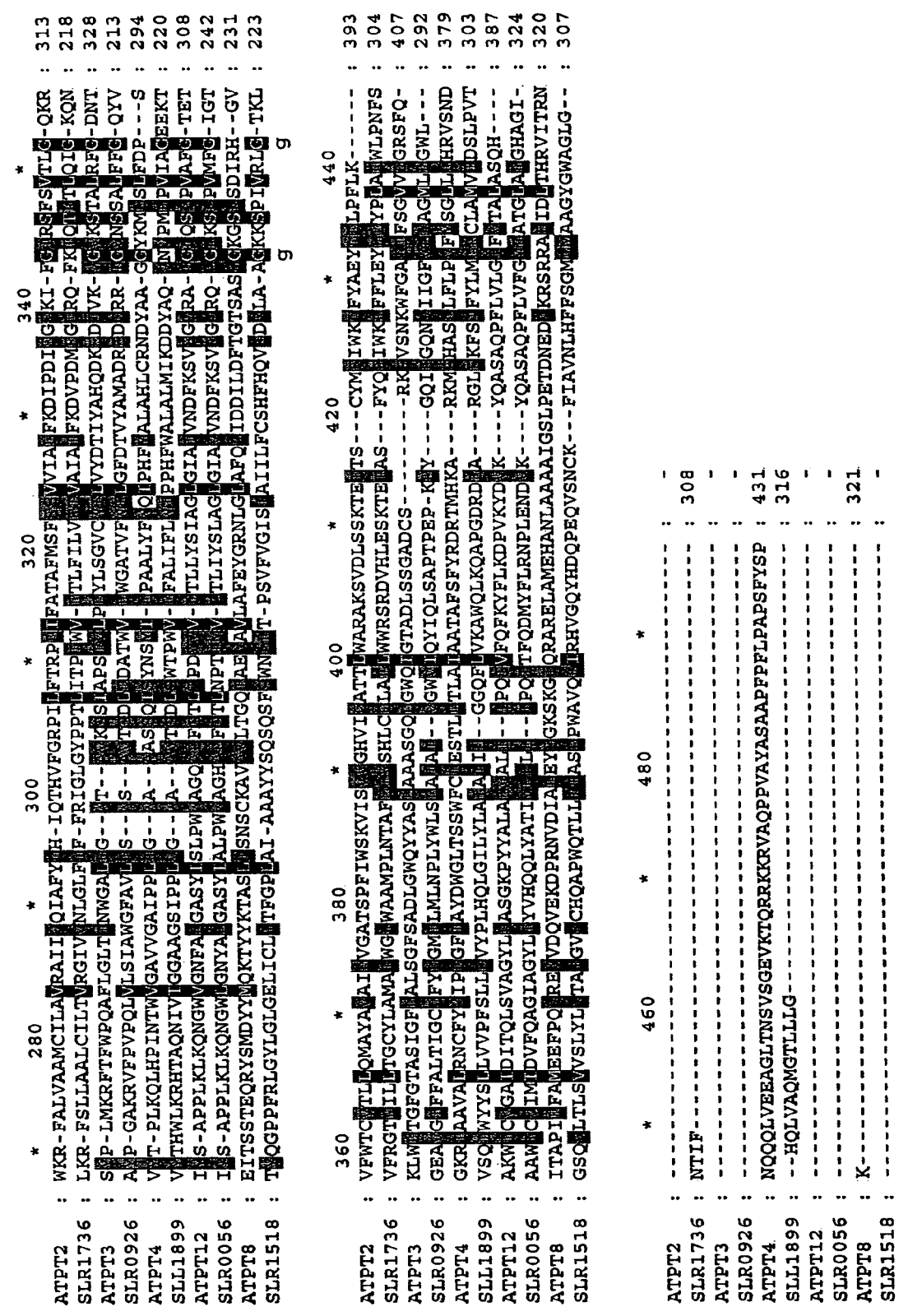

Amino acid sequence comparisons are performed using various *Arabidopsis* prenyltransferase sequences and the *Synechocystis* sequences. The comparisons are presented in Table 4 below. Provided are the percent identities, percent similarity, and the percent gap. The alignment of the sequences is provided in FIG. 22.

4C. Phytyl Prenyltransferase Enzyme Assays

[$^3$H] Homogentisic acid in 0.1% $H_3PO_4$ (specific radioactivity 40 Ci/mmol). Phytyl pyrophosphate was synthesized as described by Joo, et al. (1973) *Can J. Biochem.* 51:1527. 2-methyl-6-phytylquinol and 2,3-dimethyl-5-phytylquinol were synthesized as described by Soll, et al. (1980) *Phytochemistry* 19:215. Homogentisic acid, α, β, δ, and γ-tocopherol, and tocol, were purchased commercially.

The wild-type strain of *Synechocystis* sp. PCC 6803 was grown in BG11 medium with bubbling air at 30° C. under 50 µE.m$^{-2}$.s$^{-1}$ fluorescent light, and 70% relative humidity. The growth medium of slr1736 knock-out (potential PPT) strain of this organism was supplemented with 25 µg mL$^{-1}$ kanamycin. Cells were collected from 0.25 to 1 liter culture by centrifugation at 5000 g for 10 min and stored at −80° C.

Total membranes were isolated according to Zak's procedures with some modifications (Zak, et al. (1999) *Eur J. Biochem* 261:311). Cells were broken on a French press. Before the French press treatment, the cells were incubated for 1 hour with lysozyme (0.5%, w/v) at 30° C. in a medium containing 7 mM EDTA, 5 mM NaCl and 10 mM Hepes-NaOH, pH 7.4. The spheroplasts were collected by centrifugation at 5000 g for 10 min and resuspended at 0.1-0.5 mg chlorophyll.mL$^{-1}$ in 20 mM potassium phosphate buffer, pH 7.8. Proper amount of protease inhibitor cocktail and DNAase I from Boehringer Mannheim were added to the solution. French press treatments were performed two to three times at 100 MPa. After breakage, the cell suspension was centrifuged for 10 min at 5000 g to pellet unbroken cells, and this was followed by centrifugation at 100 000 g for 1 hour to collect total membranes. The final pellet was resuspended in a buffer containing 50 mM Tris-HCL and 4 mM $MgCl_2$.

Chloroplast pellets were isolated from 250 g of spinach leaves obtained from local markets. Devined leaf sections were cut into grinding buffer (2 l/250 g leaves) containing 2 mM EDTA, 1 mM $MgCl_2$, 1 mM $MnCl_2$, 0.33 M sorbitol, 0.1% ascorbic acid, and 50 mM Hepes at pH 7.5. The leaves

TABLE 4

|  |  | ATPT2 | slr1736 | ATPT3 | slr0926 | ATPT4 | sll1899 | ATPT12 | slr0056 | ATPT8 | slr1518 |
|---|---|---|---|---|---|---|---|---|---|---|---|
| ATPT2 | % identity |  | 29 | 9 | 9 | 8 | 8 | 12 | 9 | 7 | 9 |
|  | % similar |  | 46 | 23 | 21 | 20 | 20 | 28 | 23 | 21 | 20 |
|  | % gap |  | 27 | 13 | 28 | 23 | 29 | 11 | 24 | 25 | 24 |
| slr1736 | % identity |  |  | 9 | 13 | 8 | 12 | 13 | 15 | 8 | 10 |
|  | % similar |  |  | 19 | 28 | 19 | 28 | 26 | 33 | 21 | 26 |
|  | % gap |  |  | 34 | 12 | 34 | 15 | 26 | 10 | 12 | 10 |
| ATPT3 | % identity |  |  |  | 23 | 11 | 14 | 13 | 10 | 5 | 11 |
|  | % similar |  |  |  | 36 | 26 | 26 | 26 | 21 | 14 | 22 |
|  | % gap |  |  |  | 29 | 21 | 31 | 16 | 30 | 30 | 30 |
| slr0926 | % identity |  |  |  |  | 12 | 20 | 17 | 20 | 11 | 14 |
|  | % similar |  |  |  |  | 24 | 37 | 28 | 33 | 24 | 29 |
|  | % gap |  |  |  |  | 33 | 12 | 25 | 10 | 11 | 9 |
| ATPT4 | % identity |  |  |  |  |  | 18 | 11 | 8 | 6 | 7 |
|  | % similar |  |  |  |  |  | 33 | 23 | 18 | 16 | 19 |
|  | % gap |  |  |  |  |  | 28 | 19 | 32 | 32 | 33 |
| sll1899 | % identity |  |  |  |  |  |  | 13 | 17 | 10 | 12 |
|  | % similar |  |  |  |  |  |  | 24 | 30 | 23 | 26 |
|  | % gap |  |  |  |  |  |  | 27 | 13 | 10 | 11 |
| ATPT12 | % identity |  |  |  |  |  |  |  | 52 | 8 | 11 |
|  | % similar |  |  |  |  |  |  |  | 66 | 19 | 26 |
|  | % gap |  |  |  |  |  |  |  | 18 | 25 | 23 |
| slr0056 | % identity |  |  |  |  |  |  |  |  | 9 | 13 |
|  | % similar |  |  |  |  |  |  |  |  | 23 | 32 |
|  | % gap |  |  |  |  |  |  |  |  | 10 | 8 |
| ATPT8 | % identity |  |  |  |  |  |  |  |  |  | 7 |
|  | % similar |  |  |  |  |  |  |  |  |  | 23 |
|  | % gap |  |  |  |  |  |  |  |  |  | 7 |
| slr1518 |  |  |  |  |  |  |  |  |  |  |  | were homogenized for 3 sec three times in a 1-L blendor, and filtered through 4 layers of mirocloth. The supernatant was then centrifuged at 5000 g for 6 min. The chloroplast pellets were resuspended in small amount of grinding buffer (Douce, et al Methods in Chloroplast Molecular Biology, 239 (1982)

Chloroplasts in pellets can be broken in three ways. Chloroplast pellets were first aliquoted in 1 mg of chlorophyll per tube, centrifuged at 6000 rpm for 2 min in microcentrifuge, and grinding buffer was removed. Two hundred microliters of Triton X-100 buffer (0.1% Triton X-100, 50 mM Tris-HCl pH 7.6 and 4 mM $MgCl_2$) or swelling buffer (10 mM Tris pH 7.6 and 4 mM $MgCl_2$) was added to each tube and incubated for ½ hour at 4° C. Then the broken chloroplast pellets were used for the assay immediately. In addition, broken chloroplasts can also be obtained by freezing in liquid nitrogen and stored at −80° C. for ½ hour, then used for the assay.

In some cases chloroplast pellets were further purified with 40%/80% percoll gradient to obtain intact chloroplasts. The intact chloroplasts were broken with swelling buffer, then either used for assay or further purified for envelope membranes with 20.5%/31.8% sucrose density gradient (Sol, et al (1980) supra). The membrane fractions were centrifuged at 100 000 g for 40 min and resuspended in 50 mM Tris-HCl pH 7.6, 4 mM $MgCl_2$.

Various amounts of [$^3$H]HGA, 40 to 60 μM unlabelled HGA with specific activity in the range of 0.16 to 4 Ci/mmole were mixed with a proper amount of 1M Tris-NaOH pH 10 to adjust pH to 7.6. HGA was reduced for 4 min with a trace amount of solid $NaBH_4$. In addition to HGA, standard incubation mixture (final vol 1 mL) contained 50 mM Tris-HCl, pH 7,6,3-5 mM $MgCl_2$, and 100 μM phytyl pyrophosphate. The reaction was initiated by addition of *Synechocystis* total membranes, spinach chloroplast pellets, spinach broken chloroplasts, or spinach envelope membranes. The enzyme reaction was carried out for 2 hour at 23° C. or 30° C. in the dark or light. The reaction is stopped by freezing with liquid nitrogen, and stored at −80° C. or directly by extraction.

A constant amount of tocol was added to each assay mixture and reaction products were extracted with a 2 mL mixture of chloroform/methanol (1:2, v/v) to give a monophasic solution. NaCl solution (2 mL; 0.9%) was added with vigorous shaking. This extraction procedure was repeated three times. The organic layer containing the prenylquinones was filtered through a 20 mμ filter, evaporated under $N_2$, and then resuspended in 100 μL of ethanol.

The samples were mainly analyzed by Normal-Phase HPLC method (Isocratic 90% Hexane and 10% Methyl-t-butyl ether), and use a Zorbax silica column, 4.6×250 mm. The samples were also analyzed by Reversed-Phase HPLC method (Isocratic 0.1% $H_3PO_4$ in MeOH), and use a Vydac 201HS54 C18 column; 4.6×250 mm coupled with an All-tech C18 guard column. The amount of products were calculated based on the substrate specific radioactivity, and adjusted according to the % recovery based on the amount of internal standard.

The amount of chlorophyll was determined as described in Amon (1949) *Plant Physiol*. 24:1. Amount of protein was determined by the Bradford method using gamrnma globulin as a standard (Bradford, (1976) *Anal. Biochem*. 72:248)

Figure 23:
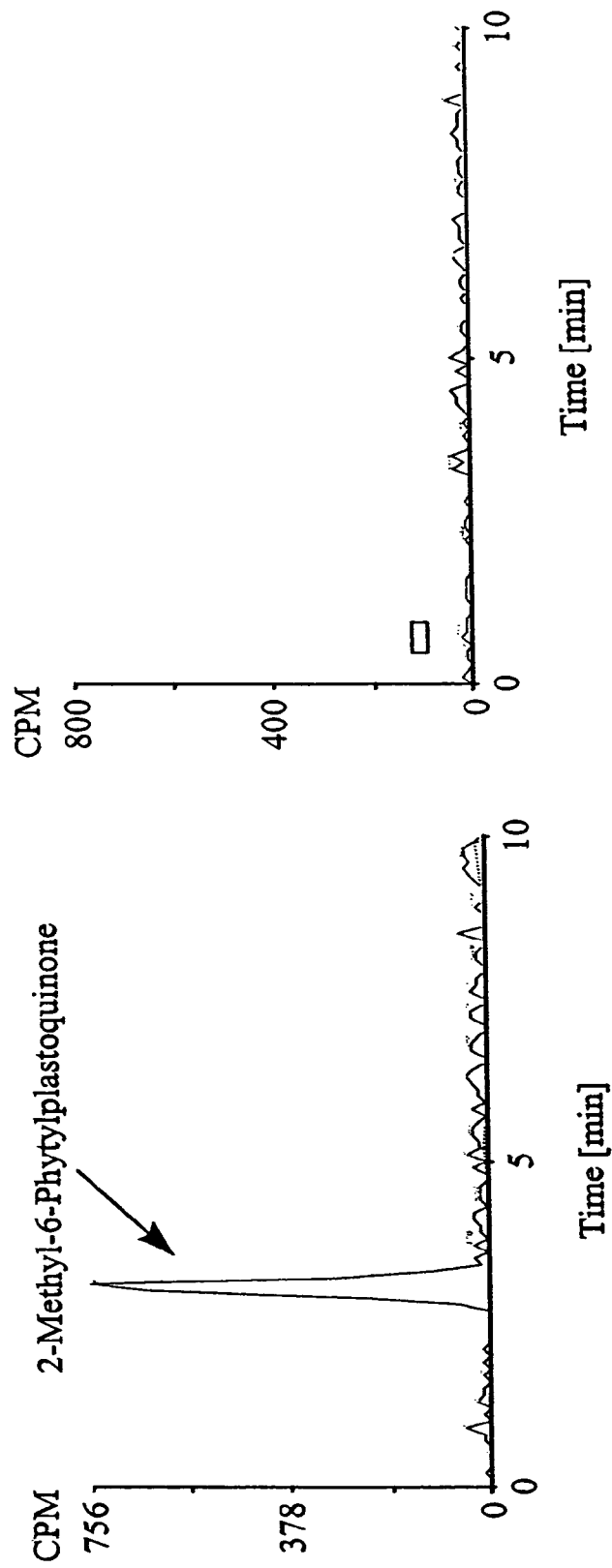
FIG. 23 provides the results of the enzymatic assay from preparations of wild type *Synechocystis* strain 6803, and *Synechocystis* slr1736 knockout.

Results of the assay demonstrate that 2-Methyl-6-Phytylplastoquinone is not produced in the *Synechocystis* slr1736 knockout preparations. The results of the phytyl prenyltransferase enzyme activity assay for the slr1736 knock out are presented in FIG. 23.

4D. Complementation of the slr1736 Knockout with ATPT2

In order to determine whether ATPT2 could complement the knockout of slr1736 in *Synechocystis* 6803, a plasmid was constructed to express the ATPT2 sequence from the TAC promoter. A vector, plasmid psl1211, was obtained from the lab of Dr. Himadri Pakrasi of Washington University, and is based on the plasmid RSF1010 which is a broad host range plasmid (Ng W.-O., Zentella R., Wang, Y., Taylor J-S. A., Pakrasi, H. B. 2000. phrA, the major photoreactivating factor in the cyanobacterium *Synechocystis* sp. strain PCC 6803 codes for a cyclobutane pyrimidine dimer specific DNA photolyase. *Arch. Microbiol*. (in press)). The ATPT2 gene was isolated from the vector pCGN10817 by PCR using the following primers. ATPT2nco.pr 5'-CCATGGATTCGAG-TAAAGTTGTCGC (SEQ ID NO:89); ATPT2ri.pr-5'-GAAT-TCACTTCAAAAAAGGTAACAG (SEQ ID NO:90). These primers will remove approximately 112 BP from the 5' end of the ATPT2 sequence, which is thought to be the chloroplast transit peptide. These primers will also add an NcoI site at the 5' end and an EcoRI site at the 3' end which can be used for sub-cloning into subsequent vectors. The PCR product from using these primers and pCGN10817 was ligated into pGEM T easy and the resulting vector pMON21689 was confirmed by sequencing using the m13forward and m13reverse primers. The NcoI/EcoRI fragment from pMON21689 was then ligated with the EagI/EcoRI and EagI/NcoI fragments from psl1211 resulting in pMON21690. The plasmid pMON21690 was introduced into the slr1736 *Synechocystis* 6803 KO strain via conjugation. Cells of s1906 (a helper strain) and DH10B cells containing pMON21690 were grown to log phase (O.D. 600=0.4) and 1 ml was harvested by centrifugation. The cell pellets were washed twice with a sterile BG-11 solution and resuspended in 200 ul of Bg-11. The following was mixed in a sterile eppendorf tube: 50 ul SL906, 50 ul DH10B cells containing pMON21690, and 100 ul of a fresh culture of the slr1736 *Synechocystis* 6803 KO strain (O.D. 730=0.2-0.4). The cell mixture was immediately transferred to a nitrocellulose filter resting on BG-11 and incubated for 24 hours at 30 C and 2500 LUX(50 ue) of light. The filter was then transferred to BG-11 supplemented with 10 ug/ml Gentamycin and incubated as above for ~5 days. When colonies appeared, they were picked and grown up in liquid Bg-11+Gentamycin 10 ug/ml. (Elhai, J. and Wolk, P. 1988. Conjugal transfer of DNA to Cyanobacteria. *Methods in Enzymology* 167, 747-54) The liquid cultures were then assayed for tocopherols by harvesting 1 ml of culture by centrifugation, extracting with ethanol/pyrogallol, and HPLC separation. The slr1736 *Synechocystis* 6803 KO strain, did not contain any detectable tocopherols, while the slr1736 *Synechocystis* 6803 KO strain transformed with pmon21690 contained detectable alpha tocopherol. A *Synechocystis* 6803 strain transformed with psl1211 (vector control) produced alpha tocopherol as well.

4E: Additional Evidence of Prenyltransferase Activity

To test the hypothesis that slr1736 or ATPT2 are sufficient as single genes to obtain phytyl prenyltransferase activity, both genes were expressed in SF9 cells and in yeast. When either slr1736 or ATPT2 were expressed in insect cells (Table 5) or in yeast, phytyl prenyltransferase activity was detectable in membrane preparations, whereas membrane preparations of the yeast vector control, or membrane preparations of insect cells did not exhibit phytyl prenyltransferase activity.

TABLE 5

Phytyl prenyltransferase activity

| Enzyme source | Enzyme activity [pmol/mg × h] |
|---|---|
| slr1736 expressed in SF9 cells | 20 |
| ATPT2 expressed in SF9 cells | 6 |
| SF9 cell control | <0.05 |
| Synechocystis 6803 | 0.25 |
| Spinach chloroplasts | 0.20 |

Example 5

Transgenic Plant Analysis

5A. Arabidopsis

Arabidopsis plants transformed with constructs for the sense or antisense expression of the ATPT proteins were analyzed by High Pressure Liquid Chromatography (HPLC) for altered levels of total tocopherols, as well as altered levels of specific tocopherols (alpha, beta, gamma, and delta tocopherol).

Extracts of leaves and seeds were prepared for HPLC as follows. For seed extracts, 10 mg of seed was added to 1 g of microbeads (Biospec) in a sterile microfuge tube to which 500 ul 1% pyrogallol (Sigma Chem)/ethanol was added. The mixture was shaken for 3 minutes in a mini Beadbeater (Biospec) on "fast" speed. The extract was filtered through a 0.2 um filter into an autosampler tube. The filtered extracts were then used in HPLC analysis described below.

Leaf extracts were prepared by mixing 30-50 mg of leaf tissue with 1 g microbeads and freezing in liquid nitrogen until extraction. For extraction, 500 ul 1% pyrogallol in ethanol was added to the leaf/bead mixture and shaken for 1 minute on a Beadbeater (Biospec) on "fast" speed. The resulting mixture was centrifuged for 4 minutes at 14,000 rpm and filtered as described above prior to HPLC analysis.

HPLC was performed on a Zorbax silica HPLC column (4.6 mm×250 mm) with a fluorescent detection, an excitation at 290 nm, an emission at 336 nm, and bandpass and slits. Solvent A was hexane and solvent B was methyl-t-butyl ether. The injection volume was 20 ul, the flow rate was 1.5 ml/min, the run time was 12 min (40° C.) using the gradient (Table 6):

TABLE 6

| Time | Solvent A | Solvent B |
|---|---|---|
| 0 min. | 90% | 10% |
| 10 min. | 90% | 10% |
| 11 min. | 25% | 75% |
| 12 min. | 90% | 10% |

Tocopherol standards in 1% pyrogallol/ethanol were also run for comparison (alpha tocopherol, gamma tocopherol, beta tocopherol, delta tocopherol, and tocopherol (tocol) (all from Matreya).

Standard curves for alpha, beta, delta, and gamma tocopherol were calculated using Chemstation software. The absolute amount of component x is: Absolute amount of x=$Response_x \times RF_x \times$dilution factor where $Response_x$ is the area of peak x, $RF_x$ is the response factor for component x ($Amount_x/Response_x$) and the dilution factor is 500 ul. The ng/mg tissue is found by: total ng component/mg plant tissue.

Figure 24:
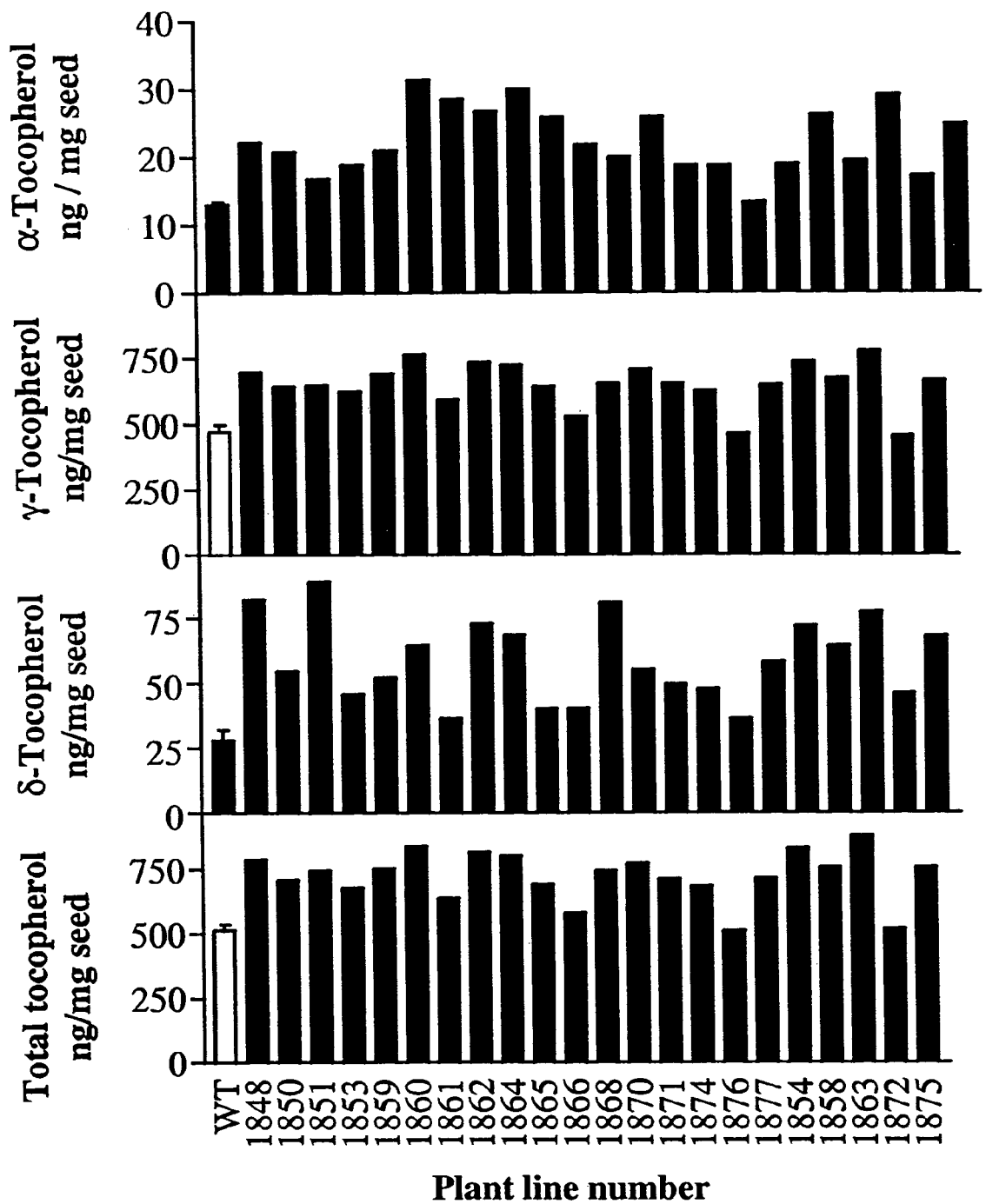
FIG. 24 provides bar graphs of HPLC data obtained from seed extracts of transgenic *Arabidopsis* containing pCGN10822, which provides of the expression of the ATPT2 sequence, in the sense orientation, from the napin promoter. Provided are graphs for alpha, gamma, and delta tocopherols, as well as total tocopherol for 22 transformed lines, as well as a nontransformed (wildtype) control.

Results of the HPLC analysis of seed extracts of transgenic Arabidopsis lines containing pMON10822 for the expression of ATPT2 from the napin promoter are provided in FIG. 24.

Figure 25:
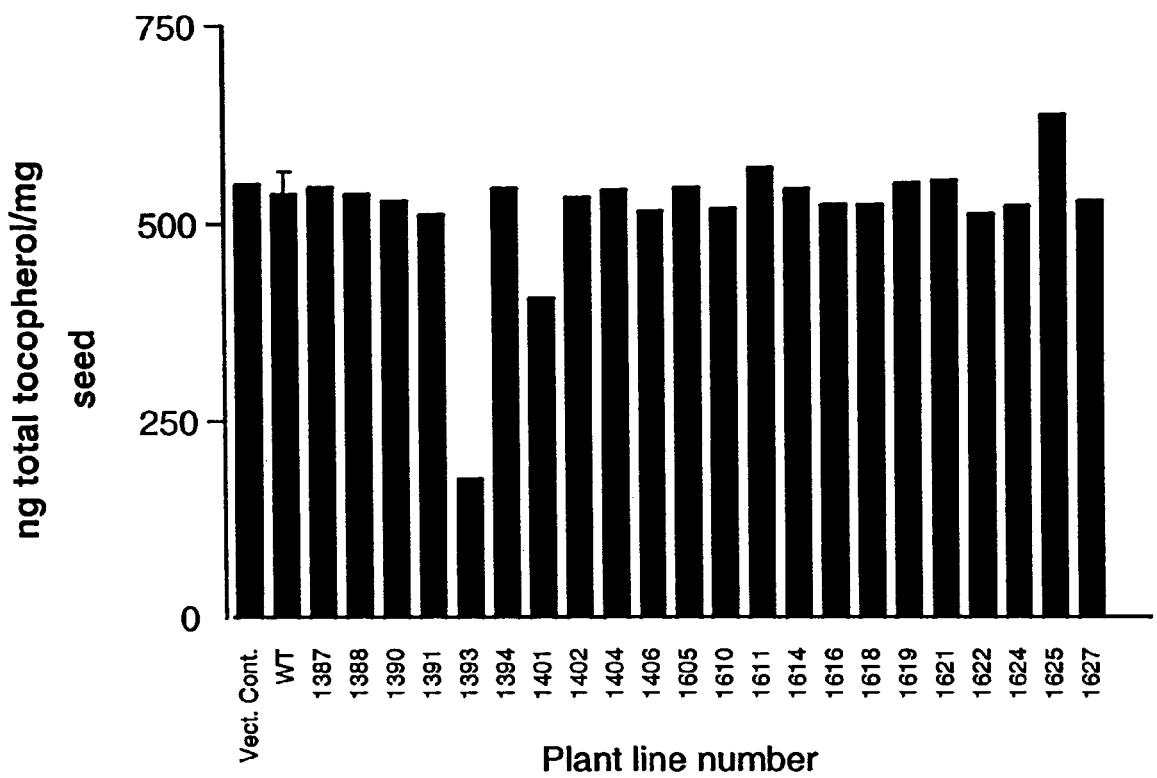
FIG. 25 provides a bar graph of HPLC analysis of seed extracts from *Arabidopsis* plants transformed with pCGN10803 (35S-ATPT2, in the antisense orientation), pCGN10822 (line 1625, napin ATPT2 in the sense orientation), pCGN10809 (line 1627, 35S-ATPT3 in the sense orientation), a nontransformed (wt) control, and an empty vector transformed control.
Figure 26:
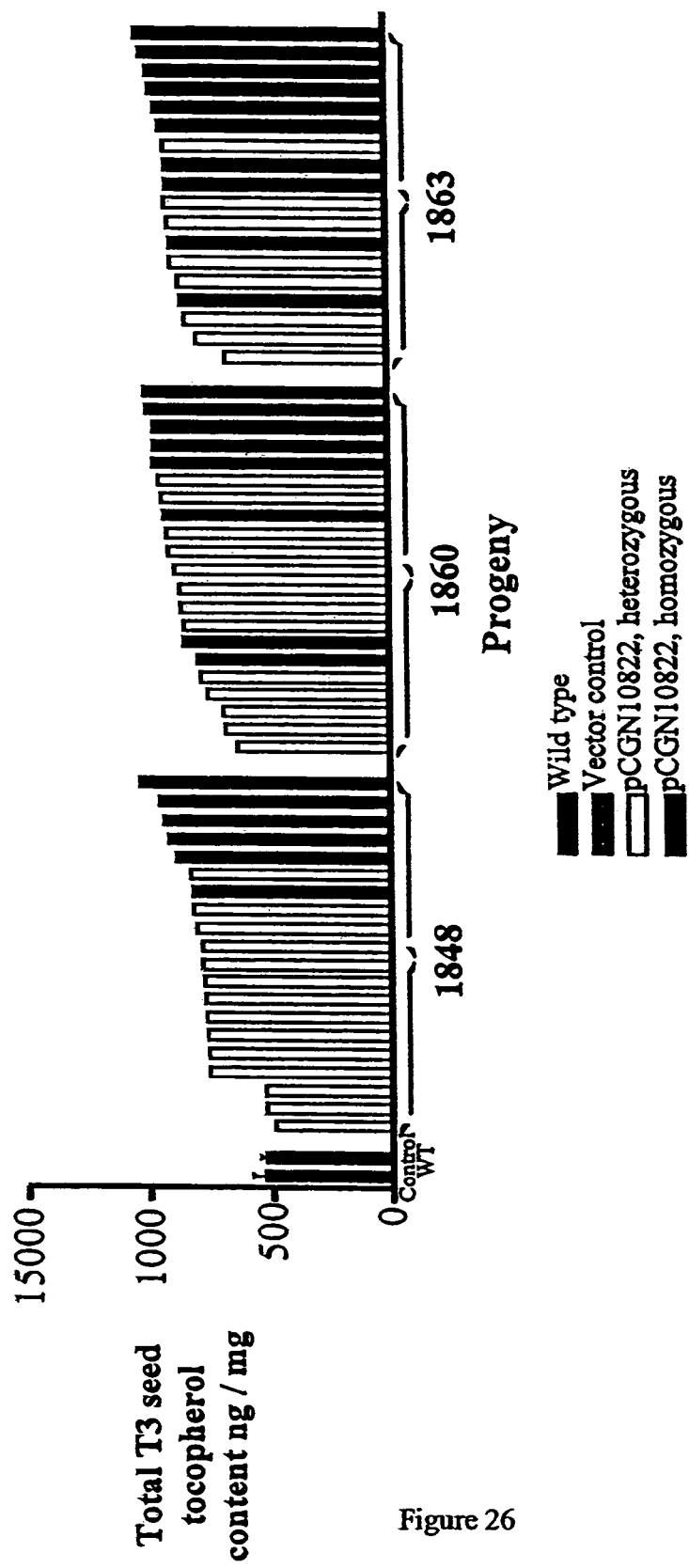
FIG. 26 shows total tocopherol levels measured in T# *Arabidopsis* seed of line.

HPLC analysis results of segregating T2 Arabidopsis seed tissue expressing the ATPT2 sequence from the napin promoter (pCGN10822) demonstrates an increased level of tocopherols in the seed. Total tocopherol levels are increased as much as 50% over the total tocopherol levels of non-transformed (wild-type) Arabidopsis plants (FIG. 25). Homozygous progeny from the top 3 lines (T3 seed) have up to a two-fold (100%) increase in total tocopherol levels over control Arabidopsis seed (FIG. 26.)

Furthermore, increases of particular tocopherols are also increased in transgenic Arabidopsis plants expressing the ATPT2 nucleic acid sequence from the napin promoter. Levels of delta tocopherol in these lines are increased greater than 3 fold over the delta tocopherol levels obtained from the seeds of wild type Arabidopsis lines. Levels of gamma tocopherol in transgenic Arabidopsis lines expressing the ATPT2 nucleic acid sequence are increased as much as about 60% over the levels obtained in the seeds of non-transgenic control lines. Furthermore, levels of alpha tocopherol are increased as much as 3 fold over those obtained from non-transgenic control lines.

Figure 27:
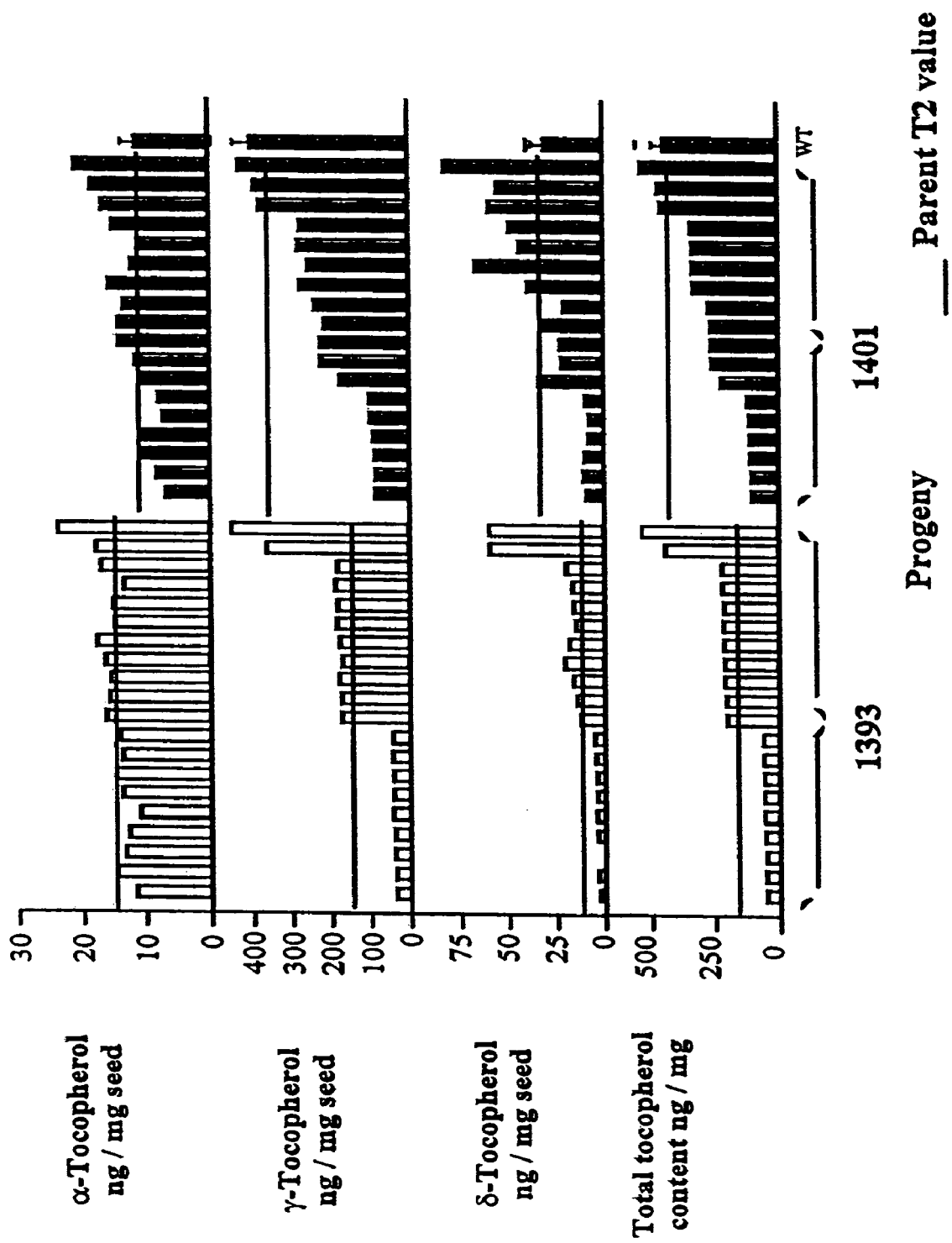
FIG. 27 shows total tocopherol levels measured in T# *Arabidopsis* seed of line.

Results of the HPLC analysis of seed extracts of transgenic Arabidopsis lines containing pCGN10803 for the expression of ATPT2 from the enhanced 35S promoter (antisense orientation) are provided in FIG. 25. Two lines were identified that have reduced total tocopherols, up to a ten-fold decrease observed in T3 seed compared to control Arabidopsis (FIG. 27.)

5B. Canola

Brassica napus, variety SP30021, was transformed with pCGN10822 (napin-ATPT2-napin 3', sense orientation) using Agrobacterium tumefaciens-mediated transformation. Flowers of the R0 plants were tagged upon pollination and developing seed was collected at 35 and 45 days after pollination (DAP).

Figure 28:
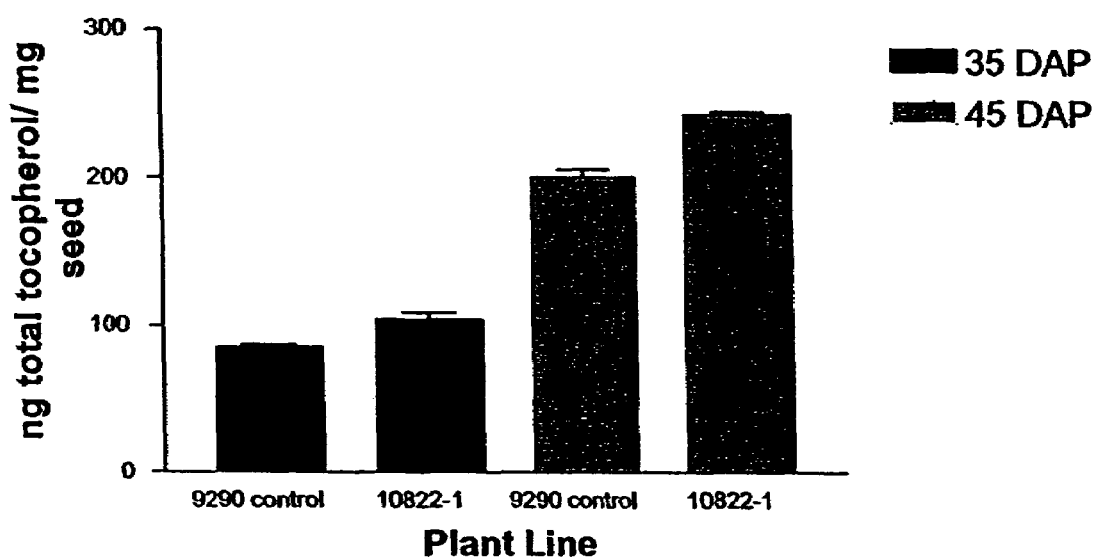
FIG. 28 shows total tocopherol levels measured in developing canola seed of line 10822-1.

Developing seed was assayed for tocopherol levels, as described above for Arabidopsis. Line 10822-1 shows a 20% increase of total tocopherols, compared to the wild-type control, at 45 DAP. FIG. 28 shows total tocopherol levels measured in developing canola seed.

Example 6

Sequences to Tocopherol Cyclase

6A. Preparation of the slr1737 Knockout

The Synechocystis sp. 6803 slr1737 knockout was constructed by the following method. The GPS™-1 Genome Priming System (New England Biolabs) was used to insert, by a Tn7 Transposase system, a Kanamycin resistance cassette into slr1737. A plasmid from a Synechocystis genomic library clone containing 652 base pairs of the targeted orf (Synechcocystis genome base pairs 1324051-1324703; the predicted orf base pairs 1323672-1324763, as annotated by Cyanobase) was used as target DNA. The reaction was performed according to the manufacturers protocol. The reaction mixture was then transformed into E. coli DH10B electrocompetent cells and plated. Colonies from this transformation were then screened for transposon insertions into the target sequence by amplifying with M13 Forward and Reverse Universal primers, yielding a product of 652 base pairs plus ~1700 base pairs, the size of the transposon kanamycin cassette, for a total fragment size of ~2300 base pairs. After this determination, it was then necessary to determine the approximate location of the insertion within the targeted orf, as 100 base pairs of orf sequence was estimated as necessary for efficient homologous recombination in *Synechocystis*. This was accomplished through amplification reactions using either of the primers to the ends of the transposon, Primer S (5' end) or N (3' end), in combination with either a M13 Forward or Reverse primer. That is, four different primer combinations were used to map each potential knockout construct: Primer S-M13 Forward, Primer S-M13 Reverse, Primer N-M13 Forward, Primer N-M13 Reverse. The construct used to transform *Synechocystis* and knockout slr1737 was determined to consist of a approximately 150 base pairs of slr1737 sequence on the 5' side of the transposon insertion and approximately 500 base pairs on the 3' side, with the transcription of the orf and kanamycin cassette in the same direction. The nucleic acid sequence of slr1737 is provided in SEQ ID NO:38 the deduced amino acid sequence is provided in SEQ ID NO:39.

Cells of *Synechocystis* 6803 were grown to a density of ~2×10$^8$ cells per ml and harvested by centrifugation. The cell pellet was re-suspended in fresh BG-11 medium at a density of 1×10$^9$ cells per ml and used immediately for transformation. 100 ul of these cells were mixed with 5 ul of mini prep DNA and incubated with light at 30 C for 4 hours. This mixture was then plated onto nylon filters resting on BG-11 agar supplemented with TES ph8 and allowed to grow for 12-18 hours. The filters were then transferred to BG-11 agar+TES+5 ug/ml kanamycin and allowed to grow until colonies appeared within 7-10 days (Packer and Glazer, 1988). Colonies were then picked into BG-11 liquid media containing 5 ug/ml kanamycin and allowed to grow for 5 days. These cells were then transferred to BG-11 media containing 10 ug/ml kanamycin and allowed to grow for 5 days and then transferred to Bg-11+kanamycin at 25 ug/ml and allowed to grow for 5 days. Cells were then harvested for PCR analysis to determine the presence of a disrupted ORF and also for HPLC analysis to determine if the disruption had any effect on tocopherol levels.

PCR analysis of the *Synechocystis* isolates, using primers to the ends of the slr1737 orf, showed complete segregation of the mutant genome, meaning no copies of the wild type genome could be detected in these strains. This suggests that function of the native gene is not essential for cell function. HPLC analysis of the strain carrying the knockout for slr1737 produced no detectable levels of tocopherol.

6B. The Relation of slr1737 and slr1736

Figure 29:
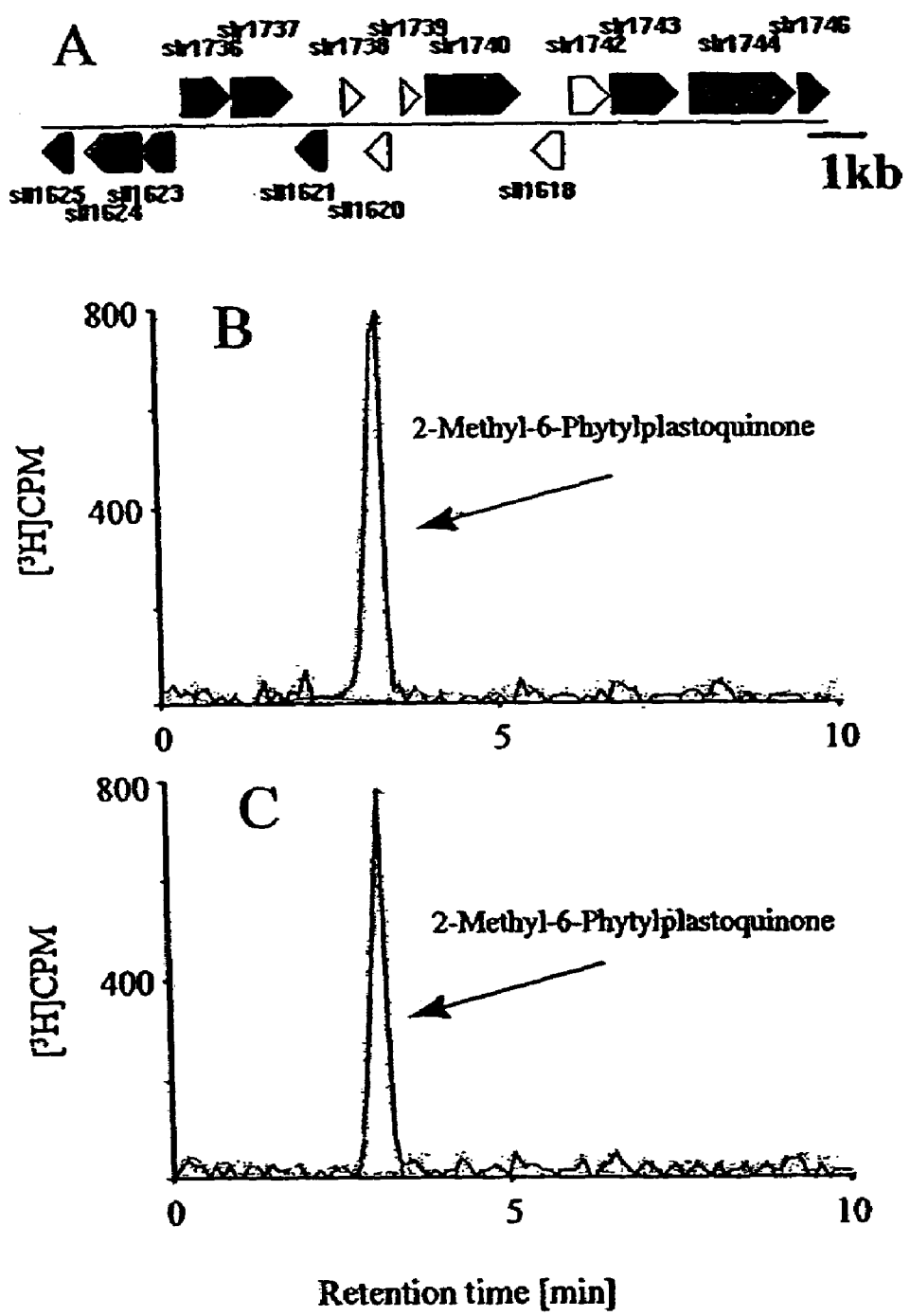
FIG. 29: shows results of phytyl prenyltransferase activity assay using *Synechocystis* wild type and slr1737 knockout mutant membrane preparations.
Figure 30A:
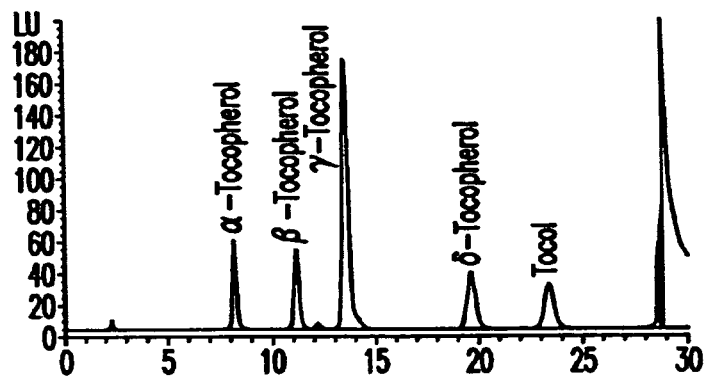
FIG. 30 is the chromatograph from an HPLC analysis of *Synechocystis* extracts.
Figure 30B:
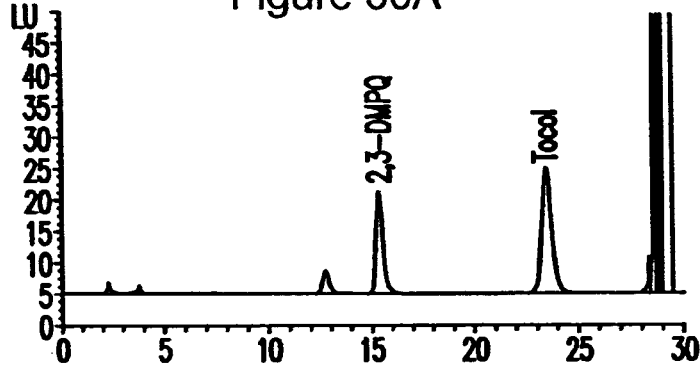
Figure 30C:
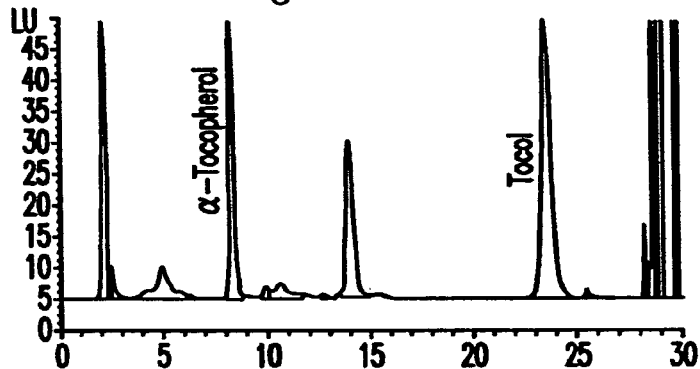
Figure 30D:
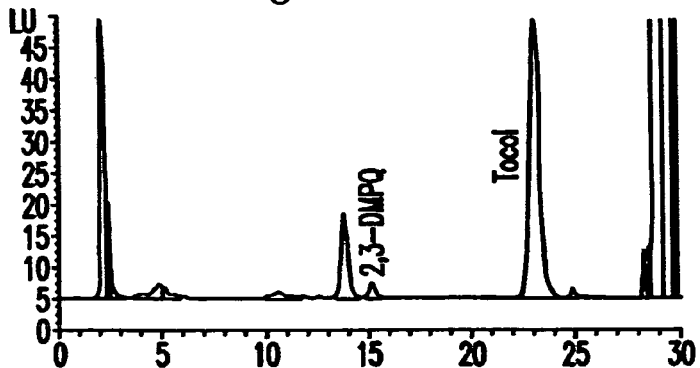

The slr1737 gene occurs in *Synechocystis* downstream and in the same orientation as slr1736, the phytyl prenyltransferase. In bacteria this proximity often indicates an operon structure and therefore an expression pattern that is linked in all genes belonging to this operon. Occasionally such operons contain several genes that are required to constitute one enzyme. To confirm that slr1737 is not required for phytyl prenyltransferase activity, phytyl prenyltransferase was measured in extracts from the *Synechocystis* slr1737 knockout mutant. FIG. 29 shows that extracts from the *Synechocystis* slr1737 knockout mutant still contain phytyl prenyltransferase activity. The molecular organization of genes in *Synechocystis* 6803 is shown in A. Figures B and C show HPLC traces (normal phase HPLC) of reaction products obtained with membrane preparations from *Synechocystis* wild type and slr1737 membrane preparations, respectively.

The fact that slr1737 is not required for the PPT activity provides additional data that ATPT2 and slr1736 encode phytyl prenyltransferases.

6C *Synechocystis* Knockouts

*Synechocystis* 6803 wild type and *Synechocystis* slr1737 knockout mutant were grown photoautotrophically. Cells from a 20 ml culture of the late logarithmic growth phase were harvested and extracted with ethanol. Extracts were separated by isocratic normal-phase HPLC using a Hexane/Methyl-t-butyl ether (95/5) and a Zorbax silica column, 4.6×250 mm. Tocopherols and tocopherol intermediates were detected by fluorescence (excitement 290 nm, emission 336 nm) (FIG. 30).

Extracts of *Synechocystis* 6803 contained a clear signal of alpha-tocopherol. 2,3-Dimethyl-5-phytylplastoquinol was below the limit of detection in extracts from the *Synechocystis* wild type (C). In contrast, extracts from the *Synechocystis* slr1737 knockout mutant did not contain alpha-tocopherol, but contained 2,3-dimethyl-5-phytylplastoquinol (D), indicating that the interruption of slr1737 has resulted in a block of the 2,3-dimethyl-5-phytylplastoquinol cyclase reaction.

Chromatograms of standard compounds alpha, beta, gamma, delta-tocopherol and 2,3-dimethyl-5-phytylplastoquinol are shown in A and B. Chromatograms of extracts form *Synechocystis* wild type and the *Synechocystis* slr1737 knockout mutant are shown in C and D, respectively. Abbreviations: 2,3-DMPQ, 2,3-dimethyl-5-phytylplastoquinol.

6D. Incubation with Lysozyme Treated *Synechocystis*

*Synechocystis* 6803 wild type and slr1737 knockout mutant cells from the late logarithmic growth phase (approximately 1 g wet cells per experiment in a total volume of 3 ml) were treated with Lysozyme and subsequently incubated with S-adenosylmethionine, and phytylpyrophosphate, plus radiolabelled homogentisic acid. After 17 h incubation in the dark at room temperature the samples were extracted with 6 ml chloroform/methanol (1/2 v/v). Phase separation was obtained by the addition of 6 ml 0.9% NaCl solution. This procedure was repeated three times. Under these conditions 2,3-dimethyl-5-phytylplastoquinol is oxidized to form 2,3-dimethyl-5-phytylplastoquinone.

The extracts were analyzed by normal phase and reverse phase HPLC. Using extracts from wild type *Synechocystis* cells radiolabelled gamma-tocopherol and traces of radiolabelled 2,3-dimethyl-5-phytylplastoquinone were detected. When extracts from the slr1737 knockout mutant were analyzed, only radiolabelled 2,3-dimethyl-5-phytylplastoquinone was detectable. The amount of 2,3-dimethyl-5-phytylplastoquinone was significantly increased compared to wild type extracts. Heat treated samples of the wild type and the slr1737 knockout mutant did not produce radiolabelled 2,3-dimethyl-5-phytylplastoquinone, nor radiolabelled tocopherols. These results further support the role of the slr1737 expression product in the cyclization of 2,3-dimethyl-5-phytylplastoquinol.

6E. *Arabidopsis* Homologue to slr1737

An *Arabidopsis* homologue to slr1737 was identified from a BLASTALL search using *Synechocystis* sp 6803 gene slr1737 as the query, in both public and proprietary databases. SEQ ID NO:109 and SEQ ID NO:110 are the DNA and translated amino acid sequences, respectively, of the *Arabidopsis* homologue to slr1737. The start if found at the ATG at base 56 in SEQ ID NO:109.

The sequences obtained for the homologue from the proprietary database differs from the public database (F4D11.30, BAC AL022537), in having a start site 471 base pairs upstream of the start identified in the public sequence. A comparison of the public and proprietary sequences is provided in FIG. 31. The correct start correlates within the public database sequence is at 12080, while the public sequence start is given as being at 11609.

Attempts to amplify a slr1737 homologue were unsuccessful using primers designed from the public database, while amplification of the gene was accomplished with primers obtained from SEQ ID NO:109.

Analysis of the protein sequence to identify transit peptide sequence predicted two potential cleavage sites, one between amino acids 48 and 49, and the other between amino acids 98 and 99.

6F. slr1737 Protein Information

Figure 32:
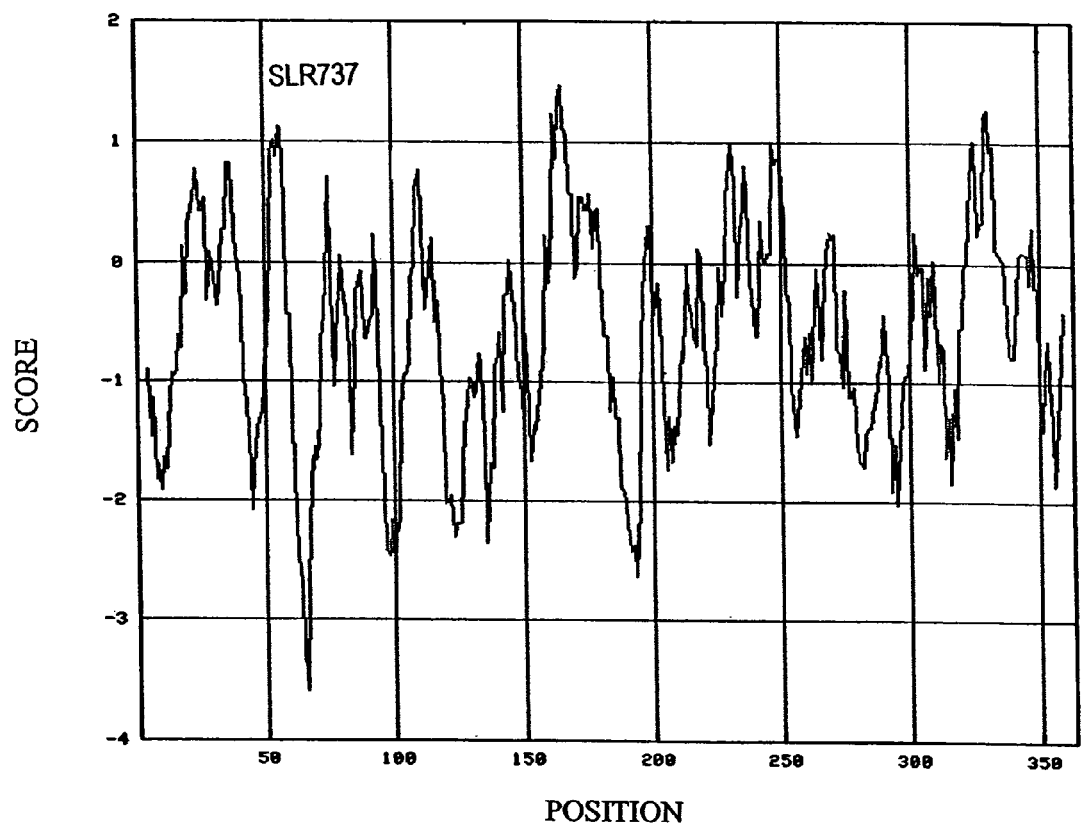
FIG. 32 shows the results of hydropathic analysis of slr1737

The slr1737 orf comprises 363 amino acid residues and has a predicted MW of 41 kDa (SEQ ID NO: 39). Hydropathic analysis indicates the protein is hydrophillic (FIG. 32).

Figure 33:
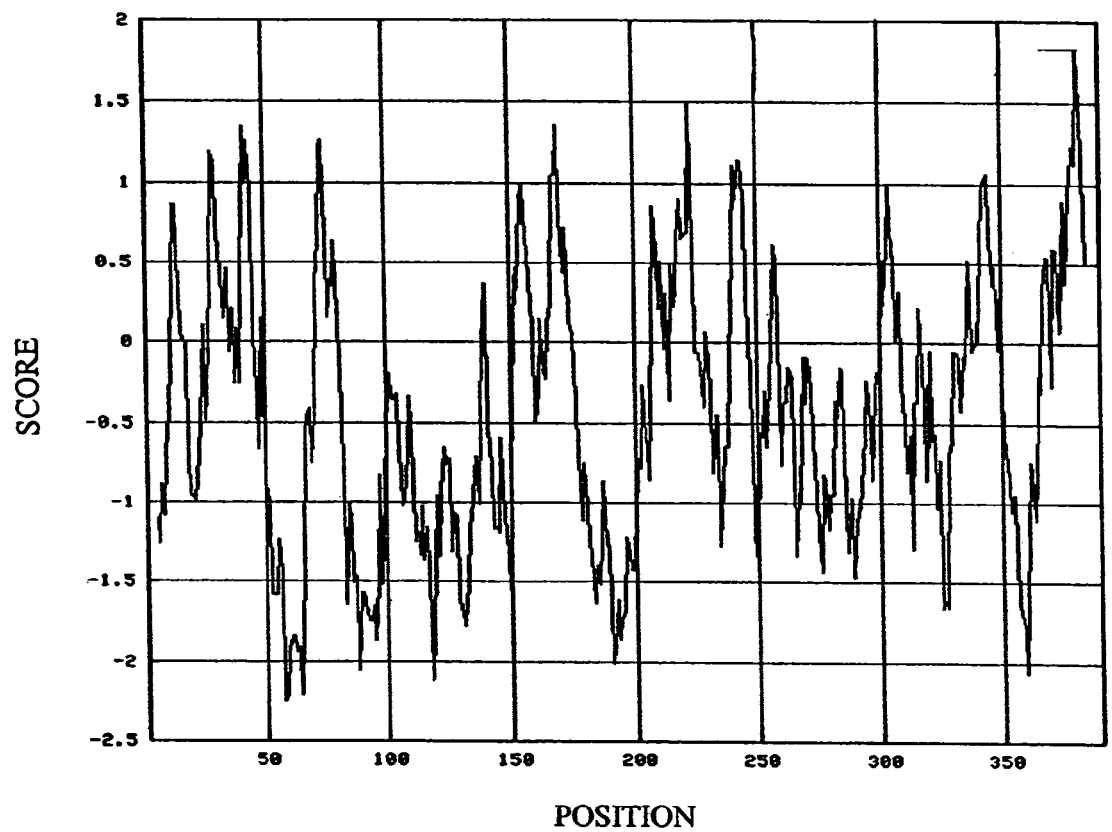
FIG. 33 shows the results of hydropathic analysis of the *Arabidopsis* homologue of slr1737.

The *Arabidopsis* homologue to slr1737 (SEQ ID NO:110) comprises 488 amino acid residues, has a predicted MW of 55 kDa, and a has a putative transit peptide sequence comprising the first 98 amino acids. The predicted MW of the mature form of the *Arabidopsis* homologue is 44 kDa. The hydropathic plot for the *Arabidopsis* homologue also reveals that it is hydrophillic (FIG. 33). Further blast analysis of the *Arabidopsis* homologue reveals limited sequence identity (25% sequence identity) with the beta-subunit of respiratory nitrate reductase. Based on the sequence identity to nitrate reductase, it suggests the slr1737 orf is an enzyme that likely involves general acid catalysis mechanism.

Figure 34:
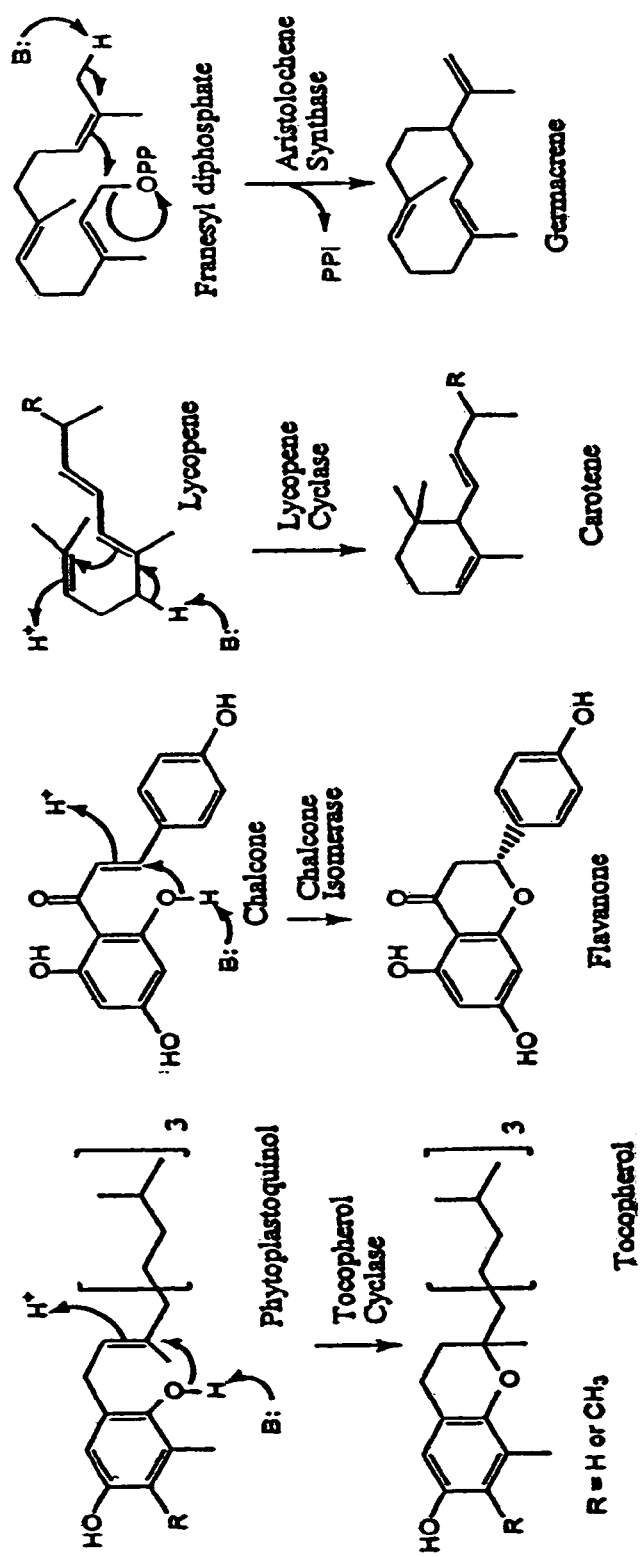
FIG. 34 shows the catalytic mechanism of various cyclase enzymes

Investigation of known enzymes involved in tocopherol metabolism indicated that the best candidate corresponding to the general acid mechanism is the tocopherol cyclase. There are many known examples of cyclases including, tocopherol cyclase, chalcone isomerase, lycopene cyclase, and aristolochene synthase. By further examination of the microscopic catalytic mechanism of phytoplastoquinol cyclization, as an example, chalcone isomerase has a catalytic mechanism most similar to tocopherol cyclase. (FIG. 34).

Multiple sequence alignment was performed between slr1737, slr1737 *Arabidopsis* homologue and the *Arabidopsis* chalcone isomerase (Genbank:P41088) (FIG. 35). 65% of the conserved residues among the three enzymes are strictly conserved within the known chalcone isomerases. The crystal structure of alfalfa chalcone isomerase has been solved (Jez, Joseph M., Bowman, Marianne E., Dixon, Richard A., and Noel, Joseph P. (2000) "Structure and mechanism of the evolutionarily unique plant enzyme chalcone isomerase". *Nature Structural Biology* 7: 786-791.) It has been demonstrated tyrosine (Y) 106 of the alfalfa chalcone isomerase serves as the general acid during cyclization reaction (Genbank: P28012). The equivalent residue in slr1737 and the slr1737 *Arabidopsis* homolog is lysine (K), which is an excellent catalytic residue as general acid.

The information available from partial purification of tocopherol cyclase from *Chlorella protothecoides* (U.S. Pat. No. 5,432,069), i.e., described as being glycine rich, water soluble and with a predicted MW of 48-50 kDa, is consistent with the protein informatics information obtained for the slr1737 and the *Arabidopsis* slr1737 homologue.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated nucleic acid comprising a nucleic acid sequence that encodes tocopherol cyclase and is selected from the group consisting of
   (a) a nucleic acid sequence comprising SEQ ID NO:109;
   (b) a nucleic acid sequence encoding a tocopherol cyclase protein comprising an amino acid sequence of SEQ ID NO:110; and
   (c) a nucleic acid sequence encoding a tocopherol cyclase protein comprising an amino acid sequence with at least 90% sequence identity to SEQ ID NO:110.

2. An isolated nucleic acid sequence according to claim 1, wherein said tocopherol cyclase is active in the cyclization of 2,3-dimethyl-5-phytylplastoquinol to tocopherol.

3. An isolated nucleic acid sequence according to claim 1, wherein said tocopherol cyclase is active in the cyclization of 2,3-dimethyl-5-geranylgeranylplastoquinol to tocotrienol.

4. An isolated DNA sequence according to claim 1, wherein said nucleic acid sequence is isolated from a eukaryotic cell source.

5. An isolated DNA sequence according to claim 4, wherein said eukaryotic cell source is selected from the group consisting of mammalian, nematode, fungal, and plant cells.

6. The isolated DNA sequence of claim 5 wherein said tocopherol cyclase protein is from *Arabidopsis*.

7. The isolated DNA sequence of claim 1, comprising the sequence of SEQ ID NO:109.

8. The isolated DNA sequence of claim 1 wherein said tocopherol cyclase protein comprises the amino acid sequence of SEQ ID NO:110.

9. The isolated DNA sequence of claim 4 wherein said tocopherol cyclase protein is from a source selected from the group consisting of *Arabidopsis*, soybean, corn, rice, wheat, leek canola, leek, cotton, and tomato.

10. A nucleic acid construct comprising as operably linked components, a transcriptional initiation region functional in a host cell, the isolated nucleic acid sequence of claim 1, and a transcriptional termination region.

11. A nucleic acid construct according to claim 10, wherein said nucleic acid sequence encoding tocopherol cyclase is obtained from an organism selected from the group consisting of a eukaryotic organism and a prokaryotic organism.

12. A nucleic acid construct according to claim 11, wherein said nucleic acid sequence encoding tocopherol cyclase is obtained from a plant source.

13. A nucleic acid construct according to claim 12, wherein said nucleic acid sequence encoding tocopherol cyclase is obtained from a source selected from the group consisting of *Arabidopsis*, soybean, corn, rice, wheat, leek canola, leek, cotton, and tomato.

14. A plant cell comprising the construct of 10.

15. A plant comprising a cell of claim 14.

16. A feed composition produced from a plant according to claim 15.

17. A seed comprising a cell of claim 14.

18. A method for the alteration of the isoprenoid content in a host cell, said method comprising; transforming said host cell with a construct comprising as operably linked components, a transcriptional initiation region functional in a host cell, the isolated nucleic acid sequence of claim 1, and a transcriptional termination region, wherein said isoprenoid compound is selected from the group consisting of tocopherols and tocotrienols.

19. The method according to claim 18, wherein said host cell is selected from the group consisting of a prokaryotic cell and a eukaryotic cell.

20. The method according to claim 19, wherein said prokaryotic cell is a *Synechocystis* sp.

21. The method according to claim 19, wherein said eukaryotic cell is a plant cell.

22. The method according to claim 21, wherein said plant cell is obtained from a plant selected from the group consisting of *Arabidopsis*, soybean, corn, rice, wheat, leek canola, leek, cotton, and tomato.

23. A method for producing an isoprenoid compound of interest in a host cell, said method comprising obtaining a transformed host cell, said host cell having and expressing in its genome: a construct having a DNA sequence according to claim 1 operably linked to a transcriptional initiation region functional in a host cell, wherein said isoprenoid compound is selected from the group consisting of tocopherols and tocotrienols.

24. The method according to claim 23, wherein said host cell is selected from the group consisting of a prokaryotic cell and a eukaryotic cell.

25. The method according to claim 24, wherein said prokaryotic cell is a *Synechocystis* sp.

26. The method according to claim 24, wherein said eukaryotic cell is a plant cell.

27. The method according to claim 26, wherein said plant cell is obtained from a plant selected from the group consisting wherein said compound selected from the group of *Arabidopsis*, soybean, corn, rice, wheat, leek canola, leek, cotton, and tomato.

28. A method for increasing the biosynthetic flux in a host cell toward production of an isoprenoid compound, said method comprising; transforming said host cell with a construct comprising as operably linked components, a transcriptional initiation region functional in a host cell, the nucleic acid sequence of claim 1, and a transcriptional termination region, wherein said isoprenoid compound is selected from the group consisting of tocopherols and tocotrienols.

29. The method according to claim 28, wherein said host cell is selected from the group consisting of a prokaryotic cell and a eukaryotic cell.

30. The method according to claim 29, wherein said prokaryotic cell is a *Synechocystis* sp.

31. The method according to claim 29, wherein said eukaryotic cell is a plant cell.

32. The method according to claim 31, wherein said plant cell is obtained from a plant selected from the group consisting *Arabidopsis*, soybean, corn, rice, wheat, leek canola, leek, cotton, and tomato.

33. The method according to claim 31, wherein said transcriptional initiation region is a seed-specific promoter.

34. The isolated nucleic acid of claim 1, wherein said nucleic acid sequence is a nucleic acid sequence encoding a tocopherol cyclase protein comprising an amino acid sequence with at least 90% sequence identity to SEQ ID NO: 110.

35. The nucleic acid construct of claim 10, wherein the isolated nucleic acid sequence comprises a nucleic acid sequence comprising SEQ ID NO: 109.

36. The nucleic acid construct of claim 10, wherein the isolated nucleic acid sequence comprises a nucleic acid sequence encoding a tocopherol cyclase protein comprising an amino acid sequence of SEQ ID NO: 110.

37. The nucleic acid construct of claim 10, wherein the isolated nucleic acid sequence comprises a nucleic acid sequence encoding a tocopherol cyclase protein comprising an amino acid sequence with at least 90% sequence identity to SEQ ID NO:1 10.

38. The plant cell of claim 14, wherein the isolated nucleic acid sequence comprises a nucleic acid sequence comprising SEQ ID NO:109.

39. The plant cell of claim 14, wherein the isolated nucleic acid sequence comprises a nucleic acid sequence encoding a tocopherol cyclase protein comprising an amino acid sequence of SEQ ID NO: 110.

40. The plant cell of claim 14, wherein the isolated nucleic acid sequence comprises a nucleic acid sequence encoding a tocopherol cyclase protein comprising an amino acid sequence with at least 90% sequence identity to SEQ ID NO:1 10.

41. The plant of claim 15, wherein the isolated nucleic acid sequence comprises a nucleic acid sequence comprising SEQ ID NO:109.

42. The plant of claim 15, wherein the isolated nucleic acid sequence comprises a nucleic acid sequence encoding a tocopherol cyclase protein comprising an amino acid sequence of SEQ ID NO: 110.

43. The plant of claim 15, wherein the isolated nucleic acid sequence comprises a nucleic acid sequence encoding a tocopherol cyclase protein comprising an amino acid sequence with at least 90% sequence identity to SEQ ID NO: 110.

44. The seed of claim 17, wherein the isolated nucleic acid sequence comprises a nucleic acid sequence comprising SEQ ID NO:109.

45. The seed of claim 17, wherein the isolated nucleic acid sequence comprises a nucleic acid sequence encoding a tocopherol cyclase protein comprising an amino acid sequence of SEQ ID NO:110.

46. The seed of claim 17, wherein the isolated nucleic acid sequence comprises a nucleic acid sequence encoding a tocopherol cyclase protein comprising an amino acid sequence with at least 90% sequence identity to SEQ ID NO: 110.

47. The method of claim 18, wherein the isolated nucleic acid sequence comprises a nucleic acid sequence comprising SEQ ID NO:109.

48. The method of claim 18, wherein the isolated nucleic acid sequence comprises a nucleic acid sequence encoding a tocopherol cyclase protein comprising an amino acid sequence of SEQ ID NO:110.

49. The method of claim 18, wherein the isolated nucleic acid sequence comprises a nucleic acid sequence encoding a tocopherol cyclase protein comprising an amino acid sequence with at least 90% sequence identity to SEQ ID NO: 110.

50. The method of claim 23, wherein the DNA sequence comprises a nucleic acid sequence comprising SEQ ID NO: 109.

51. The method of claim 23, wherein the DNA sequence comprises a nucleic acid sequence encoding a tocopherol cyclase protein comprising an amino acid sequence of SEQ ID NO:110.

52. The method of claim 23, wherein the DNA sequence comprises a nucleic acid sequence encoding a tocopherol cyclase protein comprising an amino acid sequence with at least 90% sequence identity to SEQ ID NO:110.

\* \* \* \* \*

UNITED STATES PATENT AND TRADEMARK OFFICE
CERTIFICATE OF CORRECTION

PATENT NO. : 7,420,101 B2
APPLICATION NO. : 11/092140
DATED : September 2, 2008
INVENTOR(S) : Subramaniam et al.

It is certified that error appears in the above-identified patent and that said Letters Patent is hereby corrected as shown below:

Title page In the first inventor's name, line 75, delete "Sai S. Subramaniam", and insert --S. Sai Subramaniam--.

In claim 37, column 138, line 67, delete "NO:1 10", and insert --NO:110--.

Signed and Sealed this

Twenty-eighth Day of October, 2008

JON W. DUDAS
*Director of the United States Patent and Trademark Office*

SEQUENCE LISTING

<160> NUMBER OF SEQ ID NOS: 114

<210> SEQ ID NO 1
<211> LENGTH: 1182
<212> TYPE: DNA
<213> ORGANISM: Arabidopsis sp.

<400> SEQUENCE: 1

| | | | | | |
|---|---|---|---|---|---|
| atggagtctc | tgctctctag | ttcttctctt | gtttccgctg | ctggtgggtt | ttgttggaag | 60 |
| aagcagaatc | taaagctcca | ctctttatca | gaaatccgag | ttctgcgttg | tgattcgagt | 120 |
| aaagttgtcg | caaaaccgaa | gtttaggaac | aatcttgtta | ggcctgatgg | tcaaggatct | 180 |
| tcattgttgt | tgtatccaaa | acataagtcg | agatttcggg | ttaatgccac | tgcgggtcag | 240 |
| cctgaggctt | tcgactcgaa | tagcaaacag | aagtctttta | gagactcgtt | agatgcgttt | 300 |
| tacaggtttt | ctaggcctca | tacagttatt | ggcacagtgc | ttagcatttt | atctgtatct | 360 |
| ttcttagcag | tagagaaggt | ttctgatata | tctcctttac | ttttcactgg | catcttggag | 420 |
| gctgttgttg | cagctctcat | gatgaacatt | tacatagttg | ggctaaatca | gttgtctgat | 480 |
| gttgaaatag | ataaggttaa | caagccctat | cttccattgg | catcaggaga | atattctgtt | 540 |
| aacaccggca | ttgcaatagt | agcttccttc | tccatcatga | gtttctggct | tgggtggatt | 600 |

```
gttggttcat ggccattgtt ctgggctctt tttgtgagtt tcatgctcgg tactgcatac    660
tctatcaatt tgccactttt acggtggaaa agatttgcat tggttgcagc aatgtgtatc    720
ctcgctgtcc gagctattat tgttcaaatc gcctttatc tacatattca gacacatgtg    780
tttggaagac caatcttgtt cactaggcct cttatttcg ccactgcgtt tatgagcttt    840
ttctctgtcg ttattgcatt gtttaaggat atacctgata tcgaagggga taagatattc    900
ggaatccgat cattctctgt aactctgggt cagaaacggg tgttttggac atgtgttaca    960
ctacttcaaa tggcttacgc tgttgcaatt ctagttggag ccacatctcc attcatatgg   1020
agcaaagtca tctcggttgt gggtcatgtt atactcgcaa caactttgtg ggctcgagct   1080
aagtccgttg atctgagtag caaaaccgaa ataacttcat gttatatgtt catatggaag   1140
ctcttttatg cagagtactt gctgttacct tttttgaagt ga                      1182

<210> SEQ ID NO 2
<211> LENGTH: 393
<212> TYPE: PRT
<213> ORGANISM: Arabidopsis sp.

<400> SEQUENCE: 2

Met Glu Ser Leu Leu Ser Ser Ser Leu Val Ser Ala Ala Gly Gly
  1               5                  10                  15

Phe Cys Trp Lys Lys Gln Asn Leu Lys Leu His Ser Leu Ser Glu Ile
                 20                  25                  30

Arg Val Leu Arg Cys Asp Ser Ser Lys Val Val Ala Lys Pro Lys Phe
             35                  40                  45

Arg Asn Asn Leu Val Arg Pro Asp Gly Gln Gly Ser Ser Leu Leu Leu
         50                  55                  60

Tyr Pro Lys His Lys Ser Arg Phe Arg Val Asn Ala Thr Ala Gly Gln
 65                  70                  75                  80

Pro Glu Ala Phe Asp Ser Asn Ser Lys Gln Lys Ser Phe Arg Asp Ser
                 85                  90                  95

Leu Asp Ala Phe Tyr Arg Phe Ser Arg Pro His Thr Val Ile Gly Thr
            100                 105                 110

Val Leu Ser Ile Leu Ser Val Ser Phe Leu Ala Val Glu Lys Val Ser
        115                 120                 125

Asp Ile Ser Pro Leu Leu Phe Thr Gly Ile Leu Glu Ala Val Val Ala
    130                 135                 140

Ala Leu Met Met Asn Ile Tyr Ile Val Gly Leu Asn Gln Leu Ser Asp
145                 150                 155                 160

Val Glu Ile Asp Lys Val Asn Lys Pro Tyr Leu Pro Leu Ala Ser Gly
                165                 170                 175

Glu Tyr Ser Val Asn Thr Gly Ile Ala Ile Val Ala Ser Phe Ser Ile
            180                 185                 190

Met Ser Phe Trp Leu Gly Trp Ile Val Gly Ser Trp Pro Leu Phe Trp
        195                 200                 205

Ala Leu Phe Val Ser Phe Met Leu Gly Thr Ala Tyr Ser Ile Asn Leu
    210                 215                 220

Pro Leu Leu Arg Trp Lys Arg Phe Ala Leu Val Ala Ala Met Cys Ile
225                 230                 235                 240

Leu Ala Val Arg Ala Ile Ile Val Gln Ile Ala Phe Tyr Leu His Ile
                245                 250                 255

Gln Thr His Val Phe Gly Arg Pro Ile Leu Phe Thr Arg Pro Leu Ile
            260                 265                 270
```

```
Phe Ala Thr Ala Phe Met Ser Phe Phe Ser Val Val Ile Ala Leu Phe
        275                 280                 285
Lys Asp Ile Pro Asp Ile Glu Gly Asp Lys Ile Phe Gly Ile Arg Ser
        290                 295                 300
Phe Ser Val Thr Leu Gly Gln Lys Arg Val Phe Trp Thr Cys Val Thr
305                 310                 315                 320
Leu Leu Gln Met Ala Tyr Ala Val Ala Ile Leu Val Gly Ala Thr Ser
                325                 330                 335
Pro Phe Ile Trp Ser Lys Val Ile Ser Val Val Gly His Val Ile Leu
            340                 345                 350
Ala Thr Thr Leu Trp Ala Arg Ala Lys Ser Val Asp Leu Ser Ser Lys
        355                 360                 365
Thr Glu Ile Thr Ser Cys Tyr Met Phe Ile Trp Lys Leu Phe Tyr Ala
        370                 375                 380
Glu Tyr Leu Leu Leu Pro Phe Leu Lys
385                 390

<210> SEQ ID NO 3
<211> LENGTH: 1224
<212> TYPE: DNA
<213> ORGANISM: Arabidopsis sp.

<400> SEQUENCE: 3
atggcgtttt ttgggctctc ccgtgtttca agacggttgt tgaaatcttc cgtctccgta      60
actccatctt cttcctctgc tcttttgcaa tcacaacata aatccttgtc caatcctgtg     120
actacccatt acacaaatcc tttcactaag tgttatcctt catggaatga taattaccaa     180
gtatggagta aggaagagaa attgcatcag gagaagtttt tggtgttggg ttggaattac     240
agattaattt gtggaatgtc gtcgtcttct tcggttttgg agggaaagcc gaagaaagat     300
gataaggaga gagtgatggt gttgttgttg aagaaagctt cttggataga tttgtatttta     360
ccagaagaag ttagaggtta tgctaagctt gctcgattgg ataaacccat ggaacttgg     420
ttgcttgcgt ggccttgtat gtggtcgatt gcgttggctg ctgatcctgg aagccttcca     480
agttttaaat atatggcttt atttggttgc ggagcattac ttcttagagg tgctggttgt     540
actataaatg atctgcttga tcaggacata gatacaaagg ttgatcgtac aaaactaaga     600
cctatcgcca gtggtctttt gacaccattt caagggattg gatttctcgg gctgcagttg     660
cttttaggct tagggattct tctccaactt aacaattaca gccgtgtttt aggggcttca     720
tctttgttac ttgtcttttc ctaccacctt atgaagaggt ttacattttg gcctcaagcc     780
ttttlaggtt tgaccataaa ctggggagca ttgttaggat ggactgcagt taaaggaagc     840
atagcaccat ctattgtact ccctctctat ctctccggag tctgctggac ccttgtttat     900
gatactattt atgcacatca ggacaaagaa gatgatgtaa agttggtgt taagtcaaca     960
gcccttagat tcggtgataa tacaaagctt tggttaactg gatttggcac agcatccata    1020
ggttttcttg cactttctgg attcagtgca gatctcgggt ggcaatatta cgcatcactg    1080
gccgctgcat caggacagtt aggatggcaa ataggggacg ctgacttatc atctggtgct    1140
gactgcagta gaaaatttgt gtcgaacaag tggtttggtg ctattatatt tagtggagtt    1200
gtacttggaa gagttttca ataa                                             1224

<210> SEQ ID NO 4
<211> LENGTH: 407
<212> TYPE: PRT
<213> ORGANISM: Arabidopsis sp.
```

<400> SEQUENCE: 4

```
Met Ala Phe Phe Gly Leu Ser Arg Val Ser Arg Arg Leu Leu Lys Ser
1               5                   10                  15
Ser Val Ser Val Thr Pro Ser Ser Ser Ala Leu Leu Gln Ser Gln
            20                  25                  30
His Lys Ser Leu Ser Asn Pro Val Thr Thr His Tyr Thr Asn Pro Phe
            35                  40                  45
Thr Lys Cys Tyr Pro Ser Trp Asn Asp Asn Tyr Gln Val Trp Ser Lys
        50                  55                  60
Gly Arg Glu Leu His Gln Glu Lys Phe Phe Gly Val Gly Trp Asn Tyr
65                  70                  75                  80
Arg Leu Ile Cys Gly Met Ser Ser Ser Ser Val Leu Glu Gly Lys
                    85                  90                  95
Pro Lys Lys Asp Asp Lys Glu Lys Ser Asp Gly Val Val Lys Lys
                100                 105                 110
Ala Ser Trp Ile Asp Leu Tyr Leu Pro Glu Glu Val Arg Gly Tyr Ala
            115                 120                 125
Lys Leu Ala Arg Leu Asp Lys Pro Ile Gly Thr Trp Leu Leu Ala Trp
130                 135                 140
Pro Cys Met Trp Ser Ile Ala Leu Ala Ala Asp Pro Gly Ser Leu Pro
145                 150                 155                 160
Ser Phe Lys Tyr Met Ala Leu Phe Gly Cys Gly Ala Leu Leu Arg
                    165                 170                 175
Gly Ala Gly Cys Thr Ile Asn Asp Leu Leu Asp Gln Asp Ile Asp Thr
                180                 185                 190
Lys Val Asp Arg Thr Lys Leu Arg Pro Ile Ala Ser Gly Leu Leu Thr
            195                 200                 205
Pro Phe Gln Gly Ile Gly Phe Leu Gly Leu Gln Leu Leu Gly Leu
            210                 215                 220
Gly Ile Leu Leu Gln Leu Asn Asn Tyr Ser Arg Val Leu Gly Ala Ser
225                 230                 235                 240
Ser Leu Leu Leu Val Phe Ser Tyr Pro Leu Met Lys Arg Phe Thr Phe
                    245                 250                 255
Trp Pro Gln Ala Phe Leu Gly Leu Thr Ile Asn Trp Gly Ala Leu Leu
            260                 265                 270
Gly Trp Thr Ala Val Lys Gly Ser Ile Ala Pro Ser Ile Val Leu Pro
        275                 280                 285
Leu Tyr Leu Ser Gly Val Cys Trp Thr Leu Val Tyr Asp Thr Ile Tyr
        290                 295                 300
Ala His Gln Asp Lys Glu Asp Val Lys Val Gly Val Lys Ser Thr
305                 310                 315                 320
Ala Leu Arg Phe Gly Asp Asn Thr Lys Leu Trp Leu Thr Gly Phe Gly
                325                 330                 335
Thr Ala Ser Ile Gly Phe Leu Ala Leu Ser Gly Phe Ser Ala Asp Leu
            340                 345                 350
Gly Trp Gln Tyr Tyr Ala Ser Leu Ala Ala Ala Ser Gly Gln Leu Gly
        355                 360                 365
Trp Gln Ile Gly Thr Ala Asp Leu Ser Ser Gly Ala Asp Cys Ser Arg
    370                 375                 380
Lys Phe Val Ser Asn Lys Trp Phe Gly Ala Ile Ile Phe Ser Gly Val
385                 390                 395                 400
Val Leu Gly Arg Ser Phe Gln
```

<210> SEQ ID NO 5
<211> LENGTH: 1296
<212> TYPE: DNA
<213> ORGANISM: Arabidopsis sp.

<400> SEQUENCE: 5

| | | | | | |
|---|---|---|---|---|---|
| atgtggcgaa | gatctgttgt | ttctcgttta | tcttcaagaa | tctctgtttc | ttcttcgtta | 60 |
| ccaaacccta | gactgattcc | ttggtcccgc | gaattatgtg | ccgttaatag | cttctcccag | 120 |
| cctccggtct | cgacggaatc | aactgctaag | ttagggatca | ctggtgttag | atctgatgcc | 180 |
| aatcgagttt | ttgccactgc | tactgccgcc | gctacagcta | cagctaccac | cggtgagatt | 240 |
| tcgtctagag | ttgcggcttt | ggctggatta | gggcatcact | acgctcgttg | ttattgggag | 300 |
| ctttctaaag | ctaaacttag | tatgcttgtg | gttgcaactt | ctggaactgg | gtatattctg | 360 |
| ggtacgggaa | atgctgcaat | tagcttcccg | gggctttgtt | acacatgtgc | aggaaccatg | 420 |
| atgattgctg | catctgctaa | ttccttgaat | cagattttg | agataagcaa | tgattctaag | 480 |
| atgaaaagaa | cgatgctaag | gccattgcct | caggacgta | ttagtgttcc | acacgctgtt | 540 |
| gcatgggcta | ctattgctgg | tgcttctggt | gcttgtttgt | tggccagcaa | gactaatatg | 600 |
| ttggctgctg | gacttgcatc | tgccaatctt | gtactttatg | cgtttgttta | tactccgttg | 660 |
| aagcaacttc | accctatcaa | tacatggggtt | ggcgctgttg | ttggtgctat | cccaccctttg | 720 |
| cttgggtggg | cggcagcgtc | tggtcagatt | tcatacaatt | cgatgattct | tccagctgct | 780 |
| ctttactttt | ggcagatacc | tcattttatg | gcccttgcac | atctctgccg | caatgattat | 840 |
| gcagctggag | gttacaagat | gttgtcactc | tttgatccgt | cagggaagag | aatagcagca | 900 |
| gtggctctaa | ggaactgctt | ttacatgatc | cctctcggtt | tcatcgccta | tgactggggg | 960 |
| ttaacctcaa | gttggttttg | cctcgaatca | acacttctca | cactagcaat | cgctgcaaca | 1020 |
| gcattttcat | tctaccgaga | ccggaccatg | cataaagcaa | ggaaaatgtt | ccatgccagt | 1080 |
| cttctcttcc | ttcctgtttt | catgtctggt | cttcttctac | accgtgtctc | taatgataat | 1140 |
| cagcaacaac | tcgtagaaga | agccggatta | acaaattctg | tatctggtga | agtcaaaact | 1200 |
| cagaggcgaa | agaaacgtgt | ggctcaacct | ccggtggctt | atgcctctgc | tgcaccgttt | 1260 |
| cctttcctcc | cagctccttc | cttctactct | ccatga | | | 1296 |

<210> SEQ ID NO 6
<211> LENGTH: 431
<212> TYPE: PRT
<213> ORGANISM: Arabidopsis sp.

<400> SEQUENCE: 6

Met Trp Arg Arg Ser Val Val Tyr Arg Phe Ser Ser Arg Ile Ser Val
1               5                   10                  15

Ser Ser Ser Leu Pro Asn Pro Arg Leu Ile Pro Trp Ser Arg Glu Leu
            20                  25                  30

Cys Ala Val Asn Ser Phe Ser Gln Pro Pro Val Ser Thr Glu Ser Thr
        35                  40                  45

Ala Lys Leu Gly Ile Thr Gly Val Arg Ser Asp Ala Asn Arg Val Phe
    50                  55                  60

Ala Thr Ala Thr Ala Ala Ala Thr Ala Thr Ala Thr Gly Glu Ile
65                  70                  75                  80

Ser Ser Arg Val Ala Ala Leu Ala Gly Leu Gly His His Tyr Ala Arg
                85                  90                  95

```
Cys Tyr Trp Glu Leu Ser Lys Ala Lys Leu Ser Met Leu Val Val Ala
            100                 105                 110

Thr Ser Gly Thr Gly Tyr Ile Leu Gly Thr Gly Asn Ala Ala Ile Ser
        115                 120                 125

Phe Pro Gly Leu Cys Tyr Thr Cys Ala Gly Thr Met Met Ile Ala Ala
    130                 135                 140

Ser Ala Asn Ser Leu Asn Gln Ile Phe Glu Ile Ser Asn Asp Ser Lys
145                 150                 155                 160

Met Lys Arg Thr Met Leu Arg Pro Leu Pro Ser Gly Arg Ile Ser Val
                165                 170                 175

Pro His Ala Val Ala Trp Ala Thr Ile Ala Gly Ala Ser Gly Ala Cys
            180                 185                 190

Leu Leu Ala Ser Lys Thr Asn Met Leu Ala Ala Gly Leu Ala Ser Ala
        195                 200                 205

Asn Leu Val Leu Tyr Ala Phe Val Tyr Thr Pro Leu Lys Gln Leu His
    210                 215                 220

Pro Ile Asn Thr Trp Val Gly Ala Val Gly Ala Ile Pro Pro Leu
225                 230                 235                 240

Leu Gly Trp Ala Ala Ala Ser Gly Gln Ile Ser Tyr Asn Ser Met Ile
                245                 250                 255

Leu Pro Ala Ala Leu Tyr Phe Trp Gln Ile Pro His Phe Met Ala Leu
            260                 265                 270

Ala His Leu Cys Arg Asn Asp Tyr Ala Ala Gly Gly Tyr Lys Met Leu
        275                 280                 285

Ser Leu Phe Asp Pro Ser Gly Lys Arg Ile Ala Ala Val Ala Leu Arg
    290                 295                 300

Asn Cys Phe Tyr Met Ile Pro Leu Gly Phe Ile Ala Tyr Asp Trp Gly
305                 310                 315                 320

Leu Thr Ser Ser Trp Phe Cys Leu Glu Ser Thr Leu Leu Thr Leu Ala
                325                 330                 335

Ile Ala Ala Thr Ala Phe Ser Phe Tyr Arg Asp Arg Thr Met His Lys
            340                 345                 350

Ala Arg Lys Met Phe His Ala Ser Leu Leu Phe Leu Pro Val Phe Met
        355                 360                 365

Ser Gly Leu Leu Leu His Arg Val Ser Asn Asp Asn Gln Gln Gln Leu
    370                 375                 380

Val Glu Glu Ala Gly Leu Thr Asn Ser Val Ser Gly Glu Val Lys Thr
385                 390                 395                 400

Gln Arg Arg Lys Lys Arg Val Ala Gln Pro Pro Val Ala Tyr Ala Ser
                405                 410                 415

Ala Ala Pro Phe Pro Phe Leu Pro Ala Pro Ser Phe Tyr Ser Pro
            420                 425                 430

<210> SEQ ID NO 7
<211> LENGTH: 479
<212> TYPE: DNA
<213> ORGANISM: Arabidopsis sp.

<400> SEQUENCE: 7
ggaaactccc ggagcacctg tttgcaggta ccgctaacct taatcgataa tttatttctc    60
ttgtcaggaa ttatgtaagt ctggtggaag ctcgcatac cattttttgca ttgccttttcg   120 ctatgatcgg gtttactttg ggtgtgatga gaccaggcgt ggcttatgg tatggcgaaa    180 acccattttt atccaatgct gcattccctc ccgatgattc gttctttcat tcctatacag   240
```

-continued

```
gtatcatgct gataaaactg ttactggtac tggtttgtat ggtatcagca agaagcgcgg        300
cgatggcgtt taaccggtat ctcgacaggc attttgacgc gaagaacccg cgtactgcca        360
tccgtgaaat acctgcgggc gtcatatctg ccaacagtgc gctggtgttt acgataggct        420
gctgcgtggt attctgggtg gcctgttatt tcattaacac gatctgtttt tacctggcg         479
```

<210> SEQ ID NO 8
<211> LENGTH: 551
<212> TYPE: DNA
<213> ORGANISM: Arabidopsis sp.
<220> FEATURE:
<221> NAME/KEY: misc_feature
<222> LOCATION: (1)...(551)
<223> OTHER INFORMATION: n = A,T,C or G

<400> SEQUENCE: 8

```
ttgtggctta caccttaatg agcatacgcc agnccattac ggctcgttaa tcggcgccat         60
ngccggngct gntgcaccgg tagtgggcta ctgcgccgtg accaatcagc ttgatctagc        120
ggctcttatt ctgtttttaa ttttactgtt ctggcaaatg ccgcattttt acgcgatttc        180
cattttcagg ctaaaagact tttcagcggc ctgtattccg gtgctgccca tcattaaaga        240
cctgcgctat accaaaatca gcatgctggt ttacgtgggc ttatttacac tggctgctat        300
catgccggcc ctcttagggt atgccggttg gatttatggg atagcggcct taattttagg        360
cttgtattgg ctttatattg ccatacaagg attcaagacc gccgatgatc aaaaatggtc        420
tcgtaagatg tttggatctt cgattttaat cattaccctc ttgtcggtaa tgatgcttgt        480
ttaaacttac tgcctcctga agtttatata tcgataattt cagcttaagg aggcttagtg        540
gttaattcaa t                                                            551
```

<210> SEQ ID NO 9
<211> LENGTH: 297
<212> TYPE: PRT
<213> ORGANISM: Arabidopsis sp.

<400> SEQUENCE: 9

```
Met Val Leu Ala Glu Val Pro Lys Leu Ala Ser Ala Ala Glu Tyr Phe
 1               5                  10                  15

Phe Lys Arg Gly Val Gln Gly Lys Gln Phe Arg Ser Thr Ile Leu Leu
                20                  25                  30

Leu Met Ala Thr Ala Leu Asn Val Arg Val Pro Glu Ala Leu Ile Gly
            35                  40                  45

Glu Ser Thr Asp Ile Val Thr Ser Glu Leu Arg Val Arg Gln Arg Gly
        50                  55                  60

Ile Ala Glu Ile Thr Glu Met Ile His Val Ala Ser Leu Leu His Asp
65                  70                  75                  80

Asp Val Leu Asp Asp Ala Asp Thr Arg Arg Gly Val Gly Ser Leu Asn
                85                  90                  95

Val Val Met Gly Asn Lys Val Val Ala Leu Leu Ala Thr Ala Val Glu
            100                 105                 110

His Leu Val Thr Gly Glu Thr Met Glu Ile Thr Ser Ser Thr Glu Gln
        115                 120                 125

Arg Tyr Ser Met Asp Tyr Tyr Met Gln Lys Thr Tyr Tyr Lys Thr Ala
    130                 135                 140

Ser Leu Ile Ser Asn Ser Cys Lys Ala Val Ala Val Leu Thr Gly Gln
145                 150                 155                 160
```

```
Thr Ala Glu Val Ala Val Leu Ala Phe Glu Tyr Gly Arg Asn Leu Gly
            165                 170                 175
Leu Ala Phe Gln Leu Ile Asp Asp Ile Leu Asp Phe Thr Gly Thr Ser
        180                 185                 190
Ala Ser Leu Gly Lys Gly Ser Leu Ser Asp Ile Arg His Gly Val Ile
    195                 200                 205
Thr Ala Pro Ile Leu Phe Ala Met Glu Glu Phe Pro Gln Leu Arg Glu
210                 215                 220
Val Val Asp Gln Val Glu Lys Asp Pro Arg Asn Val Asp Ile Ala Leu
225                 230                 235                 240
Glu Tyr Leu Gly Lys Ser Lys Gly Ile Gln Arg Ala Arg Glu Leu Ala
                245                 250                 255
Met Glu His Ala Asn Leu Ala Ala Ala Ile Gly Ser Leu Pro Glu
            260                 265                 270
Thr Asp Asn Glu Asp Val Lys Arg Ser Arg Arg Ala Leu Ile Asp Leu
        275                 280                 285
Thr His Arg Val Ile Thr Arg Asn Lys
290                 295
```

<210> SEQ ID NO 10
<211> LENGTH: 561
<212> TYPE: DNA
<213> ORGANISM: Arabidopsis sp.

<400> SEQUENCE: 10

```
aagcgcatcc gtcctcttct acgattgccg ccagccgcat gtatggctgc ataaccgacc     60
gcccctatcc gctcgcggcc gcggtcgaat tcattcacac cgcgacgctg ctgcatgacg    120
acgtcgtcga tgaaagcgat ttgcgccgcg ccgcgaaag cgcgcataag gttttcggca    180
atcaggcgag cgtgctcgtc ggcgatttcc ttttctcccg cgccttccag ctgatggtgg    240
aagacgctc gctcgacgcg ctgcgcattc tctcggatgc ctccgccgtg atcgcgcagg    300
gcgaagtgat gcagctcggc accgcgcgca tcttgaaac caatatgagc cagtatctcg    360
atgtgatcag cgcgaagacc gccgcgctct tgccgccgc ctgcgaaatc ggcccggtga    420
tggcgaacgc gaaggcggaa gatgctgccg cgatgtgcga atacggcatg aatctcggta    480
tcgccttcca gatcatcgac gaccttctcg attacggcac cggcggccac gccgagcttg    540
gcaagaacac gggcgacgat t                                             561
```

<210> SEQ ID NO 11
<211> LENGTH: 966
<212> TYPE: DNA
<213> ORGANISM: Arabidopsis sp.

<400> SEQUENCE: 11

```
atggtacttg ccgaggttcc aaagcttgcc tctgctgctg agtacttctt caaaagggt     60
gtgcaaggaa acagtttcg ttcaactatt tgctgctga tggcgacagc tctgaatgta    120
cgcgttccag aagcattgat tggggaatca acagatatag tcacatcaga attacgcgta    180
aggcaacggg gtattgctga aatcactgaa atgatacacg tcgcaagtct actgcacgat    240
gatgtcttgg atgatgccga tacaaggcgt ggtgttggtt ccttaaatgt tgtaatgggt    300
aacaagatgt cggtattagc aggagacttc ttgctctccc gggcttgtgg ggctctcgct    360
gctttaaaga acacagaggt tgtagcatta cttgcaactg ctgtagaaca tcttgttacc    420
ggtgaaacca tggaaataac tagttcaacc gagcagcgtt atagtatgga ctactacatg    480
```

-continued

```
cagaagacat attataagac agcatcgcta atctctaaca gctgcaaagc tgttgccgtt    540
ctcactggac aaacagcaga agttgccgtg ttagcttttg agtatgggag gaatctgggt    600
ttagcattcc aattaataga cgacattctt gatttcacgg gcacatctgc ctctctcgga    660
aagggatcgt tgtcagatat tcgccatgga gtcataacag ccccaatcct ctttgccatg    720
gaagagtttc ctcaactacg cgaagttgtt gatcaagttg aaaaagatcc taggaatgtt    780
gacattgctt tagagtatct tgggaagagc aagggaatac agagggcaag agaattagcc    840
atggaacatg cgaatctagc agcagctgca atcgggtctc tacctgaaac agacaatgaa    900
gatgtcaaaa gatcgaggcg ggcacttatt gacttgaccc atagagtcat caccagaaac    960
aagtga                                                               966
```

```
<210> SEQ ID NO 12
<211> LENGTH: 321
<212> TYPE: PRT
<213> ORGANISM: Arabidopsis sp.

<400> SEQUENCE: 12

Met Val Leu Ala Glu Val Pro Lys Leu Ala Ser Ala Ala Glu Tyr Phe
  1               5                  10                  15

Phe Lys Arg Gly Val Gln Gly Lys Gln Phe Arg Ser Thr Ile Leu Leu
                 20                  25                  30

Leu Met Ala Thr Ala Leu Asn Val Arg Val Pro Glu Ala Leu Ile Gly
             35                  40                  45

Glu Ser Thr Asp Ile Val Thr Ser Glu Leu Arg Val Arg Gln Arg Gly
         50                  55                  60

Ile Ala Glu Ile Thr Glu Met Ile His Val Ala Ser Leu Leu His Asp
 65                  70                  75                  80

Asp Val Leu Asp Asp Ala Asp Thr Arg Arg Gly Val Gly Ser Leu Asn
                 85                  90                  95

Val Val Met Gly Asn Lys Met Ser Val Leu Ala Gly Asp Phe Leu Leu
            100                 105                 110

Ser Arg Ala Cys Gly Ala Leu Ala Ala Leu Lys Asn Thr Glu Val Val
        115                 120                 125

Ala Leu Leu Ala Thr Ala Val Glu His Leu Val Thr Gly Glu Thr Met
    130                 135                 140

Glu Ile Thr Ser Ser Thr Glu Gln Arg Tyr Ser Met Asp Tyr Tyr Met
145                 150                 155                 160

Gln Lys Thr Tyr Tyr Lys Thr Ala Ser Leu Ile Ser Asn Ser Cys Lys
                165                 170                 175

Ala Val Ala Val Leu Thr Gly Gln Thr Ala Glu Val Ala Val Leu Ala
            180                 185                 190

Phe Glu Tyr Gly Arg Asn Leu Gly Leu Ala Phe Gln Leu Ile Asp Asp
        195                 200                 205

Ile Leu Asp Phe Thr Gly Thr Ser Ala Ser Leu Gly Lys Gly Ser Leu
    210                 215                 220

Ser Asp Ile Arg His Gly Val Ile Thr Ala Pro Ile Leu Phe Ala Met
225                 230                 235                 240

Glu Glu Phe Pro Gln Leu Arg Glu Val Val Asp Gln Val Glu Lys Asp
                245                 250                 255

Pro Arg Asn Val Asp Ile Ala Leu Glu Tyr Leu Gly Lys Ser Lys Gly
            260                 265                 270

Ile Gln Arg Ala Arg Glu Leu Ala Met Glu His Ala Asn Leu Ala Ala
        275                 280                 285
```

```
Ala Ala Ile Gly Ser Leu Pro Glu Thr Asp Asn Glu Asp Val Lys Arg
    290                 295                 300

Ser Arg Arg Ala Leu Ile Asp Leu Thr His Arg Val Ile Thr Arg Asn
305                 310                 315                 320

Lys

<210> SEQ ID NO 13
<211> LENGTH: 621
<212> TYPE: DNA
<213> ORGANISM: Arabidopsis sp.

<400> SEQUENCE: 13
gctttctcct tgctaattc ttgagctttc ttgatcccac cgcgatttct aactatttca     60
atcgcttctt caagcgatcc aggctcacaa aactcagact caatgatctc tcttagcctt    120
ggctcattct ctagcgcgaa gatcactggc gccgttatgt tacctttggc taagtcatta    180
gctgcaggct tacctaactg ctctgtggac tgagtgaagt ccagaatgtc atcaactact    240
tgaaaagata aaccgagatt ctccccgaac tgatacattt gctctgcgac cttgctttcg    300
actttactga aaattgctgc tccctttggtg cttgcagcta ctaatgaagc tgtcttgtag    360
taactcttta gcatgtagtc atcaagcttg acatcacaat cgaataaact cgatgcttgc    420
tttatctcac cgcttgcaaa atctttgatc acctgcaaaa agataaatca agattcagac    480
caaatgttct tgtattgag tagcttcatc taatctcaga aggaatatt acctgactta     540
tgagcttaat gacttcaagg ttttcgagat ttgtaagtac catgatgctt gagcaacatg    600
aaatccccag ctaatacagc t                                              621

<210> SEQ ID NO 14
<211> LENGTH: 741
<212> TYPE: DNA
<213> ORGANISM: Arabidopsis sp.

<400> SEQUENCE: 14
ggtgagtttt gttaatagtt atgagattca tctatttttg tcataaaatt gtttggtttg     60
gtttaaactc tgtgtataat tgcaggaaag gaaacagttc atgagctttt cggcacaaga    120
gtagcggtgc tagctggaga tttcatgttt gctcaagcgt catggtactt agcaaatctc    180
gagaatcttg aagttattaa gctcatcagt caggtactta gttactctta cattgttttt    240
ctatgaggtt gagctatgaa tctcatttcg ttgaataatg ctgtgcctca aactttttt     300
catgttttca ggtgatcaaa gactttgcaa gcggagagat aaagcaggcg tccagcttat    360
ttgactgcga caccaagctc gacgagtact tactcaaaag tttctacaag acagcctctt    420
tagtggctgc gagcaccaaa ggagctgcca ttttcagcag agttgagcct gatgtgacag    480
aacaaatgta cgagtttggg aagaatctcg gtctctcttt ccagatagtt gatgatattt    540
tggatttcac tcagtcgaca gagcagctcg ggaagccagc agggagtgat ttggctaaag    600
gtaacttaac agcacctgtg attttcgctc tggagaggga gccaaggcta agagagatca    660
ttgagtcaaa gttctgtgag gcgggttctc tggaagaagc gattgaagcg gtgacaaaag    720
gtgggggat aagagagca c                                                741

<210> SEQ ID NO 15
<211> LENGTH: 1087
<212> TYPE: DNA
<213> ORGANISM: Arabidopsis sp.
```

<400> SEQUENCE: 15

```
cctcttcagc caatccagag gaagaagaga caacttttta tctttcgtca agagtctccg      60
aaaacgcacg gttttatgct ctctcttctg ccctcacctc acaagacgca gggcacatga     120
ttcaaccaga gggaaaaagc aacgataaca actctgcttt tgatttcaag ctgtatatga     180
tccgcaaagc cgagtctgta aatgcggctc tcgacgtttc cgtaccgctt ctgaaacccc     240
ttacgatcca agaagcggtc aggtactctt tgctagccgg cggaaaacgt gtgaggcctc     300
tgctctgcat tgccgcttgt gagcttgtgg ggggcgacga ggctactgcc atgtcagccg     360
cttgcgcggt cgagatgatc cacacaagct ctctcattca tgacgatctt ccgtgcatgg     420
acaatgccga cctccgtaga ggcaagccca ccaatcacaa ggtatgttgt ttaattatat     480
gaaggctcag agataatgct gaactagtgt tgaaccaatt tttgctcaaa caaggtatat     540
ggagaagaca tggcggtttt ggcaggtgat gcactccttg cattggcgtt tgagcacatg     600
acggttgtgt cgagtgggtt ggtcgctccc gagaagatga ttcgcgccgt ggttgagctg     660
gccagggcca tagggactac agggctagtt gctggacaaa tgatagacct agccagcgaa     720
agactgaatc cagacaaggt tggattggag catctagagt tcatccatct ccacaaaacg     780
gcggcattgt tggaggcagc ggcagtttta ggggttataa tgggaggtgg aacagaggaa     840
gaaatcgaaa agcttagaaa gtatgctagg tgtattggac tactgtttca ggttgttgat     900
gacattctcg acgtaacaaa atctactgag gaattgggta agacagccgg aaaagacgta     960
atggccggaa agctgacgta tccaaggctg ataggtttgg agggatccag ggaagttgca    1020
gagcacctga ggagagaagc agaggaaaag cttaaagggt ttgatccaag tcaggcggcg    1080
cctctgg                                                             1087
```

<210> SEQ ID NO 16
<211> LENGTH: 1164
<212> TYPE: DNA
<213> ORGANISM: Arabidopsis sp.

<400> SEQUENCE: 16

```
atgacttcga ttctcaacac tgtctccacc atccactctt ccagagttac ctccgtcgat      60
cgagtcggag tcctctctct tcggaattcg gattccgttg agttcactcg ccggcgttct     120
ggtttctcga cgttgatcta cgaatcaccc gggcggagat tgttgtgcg tgcggcggag     180
actgatactg ataaagttaa atctcagaca cctgacaagg caccagccgg tggttcaagc     240
attaaccagc ttctcggtat caaggagca tctcaagaaa ctaataaatg gaagattcgt     300
cttcagctta caaaaccagt cacttggcct ccactggttt ggggagtcgt ctgtggtgct     360
gctgcttcag ggaactttca ttggaccca gaggatgttg ctaagtcgat tctttgcatg     420
atgatgtctg gtccttgtct tactggctat acacagacaa tcaacgactg gtatgataga     480
gatatcgacg caattaatga gccatatcgt ccaattccat ctggagcaat atcagagcca     540
gaggttatta cacaagtctg ggtgctatta ttgggaggtc ttggtattgc tggaatatta     600
gatgtgtggg cagggcatac cactcccact gtccttctatc ttgctttggg aggatcattg     660
ctatcttata tatactctgc tccacctctt aagctaaaac aaaatggatg ggttggaaat     720
tttgcacttg gagcaagcta tattagtttg ccatggtggg ctggccaagc attgtttggc     780
actcttacgc cagatgttgt tgttctaaca ctcttgtaca gcatagctgg gttaggaata     840
gccattgtta acgacttcaa aagtgttgaa ggagatagag cattaggact tcagtctctc     900
ccagtagctt ttggcaccga aactgcaaaa tggatatgcg ttggtgctat agacattact     960
```

```
cagctttctg ttgccggata tctattagca tctgggaaac cttattatgc gttggcgttg    1020
gttgctttga tcattcctca gattgtgttc cagtttaaat actttctcaa ggaccctgtc    1080
aaatacgacg tcaagtacca ggcaagcgcg cagccattct tggtgctcgg aatatttgta    1140
acggcattag catcgcaaca ctga                                          1164
```

<210> SEQ ID NO 17
<211> LENGTH: 387
<212> TYPE: PRT
<213> ORGANISM: Arabidopsis sp.

<400> SEQUENCE: 17

```
Met Thr Ser Ile Leu Asn Thr Val Ser Thr Ile His Ser Ser Arg Val
 1               5                  10                  15

Thr Ser Val Asp Arg Val Gly Val Leu Ser Leu Arg Asn Ser Asp Ser
                20                  25                  30

Val Glu Phe Thr Arg Arg Ser Gly Phe Ser Thr Leu Ile Tyr Glu
        35                  40                  45

Ser Pro Gly Arg Arg Phe Val Val Arg Ala Ala Glu Thr Asp Thr Asp
    50                  55                  60

Lys Val Lys Ser Gln Thr Pro Asp Lys Ala Pro Ala Gly Gly Ser Ser
65                  70                  75                  80

Ile Asn Gln Leu Leu Gly Ile Lys Gly Ala Ser Gln Glu Thr Asn Lys
                85                  90                  95

Trp Lys Ile Arg Leu Gln Leu Thr Lys Pro Val Thr Trp Pro Pro Leu
            100                 105                 110

Val Trp Gly Val Val Cys Gly Ala Ala Ala Ser Gly Asn Phe His Trp
        115                 120                 125

Thr Pro Glu Asp Val Ala Lys Ser Ile Leu Cys Met Met Met Ser Gly
    130                 135                 140

Pro Cys Leu Thr Gly Tyr Thr Gln Thr Ile Asn Asp Trp Tyr Asp Arg
145                 150                 155                 160

Asp Ile Asp Ala Ile Asn Glu Pro Tyr Arg Pro Ile Pro Ser Gly Ala
                165                 170                 175

Ile Ser Glu Pro Glu Val Ile Thr Gln Val Trp Val Leu Leu Leu Gly
            180                 185                 190

Gly Leu Gly Ile Ala Gly Ile Leu Asp Val Trp Ala Gly His Thr Thr
        195                 200                 205

Pro Thr Val Phe Tyr Leu Ala Leu Gly Gly Ser Leu Leu Ser Tyr Ile
    210                 215                 220

Tyr Ser Ala Pro Pro Leu Lys Leu Lys Gln Asn Gly Trp Val Gly Asn
225                 230                 235                 240

Phe Ala Leu Gly Ala Ser Tyr Ile Ser Leu Pro Trp Trp Ala Gly Gln
                245                 250                 255

Ala Leu Phe Gly Thr Leu Thr Pro Asp Val Val Leu Thr Leu Leu
            260                 265                 270

Tyr Ser Ile Ala Gly Leu Gly Ile Ala Ile Val Asn Asp Phe Lys Ser
        275                 280                 285

Val Glu Gly Asp Arg Ala Leu Gly Leu Gln Ser Leu Pro Val Ala Phe
    290                 295                 300

Gly Thr Glu Thr Ala Lys Trp Ile Cys Val Gly Ala Ile Asp Ile Thr
305                 310                 315                 320

Gln Leu Ser Val Ala Gly Tyr Leu Leu Ala Ser Gly Lys Pro Tyr Tyr
                325                 330                 335
```

```
Ala Leu Ala Leu Val Ala Leu Ile Ile Pro Gln Ile Val Phe Gln Phe
        340                 345                 350

Lys Tyr Phe Leu Lys Asp Pro Val Lys Tyr Asp Val Lys Tyr Gln Ala
        355                 360                 365

Ser Ala Gln Pro Phe Leu Val Leu Gly Ile Phe Val Thr Ala Leu Ala
        370                 375                 380

Ser Gln His
385

<210> SEQ ID NO 18
<211> LENGTH: 981
<212> TYPE: DNA
<213> ORGANISM: Arabidopsis sp.

<400> SEQUENCE: 18
atgttgttta gtggttcagc gatcccatta agcagcttct gctctcttcc ggagaaaccc      60
cacactcttc ctatgaaact ctctcccgct gcaatccgat cttcatcctc atctgccccg     120
gggtcgttga acttcgatct gaggacgtat tggacgactc tgatcaccga gatcaaccag     180
aagctggatg aggccatacc ggtcaagcac cctgcgggga tctacgaggc tatgagatac     240
tctgtactcg cacaaggcgc caagcgtgcc cctcctgtga tgtgtgtggc ggcctgcgag     300
ctcttcggtg gcgatcgcct cgccgctttc cccaccgcct gtgccctaga aatggtgcac     360
gcggcttcgt tgatacacga cgacctcccc tgtatggacg acgatcctgt gcgcagagga     420
aagccatcta accacactgt ctacggctct ggcatggcca ttctcgccgg tgacgccctc     480
ttcccactcg ccttccagca cattgtctcc cacacgcctc ctgaccttgt tccccgagcc     540
accatcctca gactcatcac tgagattgcc cgcactgtcg gctccactgg tatggctgca     600
ggccagtacg tcgaccttga aggaggtccc tttcctcttt cctttgttca ggagaagaaa     660
ttcggagcca tgggtgaatg ctctgccgtg tgcggtggcc tattgggcgg tgccactgag     720
gatgagctcc agagtctccg aaggtacggg agagccgtcg ggatgctgta tcaggtggtc     780
gatgacatca ccgaggacaa gaagaagagc tatgatggtg agcagagaa gggaatgatg     840 gaaatggcgg aagagctcaa ggagaaggcg aagaaggagc ttcaagtgtt tgacaacaag     900
tatggaggag agacacact tgttcctctc tacaccttcg ttgactacgc tgctcatcga     960
cattttcttc ttccctctg a                                               981

<210> SEQ ID NO 19
<211> LENGTH: 245
<212> TYPE: DNA
<213> ORGANISM: Glycine sp.

<400> SEQUENCE: 19
gcaacatctg ggactgggtt tgtcttgggg agtggtagtg ctgttgatct ttcggcactt      60
tcttgcactt gcttgggtac catgatggtt gctgcatctg ctaactcttt gaatcaggtg     120
tttgagatca ataatgatgc taaaatgaag agaacaagtc gcaggccact accctcagga     180
cgcatcacaa tacctcatgc agttggctgg gcatcctctg ttggattagc tggtacggct     240
ctact                                                                245

<210> SEQ ID NO 20
<211> LENGTH: 253
<212> TYPE: DNA
<213> ORGANISM: Glycine sp.
```

```
<400> SEQUENCE: 20
attggctttc caagatcatt gggttttctt gttgcattca tgaccttcta ctccttgggt      60
ttggcattgt ccaaggatat acctgacgtt gaaggagata agagcacgg cattgattct      120 tttgcagtac gtctaggtca gaaacgggca ttttggattt gcgtttcctt ttttgaaatg     180
gctttcggag ttggtatcct ggccggagca tcatgctcac acttttggac taaaattttc    240
acgggtatgg gaa                                                         253

<210> SEQ ID NO 21
<211> LENGTH: 275
<212> TYPE: DNA
<213> ORGANISM: Glycine sp.

<400> SEQUENCE: 21
tgatcttcta ctctctgggt atggcattgt ccaaggatat atctgacgtt aaaggagata      60
aagcatacgg catcgatact ttagcgatac gtttgggtca aaaatgggta ttttggattt     120
gcattatcct ttttgaaatg gcttttggag ttgccctctt ggcaggagca acatcttctt     180
acctttggat taaaattgtc acgggtctgg gacatgctat tcttgcttca attctcttgt     240
accaagccaa atctatatac ttgagcaaca aagtt                                275

<210> SEQ ID NO 22
<211> LENGTH: 299
<212> TYPE: DNA
<213> ORGANISM: Glycine sp.
<220> FEATURE:
<221> NAME/KEY: misc_feature
<222> LOCATION: (1)...(299)
<223> OTHER INFORMATION: n = A,T,C or G

<400> SEQUENCE: 22
ccanaatang tncatcttng aaagacaatt ggcctcttca acacacaagt ctgcatgtga      60
agaagaggcc aattgtcttt ccaagatcac ttatngtggc tattgtaatc atgaacttct     120
tctttgtggg tatggcattg gcaaaggata tacctanctg ttgaaggaga taaaatatat     180
ggcattgata cttttgcaat acgtataggt caaaaacaag tattttggat ttgtattttc     240
cttttgaaaa ggctttcgga gtttccctag tggcaggagc aacatcttct agccttggt     299

<210> SEQ ID NO 23
<211> LENGTH: 767
<212> TYPE: DNA
<213> ORGANISM: Glycine sp.

<400> SEQUENCE: 23
gtggaggctg tggttgctgc cctgtttatg aatatttata ttgttggttt gaatcaattg      60
tctgatgttg aaatagacaa gataaacaag ccgtatcttc cattagcatc tggggaatat     120
tcctttgaaa ctggtgtcac tattgttgca tcttttcaa ttctgagttt ttggcttggc     180
tgggttgtag gttcatggcc attatttggg gccctttttg taagctttgt gctaggaact     240
gcttattcaa tcaatgtgcc tctgttgaga tggaagaggt ttgcagtgct tgcagcgatg     300
tgcattctag ctgttcgggc agtaatagtt caacttgcat ttttccttca catgcagact     360
catgtgtaca agaggccacc tgtcttttca agaccattga ttttgctac tgcattcatg     420 agcttcttct ctgtagttat agcactgttt aaggatatac ctgacattga aggagataaa     480
gtatttggca tccaatcttt ttcagtgtgt ttaggtcaga agccggtgtt ctggacttgt     540
gttacccttc ttgaaatagc ttatggagtc gccctcctgg tgggagctgc atctccttgt     600
```

```
ctttggagca aaattttcac gggtctggga cacgctgtgc tggcttcaat tctctggttt    660
catgccaaat ctgtagattt gaaaagcaaa gcttcgataa catccttcta tatgtttatt    720
tggaagctat tttatgcaga atacttactc attccttttg ttagatg                  767
```

```
<210> SEQ ID NO 24
<211> LENGTH: 255
<212> TYPE: PRT
<213> ORGANISM: Glycine sp.

<400> SEQUENCE: 24
```

| | | | | | | | | | | | | | | | |
|---|---|---|---|---|---|---|---|---|---|---|---|---|---|---|---|
| Val | Glu | Ala | Val | Val | Ala | Ala | Leu | Phe | Met | Asn | Ile | Tyr | Ile | Val | Gly |
| 1 | | | | 5 | | | | | 10 | | | | | 15 | |
| Leu | Asn | Gln | Leu | Ser | Asp | Val | Glu | Ile | Asp | Lys | Ile | Asn | Lys | Pro | Tyr |
| | | | 20 | | | | | 25 | | | | | 30 | | |
| Leu | Pro | Leu | Ala | Ser | Gly | Glu | Tyr | Ser | Phe | Glu | Thr | Gly | Val | Thr | Ile |
| | | | 35 | | | | | 40 | | | | | 45 | | |
| Val | Ala | Ser | Phe | Ser | Ile | Leu | Ser | Phe | Trp | Leu | Gly | Trp | Val | Val | Gly |
| | 50 | | | | | 55 | | | | | 60 | | | | |
| Ser | Trp | Pro | Leu | Phe | Trp | Ala | Leu | Phe | Val | Ser | Phe | Val | Leu | Gly | Thr |
| 65 | | | | | 70 | | | | | 75 | | | | | 80 |
| Ala | Tyr | Ser | Ile | Asn | Val | Pro | Leu | Leu | Arg | Trp | Lys | Arg | Phe | Ala | Val |
| | | | | 85 | | | | | 90 | | | | | 95 | |
| Leu | Ala | Ala | Met | Cys | Ile | Leu | Ala | Val | Arg | Ala | Val | Ile | Val | Gln | Leu |
| | | | | 100 | | | | | 105 | | | | | 110 | |
| Ala | Phe | Phe | Leu | His | Met | Gln | Thr | His | Val | Tyr | Lys | Arg | Pro | Pro | Val |
| | | | 115 | | | | | 120 | | | | | 125 | | |
| Phe | Ser | Arg | Pro | Leu | Ile | Phe | Ala | Thr | Ala | Phe | Met | Ser | Phe | Phe | Ser |
| | 130 | | | | | 135 | | | | | 140 | | | | |
| Val | Val | Ile | Ala | Leu | Phe | Lys | Asp | Ile | Pro | Asp | Ile | Glu | Gly | Asp | Lys |
| 145 | | | | | 150 | | | | | 155 | | | | | 160 |
| Val | Phe | Gly | Ile | Gln | Ser | Phe | Ser | Val | Cys | Leu | Gly | Gln | Lys | Pro | Val |
| | | | | 165 | | | | | 170 | | | | | 175 | |
| Phe | Trp | Thr | Cys | Val | Thr | Leu | Leu | Glu | Ile | Ala | Tyr | Gly | Val | Ala | Leu |
| | | | | 180 | | | | | 185 | | | | | 190 | |
| Leu | Val | Gly | Ala | Ala | Ser | Pro | Cys | Leu | Trp | Ser | Lys | Ile | Phe | Thr | Gly |
| | | | 195 | | | | | 200 | | | | | 205 | | |
| Leu | Gly | His | Ala | Val | Leu | Ala | Ser | Ile | Leu | Trp | Phe | His | Ala | Lys | Ser |
| | 210 | | | | | 215 | | | | | 220 | | | | |
| Val | Asp | Leu | Lys | Ser | Lys | Ala | Ser | Ile | Thr | Ser | Phe | Tyr | Met | Phe | Ile |
| 225 | | | | | 230 | | | | | 235 | | | | | 240 |
| Trp | Lys | Leu | Phe | Tyr | Ala | Glu | Tyr | Leu | Leu | Ile | Pro | Phe | Val | Arg | |
| | | | | 245 | | | | | 250 | | | | | 255 | |

```
<210> SEQ ID NO 25
<211> LENGTH: 360
<212> TYPE: DNA
<213> ORGANISM: Zea sp.
<220> FEATURE:
<221> NAME/KEY: misc_feature
<222> LOCATION: (1)...(360)
<223> OTHER INFORMATION: n = A,T,C or G

<400> SEQUENCE: 25
ggcgtcttca cttgttctgg tcttctcgta tccctgatg aagaggttca cattttggcc     60
tcaggcttat cttggcctga cattcaactg gggagcttta ctagggtggg ctgctattaa   120
```

```
ggaaagcata gaccctgcaa atcatccttc cattgtatac agctggtatt tgttggacgc    180
tggtgtatga tactatatat gcgcatcagg tgtttcgcta tccctacttt catattaatc    240
cttgatgaag tggccatttc atgttgtcgc ggtggtctta tacttgcata tctccatgca    300
tctcaggaca aagangatga cctgaaagta ggagtccaag tccacagctt aagatttggg    360
```

<210> SEQ ID NO 26
<211> LENGTH: 299
<212> TYPE: DNA
<213> ORGANISM: Zea sp.
<220> FEATURE:
<221> NAME/KEY: misc_feature
<222> LOCATION: (1)...(299)
<223> OTHER INFORMATION: n = A,T,C or G

<400> SEQUENCE: 26

```
gatggttgca gcatctgcaa atacccctcaa ccaggtgttt gngataaaaa atgatgctaa    60
aatgaaaagg acaatgcgtg ccccctgcca tctggtcgca ttagtcctgc acatgctgcg   120
atgtgggcta caagtgttgg agttgcagga acagctttgt tggcctggaa ggctaatggc   180
ttggcagctg ggcttgcagc ttctaatctt gttctgtatg catttgtgta tacgccgttg   240
aagcaaatac accctgttaa tacatgggtt ggggcagtcg ttggtgccat cccaccact    299
```

<210> SEQ ID NO 27
<211> LENGTH: 255
<212> TYPE: DNA
<213> ORGANISM: Zea sp.
<220> FEATURE:
<221> NAME/KEY: misc_feature
<222> LOCATION: (1)...(255)
<223> OTHER INFORMATION: n = A,T,C or G

<400> SEQUENCE: 27

```
anacttgcat atctccatgc ntctcaggac aaagangatg acctgaaagt aggtgtcaag    60
tccacagcat taagatttgg agatttgacc nnatactgna tcagtggctt tggcgcggca   120
tgcttcggca gcttagcact cagtggttac aatgctgacc ttggttggtg tttagtgtga   180
tgcttgagcg aagaatggta tngttttttac ttgatattga ctccagacct gaaatcatgt   240
tggacagggt ggccc                                                    255
```

<210> SEQ ID NO 28
<211> LENGTH: 257
<212> TYPE: DNA
<213> ORGANISM: Zea sp.

<400> SEQUENCE: 28

```
attgaagggg ataggactct ggggcttcag tcacttcctg ttgcttttgg gatggaaact    60
gcaaaatgga tttgtgttgg agcaattgat atcactcaat tatctgttgc aggttaccta   120
ttgagcaccg gtaagctgta ttatgccctg gtgttgcttg ggctaacaat tcctcaggtg   180
ttctttcagt tccagtactt cctgaaggac cctgtgaagt atgatgtcaa atatcaggca   240
agcgcacaac cattctt                                                  257
```

<210> SEQ ID NO 29
<211> LENGTH: 368
<212> TYPE: DNA
<213> ORGANISM: Zea sp.

<400> SEQUENCE: 29

```
atccagttgc aaataataat ggcgttcttc tctgttgtaa tagcactatt caaggatata    60
```

```
cctgacatcg aaggggaccg catattcggg atccgatcct tcagcgtccg gttagggcaa    120
aagaaggtct tttggatctg cgttggcttg cttgagatgg cctacagcgt tgcgatactg    180
atgggagcta cctcttcctg tttgtggagc aaaacagcaa ccatcgctgg ccattccata    240
cttgccgcga tcctatggag ctgcgcgcga tcggtggact tgacgagcaa agccgcaata    300
acgtccttct acatgttcat ctggaagctg ttctacgcgg agtacctgct catccctctg    360
gtgcggtg                                                             368
```

```
<210> SEQ ID NO 30
<211> LENGTH: 122
<212> TYPE: PRT
<213> ORGANISM: Zea sp.

<400> SEQUENCE: 30

Ile Gln Leu Gln Ile Ile Met Ala Phe Phe Ser Val Val Ile Ala Leu
 1               5                  10                  15

Phe Lys Asp Ile Pro Asp Ile Glu Gly Asp Arg Ile Phe Gly Ile Arg
                20                  25                  30

Ser Phe Ser Val Arg Leu Gly Gln Lys Lys Val Phe Trp Ile Cys Val
            35                  40                  45

Gly Leu Leu Glu Met Ala Tyr Ser Val Ala Ile Leu Met Gly Ala Thr
        50                  55                  60

Ser Ser Cys Leu Trp Ser Lys Thr Ala Thr Ile Ala Gly His Ser Ile
    65                  70                  75                  80

Leu Ala Ala Ile Leu Trp Ser Cys Ala Arg Ser Val Asp Leu Thr Ser
                85                  90                  95

Lys Ala Ala Ile Thr Ser Phe Tyr Met Phe Ile Trp Lys Leu Phe Tyr
               100                 105                 110

Ala Glu Tyr Leu Leu Ile Pro Leu Val Arg
           115                 120
```

```
<210> SEQ ID NO 31
<211> LENGTH: 278
<212> TYPE: DNA
<213> ORGANISM: Zea sp.

<400> SEQUENCE: 31
tattcagcac cacctctcaa gctcaagcag aatggatgga ttgggaactt cgctctgggt     60
gcgagttaca tcagcttgcc ctggtgggct ggccaggcgt tatttggaac tcttacacca    120
gatatcattg tcttgactac tttgtacagc atagctgggc tagggattgc tattgtaaat    180
gatttcaaga gtattgaagg ggataggact ctggggcttc agtcacttcc tgttgctttt    240
gggatggaaa ctgcaaaatg gatttgtgtt ggagcaat                            278
```

```
<210> SEQ ID NO 32
<211> LENGTH: 292
<212> TYPE: PRT
<213> ORGANISM: Synechocystis sp.

<400> SEQUENCE: 32

Met Val Ala Gln Thr Pro Ser Ser Pro Pro Leu Trp Leu Thr Ile Ile
 1               5                  10                  15

Tyr Leu Leu Arg Trp His Lys Pro Ala Gly Arg Leu Ile Leu Met Ile
                20                  25                  30

Pro Ala Leu Trp Ala Val Cys Leu Ala Ala Gln Gly Leu Pro Pro Leu
            35                  40                  45
```

-continued

```
Pro Leu Leu Gly Thr Ile Ala Leu Gly Thr Leu Ala Thr Ser Gly Leu
     50                  55                  60

Gly Cys Val Val Asn Asp Leu Trp Asp Arg Asp Ile Asp Pro Gln Val
 65                  70                  75                  80

Glu Arg Thr Lys Gln Arg Pro Leu Ala Ala Arg Ala Leu Ser Val Gln
                 85                  90                  95

Val Gly Ile Gly Val Ala Leu Val Ala Leu Leu Cys Ala Ala Gly Leu
            100                 105                 110

Ala Phe Tyr Leu Thr Pro Leu Ser Phe Trp Leu Cys Val Ala Ala Val
            115                 120                 125

Pro Val Ile Val Ala Tyr Pro Gly Ala Lys Arg Val Phe Pro Val Pro
    130                 135                 140

Gln Leu Val Leu Ser Ile Ala Trp Gly Phe Ala Val Leu Ile Ser Trp
145                 150                 155                 160

Ser Ala Val Thr Gly Asp Leu Thr Asp Ala Thr Trp Val Leu Trp Gly
                165                 170                 175

Ala Thr Val Phe Trp Thr Leu Gly Phe Asp Thr Val Tyr Ala Met Ala
            180                 185                 190

Asp Arg Glu Asp Asp Arg Arg Ile Gly Val Asn Ser Ser Ala Leu Phe
        195                 200                 205

Phe Gly Gln Tyr Val Gly Glu Ala Val Gly Ile Phe Phe Ala Leu Thr
    210                 215                 220

Ile Gly Cys Leu Phe Tyr Leu Gly Met Ile Leu Met Leu Asn Pro Leu
225                 230                 235                 240

Tyr Trp Leu Ser Leu Ala Ile Ala Ile Val Gly Trp Val Ile Gln Tyr
                245                 250                 255

Ile Gln Leu Ser Ala Pro Thr Pro Glu Pro Lys Leu Tyr Gly Gln Ile
            260                 265                 270

Phe Gly Gln Asn Val Ile Gly Phe Val Leu Leu Ala Gly Met Leu
        275                 280                 285

Leu Gly Trp Leu
    290

<210> SEQ ID NO 33
<211> LENGTH: 316
<212> TYPE: PRT
<213> ORGANISM: Synechocystis sp.

<400> SEQUENCE: 33

Met Val Thr Ser Thr Lys Ile His Arg Gln His Asp Ser Met Gly Ala
 1               5                  10                  15

Val Cys Lys Ser Tyr Tyr Gln Leu Thr Lys Pro Arg Ile Ile Pro Leu
            20                  25                  30

Leu Leu Ile Thr Thr Ala Ala Ser Met Trp Ile Ala Ser Glu Gly Arg
        35                  40                  45

Val Asp Leu Pro Lys Leu Leu Ile Thr Leu Gly Gly Thr Leu Ala
    50                  55                  60

Ala Ala Ser Ala Gln Thr Leu Asn Cys Ile Tyr Asp Gln Asp Ile Asp
 65                  70                  75                  80

Tyr Glu Met Leu Arg Thr Arg Ala Arg Pro Ile Pro Ala Gly Lys Val
                 85                  90                  95

Gln Pro Arg His Ala Leu Ile Phe Ala Leu Ala Leu Gly Val Leu Ser
            100                 105                 110

Phe Ala Leu Leu Ala Thr Phe Val Asn Val Leu Ser Gly Cys Leu Ala
```

-continued

```
                115                 120                 125
Leu Ser Gly Ile Val Phe Tyr Met Leu Val Tyr Thr His Trp Leu Lys
    130                 135                 140

Arg His Thr Ala Gln Asn Ile Val Ile Gly Gly Ala Ala Gly Ser Ile
145                 150                 155                 160

Pro Pro Leu Val Gly Trp Ala Ala Val Thr Gly Asp Leu Ser Trp Thr
                165                 170                 175

Pro Trp Val Leu Phe Ala Leu Ile Phe Leu Trp Thr Pro Pro His Phe
            180                 185                 190

Trp Ala Leu Ala Leu Met Ile Lys Asp Asp Tyr Ala Gln Val Asn Val
        195                 200                 205

Pro Met Leu Pro Val Ile Ala Gly Glu Glu Lys Thr Val Ser Gln Ile
    210                 215                 220

Trp Tyr Tyr Ser Leu Leu Val Val Pro Phe Ser Leu Leu Leu Val Tyr
225                 230                 235                 240

Pro Leu His Gln Leu Gly Ile Leu Tyr Leu Ala Ile Ala Ile Ile Leu
                245                 250                 255

Gly Gly Gln Phe Leu Val Lys Ala Trp Gln Leu Lys Gln Ala Pro Gly
            260                 265                 270

Asp Arg Asp Leu Ala Arg Gly Leu Phe Lys Phe Ser Ile Phe Tyr Leu
        275                 280                 285

Met Leu Leu Cys Leu Ala Met Val Ile Asp Ser Leu Pro Val Thr His
    290                 295                 300

Gln Leu Val Ala Gln Met Gly Thr Leu Leu Gly
305                 310                 315

<210> SEQ ID NO 34
<211> LENGTH: 324
<212> TYPE: PRT
<213> ORGANISM: Synechocystis sp.

<400> SEQUENCE: 34

Met Ser Asp Thr Gln Asn Thr Gly Gln Asn Gln Ala Lys Ala Arg Gln
1               5                   10                  15

Leu Leu Gly Met Lys Gly Ala Ala Pro Gly Glu Ser Ser Ile Trp Lys
            20                  25                  30

Ile Arg Leu Gln Leu Met Lys Pro Ile Thr Trp Ile Pro Leu Ile Trp
        35                  40                  45

Gly Val Val Cys Gly Ala Ala Ser Ser Gly Gly Tyr Ile Trp Ser Val
    50                  55                  60

Glu Asp Phe Leu Lys Ala Leu Thr Cys Met Leu Leu Ser Gly Pro Leu
65                  70                  75                  80

Met Thr Gly Tyr Thr Gln Thr Leu Asn Asp Phe Tyr Asp Arg Asp Ile
                85                  90                  95

Asp Ala Ile Asn Glu Pro Tyr Arg Pro Ile Pro Ser Gly Ala Ile Ser
            100                 105                 110

Val Pro Gln Val Val Thr Gln Ile Leu Ile Leu Leu Val Ala Gly Ile
        115                 120                 125

Gly Val Ala Tyr Gly Leu Asp Val Trp Ala Gln His Asp Phe Pro Ile
    130                 135                 140

Met Met Val Leu Thr Leu Gly Gly Ala Phe Val Ala Tyr Ile Tyr Ser
145                 150                 155                 160

Ala Pro Pro Leu Lys Leu Lys Gln Asn Gly Trp Leu Gly Asn Tyr Ala
                165                 170                 175
```

```
Leu Gly Ala Ser Tyr Ile Ala Leu Pro Trp Trp Ala Gly His Ala Leu
            180                 185                 190

Phe Gly Thr Leu Asn Pro Thr Ile Met Val Leu Thr Leu Ile Tyr Ser
            195                 200                 205

Leu Ala Gly Leu Gly Ile Ala Val Val Asn Asp Phe Lys Ser Val Glu
            210                 215                 220

Gly Asp Arg Gln Leu Gly Leu Lys Ser Leu Pro Val Met Phe Gly Ile
225                 230                 235                 240

Gly Thr Ala Ala Trp Ile Cys Val Ile Met Ile Asp Val Phe Gln Ala
                245                 250                 255

Gly Ile Ala Gly Tyr Leu Ile Tyr Val His Gln Gln Leu Tyr Ala Thr
                260                 265                 270

Ile Val Leu Leu Leu Leu Ile Pro Gln Ile Thr Phe Gln Asp Met Tyr
            275                 280                 285

Phe Leu Arg Asn Pro Leu Glu Asn Asp Val Lys Tyr Gln Ala Ser Ala
            290                 295                 300

Gln Pro Phe Leu Val Phe Gly Met Leu Ala Thr Gly Leu Ala Leu Gly
305                 310                 315                 320

His Ala Gly Ile

<210> SEQ ID NO 35
<211> LENGTH: 307
<212> TYPE: PRT
<213> ORGANISM: Synechocystis sp.

<400> SEQUENCE: 35

Met Thr Glu Ser Ser Pro Leu Ala Pro Ser Thr Ala Pro Ala Thr Arg
1               5                   10                  15

Lys Leu Trp Leu Ala Ala Ile Lys Pro Pro Met Tyr Thr Val Ala Val
            20                  25                  30

Val Pro Ile Thr Val Gly Ser Ala Val Ala Tyr Gly Leu Thr Gly Gln
            35                  40                  45

Trp His Gly Asp Val Phe Thr Ile Phe Leu Leu Ser Ala Ile Ala Ile
        50                  55                  60

Ile Ala Trp Ile Asn Leu Ser Asn Asp Val Phe Asp Ser Asp Thr Gly
65              70                  75                  80

Ile Asp Val Arg Lys Ala His Ser Val Val Asn Leu Thr Gly Asn Arg
            85                  90                  95

Asn Leu Val Phe Leu Ile Ser Asn Phe Phe Leu Leu Ala Gly Val Leu
            100                 105                 110

Gly Leu Met Ser Met Ser Trp Arg Ala Gln Asp Trp Thr Val Leu Glu
            115                 120                 125

Leu Ile Gly Val Ala Ile Phe Leu Gly Tyr Thr Tyr Gln Gly Pro Pro
            130                 135                 140

Phe Arg Leu Gly Tyr Leu Gly Leu Gly Glu Leu Ile Cys Leu Ile Thr
145                 150                 155                 160

Phe Gly Pro Leu Ala Ile Ala Ala Tyr Tyr Ser Gln Ser Gln Ser
            165                 170                 175

Phe Ser Trp Asn Leu Leu Thr Pro Ser Val Phe Val Gly Ile Ser Thr
            180                 185                 190

Ala Ile Ile Leu Phe Cys Ser His Phe His Gln Val Glu Asp Asp Leu
            195                 200                 205

Ala Ala Gly Lys Lys Ser Pro Ile Val Arg Leu Gly Thr Lys Leu Gly
            210                 215                 220
```

```
Ser Gln Val Leu Thr Leu Ser Val Val Ser Leu Tyr Leu Ile Thr Ala
225                 230                 235                 240

Ile Gly Val Leu Cys His Gln Ala Pro Trp Gln Thr Leu Leu Ile Ile
                245                 250                 255

Ala Ser Leu Pro Trp Ala Val Gln Leu Ile Arg His Val Gly Gln Tyr
                260                 265                 270

His Asp Gln Pro Glu Gln Val Ser Asn Cys Lys Phe Ile Ala Val Asn
            275                 280                 285

Leu His Phe Phe Ser Gly Met Leu Met Ala Ala Gly Tyr Gly Trp Ala
        290                 295                 300

Gly Leu Gly
305

<210> SEQ ID NO 36
<211> LENGTH: 927
<212> TYPE: DNA
<213> ORGANISM: Synechocystis sp.

<400> SEQUENCE: 36
atggcaacta tccaagcttt ttggcgcttc tcccgccccc ataccatcat tggtacaact      60
ctgagcgtct gggctgtgta tctgttaact attctcgggg atggaaactc agttaactcc     120
cctgcttccc tggatttagt gttcggcgct tggctggcct gcctgttggg taatgtgtac     180
attgtcggcc tcaaccaatt gtgggatgtg gacattgacc gcatcaataa gccgaatttg     240
cccctagcta acgagatttt tctatcgcc caggccgtt ggattgtggg actttgtggc       300
gttgcttcct tggcgatcgc ctggggatta gggctatggc tggggctaac ggtgggcatt     360
agtttgatta ttggcacggc ctattcggtg ccgccagtga ggttaaagcg cttttccctg     420
ctggcggccc tgtgtattct gacggtgcgg ggaattgtgg ttaacttggg cttattttta     480
ttttttagaa ttggtttagg ttatcccccc actttaataa cccccatctg ggttttgact     540
ttatttatct tagttttcac cgtggcgatc gccattttta aagatgtgcc agatatggaa     600
ggcgatcggc aatttaagat tcaaacttta actttgcaaa tcggcaaaca aaacgttttt     660
cggggaacct taattttact cactggttgt tatttagcca tggcaatctg gggcttatgg     720
gcggctatgc ctttaaatac tgctttcttg attgtttccc atttgtgctt attagcctta     780
ctctggtggc ggagtcgaga tgtacactta gaaagcaaaa ccgaaattgc tagttttat      840 cagtttattt ggaagctatt tttcttagag tacttgctgt atcccttggc tctgtggtta     900
cctaattttt ctaatactat tttttag                                         927

<210> SEQ ID NO 37
<211> LENGTH: 308
<212> TYPE: PRT
<213> ORGANISM: Synechocystis sp.

<400> SEQUENCE: 37

Met Ala Thr Ile Gln Ala Phe Trp Arg Phe Ser Arg Pro His Thr Ile
1               5                   10                  15

Ile Gly Thr Thr Leu Ser Val Trp Ala Val Tyr Leu Leu Thr Ile Leu
            20                  25                  30

Gly Asp Gly Asn Ser Val Asn Ser Pro Ala Ser Leu Asp Leu Val Phe
        35                  40                  45

Gly Ala Trp Leu Ala Cys Leu Leu Gly Asn Val Tyr Ile Val Gly Leu
    50                  55                  60

Asn Gln Leu Trp Asp Val Asp Ile Asp Arg Ile Asn Lys Pro Asn Leu
```

```
                65                  70                  75                  80
Pro Leu Ala Asn Gly Asp Phe Ser Ile Ala Gln Gly Arg Trp Ile Val
                    85                  90                  95
Gly Leu Cys Gly Val Ala Ser Leu Ala Ile Ala Trp Gly Leu Gly Leu
                100                 105                 110
Trp Leu Gly Leu Thr Val Gly Ile Ser Leu Ile Ile Gly Thr Ala Tyr
                115                 120                 125
Ser Val Pro Pro Val Arg Leu Lys Arg Phe Ser Leu Leu Ala Ala Leu
            130                 135                 140
Cys Ile Leu Thr Val Arg Gly Ile Val Val Asn Leu Gly Leu Phe Leu
145                 150                 155                 160
Phe Phe Arg Ile Gly Leu Gly Tyr Pro Pro Thr Leu Ile Thr Pro Ile
                165                 170                 175
Trp Val Leu Thr Leu Phe Ile Leu Val Phe Thr Val Ala Ile Ala Ile
                180                 185                 190
Phe Lys Asp Val Pro Asp Met Glu Gly Asp Arg Gln Phe Lys Ile Gln
            195                 200                 205
Thr Leu Thr Leu Gln Ile Gly Lys Gln Asn Val Phe Arg Gly Thr Leu
        210                 215                 220
Ile Leu Leu Thr Gly Cys Tyr Leu Ala Met Ala Ile Trp Gly Leu Trp
225                 230                 235                 240
Ala Ala Met Pro Leu Asn Thr Ala Phe Leu Ile Val Ser His Leu Cys
                245                 250                 255
Leu Leu Ala Leu Leu Trp Trp Arg Ser Arg Asp Val His Leu Glu Ser
                260                 265                 270
Lys Thr Glu Ile Ala Ser Phe Tyr Gln Phe Ile Trp Lys Leu Phe Phe
            275                 280                 285
Leu Glu Tyr Leu Leu Tyr Pro Leu Ala Leu Trp Leu Pro Asn Phe Ser
        290                 295                 300
Asn Thr Ile Phe
305

<210> SEQ ID NO 38
<211> LENGTH: 1092
<212> TYPE: DNA
<213> ORGANISM: Synechocystis sp.

<400> SEQUENCE: 38
atgaaatttc cgccccacag tggttaccat tggcaaggtc aatcaccttt ctttgaaggt      60
tggtacgtgc gcctgctttt gccccaatcc ggggaaagtt ttgcttttat gtactccatc     120
gaaaatcctg ctagcgatca tcattacggc ggcggtgctg tgcaaatttt agggccggct     180
acgaaaaaac aagaaaatca ggaagaccaa cttgtttggc ggacatttcc ctcggtaaaa     240
aaattttggg ccagtcctcg ccagtttgcc ctagggcatt ggggaaaatg tagggataac     300
aggcaggcga aacccctact ctccgaagaa ttttttgcca cggtcaagga aggttatcaa     360
atccatcaaa atcagcacca aggacaaatc attcatggcg atcgccattg tcgttggcag     420
ttcaccgtag aaccggaagt aacttggggg agtcctaacc gatttcctcg ggctacagcg     480
ggttggcttt cctttttacc cttgtttgat cccggttggc aaattctttt agcccaaggt     540
agagcgcacg gctggctgaa atggcagagg gaacagtatg aatttgacca cgccctagtt     600
tatgccgaaa aaaattgggg tcactccttt ccctcccgct ggttttggct ccaagcaaat     660 tatttttcctg accatccagg actgagcgtc actgccgctg cggggaacg gattgttctt     720
```

-continued

```
ggtcgccccg aagaggtagc tttaattggc ttacatcacc aaggtaattt ttacgaattt    780
ggcccgggcc atggcacagt cacttggcaa gtagctccct ggggccgttg gcaattaaaa    840
gccagcaatg ataggtattg ggtcaagttg tccggaaaaa cagataaaaa aggcagttta    900
gtccacactc ccaccgccca gggcttacaa ctcaactgcc gagataccac tagggggctat   960 ttgtatttgc aattgggatc tgtgggtcac ggcctgatag tgcaagggga aacggacacc   1020
gcggggctag aagttggagg tgattgggt taacagagg aaaatttgag caaaaaaaca    1080
gtgccattct ga                                                       1092
```

<210> SEQ ID NO 39
<211> LENGTH: 363
<212> TYPE: PRT
<213> ORGANISM: Synechocystis sp.

<400> SEQUENCE: 39

```
Met Lys Phe Pro Pro His Ser Gly Tyr His Trp Gln Gly Gln Ser Pro
  1               5                  10                  15

Phe Phe Glu Gly Trp Tyr Val Arg Leu Leu Pro Gln Ser Gly Glu
             20                  25                  30

Ser Phe Ala Phe Met Tyr Ser Ile Glu Asn Pro Ala Ser Asp His His
         35                  40                  45

Tyr Gly Gly Gly Ala Val Gln Ile Leu Gly Pro Ala Thr Lys Lys Gln
     50                  55                  60

Glu Asn Gln Glu Asp Gln Leu Val Trp Arg Thr Phe Pro Ser Val Lys
 65                  70                  75                  80

Lys Phe Trp Ala Ser Pro Arg Gln Phe Ala Leu Gly His Trp Gly Lys
                 85                  90                  95

Cys Arg Asp Asn Arg Gln Ala Lys Pro Leu Leu Ser Glu Glu Phe Phe
            100                 105                 110

Ala Thr Val Lys Glu Gly Tyr Gln Ile His Gln Asn Gln His Gln Gly
        115                 120                 125

Gln Ile Ile His Gly Asp Arg His Cys Arg Trp Gln Phe Thr Val Glu
    130                 135                 140

Pro Glu Val Thr Trp Gly Ser Pro Asn Arg Phe Pro Arg Ala Thr Ala
145                 150                 155                 160

Gly Trp Leu Ser Phe Leu Pro Leu Phe Asp Pro Gly Trp Gln Ile Leu
                165                 170                 175

Leu Ala Gln Gly Arg Ala His Gly Trp Leu Lys Trp Gln Arg Glu Gln
            180                 185                 190

Tyr Glu Phe Asp His Ala Leu Val Tyr Ala Glu Lys Asn Trp Gly His
        195                 200                 205

Ser Phe Pro Ser Arg Trp Phe Trp Leu Gln Ala Asn Tyr Phe Pro Asp
    210                 215                 220

His Pro Gly Leu Ser Val Thr Ala Ala Gly Gly Glu Arg Ile Val Leu
225                 230                 235                 240

Gly Arg Pro Glu Glu Val Ala Leu Ile Gly Leu His His Gln Gly Asn
                245                 250                 255

Phe Tyr Glu Phe Gly Pro Gly His Gly Thr Val Thr Trp Gln Val Ala
            260                 265                 270

Pro Trp Gly Arg Trp Gln Leu Lys Ala Ser Asn Asp Arg Tyr Trp Val
        275                 280                 285

Lys Leu Ser Gly Lys Thr Asp Lys Lys Gly Ser Leu Val His Thr Pro
    290                 295                 300
```

```
Thr Ala Gln Gly Leu Gln Leu Asn Cys Arg Asp Thr Thr Arg Gly Tyr
305                 310                 315                 320

Leu Tyr Leu Gln Leu Gly Ser Val Gly His Gly Leu Ile Val Gln Gly
            325                 330                 335

Glu Thr Asp Thr Ala Gly Leu Glu Val Gly Gly Asp Trp Gly Leu Thr
            340                 345                 350

Glu Glu Asn Leu Ser Lys Lys Thr Val Pro Phe
        355                 360
```

<210> SEQ ID NO 40
<211> LENGTH: 56
<212> TYPE: DNA
<213> ORGANISM: Artificial Sequence
<220> FEATURE:
<223> OTHER INFORMATION: oligonucleotide adapter

<400> SEQUENCE: 40
cgcgatttaa atggcgcgcc ctgcaggcgg ccgcctgcag ggcgcgccat ttaaat        56

<210> SEQ ID NO 41
<211> LENGTH: 32
<212> TYPE: DNA
<213> ORGANISM: Artificial Sequence
<220> FEATURE:
<223> OTHER INFORMATION: oligonucleotide

<400> SEQUENCE: 41
tcgaggatcc gcggccgcaa gcttcctgca gg                                  32

<210> SEQ ID NO 42
<211> LENGTH: 32
<212> TYPE: DNA
<213> ORGANISM: Artificial Sequence
<220> FEATURE:
<223> OTHER INFORMATION: oligonucleotide

<400> SEQUENCE: 42
tcgacctgca ggaagcttgc ggccgcggat cc                                  32

<210> SEQ ID NO 43
<211> LENGTH: 32
<212> TYPE: DNA
<213> ORGANISM: Artificial Sequence
<220> FEATURE:
<223> OTHER INFORMATION: oligonucleotide

<400> SEQUENCE: 43
tcgacctgca ggaagcttgc ggccgcggat cc                                  32

<210> SEQ ID NO 44
<211> LENGTH: 32
<212> TYPE: DNA
<213> ORGANISM: Artificial Sequence
<220> FEATURE:
<223> OTHER INFORMATION: oligonucleotide

<400> SEQUENCE: 44
tcgaggatcc gcggccgcaa gcttcctgca gg                                  32

<210> SEQ ID NO 45
<211> LENGTH: 36
<212> TYPE: DNA
<213> ORGANISM: Artificial Sequence
<220> FEATURE:
<223> OTHER INFORMATION: oligonucleotide

<400> SEQUENCE: 45
tcgaggatcc gcggccgcaa gcttcctgca ggagct    36

<210> SEQ ID NO 46
<211> LENGTH: 28
<212> TYPE: DNA
<213> ORGANISM: Artificial Sequence
<220> FEATURE:
<223> OTHER INFORMATION: oligonucleotide

<400> SEQUENCE: 46
cctgcaggaa gcttgcggcc gcggatcc    28

<210> SEQ ID NO 47
<211> LENGTH: 36
<212> TYPE: DNA
<213> ORGANISM: Artificial Sequence
<220> FEATURE:
<223> OTHER INFORMATION: oligonucleotide

<400> SEQUENCE: 47
tcgacctgca ggaagcttgc ggccgcggat ccagct    36

<210> SEQ ID NO 48
<211> LENGTH: 28
<212> TYPE: DNA
<213> ORGANISM: Artificial Sequence
<220> FEATURE:
<223> OTHER INFORMATION: oligonucleotide

<400> SEQUENCE: 48
ggatccgcgg ccgcaagctt cctgcagg    28

<210> SEQ ID NO 49
<211> LENGTH: 39
<212> TYPE: DNA
<213> ORGANISM: Artificial Sequence
<220> FEATURE:
<223> OTHER INFORMATION: oligonucleotide

<400> SEQUENCE: 49
gatcacctgc aggaagcttg cggccgcgga tccaatgca    39

<210> SEQ ID NO 50
<211> LENGTH: 31
<212> TYPE: DNA
<213> ORGANISM: Artificial Sequence
<220> FEATURE:
<223> OTHER INFORMATION: oligonucleotide

<400> SEQUENCE: 50
ttggatccgc ggccgcaagc ttcctgcagg t    31

<210> SEQ ID NO 51
<211> LENGTH: 41
<212> TYPE: DNA
<213> ORGANISM: Artificial Sequence
<220> FEATURE:
<223> OTHER INFORMATION: Synthetic Oligonucleotides

<400> SEQUENCE: 51
ggatccgcgg ccgcacaatg gagtctctgc tctctagttc t    41

<210> SEQ ID NO 52

```
<211> LENGTH: 38
<212> TYPE: DNA
<213> ORGANISM: Artificial Sequence
<220> FEATURE:
<223> OTHER INFORMATION: Synthetic Oligonucleotides

<400> SEQUENCE: 52
ggatcctgca ggtcacttca aaaaaggtaa cagcaagt                                38

<210> SEQ ID NO 53
<211> LENGTH: 45
<212> TYPE: DNA
<213> ORGANISM: Artificial Sequence
<220> FEATURE:
<223> OTHER INFORMATION: Synthetic Oligonucleotides

<400> SEQUENCE: 53
ggatccgcgg ccgcacaatg gcgttttttg ggctctcccg tgttt                        45

<210> SEQ ID NO 54
<211> LENGTH: 40
<212> TYPE: DNA
<213> ORGANISM: Artificial Sequence
<220> FEATURE:
<223> OTHER INFORMATION: Synthetic Oligonucleotides

<400> SEQUENCE: 54
ggatcctgca ggttattgaa aacttcttcc aagtacaact                              40

<210> SEQ ID NO 55
<211> LENGTH: 38
<212> TYPE: DNA
<213> ORGANISM: Artificial Sequence
<220> FEATURE:
<223> OTHER INFORMATION: Synthetic Oligonucleotides

<400> SEQUENCE: 55
ggatccgcgg ccgcacaatg tggcgaagat ctgttgtt                                38

<210> SEQ ID NO 56
<211> LENGTH: 37
<212> TYPE: DNA
<213> ORGANISM: Artificial Sequence
<220> FEATURE:
<223> OTHER INFORMATION: Synthetic Oligonucleotides

<400> SEQUENCE: 56
ggatcctgca ggtcatggag agtagaagga aggagct                                 37

<210> SEQ ID NO 57
<211> LENGTH: 50
<212> TYPE: DNA
<213> ORGANISM: Artificial Sequence
<220> FEATURE:
<223> OTHER INFORMATION: Synthetic Oligonucleotides

<400> SEQUENCE: 57
ggatccgcgg ccgcacaatg gtacttgccg aggttccaaa gcttgcctct                   50

<210> SEQ ID NO 58
<211> LENGTH: 38
<212> TYPE: DNA
<213> ORGANISM: Artificial Sequence
<220> FEATURE:
<223> OTHER INFORMATION: Synthetic Oligonucleotides

<400> SEQUENCE: 58
```

```
ggatcctgca ggtcacttgt ttctggtgat gactctat                              38

<210> SEQ ID NO 59
<211> LENGTH: 38
<212> TYPE: DNA
<213> ORGANISM: Artificial Sequence
<220> FEATURE:
<223> OTHER INFORMATION: Synthetic Oligonucleotides

<400> SEQUENCE: 59
ggatccgcgg ccgcacaatg acttcgattc tcaacact                              38

<210> SEQ ID NO 60
<211> LENGTH: 36
<212> TYPE: DNA
<213> ORGANISM: Artificial Sequence
<220> FEATURE:
<223> OTHER INFORMATION: Synthetic Oligonucleotides

<400> SEQUENCE: 60
ggatcctgca ggtcagtgtt gcgatgctaa tgccgt                                36

<210> SEQ ID NO 61
<211> LENGTH: 22
<212> TYPE: DNA
<213> ORGANISM: Artificial Sequence
<220> FEATURE:
<223> OTHER INFORMATION: Region of slr1736 open reading frame

<400> SEQUENCE: 61
taatgtgtac attgtcggcc tc                                               22

<210> SEQ ID NO 62
<211> LENGTH: 60
<212> TYPE: DNA
<213> ORGANISM: Artificial Sequence
<220> FEATURE:
<223> OTHER INFORMATION: Region of slr1736 open reading frame

<400> SEQUENCE: 62
gcaatgtaac atcagagatt ttgagacaca acgtggcttt ccacaattcc ccgcaccgtc      60

<210> SEQ ID NO 63
<211> LENGTH: 22
<212> TYPE: DNA
<213> ORGANISM: Artificial Sequence
<220> FEATURE:
<223> OTHER INFORMATION: Region of slr1736 open reading frame

<400> SEQUENCE: 63
aggctaataa gcacaaatgg ga                                               22

<210> SEQ ID NO 64
<211> LENGTH: 63
<212> TYPE: DNA
<213> ORGANISM: Artificial Sequence
<220> FEATURE:
<223> OTHER INFORMATION: Region of slr1736 open reading frame

<400> SEQUENCE: 64
ggtatgagtc agcaacacct tcttcacgag gcagacctca gcggaattgg tttaggttat      60
ccc                                                                    63

<210> SEQ ID NO 65
```

```
<211> LENGTH: 26
<212> TYPE: DNA
<213> ORGANISM: Artificial Sequence
<220> FEATURE:
<223> OTHER INFORMATION: Primer

<400> SEQUENCE: 65
ggatccatgg ttgcccaaac cccatc                                          26

<210> SEQ ID NO 66
<211> LENGTH: 61
<212> TYPE: DNA
<213> ORGANISM: Artificial Sequence
<220> FEATURE:
<223> OTHER INFORMATION: Primer

<400> SEQUENCE: 66 caatgtaac atcagagatt ttgagacaca acgtggcttt gggtaagcaa caatgaccgg      60
c                                                                    61

<210> SEQ ID NO 67
<211> LENGTH: 25
<212> TYPE: DNA
<213> ORGANISM: Artificial Sequence
<220> FEATURE:
<223> OTHER INFORMATION: Oligonucleotide primer

<400> SEQUENCE: 67
gaattctcaa agccagccca gtaac                                           25

<210> SEQ ID NO 68
<211> LENGTH: 63
<212> TYPE: DNA
<213> ORGANISM: Artificial Sequence
<220> FEATURE:
<223> OTHER INFORMATION: Oligonucleotide primer

<400> SEQUENCE: 68
ggtatgagtc agcaacacct tcttcacgag gcagacctca gcgggtgcga aagggttttt    60
ccc                                                                  63

<210> SEQ ID NO 69
<211> LENGTH: 23
<212> TYPE: DNA
<213> ORGANISM: Artificial Sequence
<220> FEATURE:
<223> OTHER INFORMATION: End of open reading frame fragment

<400> SEQUENCE: 69
ccagtggttt aggctgtgtg gtc                                             23

<210> SEQ ID NO 70
<211> LENGTH: 21
<212> TYPE: DNA
<213> ORGANISM: Artificial Sequence
<220> FEATURE:
<223> OTHER INFORMATION: End of open reading frame fragment

<400> SEQUENCE: 70
ctgagttgga tgtattggat c                                               21

<210> SEQ ID NO 71
<211> LENGTH: 28
<212> TYPE: DNA
<213> ORGANISM: Artificial Sequence
```

```
<220> FEATURE:
<223> OTHER INFORMATION: Primer

<400> SEQUENCE: 71
ggatccatgg ttacttcgac aaaaatcc                                        28

<210> SEQ ID NO 72
<211> LENGTH: 60
<212> TYPE: DNA
<213> ORGANISM: Artificial Sequence
<220> FEATURE:
<223> OTHER INFORMATION: Primer

<400> SEQUENCE: 72
gcaatgtaac atcagagatt ttgagacaca acgtggcttt gctaggcaac cgcttagtac    60

<210> SEQ ID NO 73
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 73
gaattcttaa cccaacagta aagttccc                                        28

<210> SEQ ID NO 74
<211> LENGTH: 63
<212> TYPE: DNA
<213> ORGANISM: Artificial Sequence
<220> FEATURE:
<223> OTHER INFORMATION: Oligonucleotide primer

<400> SEQUENCE: 74
ggtatgagtc agcaacacct tcttcacgag gcagacctca gcgccggcat tgtcttttac    60
atg                                                                   63

<210> SEQ ID NO 75
<211> LENGTH: 20
<212> TYPE: DNA
<213> ORGANISM: Artificial Sequence
<220> FEATURE:
<223> OTHER INFORMATION: Open reading frame fragment

<400> SEQUENCE: 75
ggaacccttg cagccgcttc                                                 20

<210> SEQ ID NO 76
<211> LENGTH: 22
<212> TYPE: DNA
<213> ORGANISM: Artificial Sequence
<220> FEATURE:
<223> OTHER INFORMATION: Open reading frame fragment

<400> SEQUENCE: 76
gtatgcccaa ctggtgcaga gg                                              22

<210> SEQ ID NO 77
<211> LENGTH: 28
<212> TYPE: DNA
<213> ORGANISM: Artificial Sequence
<220> FEATURE:
<223> OTHER INFORMATION: Primer

<400> SEQUENCE: 77
```

```
ggatccatgt ctgacacaca aaataccg                                          28
```

<210> SEQ ID NO 78
<211> LENGTH: 62
<212> TYPE: DNA
<213> ORGANISM: Artificial Sequence
<220> FEATURE:
<223> OTHER INFORMATION: Primer

<400> SEQUENCE: 78

```
gcaatgtaac atcagagatt ttgagacaca acgtggcttt cgccaatacc agccaccaac      60
ag                                                                     62
```

<210> SEQ ID NO 79
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 79

```
gaattctcaa atccccgcat ggcctag                                          27
```

<210> SEQ ID NO 80
<211> LENGTH: 65
<212> TYPE: DNA
<213> ORGANISM: Artificial Sequence
<220> FEATURE:
<223> OTHER INFORMATION: Synthetic oligonucleotide primer

<400> SEQUENCE: 80

```
ggtatgagtc agcaacacct tcttcacgag gcagacctca gcggcctacg gcttggacgt      60
gtggg                                                                  65
```

<210> SEQ ID NO 81
<211> LENGTH: 21
<212> TYPE: DNA
<213> ORGANISM: Artificial Sequence
<220> FEATURE:
<223> OTHER INFORMATION: Open reading frame fragment

<400> SEQUENCE: 81

```
cacttggatt cccctgatct g                                                21
```

<210> SEQ ID NO 82
<211> LENGTH: 21
<212> TYPE: DNA
<213> ORGANISM: Artificial Sequence
<220> FEATURE:
<223> OTHER INFORMATION: Open reading frame fragment

<400> SEQUENCE: 82

```
gcaatacccg cttggaaaac g                                                21
```

<210> SEQ ID NO 83
<211> LENGTH: 29
<212> TYPE: DNA
<213> ORGANISM: Artificial Sequence
<220> FEATURE:
<223> OTHER INFORMATION: Primer

<400> SEQUENCE: 83

```
ggatccatga ccgaatcttc gccCctagc                                        29
```

```
<210> SEQ ID NO 84
<211> LENGTH: 61
<212> TYPE: DNA
<213> ORGANISM: Artificial Sequence
<220> FEATURE:
<223> OTHER INFORMATION: Primer

<400> SEQUENCE: 84
gcaatgtaac atcagagatt ttgagacaca acgtggcttt caatcctagg tagccgaggc      60
g                                                                      61

<210> SEQ ID NO 85
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 85
gaattcttag cccaggccag cccagcc                                          27

<210> SEQ ID NO 86
<211> LENGTH: 66
<212> TYPE: DNA
<213> ORGANISM: Artificial Sequence
<220> FEATURE:
<223> OTHER INFORMATION: Synthetic oligonucleotide primer

<400> SEQUENCE: 86
ggtatgagtc agcaacacct tcttcacgag gcagacctca gcggggaatt gatttgttta      60
attacc                                                                 66

<210> SEQ ID NO 87
<211> LENGTH: 21
<212> TYPE: DNA
<213> ORGANISM: Artificial Sequence
<220> FEATURE:
<223> OTHER INFORMATION: Open reading frame fragment

<400> SEQUENCE: 87
gcgatcgcca ttatcgcttg g                                                21

<210> SEQ ID NO 88
<211> LENGTH: 24
<212> TYPE: DNA
<213> ORGANISM: Artificial Sequence
<220> FEATURE:
<223> OTHER INFORMATION: Open reading frame fragment

<400> SEQUENCE: 88
gcagactggc aattatcagt aacg                                             24

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
ccatggattc gagtaaagtt gtcgc                                            25

<210> SEQ ID NO 90
<211> LENGTH: 25
<212> TYPE: DNA
```

<213> ORGANISM: Artificial Sequence
<220> FEATURE:
<223> OTHER INFORMATION: Primer

<400> SEQUENCE: 90
gaattcactt caaaaaaggt aacag                                   25

<210> SEQ ID NO 91
<211> LENGTH: 4550
<212> TYPE: DNA
<213> ORGANISM: Arabidopsis sp.

<400> SEQUENCE: 91

| | | | | | |
|---|---|---|---|---|---|
| attttacacc | aatttgatca | cttaactaaa | ttaattaaat | tagatgatta | tcccaccata | 60 |
| tttttgagca | ttaaaccata | aaccatagt | tataagtaac | tgttttaatc | gaatatgact | 120 |
| cgattaagat | taggaaaaat | ttataaccgg | taattaagaa | acattaacc | gtagtaaccg | 180 |
| taaatgccga | ttcctcccct | gtctaaaaga | cagaaaacat | atatttttatt | ttgccccata | 240 |
| tgtttcactc | tatttaattt | caggcacaat | acttttggtt | ggtaacaaaa | ctaaaaagga | 300 |
| caacacgtga | tactttttcct | cgtccgtcag | tcagattttt | tttaaactag | aaacaagtgg | 360 |
| caaatctaca | ccacattttt | tgcttaatct | attaacttgt | aagttttaaa | ttcctaaaaa | 420 |
| agtctaacta | attcttctaa | tataagtaca | ttccctaaat | ttcccaaaaa | gtcaaattaa | 480 |
| taattttcaa | aatctaatct | aaatatctaa | taattcaaaa | tcattaaaaa | gacacgcaac | 540 |
| aatgacacca | attaatcatc | ctcgacccac | acaattctac | agttctcatg | ctaaaccata | 600 |
| tttttttgctc | tctgttcctt | caaaatcatt | tctttctctt | ctttgattcc | caaagatcac | 660 |
| ttctttgtct | ttgattttttg | attttttttttc | tctctggcgt | gaaggaagaa | gctttatttc | 720 |
| atggagtctc | tgctctctag | ttcttctctt | gtttccgctg | gtaaatctcg | tccttttctg | 780 |
| gtttcaggtt | ttatttgttg | tttaggtttc | gttttttgtga | ttcagaacca | tacaaaaagt | 840 |
| ttgaactttt | ctgaatataa | aataaggaaa | aagtttcgat | ttttataatg | aattgtttac | 900 |
| tagatcgaag | taggtgacaa | aggttattgt | gtggagaagc | ataatttctg | ggcttgactt | 960 |
| tgaatttttgt | ttctcatgca | tgcaacttat | caatcagctg | gtgggttttg | ttggaagaag | 1020 |
| cagaatctaa | agctccactc | tttatcaggt | tcgttagggt | tttatgggtt | tttgaaatta | 1080 |
| aatactcaat | catcttagtc | tcattattct | attggttgaa | tcacattttc | taatttggaa | 1140 |
| tttatgagac | aatgtatgtt | ggacttagtt | gaagttcttc | tctttggtta | tagttgaagt | 1200 |
| gttactgatg | ttgtttagct | ctttacacca | atatatacac | ccaattttgc | agaaatccga | 1260 |
| gttctgcgtt | gtgattcgag | taaagttgtc | gcaaaaccga | agtttaggaa | caatcttgtt | 1320 |
| aggcctgatg | gtcaaggatc | ttcattgttg | ttgtatccaa | aacataagtc | gagatttcgg | 1380 |
| gttaatgcca | ctgcgggtca | gcctgaggct | ttcgactcga | atagcaaaca | gaagtctttt | 1440 |
| agagactcgt | tagatgcgtt | ttacaggttt | tctaggcctc | atacagttat | tggcacagtt | 1500 |
| aagtttctct | ttaaaaatgt | aactctttta | aaacgcaatc | tttcagggtt | tcaaggaga | 1560 |
| taacattagc | tctgtgattg | gatttgcagg | tgcttagcat | tttatctgta | tctttcttag | 1620 |
| cagtagagaa | ggtttctgat | atatctcctt | tacttttcac | tggcatcttg | gaggtaatga | 1680 |
| atatataaca | cataatgacc | gatgaagaag | atacattttt | ttcgtctctc | tgtttaaaca | 1740 |
| attgggtttt | gttttcaggc | tgttgttgca | gctctcatga | tgaacattta | catagttggg | 1800 |
| ctaaatcagt | tgtctgatgt | tgaaatagat | aaggtaacat | gcaaattttc | ttcatatgag | 1860 |
| ttcgagagac | tgatgagatt | aatagcagct | agtgcctaga | tcatctctat | gtgggttttt | 1920 |

-continued

```
gcaggttaac aagccctatc ttccattggc atcaggagaa tattctgtta acaccggcat    1980
tgcaatagta gcttccttct ccatcatggt atggtgccat tttcacaaaa tttcaacttt    2040
tagaattcta taagttactg aaatagtttg ttataaatcg ttatagagtt tctggcttgg    2100
gtggattgtt ggttcatggc cattgttctg ggctcttttt gtgagtttca tgctcggtac    2160
tgcatactct atcaatgtaa gtaagttttct caatactaga atttggctca atcaaaatc    2220 tgcagtttct agttttaggt taatgaggtt ttaataactt acttctacta caaacagttg    2280
ccacttttac ggtggaaaag atttgcattg gttgcagcaa tgtgtatcct cgctgtccga    2340
gctattattg ttcaaatcgc cttttatcta catattcagg tactaaacca ttttccttat    2400
gttttgtagt tgttttcatc aaaatcactt ttatattact aaagctgtga aactttgttg    2460
cagacacatg tgtttggaag accaatcttg ttcactaggc ctcttatttt cgccactgcg    2520
tttatgagct ttttctctgt cgttattgca ttgtttaagg taaacaaaga tggaaaaaga    2580
ttaaatctat gtatacttaa agtaaagcat tctactgtta ttgatgagaa gttttctttt    2640
ttggttggat gcaggatata cctgatatcg aagggagataa gatattcgga atccgatcat    2700
tctctgtaac tctgggtcag aaacgggtac gatatctaaa ctaaagaaat tgttttgact    2760
caagtgttgg attaagatta cagaagaaag aaaactgttt ttgtttcttg caaaattcag    2820
gtgttttgga catgtgttac actacttcaa atggcttacg ctgttgcaat tctagttgga    2880 gcccacatctc cattcatatg gagcaaagtc atctcggtaa caatctttct ttacccatcg    2940
aaaactcgct aattcatcgt ttgagtggta ctggtttcat tttgttccgt tctgttgatt    3000 tttttttcagg ttgtgggtca tgttatactc gcaacaactt tgtgggctcg agctaagtcc    3060
gttgatctga gtagcaaaac cgaaataact tcatgttata tgttcatatg gaaggttaga    3120
ttcgtttata aatagagtct ttactgcctt tttatgcgct ccaatttgga attaaaatag    3180
cctttcagtt tcatcgaatc accattatac tgataaattc tcatttctgc atcagctctt    3240
ttatgcagag tacttgctgt tacctttttt gaagtgactg acattagaag agaagaagat    3300
ggagataaaa gaataagtca tcactatgct tctgttttta ttacaagttc atgaaattag    3360
gtagtgaact agtgaattag agttttattc tgaaacatgg cagactgcaa aaatatgtca    3420
aagatatgaa tttctgttgg gtaaagaagt ctctgcttgg gcaaaatctt aaggttcggt    3480
gtgttgatat aatgctaagc gaagaaatcg attctatgta gaaatttccg aaactatgtg    3540
taaacatgtc agaacatctc cattctatat cttcttctgc aagaaagctc tgtttttatc    3600
acctaaactc tttatctctg tgtagttaag atatgtatat gtacgtgact acattttttt    3660
gttgatgtaa tttgcagaac gtatggattt ttgttagaaa gcatgagttc gaaagtatat    3720
gtttatatat atggataatt cagacctaac gtcgaagctc acaagcataa attcactact    3780
atagtttgct ctgtaataga tagttccatt gatgtcttga aactgtacgt aactgcctgg    3840 gcgtttgtg gttgatactg actactgagt gttctttgtg agtgttgtaa gtatacaaga    3900
agaagaatat aggctcacgg gaacgactgt ggtggaagat gaaatggaga tcatcacgta    3960
gcggctttgc caaagaccga gtcacgatcg agtctatgaa gtctttacag ctgctgatta    4020
tgattgacca ttgcttagag acgcattgga atcttactag ggacttgcct gggagtttct    4080
tcaagtacgt gtcagatcat acgatgtagg agatttcacg gctttgatgt gtttgtttgg    4140
agtcacaatg cttaatgggc ttattggccc aataatagct agctcttttg ctttagccgt    4200
ttcgtttgtc ccctggtggt gagtattatt agggtatggt gtgaccaaag tcaccagacc    4260
```

```
tagagtgaat ctagtagagt cctagaccat ggtccatggc ttttatttgt aatttgaaaa    4320
atgaacaatt cttttgtaa ggaaaacttt tatatagtag acgtttacta tatagaaact    4380
agttgaacta acttcgtgca attgcataat aatggtgtga aatagagggt gcaaaactca    4440
ataaacattt cgacgtacca agagttcgaa acaataagca aaatagattt ttttgcttca    4500
gactaatttg tacaatgaat ggttaataaa ccattgaagc ttttattaat                4550

<210> SEQ ID NO 92
<211> LENGTH: 4450
<212> TYPE: DNA
<213> ORGANISM: Arabidopsis sp.

<400> SEQUENCE: 92
tttaggttac aaaatcaatg atattgcgta tgtcaactat aaaagccaaa agtaaagcct      60
cttgtttgac cagaaggtca tgatcattgt atacatacag ccaaactacc tcctggaaga    120
aaagacatgg atcccaaaca acaacaatag cttcttttac aagaaccagt agtaactagt    180
cactaatcta aaagagttaa gtttcagctt ttctggcaat ggctccttga tcatttcaat    240
cctgaaggag acccactttg tagcaagacc atgtcctctg tttcacttac agtgtgtctc    300
aaaagtctac ttcaattctt catatatagg ttcctcacac tacagcttca tcctcattcg    360
ttgacagaga gagagtcttt attgaaaact tcttccaagt acaactccac taaatataat    420
agcaccaaac cacttgttcg acacaaatct gtacagatat aaaaacacta ttaggttttc    480
caaggcaaat cacataattg gattgtgaaa gagtacaaaa gataaaccca aattttcata    540 cttttctactg cagtcagcac cagatgataa gtcagctgtc cctatttgcc atcctaactg    600
tcctgatgca gcggccagtg atgcgtaata ttgccaccct taatcattag agcgagaaac    660
aaaaagaatc aaaagacagt aaatggaatt aggaatcaca aatgagtcct tgtaaagttt    720
attgagtacc gagatctgca ctgaatccag aaagtgcaag aaaacctatg gatgctgtgc    780
caaatccagt taaccaaagc tttgtattat caccgaatct aagggctgtt gacttaacac    840
caacttttac atcatcttct ttgtcctgga gacacaatat attagacatt agtccatgga    900
aaaaaaatga tttaacctag aatatctcaa aattacttgc ataaaaactg aacttgagct    960
gaaattttgg gttcgtagct tgtggcatat actatttcat tttcaatggg ccacaaaggt   1020
aactttcttt tctcacttct gttgcaaacg ggaagacttt tatggggcta actcttcact   1080
taaagtatag aaatcagatg gaaaggtgg gagatcaggg taattttctt ctttatgatt   1140
gacaaaagtc gaacatcgaa atggatgcat ttgcatgaga catgaaacaa aagctgaaaa   1200
agaaatctgt ggtggtgaag ctagaaaaag aaaacaaagc aagcaatatg cacacattga   1260
gattaactac tttgctactg gtcataatca aatagatttt gaagctaaaa aataaaaagt   1320
gaatatacct gatgtgcata aatagtatca taaacaaggg tccagcagac tccggagaga   1380
tagagaggga gtacaataga tggtgctatg cttcctttaa ctgcagtcca tcctaacaat   1440
gctccccagt ttatggtcaa acctaaaaag gcttgaggct gcaattataa aaacgaatca   1500
atcataagaa aatcagaaaa tatataatgt ctaactttga gaagccagaa tagatttaaa   1560
ttacccaaaa tgtaaacctc ttcataagtg ggtaggaaaa gacaagtaac aaagatgaag   1620
cccctaaaac acggctgcag aatatacata ctgaaatgag ctcaagtaga aaagaatttg   1680
atcacaaaac taaagacaag acctgagaac atatcttcag aatttgggcc aactacataa   1740
gggtgaacca tatgtgtatg tgaattttta aacaaacact tgcaaatacg cgactttagg   1800
gcaagtaaaa aatccaaaca aacctgtaat tgttaagttg gagaagaatc cctaagccta   1860
```

-continued

| | |
|---|---|
| aaagcaactg cagcccgaga atccaatccc cttgaaatgg tgtcaaaaga ccactggcga | 1920 |
| taggtcttag ttttgtacga tcaacctgga tataaaagaa atttgtaaga caacataatc | 1980 |
| taaaacaaaa caaccataca aaatcttgag ctttacatac aagcaaccca tctttgttta | 2040 |
| tggaagaatg aatccagtta catgaatgct gtgtatctac cctaactact aaacacatat | 2100 |
| ttcaatcgaa aaacatattc caccttcacc atatctaaca cctgaagtct ttcacttttt | 2160 |
| gaacgaagtc atcagaacat gcagataagc tattacccaa aacagagata tgactggaaa | 2220 |
| tgttgtcgta aattgatcca acatagaaaa atcaagacca gttccagatg tcaaagcaat | 2280 |
| aacactttcc caccatggtt acagaaacca tagttacaca aaacatgttt cctaaaccaa | 2340 |
| catactaaag ggatatataa atttgacatc actttatcac cataccataa gatagcttaa | 2400 |
| aaacaaactg acctttgtat ctatgtcctg atcaagcaga tcatttatag tacaaccagc | 2460 |
| acctctaaga agtaatgctc cgcaaccaaa taaagccata tatttaaaac ttggaaggct | 2520 |
| tccaggatca gcagccaacg caatcgacct atacaacaat gatggagatt cagagtatcg | 2580 |
| atctatttac atagctctgg aactagatcc atgacgaaac atggaacatc gttataatat | 2640 |
| ctaaagactt ccaaacagat tcctgagtaa gaaacccagt ggaactatag tactgtaaca | 2700 |
| tatataaaat caaagaaaac tcaggtttat agcattatcc aatcctgatt tctgccaatc | 2760 |
| cttaaccact ctcccatgct atcaaaaacc tcagctcaag atcatactac ctaattgcct | 2820 |
| atgagctctt gggaagatca ttatggattt gataactgaa aaaagtaaca gagaaatagc | 2880 |
| agactgcaag aactactcca aacttctcca ctgatatgta tgtagtctaa caataataaa | 2940 |
| cagacataaa ttcttttatc aagcttcaag agcaagttag tcagaaaaca tcacagccaa | 3000 |
| accaaccagg aaaacacata actttatcac ataaaactaa atttaatgta atctgactta | 3060 |
| acataaaacca tcctttggga cgaaaggaaa ctatataaac atgcagtctt tctttccctc | 3120 |
| agctattctt tcgatggat tataatgaat ctcaaaagtg aaatgtcttg attctcagct | 3180 |
| acattactca aaggcgaaga taaacttacc acatacaagg ccacgcaagc aaccaagttc | 3240 |
| caatgggttt atccaatcga gcaagcttag cataacctct aacttcttct ggtaaataca | 3300 |
| aatctatcca agaagcttcc ttaacaacaa caccatcact cttctcctta tcatctttct | 3360 |
| tcggcttttcc ctccaaaacc gaagaagacg acgacattcc acaaattaat ctgtaattcc | 3420 |
| aaccaacacc aaaaaacttc tcctgatgca attctcttcc tttactccat acttggtaat | 3480 |
| tatcattcca tgaaggataa cacttagtga aaggatttgt gtaatgggta gtcacaggat | 3540 |
| tggacaagga tttatgttgt gattgcaaaa gagcagagga agaagatgga gttacggaga | 3600 |
| cggaagattt caacaaccgt cttgaaacac gggagagccc aaaaaacgcc atctttgaga | 3660 |
| gaaattgttg cctggaagaa acaaagactt gagatttcaa acgtaagtga attcttacga | 3720 |
| acgaaagcta acttctcaag agaatcagat tagtgattcc tcaaaaacaa acaaaactat | 3780 |
| ctaatttcag tttcgagtga tgaagcctta agaatctaga acctccatgg cgtttctaat | 3840 |
| ctctcagaga taatcgaatt ccttaaacaa tcaaagctta gaaagagaag aacaacaaca | 3900 |
| acaacaaaaa aaatcagatt aacaaccgac cagagagcaa cgacgacgcc ggcgagaaag | 3960 |
| agcacgtcgt ctcggagcaa gacttcttct ccagtaaccc ggatggatcg ttaatgggcc | 4020 |
| tgtagattat tatatttggg ccgaaacaat tgggtcagca aaaacttggg ggataatgaa | 4080 |
| gaaacacgta cagtatgcat ttaggctcca aattaattgg ccatataatt cgaatcagat | 4140 |
| aaactaatca accccctacct tactattttc tcactgtttt tatttctacc ttagtagttg | 4200 |

```
aagaaacact tttatttatc ttttcgggac ccaaatttga taggatcggg ccattactca    4260
tgagcgtcag acacatatta gccttatcag attagtgggg taaggttttt ttaattcggt    4320
aagaagcaac aatcaatgtc ggagaaatta aagaatctgc atgggcgtgg cgtgatgata    4380
tgtgcatatg gagtcagttg ccgatcatat ataactattt ataaactaca tataaagact    4440
actaatagat                                                           4450
```

<210> SEQ ID NO 93
<211> LENGTH: 2850
<212> TYPE: DNA
<213> ORGANISM: Arabidopsis sp.

<400> SEQUENCE: 93

```
aattaaaatt tgagcggtct aaaccattag accgtttaga gatccctcca acccaaaata      60
gtcgattttc acgtcttgaa catatattgg gccttaatct gtgtggttag taaagacttt     120
tattggtcaa agaaaaacaa ccatggccca acatgttgat actttttattt aattatacaa    180 gtacccctga attctctgaa atatatttga ttgacccaga tattaatttt aattatcatt     240
tcctgtaaaa gtgaaggagt caccgtgact cgtcgtaatc tgaaaccaat ctgttcatat     300
gatgaagaag tttctctcgt tctcctccaa cgcgtagaaa attctgacgg cttaacgatg     360
tggcgaagat ctgttgttta tcgtttctct tcaagaatct ctgtttcttc ttcgttacca     420
aaccctagac tgattccttg gtcccgcgaa ttatgtgccg ttaatagctt ctcccagcct     480
ccggtctcga cggaatcaac tgctaagtta gggatcactg tgttagatc tgatgccaat      540 cgagttttg ccactgctac tgccgccgct acagctacag ctaccaccgg tgagatttcg      600
tctagagttg cggctttggc tggattaggg catcactacg ctcgttgtta ttgggagctt     660
tctaaagcta aacttaggta tgtgtttact tttcttttct catgaaaaat ctgaaaattt     720
ccaattgttg gattcttaaa ttctcatttg ttttatggtt gtagtatgct tgtggttgca     780
acttctggaa ctgggtatat tctgggtacg ggaaatgctg caattagctt cccggggctt     840
tgttacacat gtgcaggaac catgatgatt gctgcatctg ctaattcctt gaatcaggtc     900
attgaaatgt tgagaagttc ataaatttcg aatccttgtt gtgtttatgt agttgatctt     960
gcttgcttat gtttatgtag ttgaaaagtt taaaaatttc taatccttgg tagttgatct    1020
cgcttgtttg tttttttcatt ttctagattt ttgagataag caatgattct aagatgaaaa   1080
gaacgatgct aaggccattg ccttcaggac gtattagtgt tccacacgct gttgcatggg    1140
ctactattgc tggtgcttct ggtgcttgtt tgttggccag caaggtgaat gttgttttt     1200 ttatatgtga tttctttgtt ttatgaatgg gtgattgaga gattatggat ctaaactttt    1260
gcttccacga caaggttatt gcagactaat atgttggctg ctggacttgc atctgccaat    1320
cttgtacttt atgcgtttgt ttatactccg ttgaagcaac ttcaccctat caatacatgg    1380
gttggcgctg ttgttggtgc tatcccaccc ttgcttgggt aaattttgt tcctttttctt    1440 ctttattta gcagattctg ttttgttgga tactgctttt aattcaaaat gtagtcatgg      1500
ttcaccaatt ctatgcttat ctatttgtgt gttgtcagg tgggcggcag cgtctggtca     1560
gatttcatac aattcgatga ttcttccagc tgctctttac ttttggcaga tacctcattt    1620
tatgcccctt gcacatctct gccgcaatga ttatgcagct ggagggtaag accatatggt    1680
gtcatatgag attagaatgt ctccttccat gtagtgttga tcttgaacta gttcaatttc    1740
gtggaatgat cagagtgtcc tagatagtgt cacagcagtc gacatttag tggctagata     1800 atgagttctt tccgttagag ataaacattc gcgaacattg tttccagctt ccgcgaccca    1860
```

```
acttctgatt ttgtttcttg gtaccttgtt ttcagttaca agatgttgtc actctttgat    1920
ccgtcaggga agagaatagc agcagtggct ctaaggaact gcttttacat gatccctctc    1980
ggtttcatcg cctatgactg tgagtcttgt agattcatct tttttttgta gtttattgac    2040
tgcattgctg tatctgattt ttgctgttcc ttccaatttt tgtgacaggg gggttaacct    2100
caagttggtt ttgcctcgaa tcaacacttc tcacactagc aatcgctgca acagcatttt    2160
cattctaccg agaccggacc atgcataaag caaggaaaat gttccatgcc agtcttctct    2220
tccttcctgt tttcatgtct ggtcttcttc tacaccgtgt ctctaatgat aatcagcaac    2280
aactcgtaga agaagccgga ttaacaaatt ctgtatctgg tgaagtcaaa actcagaggc    2340
gaaagaaacg tgtggctcaa cctccggtgg cttatgcctc tgctgcaccg tttcctttcc    2400
tcccagctcc ttccttctac tctccatgat aacctttaag caagctattg aattttttgga   2460 aacagaaatt aaaaaaaaaa tctgaaaagt tcttaagttt aatctttggt taataatgaa    2520
gtggagaacg catacaagtt tatgtatttt ttctcatctc cacataattg tatttttttct   2580 ctaagtatgt ttcaaatgat acaaaataca tactttatca attatctgat caaattgatg    2640 aattttttgag ctttgacgtg ttaggtctat ctaataaacg tagtaacgaa tttggttttg    2700
gaaatgaaat ccgataaccg atgatggtgt agagttaaac gattaaaccg ggttggttaa    2760
aggtctcgag tctcgacggc tgcggaaatc ggaaaatcac gattgaggac tttgagctgc    2820
cacgaagatg gcgatgaggt tgaaatcaat                                     2850

<210> SEQ ID NO 94
<211> LENGTH: 3660
<212> TYPE: DNA
<213> ORGANISM: Arabidopsis sp.

<400> SEQUENCE: 94
tatttgtatt tttattgtta aattttatga tttcacccgg tatatatcat cccatattaa      60
tattagattt attttttggg ctttatttgg gttttcgatt taaactgggc ccattctgct     120
tcaatgaaac cctaatgggt tttgtttggg ctttggattt aaaccgggcc cattctgctt     180
caatgaaggt cctttgtcca acaaaactaa catccgacac aactagtatt gccaagagga     240
tcgtgccaca tggcagttat tgaatcaaag gccgccaaaa ctgtaacgta gacattactt     300
atctccggta acggacaacc actcgtttcc cgaaacagca actcacagac tcacaccact     360
ccagtctccg gcttaactac caccagagac gattctctct tccgtcggtt ctatgacttc     420
gattctcaac actgtctcca ccatccactc ttccagagtt acctccgtcg atcgagtcgg     480
agtcctctct cttcggaatt cggattccgt tgagttcact cgccggcgtt ctggtttctc     540
gacgttgatc tacgaatcac ccggtagtta gcattctgtt ggatagattg atgaatgttt     600
tcttcgattt ttttttttact gatcttgttg tggatctctc gtagggcgga gatttgttgt     660
gcgtgcggcg gagactgata ctgataaagg tatgattttt tagttgtttt tatttctct      720 ctcttcaaaa ttctctttc aaacactgtg gcgtttgaat ttccgacggc agttaaatct      780
cagacacctg acaaggcacc agccggtggt tcaagcatta accagcttct cggtatcaaa    840
ggagcatctc aagaaactgt aattttgttc atctcctcag aatcttttaa attatcatat    900
ttgtggataa tgatgtgtta gtttaggaat tttcctacta aaggtaatct ctttttgagga   960 caagtcttgt tttagctta gaatgatgt gaaaatgttg tttgttagct aaaaagagtt      1020
tgttgttata ttctgtattc agaataaatg gaagattcgt cttcagctta caaaccagt     1080
```

```
cacttggcct ccactggttt ggggagtcgt ctgtggtgct gctgcttcag gtaatcatac    1140
gaacctcttt tggatcatgc aatactgtac agaaagtttt tcattttcc ttccaattgt    1200 ttcttctggc agggaacttt cattggaccc cagaggatgt tgctaagtcg attctttgca    1260
tgatgatgtc tggtccttgt cttactggct atacacaggt ctggttttac acaacaaaaa    1320
gctgacttgt tcttattcta gtgcatttgc ttggtgctac aataacctag acttgtcgat    1380
ttccagacaa tcaacgactg gtatgataga gatatcgacg caattaatga gccatatcgt    1440
ccaattccat ctggagcaat atcagagcca gaggtaactg agacagaaca ttgtgagctt    1500
ttatctcttt tgtgattctg atttctcctt actccttaaa atgcaggtta ttacacaagt    1560
ctgggtgcta ttattgggag gtcttggtat tgctggaata ttagatgtgt gggtaagttg    1620
gcccttctga cattaactag tacagttaaa gggcacatca gatttgctaa aatcttccct    1680
tatcaggcag ggcataccac tcccactgtc ttctatcttg ctttgggagg atcattgcta    1740
tcttatatat actctgctcc acctcttaag gtaagtttta ttcctaactt ccactctcta    1800
gtgataagac actccatcca agttttggag ttttgaatat cgatatctga actgatctca    1860
ttgcagctaa aacaaaatgg atgggttgga aattttgcac ttggagcaag ctatattagt    1920
ttgccatggt aagatatctc gtgtatcaat aatatatggc gttgttctca tctcattgat    1980
ttgtttcttg ctcacttgac tgataggtgg gctggccaag cattgtttgg cactcttacg    2040
ccagatgttg ttgttctaac actcttgtac agcatagctg gggtactctt ttggcaaacc    2100
ttttatgttg cttttttcgt tatctgttgt aatatgctct tgcttcatgt tgtaccttg    2160 tgataatgca gttaggaata gccattgtta acgacttcaa aagtgttgaa ggagatagag    2220
cattaggact tcagtctctc ccagtagctt ttggcaccga aactgcaaaa tggatatgcg    2280
ttggtgctat agacattact cagctttctg ttgccggtat gtactatcca ctgtttttgt    2340
gcagctgtgg cttctatttc ttttccttga tcttatcaac tggatattca ccaatggtaa    2400
agcacaaatt aatgaagctg aatcaacaaa ggcaaaacat aaaagtacat tctaatgaaa    2460
tgagctaatg aagaggaggc atctactttt atgtttcatt agtgtgattg atggattttc    2520
atttcatgct tctaaaacaa gtattttcaa cagtgtcatg aaataacaga acttatatct    2580
tcatttgtac ttttactagt ggatgagtta cacaatcatt gttatagaac caaatcaaag    2640
gtagagatca tcattagtat atgtctattt tggttgcagg atatctatta gcatctggga    2700
aaccttatta tgcgttggcg ttggttgctt tgatcattcc tcagattgtg ttccaggtaa    2760
agacgttaac agtctcacat tataattaat caaattcttg tcactcgtct gattgctaca    2820
ctcgcttcta taaactgcag tttaaatact ttctcaagga ccctgtcaaa tacgacgtca    2880
agtaccaggt aagtcaactt agtacacatg tttgtgttct tttgaaatat ctttgagagg    2940
tctcttaatc agaagttgct tgaaacactc atcttgatta caggcaagcg cgcagccatt    3000
cttggtgctc ggaatatttg taacggcatt agcatcgcaa cactgaaaaa ggcgtatttt    3060
gatgggtttt tgtcgaaagc agaggtgttg acacatcaaa tgtgggcaag tgatggcatc    3120
aactagttta aaagattttg taaaatgtat gtaccgttat tactagaaac aactcctgtt    3180
gtatcaattt agcaaaacgg ctgagaaatt gtaattgatg ttaccgtatt tgcgctccat    3240
ttttgcattt cctgctcata tcgaggattg gggtttatgt tagttctgtc acttctctgc    3300
tttcagaatg tttttgtttt ctgtagtgga ttttaactat tttcatcact ttttgtattg    3360
attctaaaca tgtatccaca taaaaacagt aatatacaaa aatgatactt cctcaaactt    3420
tttataatct aaatctaaca actagctagt aacccaacta acttcataca attaatttga    3480
```

| | |
|---|---|
| gaaactacaa agactagact atacatatgt tatttaacaa cttgaaactg tgttattact | 3540 |
| acctgatttt tttctattct acagccattt gatatgctgc aatcttaaca tatcaagtct | 3600 |
| cacgttgttg gacacaacat actatcacaa gtaagacacg aagtaaaacc aaccggcaac | 3660 |

<210> SEQ ID NO 95
<211> LENGTH: 1236
<212> TYPE: DNA
<213> ORGANISM: Glycine sp.

<400> SEQUENCE: 95

| | |
|---|---|
| atggattcac tgcttcttcg atctttccct aatattaata acgcctcttc tctcaccacc | 60 |
| actggtgcaa atttctccag gactaaatct ttcgccaaca tttaccatgc aagttcttat | 120 |
| gtgccaaatg cttcatggca caataggaaa atccaaaaag aatataattt tttgaggttt | 180 |
| cggtggccaa gtttgaacca tcattacaaa ggcattgagg gagcgtgtac atgtaaaaaa | 240 |
| tgtaatataa aatttgttgt gaaagcgacc tctgaaaaat ctcttgagtc tgaacctcaa | 300 |
| gcttttgatc caaaaagcat tttggactct gtcaagaatt ccttggatgc tttctacagg | 360 |
| ttttccaggc ctcacacagt tattggcaca gcattaagca taatttctgt gtctcttctt | 420 |
| gctgttgaga aaatatcaga tatatctcca ttatttttta ctggtgtgtt ggaggctgtg | 480 |
| gttgctgccc tgtttatgaa tatttatatt gttggtttga atcaattgtc tgatgttgaa | 540 |
| atagacaaga taaacaagcc gtatcttcca ttagcatctg gggaatattc ctttgaaact | 600 |
| ggtgtcacta ttgttgcatc ttttttcaatt ctgagttttt ggcttggctg ggttgtaggt | 660 |
| tcatggccat tattttgggc cctttttgta agctttgtgc taggaactgc ttattcaatc | 720 |
| aatgtgcctc tgttgagatg gaagaggttt gcagtgcttg cagcgatgtg cattctagct | 780 |
| gttcgggcag taatagttca acttgcattt ttccttcaca tgcagactca tgtgtacaag | 840 |
| aggccacctg tcttttcaag accattgatt tttgctactg cattcatgag cttcttctct | 900 |
| gtagttatag cactgtttaa ggatatacct gacattgaag gagataaagt atttggcatc | 960 |
| caatctttttt cagtgcgttt aggtcagaag ccggtgttct ggacttgtgt tacccttctt | 1020 |
| gaaatagctt atggagtcgc cctcctggtg ggagctgcat ctccttgtct ttggagcaaa | 1080 |
| attttcacgg gtctgggaca cgctgtgctg gcttcaattc tctggtttca tgccaaatct | 1140 |
| gtagatttga aaagcaaagc ttcgataaca tccttctata tgtttatttg gaagctattt | 1200 |
| tatgcagaat acttactcat tccttttgtt agatga | 1236 |

<210> SEQ ID NO 96
<211> LENGTH: 1188
<212> TYPE: DNA
<213> ORGANISM: Glycine sp.

<400> SEQUENCE: 96

| | |
|---|---|
| atggattcga tgcttcttcg atctttttcct aatattaaca acgcttcttc tctcgccacc | 60 |
| actggttctt atttgccaaa tgcttcatgg cacaatagga aatccaaaaa agaatataat | 120 |
| tttttgaggt ttcggtggcc aagtttgaac caccattaca aaagcattga aggagggtgt | 180 |
| acatgtaaaa aatgtaatat aaaatttgtt gtgaaagcga cctctgaaaa atcttttgag | 240 |
| tctgaacccc aagcttttga tccaaaaagc attttggact ctgtcaagaa ttccttggat | 300 |
| gctttctaca ggttttccag acctcacaca gttattggca cagcattaag cataatttct | 360 |
| gtgtccctcc ttgctgttga gaaaatatca gatatatctc cattattttt tactggtgtg | 420 |

-continued

```
ttggaggctg tggttgctgc cctgtttatg aatatttata ttgttggttt gaatcaattg    480
tctgatgttg aaatagacaa gataaacaag ccgtatcttc cattagcatc tggggaatat    540
tcctttgaaa ctggtgtcac tattgttgca tcttttttca attctgagttt ttggcttggc   600 tgggttgtag gttcatggcc attatttttgg gccctttttg taagctttgt gctaggaact   660
gcttattcaa tcaatgtgcc tctgttgaga tggaagaggt ttgcagtgct gcagcgatg    720 tgcattctag ctgttcgggc agtaatagtt caacttgcat ttttccttca catccagact    780
catgtataca agaggccacc tgtctttttca agatcattga ttttttgctac tgcattcatg   840 agcttcttct ctgtagttat agcactgttt aaggatatac ctgacattga aggagataaa    900
gtatttggca tccaatcttt ttcagtgcgt ttaggtcaga agccggtatt ctggacttgt    960
gttatccttc ttgaaatagc ttatggagtc gccctcctgg tgggagctgc atctccttgt   1020
ctttggagca aaattgtcac gggtctggga cacgctgttc tggcttcaat tctctggttt   1080
catgccaaat ctgtagattt gaaaagcaaa gcttcgataa catccttcta tatgtttatt   1140
tggaagctat tttatgcaga atacttactc attccttttg ttagatga                 1188
```

<210> SEQ ID NO 97
<211> LENGTH: 395
<212> TYPE: PRT
<213> ORGANISM: Glycine sp.

<400> SEQUENCE: 97

```
Met Asp Ser Met Leu Leu Arg Ser Phe Pro Asn Ile Asn Asn Ala Ser
1               5                   10                  15

Ser Leu Ala Thr Thr Gly Ser Tyr Leu Pro Asn Ala Ser Trp His Asn
            20                  25                  30

Arg Lys Ile Gln Lys Glu Tyr Asn Phe Leu Arg Phe Arg Trp Pro Ser
        35                  40                  45

Leu Asn His His Tyr Lys Ser Ile Glu Gly Gly Cys Thr Cys Lys Lys
    50                  55                  60

Cys Asn Ile Lys Phe Val Val Lys Ala Thr Ser Glu Lys Ser Phe Glu
65                  70                  75                  80

Ser Glu Pro Gln Ala Phe Asp Pro Lys Ser Ile Leu Asp Ser Val Lys
                85                  90                  95

Asn Ser Leu Asp Ala Phe Tyr Arg Phe Ser Arg Pro His Thr Val Ile
            100                 105                 110

Gly Thr Ala Leu Ser Ile Ile Ser Val Ser Leu Leu Ala Val Glu Lys
        115                 120                 125

Ile Ser Asp Ile Ser Pro Leu Phe Phe Thr Gly Val Leu Glu Ala Val
    130                 135                 140

Val Ala Ala Leu Phe Met Asn Ile Tyr Ile Val Gly Leu Asn Gln Leu
145                 150                 155                 160

Ser Asp Val Glu Ile Asp Lys Ile Asn Lys Pro Tyr Leu Pro Leu Ala
                165                 170                 175

Ser Gly Glu Tyr Ser Phe Glu Thr Gly Val Thr Ile Val Ala Ser Phe
            180                 185                 190

Ser Ile Leu Ser Phe Trp Leu Gly Trp Val Val Gly Ser Trp Pro Leu
        195                 200                 205

Phe Trp Ala Leu Phe Val Ser Phe Val Leu Gly Thr Ala Tyr Ser Ile
    210                 215                 220

Asn Val Pro Leu Leu Arg Trp Lys Arg Phe Ala Val Leu Ala Ala Met
225                 230                 235                 240
```

-continued

```
Cys Ile Leu Ala Val Arg Ala Val Ile Val Gln Leu Ala Phe Phe Leu
                245                 250                 255

His Ile Gln Thr His Val Tyr Lys Arg Pro Pro Val Phe Ser Arg Ser
            260                 265                 270

Leu Ile Phe Ala Thr Ala Phe Met Ser Phe Ser Val Val Ile Ala
        275                 280                 285

Leu Phe Lys Asp Ile Pro Asp Ile Glu Gly Asp Lys Val Phe Gly Ile
    290                 295                 300

Gln Ser Phe Ser Val Arg Leu Gly Gln Lys Pro Val Phe Trp Thr Cys
305                 310                 315                 320

Val Ile Leu Leu Glu Ile Ala Tyr Gly Val Ala Leu Leu Val Gly Ala
                325                 330                 335

Ala Ser Pro Cys Leu Trp Ser Lys Ile Val Thr Gly Leu Gly His Ala
            340                 345                 350

Val Leu Ala Ser Ile Leu Trp Phe His Ala Lys Ser Val Asp Leu Lys
        355                 360                 365

Ser Lys Ala Ser Ile Thr Ser Phe Tyr Met Phe Ile Trp Lys Leu Phe
    370                 375                 380

Tyr Ala Glu Tyr Leu Leu Ile Pro Phe Val Arg
385                 390                 395

<210> SEQ ID NO 98
<211> LENGTH: 411
<212> TYPE: PRT
<213> ORGANISM: Glycine sp.

<400> SEQUENCE: 98

Met Asp Ser Leu Leu Arg Ser Phe Pro Asn Ile Asn Asn Ala Ser
1               5                   10                  15

Ser Leu Thr Thr Thr Gly Ala Asn Phe Ser Arg Thr Lys Ser Phe Ala
                20                  25                  30

Asn Ile Tyr His Ala Ser Ser Tyr Val Pro Asn Ala Ser Trp His Asn
            35                  40                  45

Arg Lys Ile Gln Lys Glu Tyr Asn Phe Leu Arg Phe Arg Trp Pro Ser
        50                  55                  60

Leu Asn His His Tyr Lys Gly Ile Glu Gly Ala Cys Thr Cys Lys Lys
65                  70                  75                  80

Cys Asn Ile Lys Phe Val Lys Ala Thr Ser Glu Lys Ser Leu Glu
                85                  90                  95

Ser Glu Pro Gln Ala Phe Asp Pro Lys Ser Ile Leu Asp Ser Val Lys
            100                 105                 110

Asn Ser Leu Asp Ala Phe Tyr Arg Phe Ser Arg Pro His Thr Val Ile
        115                 120                 125

Gly Thr Ala Leu Ser Ile Ile Ser Val Ser Leu Leu Ala Val Glu Lys
    130                 135                 140

Ile Ser Asp Ile Ser Pro Leu Phe Phe Thr Gly Val Leu Glu Ala Val
145                 150                 155                 160

Val Ala Ala Leu Phe Met Asn Ile Tyr Ile Val Gly Leu Asn Gln Leu
                165                 170                 175

Ser Asp Val Glu Ile Asp Lys Ile Asn Lys Pro Tyr Leu Pro Leu Ala
            180                 185                 190

Ser Gly Glu Tyr Ser Phe Glu Thr Gly Val Thr Ile Val Ala Ser Phe
        195                 200                 205

Ser Ile Leu Ser Phe Trp Leu Gly Trp Val Val Gly Ser Trp Pro Leu
    210                 215                 220
```

```
Phe Trp Ala Leu Phe Val Ser Phe Val Leu Gly Thr Ala Tyr Ser Ile
225                 230                 235                 240

Asn Val Pro Leu Leu Arg Trp Lys Arg Phe Ala Val Leu Ala Ala Met
            245                 250                 255

Cys Ile Leu Ala Val Arg Ala Val Ile Val Gln Leu Ala Phe Phe Leu
        260                 265                 270

His Met Gln Thr His Val Tyr Lys Arg Pro Pro Val Phe Ser Arg Pro
            275                 280                 285

Leu Ile Phe Ala Thr Ala Phe Met Ser Phe Ser Val Val Ile Ala
        290                 295                 300

Leu Phe Lys Asp Ile Pro Asp Ile Glu Gly Asp Lys Val Phe Gly Ile
305                 310                 315                 320

Gln Ser Phe Ser Val Arg Leu Gly Gln Lys Pro Val Phe Trp Thr Cys
                325                 330                 335

Val Thr Leu Leu Glu Ile Ala Tyr Gly Val Ala Leu Leu Val Gly Ala
            340                 345                 350

Ala Ser Pro Cys Leu Trp Ser Lys Ile Phe Thr Gly Leu Gly His Ala
        355                 360                 365

Val Leu Ala Ser Ile Leu Trp Phe His Ala Lys Ser Val Asp Leu Lys
370                 375                 380

Ser Lys Ala Ser Ile Thr Ser Phe Tyr Met Phe Ile Trp Lys Leu Phe
385                 390                 395                 400

Tyr Ala Glu Tyr Leu Leu Ile Pro Phe Val Arg
            405                 410

<210> SEQ ID NO 99
<211> LENGTH: 964
<212> TYPE: DNA
<213> ORGANISM: Oryza sp.

<400> SEQUENCE: 99
gagcagcact gggtcttaca ttccaatgga gctcgcctgt tgctttcatt acatgcttcg    60
tgactttatt tgctttggtc attgctataa ccaaagatct cccagatgtt gaagggatc    120
ggaagtatca aatatcaact ttggcgacaa agctcggtgt cagaaacatt gcatttcttg    180
gctctggttt attgatagca aatttatgttg ctgctattgc tgtagctttt ctcatgcctc    240
aggctttcag gcgcactgta atggtgcctg tgcatgctgc ccttgccgtt ggtataattt    300
tccagacatg ggttctggag caagcaaaat atactaagga tgctatttca cagtactacc    360
ggttcatttg gaatctcttc tatgctgaat acatcttctt cccgttgata tagagaccaa    420
gcaatctgat atggtctgca tgttgagtgc ggcaaaaact agaagcccat atgaacagtg    480
ggagtagggg aacgaacatg ccatccatgg gaagactctg ataactctct ctcgcccggg    540
ctgtaaaggg taagcactgt tgggcatata tatgaaagga aggtgataaa gcagggatgc    600
taaattgcta ctgggatcct caaaggctta tagtggtcac cagtggaatg tgccttaata    660
atttggttac ccagcagagc aagttttttgc aggttattag gtaatatctt tgagggaatg    720
aacttagatt tcattgtttt aaggtctggt cacacaacgg gtagtagtgc tggagcggca    780
aaaaacgacc ttgttttaca ctaccaaggg aggttaactc tagttttcat gtgaccactt    840
accttgagag ttgagaccat ggaatcactt gtcgactcct cggcttgtat atttctagtg    900
tcagcatttg cattctcctc cccacttgta cttgaaaagt tgaagacaac ttttttgttt    960
gtgt                                                                964
```

<210> SEQ ID NO 100
<211> LENGTH: 421
<212> TYPE: DNA
<213> ORGANISM: Triticum sp.

<400> SEQUENCE: 100

```
cgtccgcgga cgcgtgggtg cttattcagt caatctgccg cactttctat ggaagagatc        60
tgctgttgtt gcagcactct gcatattagc agtgcgtgcg gtgatagttc aactggcatt       120
ttttctccac attcagacat ttgttttcag aaggccggca gacttttcaa agccattgat       180
atttgcaact gccttcatga cattcttctc agttgtaata gcattattca aggatatacc       240
cgatattgaa ggggaccgca tctttggaat ccaatctttt agtggtagac taggtcaaag       300
caggggtttc tggacttgcg ttggcctact tgaggttgcc tacggtgttg cgatactgag       360
ggggtaact tcttccagtt tgtggagcaa atctataact gttgtgggcc atgcaatcct       420
c                                                                        421
```

<210> SEQ ID NO 101
<211> LENGTH: 705
<212> TYPE: DNA
<213> ORGANISM: Allium porrum

<400> SEQUENCE: 101

```
gtttccccccc ctcgaatttt tttttttttt tttacttca tttttctgtg aataaattct        60
taaaaagac aaagaaaacc actggatatc ctaaattcaa cataggctat tgtcattcaa       120
tgataatctt taacacaaca tacaacatga atataattaa ggagaaatga tctgcaattg       180
ttgaaagaac tctccgtttt taagatgaca attaaagcgt tgttaattcc agccatttct       240
gcctccatta tctactcatc ttctcttgcg attcttttcc atgtaggtca taaaccctca       300
tcttacaaaa ggaatgagca agtactcagc atagaagagc ttccacacga acatataaaa       360
agatgtaata gtggttttgg tcattggtcc atgagatcta gcacgattcc aaagtaacga       420
cccaagaatt gcatgaccta tcactgttaa gcatttgctc cataggcatg aggaagtagc       480
tccaacaacc atgacaacag tgtaggccat ctcaaggaga tatatacata tccaaaacac       540
cctctcctgg ccaaggcgca cgctgaaaga atggatgcca aatattttgt ctccgtctat       600
atcaggtata tccttaaata gagcaataac aactgagaag aagctcatga aggcagttgc       660
aaatatcaat ggccttgtga aacttgctgg tcttttgaaa acaaa                       705
```

<210> SEQ ID NO 102
<211> LENGTH: 637
<212> TYPE: DNA
<213> ORGANISM: Allium porrum
<220> FEATURE:
<221> NAME/KEY: misc_feature
<222> LOCATION: (1)...(637)
<223> OTHER INFORMATION: n = A, T, C, or G

<400> SEQUENCE: 102

```
nattcggcac gagttttgaa gaagttaagc atggactccc tccttaccaa gccagttgta        60
atacctctgc cttctccagt ttgttcacta ccaatcttgc gaggcagttc tgcaccaggg       120
cagtattcat gtagaaacta caatccaata agaattcaaa ggtgcctcgt aaattatgaa       180
catgtgaaac caaggtttac aacatgtagt aggtctcaaa aacttggtca tgtaaaagcc       240
acatccgagc attctttaga atctggatcc gaaggataca ctcctagaag catatgggaa       300
gccgtactag cttcactgaa tgttctatac aaattttcac gacctcacac aataatagga       360
```

```
acagcaatgg gcataatgtc agtttctttg cttgttgtcg agagcctatc cgatatttct    420
cctctgtttt ttgtgggatt attagaggct gtggttgctg cattgtttat gaatgtttac    480
attgtaggtc tgaatcaatt atttgacata gaaatagaca aggtcaataa acctgatctt    540
cctcttgcat ctggagaata ctcaccaaga gctggtactg ctattgtcat tgcttcagcc    600
atcatgagct ttggcattgg atggttagtt ggctctt                             637

<210> SEQ ID NO 103
<211> LENGTH: 677
<212> TYPE: DNA
<213> ORGANISM: Brassica napus

<400> SEQUENCE: 103
tttttttttt tttttttcaa aaagaccaat cctttagtat gtacatgaac aaagtgattt    60
tgtctccaag ctacaaagaa gaagaagaga ggtatacaaa gaaaactaca atgttcacc    120 atgaatgcta aagaaggggg aataacagat actctgcgta aagagattc catataaacc    180 ggtaatatcc tgctatagct tcctttgtgt agtttgcttt tctagcacc catgtctgga    240 aaaccaagca tgaagccaag atcatatgtg caggaatcat caagctacct ctaaaaacct    300
gaggcatgta aaagctagt gatatggcag aaatatagtt cactagcaga agtccagaac    360
cgaggaatgc aatgttcctc actccaagct ttgttgctag tgttgatat tggaacttgc    420 gatctccttc aacatcagga agatcttttg taatagcaat gactagtgca aacagtgtca    480
caaaagacgt gatgaaagcc acaggtgcac tccactgaaa cgaaagtcca agagcagctc    540
tagtagcatg gtacacacca aaattaagaa gaaaacctcg taccgtggca ataataagaa    600
acgctgcaac tggaaatctc ttcattctaa atggtggaac agaatagatg gtccccagat    660
cggacgcgtg ggtcgac                                                   677

<210> SEQ ID NO 104
<211> LENGTH: 1431
<212> TYPE: DNA
<213> ORGANISM: Zea sp.

<400> SEQUENCE: 104
ccacgcgtcc gcccggccaa gggatggacg cgcttcgcct acggccgtcc ctcctccccg    60
tgcggcccgg cgcggcccgc ccgcgagatc attttctacc accatgttgt tccatacaac    120
gaaatggtga aggacgaatt tgcttttcta gccaaaggac ccaaggtcct accttgcatc    180
accatcagaa attcttcgaa tggaaatcct cctattgtag gatatcacat cggtcattaa    240
atacttctgt taatgcttcg gggcaacagc tgcagtctga acctgaaaca catgattcta    300
caaccatctg gagggcaata tcatcttctc tagatgcatt ttacagattt tcccggccac    360
atactgtcat aggaacagca ttaagcatag tctcagtttc ccttctagct gtccagagct    420
tgtctgatat atcacctttg ttcctcactg gtttgctgga ggcagtggta gctgcccttt    480
tcatgaatat ctatattgtt ggactgaacc agttattcga cattgagata gacaaggtta    540
acaagccaac tcttccattg gcatctgggg aatacaccct tgcaactggg gttgcaatag    600
tttcggtctt tgccgctatg agctttggcc ttggatgggc tgttggatca caacctctgt    660
tttgggctct tttcataagc tttgttcttg ggactgcata ttcaatcaat ctgccgtacc    720
ttcgatggaa gagatttgct gttgttgcag cactgtgcat attagcagtt cgtgcagtga    780
ttgttcagct ggccttttttt ctccacattc agactttgt tttcaggaga ccggcagtgt    840
```

| | |
|---|---|
| tttctaggcc attattattt gcaactggat ttatgacgtt cttctctgtt gtaatagcac | 900 |
| tattcaagga tatacctgac atcgaaggga accgcatatt cgggatccga tccttcagcg | 960 |
| tccggttagg gcaaaagaag gtcttttgga tctgcgttgg cttgcttgag atggcctaca | 1020 |
| gcgttgcgat actgatggga gctacctctt cctgtttgtg gagcaaaaca gcaaccatcg | 1080 |
| ctggccattc catacttgcc gcgatcctat ggagctgcgc gcgatcggtg gacttgacga | 1140 |
| gcaaagccgc aataacgtcc ttctacatgt tcatctggaa gctgttctac gcggagtacc | 1200 |
| tgctcatccc tctggtgcgg tgagcgcgag gcgaggtggt ggcagacgga tcggcgtcgg | 1260 |
| cggggcggca aacaactcca cgggagaact gagtgccgg aagtaaactc ccgtttgaaa | 1320 |
| gttgaagcgt gcaccaccgg caccgggcag agagagacac ggtggctgga tggatacgga | 1380 |
| tggccccccc aataaattcc cccgtgcatg gtaaaaaaaa aaaaaaaaa a | 1431 |

<210> SEQ ID NO 105
<211> LENGTH: 1870
<212> TYPE: DNA
<213> ORGANISM: Zea sp.

<400> SEQUENCE: 105

| | |
|---|---|
| gccgcgcagc gcgacgagcg ccacctgctt gctgccgcgt gcctgcgtgc gtgtgcgtcc | 60 |
| accactgacc ccgcgcccgc ccgcgcgccc tgccccctcca ctccacttgc tcactcgtcg | 120 |
| cggcccgctt ccccccccggc caagggatgg acgcgcttcg cctacggccg tccctcctcc | 180 |
| ccgtgcggcc cggcgcggcc cgcccgcgag atcattttct accaccatgt tgttccatac | 240 |
| aacgaaatgg tgaaggacga atttgctttt ctagccaaag gacccaaggt cctaccttgc | 300 |
| atcaccatca gaaattcttc gaatggaaat cctcctattg taggatatca catcggtcat | 360 |
| taaatacttc tgttaatgct tcgggcaac agctgcagtc tgaacctgaa acacatgatt | 420 |
| ctacaaccat ctggagggca atatcatctt ctctagatgc attttacaga ttttcccggc | 480 |
| cacatactgt cataggaaca gcattaagca tagtctcagt ttcccttcta gctgtccaga | 540 |
| gcttgtctga tatatcacct tgttcctca ctggtttgct ggaggcagtg gtagctgccc | 600 |
| ttttcatgaa tatctatatt gttggactga accagttatt cgacattgag atagacaagg | 660 |
| ttaacaagcc aactcttcca ttggcatctg gggaatacac ccttgcaact ggggttgcaa | 720 |
| tagtttcggt ctttgccgct atgagctttg gccttggatg ggctgttgga tcacaacctc | 780 |
| tgttttgggc tcttttcata agctttgttc ttgggactgc atattcaatc aatctgccgt | 840 |
| accttcgatg gaagagattt gctgttgttg cagcactgtg catattagca gttcgtgcag | 900 |
| tgattgttca gctggccttt tttctccaca ttcagacttt tgttttcagg agaccggcag | 960 |
| tgttttctag gccattatta tttgcaactg gatttatgac gttcttctct gttgtaatag | 1020 |
| cactattcaa ggatatacct gacatcgaag gggaccgcat attcgggatc cgatccttca | 1080 |
| gcgtccggtt agggcaaaag aaggtctttt ggatctgcgt tggcttgctt gagatggcct | 1140 |
| acagcgttgc gatactgatg ggagctacct cttcctgttt gtggagcaaa acagcaacca | 1200 |
| tcgctggcca ttccatactt gccgcgatcc tatggagctg cgcgcgatcg gtggacttga | 1260 |
| cgagcaaagc cgcaataacg tccttctaca tgttcatctg gaagctgttc tacgcggagt | 1320 |
| acctgctcat ccctctggtg cggtgagcgc gaggcgaggt ggtggcagac ggatcggcgt | 1380 |
| cggcggggcg gcaaacaact ccacgggaga acttgagtgc cggaagtaaa ctcccgtttg | 1440 |
| aaagttgaag cgtgcaccac cggcaccggg cagagagaga cacggtggct ggatggatac | 1500 |
| ggatggcccc cccaataaat tccccccgtgc atggtacccc acgctgcttg atgatatccc | 1560 |

-continued

| | |
|---|---|
| atgtgtccgg gtgaccggac ctgatcgtct ctagagagat tggttgcaca acgtccaaca | 1620 |
| tagcccgtag gtattgctac cactgctagt atgatactcc ttcctagtcc ttgccagcac | 1680 |
| cagtgaccca aacttggtcg gctgagctca gcgctcagca gctttacgtg catctgcgcc | 1740 |
| ttgacttgtg cagtgggcgt cgctagcatg aatgatgtat ggtgcgtcac ggcctgacgg | 1800 |
| ttcgtcagtc tgggccgtgt tttgtgtccg aggaagatcg tctgtcagag atctggattg | 1860 |
| cctcgctgct | 1870 |

<210> SEQ ID NO 106
<211> LENGTH: 642
<212> TYPE: DNA
<213> ORGANISM: Zea sp.

<400> SEQUENCE: 106

| | |
|---|---|
| cggccggact cttctgactt ggcaaccgcc gcgcagcgcg acgagcgcca cctgcttgct | 60 |
| gccgcgtgcc tgcgtgcgtg tgcgtccacc actgaccccg cgcccgcccg ccgcccctgc | 120 |
| ccctccactc cacttgctca ctcgtcggct cgtcgcggcc cgcttccccc ccggccaagg | 180 |
| gatggacgcg cttcgcctac ggccgtccct cctcccccgtg cggcccggcg cggcccgccc | 240 |
| gcgaggcagt ggtagctgcc cttttcatga atatctatat tgttggactg aaccagttat | 300 |
| tcgacattga gatagacaag gttaacaagc caactcttcc attggcatct ggggaataca | 360 |
| cccttgcaac tggggttgca atagtttcgg tctttgccgc tatgagcttt ggccttggat | 420 |
| gggctgttgg atcacaacct ctgttttggg ctcttttcat aagctttgtt cttgggactg | 480 |
| catattcaat caatctgccg taccttcgat ggaagagatt tgctgttgtt gcagcactgt | 540 |
| gcatattagc agttcgtgca gtgattgttc agctggcctt ttttctccac attcagactt | 600 |
| ttgttttcag gagaccggca gtgttttcta ggccattatt at | 642 |

<210> SEQ ID NO 107
<211> LENGTH: 362
<212> TYPE: DNA
<213> ORGANISM: Gossypium sp.

<400> SEQUENCE: 107

| | |
|---|---|
| cccacgcgtc cgaacattgt ttgcacttgt tattgccata accaaggatc ttccagatgt | 60 |
| agaaggagat cgcaaatttc aaatatcaac attagcaaca aagcttggag ttagaaatat | 120 |
| tgcatttctt ggttccggac ttctactggt gaattatgtt gctgctgtgt tggctgcaat | 180 |
| atacatgcct caggctttca ggcgtagttt aatgatacct gctcatatct ttttggcggt | 240 |
| ctgcttgatt tttcagacat gggtgttgga acaagcaaat tacaaaaagg aagcaatctc | 300 |
| ggggttctat cgtttcatat ggaatctctt ctatgcagag tatgcgattt tccccttcgt | 360 |
| gt | 362 |

<210> SEQ ID NO 108
<211> LENGTH: 575
<212> TYPE: DNA
<213> ORGANISM: Lycopersicon sp.

<400> SEQUENCE: 108

| | |
|---|---|
| cagatcaatt ccagttcctg ctgagttttc tccactcaaa accagttcac atgcaatagt | 60 |
| acgggttttg aaatgtaaag catggaagag accaaaaaag cactattcct cttcaatgaa | 120 |
| gttgcagcgg cagtatatca cgcaagagca tgttggagga agtgatctaa gcactattgc | 180 |

| | |
|---|---:|
| tgctgataaa aaacttaaag ggagattttt ggtgcacgca tcatctgaac accctcttga | 240 |
| atctcaacct tctaaaagtc cttgggactc agttaatgat gccgtagatg ctttctacag | 300 |
| gttctcgcgg ccccatacca taataggaac agcattgagc ataatttcag tttctctcct | 360 |
| tgcagttgag aagttctctg atttttctcc attattttc actggggtgt tagaggccat | 420 |
| tgttgctgcc ctattcatga acatttacat agttggttta aaccagttgt ctgacatcga | 480 |
| aatagacaag gtaaacaagc catatcttcc attggcatca ggggaatact ctgtacaaac | 540 |
| tggagtgatt gttgtgtcgt cttttgccat tttga | 575 |

<210> SEQ ID NO 109
<211> LENGTH: 1663
<212> TYPE: DNA
<213> ORGANISM: Arabidopsis sp.

<400> SEQUENCE: 109

| | |
|---|---:|
| aacaccaaac acacaatttc acattctttt gcatatttct tcttcttctt ccattatgga | 60 |
| gatacggagc ttgattgttt ctatgaaccc taatttatct tcctttgagc tctctcgccc | 120 |
| tgtatctcct ctcactcgct cactagttcc gttccgatcg actaaactag ttccccgctc | 180 |
| catttctagg gggatcccgt cgatctccac cccgaatagt gaaactgaca agatctccgt | 240 |
| taaacctgtt tacgtcccga cgtctcccaa tcgcgaactc cggactcctc acagtggata | 300 |
| ccatttcgat ggaacacctc ggaagttctt cgagggatgg tggatccggg tttccatccc | 360 |
| agagaagagg gagagttttt gttttatgta ttctgtggag aatcctgcat tcggcagag | 420 |
| tttgtcacca ttggaagtgg ctctatatgg acctagattc actggtgttg gagctcagat | 480 |
| tcttggcgct aatgataaat attttatgcca atacgaacaa gactctcaca atttctgggg | 540 |
| agatcgacat gagctagttt tggggaatac ttttagtgct gtgccaggcg caaaggctcc | 600 |
| aaacaaggag gttccaccag aggaatttaa cagaagagtg tccgaagggt tccaagctac | 660 |
| tccattttgg catcaaggtc acatttgcga tgatggccgt actgactatg cggaaactgt | 720 |
| gaaatctgct cgttgggagt atagtactcg tcccgtttac ggttgggtg atgttggggc | 780 |
| caaacagaag tcaactgcag gctggcctgc agctttcct gtatttgagc ctcattggca | 840 |
| gatatgcatg gcaggaggcc tttccacagg gtggatagaa tggggcggtg aaaggtttga | 900 |
| gtttcgggat gcaccttctt attcagagaa gaattggggt ggaggcttcc aagaaaatg | 960 |
| gttttgggtc cagtgtaatg tcttgaagg ggcaactgga gaagttgctt taaccgcagg | 1020 |
| tggcgggttg aggcaattgc ctggattgac tgagacctat gaaaatgctg cactggtttg | 1080 |
| tgtacactat gatggaaaaa tgtacgagtt tgttccttgg aatggtgttg ttagatggga | 1140 |
| aatgtctccc tggggttatt ggtatataac tgcagagaac gaaaaccatg tggtggaact | 1200 |
| agaggcaaga acaaatgaag cgggtacacc tctgcgtgct cctaccacag aagttgggct | 1260 |
| agctacggct tgcagagata gttgttacgg tgaattgaag ttgcagatat gggacggctc | 1320 |
| atatgatgga agtaaaggca aggtgatatt agagacaaag agctcaatgg cagcagtgga | 1380 |
| gataggagga ggaccgtggt ttgggacatg gaaaggagat acgagcaaca cgcccgagct | 1440 |
| actaaaacag gctcttcagg tcccattgga tcttgaaagc gccttaggtt tggtcccttt | 1500 |
| cttcaagcca ccgggtctgt aacattgatg agtgttttgt ttgttgatag agacccatgt | 1560 |
| gatgaatgaa gccttagtca tgtcattgct agcttcacta ttatgtatgt atgatttag | 1620 |
| ttcgttcggt ccttgtggta aatgatacgg gccagtgtaa agt | 1663 |

<210> SEQ ID NO 110
<211> LENGTH: 488
<212> TYPE: PRT
<213> ORGANISM: Arabidopsis sp.

<400> SEQUENCE: 110

```
Met Glu Ile Arg Ser Leu Ile Val Ser Met Asn Pro Asn Leu Ser Ser
1               5                   10                  15

Phe Glu Leu Ser Arg Pro Val Ser Pro Leu Thr Arg Ser Leu Val Pro
            20                  25                  30

Phe Arg Ser Thr Lys Leu Val Pro Arg Ser Ile Ser Arg Val Ser Ala
        35                  40                  45

Ser Ile Ser Thr Pro Asn Ser Glu Thr Asp Lys Ile Ser Val Lys Pro
    50                  55                  60

Val Tyr Val Pro Thr Ser Pro Asn Arg Glu Leu Arg Thr Pro His Ser
65                  70                  75                  80

Gly Tyr His Phe Asp Gly Thr Pro Arg Lys Phe Phe Glu Gly Trp Tyr
                85                  90                  95

Phe Arg Val Ser Ile Pro Glu Lys Arg Glu Ser Phe Cys Phe Met Tyr
            100                 105                 110

Ser Val Glu Asn Pro Ala Phe Arg Gln Ser Leu Ser Pro Leu Glu Val
        115                 120                 125

Ala Leu Tyr Gly Pro Arg Phe Thr Gly Val Gly Ala Gln Ile Leu Gly
    130                 135                 140

Ala Asn Asp Lys Tyr Leu Cys Gln Tyr Glu Gln Asp Ser His Asn Phe
145                 150                 155                 160

Trp Gly Asp Arg His Glu Leu Val Leu Gly Asn Thr Phe Ser Ala Val
                165                 170                 175

Pro Gly Ala Lys Ala Pro Asn Lys Glu Val Pro Pro Glu Glu Phe Asn
            180                 185                 190

Arg Arg Val Ser Glu Gly Phe Gln Ala Thr Pro Phe Trp His Gln Gly
        195                 200                 205

His Ile Cys Asp Asp Gly Arg Thr Asp Tyr Ala Glu Thr Val Lys Ser
    210                 215                 220

Ala Arg Trp Glu Tyr Ser Thr Arg Pro Val Tyr Gly Trp Gly Asp Val
225                 230                 235                 240

Gly Ala Lys Gln Lys Ser Thr Ala Gly Trp Pro Ala Ala Phe Pro Val
                245                 250                 255

Phe Glu Pro His Trp Gln Ile Cys Met Ala Gly Gly Leu Ser Thr Gly
            260                 265                 270

Trp Ile Glu Trp Gly Gly Glu Arg Phe Glu Phe Arg Asp Ala Pro Ser
        275                 280                 285

Tyr Ser Glu Lys Asn Trp Gly Gly Phe Pro Arg Lys Trp Phe Trp
    290                 295                 300

Val Gln Cys Asn Val Phe Glu Gly Ala Thr Gly Glu Val Ala Leu Thr
305                 310                 315                 320

Ala Gly Gly Gly Leu Arg Gln Leu Pro Gly Leu Thr Glu Thr Tyr Glu
                325                 330                 335

Asn Ala Ala Leu Val Cys Val His Tyr Asp Gly Lys Met Tyr Glu Phe
            340                 345                 350

Val Pro Trp Asn Gly Val Val Arg Trp Glu Met Ser Pro Trp Gly Tyr
        355                 360                 365

Trp Tyr Ile Thr Ala Glu Asn Glu Asn His Val Val Glu Leu Glu Ala
    370                 375                 380
```

```
Arg Thr Asn Glu Ala Gly Thr Pro Leu Arg Ala Pro Thr Thr Glu Val
385                 390                 395                 400

Gly Leu Ala Thr Ala Cys Arg Asp Ser Cys Tyr Gly Glu Leu Lys Leu
            405                 410                 415

Gln Ile Trp Glu Arg Leu Tyr Asp Gly Ser Lys Gly Lys Val Ile Leu
        420                 425                 430

Glu Thr Lys Ser Ser Met Ala Ala Val Glu Ile Gly Gly Pro Trp
        435                 440                 445

Phe Gly Thr Trp Lys Gly Asp Thr Ser Asn Thr Pro Glu Leu Leu Lys
    450                 455                 460

Gln Ala Leu Gln Val Pro Leu Asp Leu Glu Ser Ala Leu Gly Leu Val
465                 470                 475                 480

Pro Phe Phe Lys Pro Pro Gly Leu
                485

<210> SEQ ID NO 111
<211> LENGTH: 246
<212> TYPE: PRT
<213> ORGANISM: Arabidopsis sp.

<400> SEQUENCE: 111

Met Ser Ser Ser Asn Ala Cys Ala Ser Pro Ser Pro Phe Pro Ala Val
1               5                   10                  15

Thr Lys Leu His Val Asp Ser Val Thr Phe Val Pro Ser Val Lys Ser
            20                  25                  30

Pro Ala Ser Ser Asn Pro Leu Phe Leu Gly Gly Ala Gly Val Arg Gly
        35                  40                  45

Leu Asp Ile Gln Gly Lys Phe Val Ile Phe Thr Val Ile Gly Val Tyr
50                  55                  60

Leu Glu Gly Asn Ala Val Pro Ser Leu Ser Val Lys Trp Lys Gly Lys
65                  70                  75                  80

Thr Thr Glu Glu Leu Thr Glu Ser Ile Pro Phe Phe Arg Glu Ile Val
                85                  90                  95

Thr Gly Ala Phe Glu Lys Phe Ile Lys Val Thr Met Lys Leu Pro Leu
            100                 105                 110

Thr Gly Gln Gln Tyr Ser Glu Lys Val Thr Glu Asn Cys Val Ala Ile
        115                 120                 125

Trp Lys Gln Leu Gly Leu Tyr Thr Asp Cys Glu Ala Lys Ala Val Glu
130                 135                 140

Lys Phe Leu Glu Ile Phe Lys Glu Glu Thr Phe Pro Pro Gly Ser Ser
145                 150                 155                 160

Ile Leu Phe Ala Leu Ser Pro Thr Gly Ser Leu Thr Val Ala Phe Ser
                165                 170                 175

Lys Asp Asp Ser Ile Pro Glu Thr Gly Ile Ala Val Ile Glu Asn Lys
            180                 185                 190

Leu Leu Ala Glu Ala Val Leu Glu Ser Ile Ile Gly Lys Asn Gly Val
        195                 200                 205

Ser Pro Gly Thr Arg Leu Ser Val Ala Glu Arg Leu Ser Gln Leu Met
210                 215                 220

Met Lys Asn Lys Asp Glu Lys Glu Val Ser Asp His Ser Leu Glu Glu
225                 230                 235                 240

Lys Leu Ala Lys Glu Asn
                245

<210> SEQ ID NO 112
```

<211> LENGTH: 3115
<212> TYPE: DNA
<213> ORGANISM: Arabidopsis sp.

<400> SEQUENCE: 112

```
cacacgttct cgtcctttc ttcttcctct ctgcattctt cacagagttt gtcaccacca        60
acaccaaaca cacaatttca cattcttttg catatttctt cttcttcttc cattatggag       120
atacggagct tgattgtttc tatgaaccct aatttatctt cctttgagct ctctcgccct       180
gtatctcctc tcactcgctc actagttccg ttccgatcga ctaaactagt tccccgctcc       240
atttctaggg tttcggcgtc gatctccacc ccgaatagtg aaactgacaa gatctccgtt       300
aaacctgttt acgtcccgac gtctcccaat cgcgaactcc ggactcctca cagtgggtaa       360
attgatccat tccattccat ttctcttctc ttgtttgttt tattaagctc caatttcagt       420
ttcgtctttt aatttatatg ttcttcttac gatcagtggg acttaaaaaa ttgctccttt       480
aaatgcttca gtatgttttg agtattacaa agttgtaaga tttatttttt attcatttgg       540
tggctcacca ttcgacgact acttttgaat ttgagttttt gaaaaatgca atttaacatc       600
agagagtttt tttttttatg gttgataact tattgtttaa cttttgaaaa atgcagatac       660
catttcgatg gaacacctcg gaagttcttc gagggatggt atttcagggt tccatccca        720
gagaagaggg agagttttg ttttatgtat tctgtggaga atcctgcatt cggcagagt        780
ttgtcaccat tggaagtggc tctatatgga cctagattca ctggtgttgg agctcagatt       840
cttggcgcta atgataaata tttatgccaa tacgaacaag actctcacaa tttctgggga       900
ggtaactcct tgacccttaa aatgctgtgt catgacaata agaaatcata tctgagtctt       960
ttctctactt ctagtactaa tgttcgttat tgttgttaaa gatctaagtc ttatctgaat      1020
tttgttacat tttggttctg gtgctttctc aacatgaatt tgtatatatg actttaaaga      1080
ttgcttacct aaagttttta ctcatgcata gatcgacatg agctagtttt ggggaatact      1140
tttagtgctg tgccaggcgc aaaggctcca acaaggagg ttccaccaga ggttctcact       1200
cctcccttgt tggttacttt gttatctgtt aaatagtttt ccaattgtat ccggatagtg      1260
ttctacttct ccttgtagaa aatctcaagt ttttgttact cttgctattc tcttggatgt      1320
tgatttgtaa agcatgtcgt tttattgtag gaatttaaca gaaagtgtc cgaagggttc       1380
caagctactc cattttggca tcaaggtcac atttgcgatg atggccggta attatatgat      1440
tctatgcaca acaagaattc actatattat aaatattgga ttgagtat ttttgttgaa        1500
aatttctgtg tttaaatctg acttgacttg ttttgtcagt actgactatg cggaaactgt      1560
gaaatctgct cgttgggagt atagtactcg tcccgtttac ggttggggtg atgttggggc      1620
caaacagaag tcaactgcag gctggcctgc agcttttcct gtatttgagc ctcattggca      1680
gatatgcatg gcaggaggcc tttccacagg tgtgagcttt gcttgattga cttaaagtta      1740
ataaatagac ggttaagttt acttgcctag tactaacaga aaattaagaa agaaaccacc      1800
ctctttctat cagcagaaac tgctattgta gttcttattt tttctcttgt atttgcaggg      1860
tggatagaat ggggcggtga aaggtttgag tttcggatg caccttctta ttcagagaag       1920
aattggggtg gaggcttccc aagaaaatgg ttttgggtaa acatttcat cctttgcta         1980
catttcttgt tgcagacttt agttagctag tggacctgtg tatacaccca catgtagtat      2040
acttgtttga tagctttatt tgtcaatgtc tctttacagg tccagtgtaa tgtctttgaa      2100
ggggcaactg gagaagttgc tttaaccgca ggtggcgggt tgaggcaatt gcctggattg      2160
actgagacct atgaaaatgc tgcactggta tgcacttata agatcttctt aagcaatgac      2220
```

```
agtgagtatt agaaggcaga tagtttacaa aagctctggg cccttgtaaa tctgcaggtt    2280
tgtgtacact atgatggaaa aatgtacgag tttgttcctt ggaatggtgt tgttagatgg    2340
gaaatgtctc cctggggtta ttggtatata actgcagaga acgaaaacca tgtggtaaat    2400
ttgttttact agtttcattc agttttactt ttgacatcat atcattccct tatggctaga    2460
ttccaacacc cgatgaatgt cttgtgacag gtggaactag aggcaagaac aaatgaagcg    2520
ggtacacctc tgcgtgctcc taccacagaa gttgggctag ctacggcttg cagagatagt    2580
tgttacggtg aattgaagtt gcagatatgg gaacggctat atgatggaag taaaggcaag    2640
gtatgtatgc taatgtgatc caatccctgt agttaaaagt cttaacaaat cctaaggcag    2700
tgaaagaaga ttatgaacgt ttgttatggt taacaatgat gcaggtgata ttagagacaa    2760
agagctcaat ggcagcagtg gagataggag gaggaccgtg gtttgggaca tggaaaggag    2820
atacgagcaa cacgcccgag ctactaaaac aggctcttca ggtcccattg gatcttgaaa    2880
gcgccttagg tttggtccct tcttcaagc caccgggtct gtaacattga tgagtgtttt    2940
gtttgttgat agagacccat gtgatgaatg aagccttagt catgtcattg ctagcttcac    3000
tattatgtat gtatgatttt agttcgttcg gtccttgtgg taaatgatac gggccagtgt    3060
aaagtctagt tcaataaaag ccttgagtcg cataatttca atttcaaatt gcatc         3115

<210> SEQ ID NO 113
<211> LENGTH: 536
<212> TYPE: DNA
<213> ORGANISM: Arabidopsis sp.

<400> SEQUENCE: 113
caccccaaac atcacaattt cacattcttt tgcatatttc ttcttcttct tccattatgg     60
agatacggag cttgattgtt tctatgaacc ctaatttatc ttcctttgag ctctctcgcc    120
ctgtatctcc tctcactcgc tcactagttc cgttccgatc gactaaacta gttccccgct    180
ccatttctag ggtttcggcg tcgatctcca ccccgaatag tgaaactgac aagatctccg    240
ttaaacctgt ttacgtcccg acgtctccca atcgcgaact ccggactcct cacagtggat    300
accatttcga tggaacacct cggaagttct tcgagggatg gtatttcagg gtttccatcc    360
cagagaagag ggagagtttt tgttttatgt attctgtgga gaatcctgca tttcggcaga    420
gtttgtcacc attggaagtg gctctatatg gacctagatt cactggtgtt ggagctcaga    480
ttcttggcgc taatgataaa tatttatgcc aatacgaaca agactctcac aatttc        536

<210> SEQ ID NO 114
<211> LENGTH: 411
<212> TYPE: PRT
<213> ORGANISM: Arabidopsis sp.
<220> FEATURE:
<223> OTHER INFORMATION: Peptide PIR: T04448 shown in Figure 31

<400> SEQUENCE: 114

Pro Glu Lys Arg Glu Ser Phe Cys Phe Met Tyr Ser Val Glu Asn Pro
1               5                   10                  15

Ala Phe Arg Gln Ser Leu Ser Pro Leu Glu Val Ala Leu Tyr Gly Pro
            20                  25                  30

Arg Phe Thr Gly Val Gly Ala Gln Ile Leu Gly Ala Asn Asp Lys Tyr
        35                  40                  45

Leu Cys Gln Tyr Glu Gln Asp Ser His Asn Phe Trp Gly Asp Arg His
    50                  55                  60
```

-continued

```
Glu Leu Val Leu Gly Asn Thr Phe Ser Ala Val Pro Gly Ala Lys Ala
 65                  70                  75                  80

Pro Asn Lys Glu Val Pro Pro Glu Glu Phe Asn Arg Arg Val Ser Glu
                 85                  90                  95

Gly Phe Gln Ala Thr Pro Phe Trp His Gln Gly His Ile Cys Asp Asp
            100                 105                 110

Gly Arg Thr Asp Tyr Ala Glu Thr Val Lys Ser Ala Arg Trp Glu Tyr
            115                 120                 125

Ser Thr Arg Pro Val Tyr Gly Trp Gly Asp Val Gly Ala Lys Gln Lys
130                 135                 140

Ser Thr Ala Gly Trp Pro Ala Ala Phe Pro Val Phe Glu Pro His Trp
145                 150                 155                 160

Gln Ile Cys Met Ala Gly Gly Leu Ser Thr Gly Trp Ile Glu Trp Gly
                165                 170                 175

Gly Glu Arg Phe Glu Phe Arg Asp Ala Pro Ser Tyr Ser Glu Lys Asn
            180                 185                 190

Trp Gly Gly Phe Pro Arg Lys Trp Phe Trp Val Gln Cys Asn Val
            195                 200                 205

Phe Glu Gly Ala Thr Gly Glu Val Ala Leu Thr Ala Gly Gly Leu
210                 215                 220

Arg Gln Leu Pro Gly Leu Thr Glu Thr Tyr Glu Asn Ala Ala Leu Val
225                 230                 235                 240

Cys Val His Tyr Asp Gly Lys Met Tyr Glu Phe Val Pro Trp Asn Gly
                245                 250                 255

Val Val Arg Trp Glu Met Ser Pro Trp Gly Tyr Trp Tyr Ile Thr Ala
            260                 265                 270

Glu Asn Glu Asn His Val Val Glu Leu Glu Ala Arg Thr Asn Glu Ala
            275                 280                 285

Gly Thr Pro Leu Arg Ala Pro Thr Thr Glu Val Gly Leu Ala Thr Ala
290                 295                 300

Cys Arg Asp Ser Cys Tyr Gly Glu Leu Lys Leu Gln Ile Trp Glu Arg
305                 310                 315                 320

Leu Tyr Asp Gly Ser Lys Gly Lys Leu Lys Val Leu Thr Asn Pro Lys
                325                 330                 335

Ala Val Lys Glu Asp Tyr Glu Arg Leu Leu Trp Leu Thr Met Met Gln
            340                 345                 350

Val Ile Leu Glu Thr Lys Ser Ser Met Ala Ala Val Glu Ile Gly Gly
            355                 360                 365

Gly Pro Trp Phe Gly Thr Trp Lys Gly Asp Thr Ser Asn Thr Pro Glu
370                 375                 380

Leu Leu Lys Gln Ala Leu Gln Val Pro Leu Asp Leu Glu Ser Ala Leu
385                 390                 395                 400

Gly Leu Val Pro Phe Phe Lys Pro Pro Gly Leu
                405                 410
```